United States Patent
Schlessinger et al.

(10) Patent No.: US 6,391,584 B1
(45) Date of Patent: May 21, 2002

(54) EXPRESSION-CLONING METHOD FOR IDENTIFYING TARGET PROTEINS FOR EUKARYOTIC TYROSINE KINASES AND NOVEL TARGET PROTEINS

(75) Inventors: Joseph Schlessinger; Edward Y. Skolnik, both of New York, NY (US); Benjamin L. Margolis, Ann Arbor, MI (US)

(73) Assignee: New York University Medical Center, New York, NY (US)

(*) Notice: Subject to any disclaimer, the term of this patent is extended or adjusted under 35 U.S.C. 154(b) by 0 days.

(21) Appl. No.: 09/280,598

(22) Filed: Mar. 29, 1999

Related U.S. Application Data

(60) Division of application No. 08/252,820, filed on Jun. 2, 1994, now Pat. No. 5,889,150, and a continuation-in-part of application No. 08/208,887, filed on Mar. 11, 1994, now Pat. No. 5,677,421, and a continuation-in-part of application No. 08/167,035, filed on Dec. 16, 1993, now Pat. No. 5,618,691, and a continuation-in-part of application No. 07/906,349, filed on Jun. 30, 1992, now Pat. No. 5,434,064, and a division of application No. 08/167,035, filed on Dec. 16, 1993, now Pat. No. 5,618,691, and a division of application No. 07/906,349, filed on Jun. 30, 1992, now Pat. No. 5,434,064, which is a continuation-in-part of application No. 07/643,237, filed on Jan. 18, 1991, now abandoned.

(51) Int. Cl.[7] .............. C07K 14/705; C07K 16/28; C12N 15/12

(52) U.S. Cl. ........... 435/69.1; 435/252.3; 435/320.1; 530/350; 530/388.22; 536/23.5

(58) Field of Search .................... 435/69.1, 252.3, 435/320.1; 530/350, 388.22; 536/23.5

(56) References Cited

U.S. PATENT DOCUMENTS 4,675,285 A  6/1987  Clark et al. ................... 435/6

FOREIGN PATENT DOCUMENTS

| WO | WO 90/08160 | 7/1990 |
| WO | WO 90/10234 | 9/1990 |

OTHER PUBLICATIONS

Anderson et al., 1990, "Binding of SH2 Domains of Phospholipase Cγ1, GAP, and Arc to Activated Growth Factor Receptors", Science 250:979–982.

Cobb et al., 1989, "Autophosphorylation Activates the Soluble Cytoplasmic Domain of the Insulin Receptor in an Intermolecular Reaction", J. Biol. Chem. 264:18701–18706.

Ellis et al., 1990, "Phosphorylation of GAP and GAP–Associated Proteins by Transforming and Mitogenic Tyrosine Kinases", Nature 343:377–380.

Escobedo et al., 1991, "cDNA Cloning of a Novel 85kd Protein that has SH2 Domains and Regulates Binding of P13–kinase to the PGDF β–Receptor", Cell 65:75–82.

Kaplan et al., 1990, "PDGF β–Receptor Stimulates Tyrosine Phosphorylation of GAP and Association of GAP with a Signaling Complex", Cell 61:125–133.

Kazlauskas et al., 1990, "Binding of GAP to Activated PDGF Receptors", Science 247:1578–1581.

King and Sale, 1988, "Assay of Phosphotyrosyl Protein Phosphatase Using Synyhetic Peptide 1142–1153 of the Insulin Receptor", FEBS Lett. 237:137–140.

Krueger et al., 1990, "Structural Diversity and Evolution of Human Receptor–Like Protein Tyrosine Phosphatases", EMBO J. 9:3241–3252.

MacGregor et al., 1990, "Direct Cloning of Leucine Zipper Proteins: Jun Binds Cooperatively to the CRE with CRE–BP1", Oncogene 5:451–458.

Margolis et al., 1989, "EGF Induces Tyrosine Phosphorylation of Phospholipase C–11: A Potential Mechanism for EGF Receptor Signalling", Cell 57:1101–1107.

Margolis et al., 1990, "The Tyrosine Phosphorylated Carboxyterminus of the EGF Receptor is a Binding Site for GAP and PLC–γ", EMBO J. 9:4375–4380.

Margolis et al., 1990, "Tyrosine Kinase Activity is Essential for the Association of Phospholipase C–γ with the Epidermal Growth Factor Receptor", Mol. Cell. Biol. 10:435–441.

Margolis et al., 1990, "Effect of Phospholipase $C_T$ Overexpression on PDGF–Induced Second Messengers and Mitogenesis", Science 248:607–610.

Matsuda et al., 1990, "Binding of Transforming Protein $P4^{gag-crk}$ to a Broad Range of Phosphotyrosine–Containing Proteins", Science 248:1537–1539.

Mayer et al., 1988, "A Novel Viral Oncogene with Structural Similarity to Phospholipase C", Nature 332:272–275.

Mayer et al., "Association of the v–crk Oncogene Product with Phosphotytosine–Containing Proteins and Protein Kinase Activity", Proc. Nat. Acad. Sci USA 87:2638–2642.

Meisenhelder et al., 1989, "Phospholipase C–γ is a Substrate for the PGDF and EGF Receptor Protein–Tyrosine Kinases In Vivo and In Vitro", Cell 57:1109–1122.

Otsu et al., 1991, "Characterization of Two 85kd Proteins that Associate with Receptor Tyrosine Kinases, Middle–T/pp60(c–src) Complexes, and P13–Kinase", Cell 65:91–103.

Pike, 1987, "Assay of Growth Factor–Stimulated Tyrosine Kinases Using Synthetic Peptide Substrates", Meth. Enzymol. 146:355–362.

(List continued on next page.)

Primary Examiner—John Ulm
(74) Attorney, Agent, or Firm—Pennie & Edmonds LLP

(57) ABSTRACT

The present invention relates to a novel method, based on direct expression cloning, for identifying target proteins capable of binding to and/or serving as substrates for receptor or cytoplasmic tyrosine kinases. The present invention also relates to novel proteins identified using this method, and to methods for identifying compounds that disrupt the interaction of such novel proteins with the receptor or cytoplasmic tyrosine kinases.

14 Claims, 74 Drawing Sheets

OTHER PUBLICATIONS

Sadowski et al., 1986, "A Noncatalytic Domain Conserved Among Cytoplasmic Protein–Tyrosine Kinases Modifies the Kinase Fuction and Transforming Activity of Fujinami Sarcoma Virus P130$^{gag-fps}$", Molec. Cell. Biol. 6:4396–4408.

Skolnik et al., 1991, "Cloning of P13 Kinase–Associated p85 Utilizing a Novel Method for Expression/Cloning of Target Proteins for Receptor Tyrosine Kinases", Cell 65:83–89.

Snyder et al., 1987, "λgt 11: Gene Isolation with Antibody Probes and Other Applications", Meth. Enzymol. 154:107–128.

Stahl et al., 1988, "Sequence Similarity of Phospholipase c with the Non–Catalytic Region of src", Nature 332:269–272.

Ullrich et al., 1990, "Signal Transduction by Receptors with Tyrosine Kinase Activity", Cell 61:203–211.

Vogel et al., 1988, "Cloning of Bovine GAP and its Interaction with Oncogenic ras p21", Nature 335:90–93.

Wahl et al., 1989, "Epidermal Growth Factor Stimulates Tyrosine Phosphorylation of Phospholipase C–11 Independently of Receptor Internalization and Extracellular Calcium", Proc. Nat. Acad, Sci. USA 86:1568–1572.

Moran et al., 1990, "Src Homology Region 2 Domains Direct Protein–Protein Interaction in Signal Transduction", Proc. Nat. Acad. Sci. USA 87:8622–8626.

Fazioli et al., 1993, "Eps8, a Substrate for the Epidermal Growth Factor Receptor Kinase, Enhances EGF–Dependent Mitogenic Signals", EMBO J. 12:3799–3808.

Margolis et al., 1992, "High–Efficiency Expression/Cloning of Epidermal Growth Factor–Receptor Binding Proteins with Src Homology 2 Domains", Proc. Nat. Acad Sci. USA 89:8894–8898.

White et al., 1987, "Characterization of an Endogenous Substrate of the Insulin Receptor in Cultured Cells", J. Biol. Chem. 262:9769–9777.

Mannervik and Danielson, 1988, "Glutathione Transferases—Structure and Catalytic Activity", CRC Crit. Rev. Biochem. 23:283–337.

Sulston et al., 1992, "The C. elegans Genome Sequencing Project: A Beginning", Nature 356:37–40.

Mayer et al., 1993, "A Putative Modulator Domain Present in Diverse Signalling Proteins", Cell 73:629–630.

Lehmann et al., 1990, "Nck, a Melanoma cDNA Encoding a Cytoplasmic Protein Consisting of the src Homology Units SH2 and SH3", Nucl. Acids Res. 18:1048.

Matsuda et al., 1992, "Two Species of Human CRK cDNA Encode Proteins with Distinct Biological Activities", Mol. Cell. Biol. 12:3482–3489.

Reichman et al., 1992, "The Product of the Cellular crk Gene Consists Primarily of SH2 and SH3 Regions", Cell Growth & Differentiation 3:451–460.

Cantley et al., 1991, "Oncogenes and Signal Transduction", Cell 64:281–302.

Carpenter and Cohen, 1990, "Epidermal Growth Factor", J. Biol. Chem. 265:7709–7712.

Clark et al., 1992, "Genes Involved in Two *Caenorhabditis elegans* Cell–Signaling Pathways", Cold Spring Harb. Symp. Quant. Biol. 57:363–373.

Coughlin et al., 1989, "Role of Phosphatidylinositol Kinase in PGDF Receptor Signal Transduction", Science 243:1191–1194.

Gould and Hunter, 1988, "Platelet–Derived Growth Factor Induces Multisite Phosphorylation of pp60$^{c-src}$ and Increases Its Protein–Tyrosine Kinase Activity", Mol. Cell. Biol. 8:3345–3356.

Heldin, 1991, "SH2 Domains: Elements that Control Protein Interactions During Signal Transduction", TIBS 16:450–452.

Kaplan et al., 1990, "Cloning of Three Human Tyrosine Phosphatases Reveals a Multigne Family of Receptor–Linked Protein–Tyrosine–Phosphatases Expressed in Brain", Proc. Natl. Acad. Sci. USA 87:7000–7004.

Kaplan et al., 1987, "Common Elements in Growht Factor Stimulation and Oncogenic Transformation: 85 kd Phosphoprotein and Phosphatidylinositol Kinase Activity", Cell 50:1021–1029.

Kazlauskas and Cooper, 1990, "Phosphorylation of the PDGF Receptor β Subunit Creates a Tight Binding Site for Phosphatidylinositol 3 Kinase", Embo J. 9:3279–3286.

Kazlauskas and Cooper, 1989, "Autophosphorylation of the PDGF Receptor in the Kinase Insert Region Regulations Interactions with Cell Proteins", Cell 58:1121–1133.

Kishimoto et al., 1985, "Studies on the Phosphorylation of Myelin Basic Protein by Protein Kinase C and Adenosine 3':5'–Monophosphate–Dependent Protein Kinase", J. Biol. Chem. 206:12492–12499.

Klee and Guerini, 1990, "Structure and Regulation of Calcineurin, a Calmodulin–Stimulated Protein Phosphatase", FASEB J. 4:A2172.

Koch et al., 1991, "SH2 and SH3 Domains: Elements that Control Interactions of Cytoplasmic Signaling Proteins", Science 252:668–674.

Kuenzel et al., 1987, "Substrate Specificity Determinants for Casein Kinase II as Deduced from Studies with Synthetic Peptides", J. Biol. Chem. 262:9136–9140.

Kumjian et al., 1989, "Platelet–Derived Growth Factor (PDGF) Binding Promotes Physical Association of PDGF Receptor with Phospholipase C", Proc. Natl. Acad. Sci. USA 86:8232–8236.

Kypta et al., 1990, "Association Between the PDGF Receptor and Members of the src Family of Tyrosine Kinases", Cell 62:481–492.

Margolis, 1992, "Proteins with SH2 Domains: Transducers in the Tyrosine Kinase Signaling Pathway", Cell Growth and Differentiation 3:73–80.

Margolis et al., 1992, "Tyrosine Phosphorylation of vav Proto–Oncogene Product Containing SH2 Domain and Transcription Factor Motifs", Nature 356:71–74.

Marin et al., 1986, "Site Specificity of Casein Kinase–2 (TS) from Rat Liver Cytosol. A Study with Model Peptide Substrates.", Eur. J. Biochem. 160:239–244.

Martin et al., 1992, "GAP Domains Responsible for Ras p21–Dependent Inhibition of Muscarinic Atrial K$^+$ Channel Currents", Science 255:192–194.

McGlade et al., 1992, "SH2 Domains of the p85α Subunit of Phosphatidylinositol 3–Kinase Regulate Binding to Growth Factor Receptors", Mol. Cell. Biol. 12:991–997.

Molloy et al., 1989, "PDGF Induction of Tyrosine Phosphorylation of GTPase Activating Protein", Nature 342:711–714.

Morrison et al., 1989, "Direct Activation of the Serine/Threonine Kinase Activity of Raf–1 Through Tyrosine Phosphorylation by the PDGF β–Receptor", Cell 58:649–657.

Pawson, 1988, "Non–Catalytic Domains of Cytoplasmic Protein–Tyrosine Kinases: Regulatory Elements in Signal Transduction", Oncogene 3:491–495.

Reedijk et al., 1990, "Interactions of Phosphatidylinositol Kinase, GTPase–Activating Protein (GAP), and GAP–Associated Proteins with the Colony–Stimulating Factor–1 Receptor", Mol. Cell. Biol. 10:5601–5608.

Sap et al., 1990, "Cloning and Expression of a Widely Expressed Receptor Tyrosine Phosphatase", Proc. Natl. Acad. Sci. USA 87:6112–6116.

Shurtleff et al., 1990, "Structural Features of the Colony–Stimulating Factor 1 Receptor that Affect Its Association with Phosphatidylinositol 3–Kinase", EMBO J. 9:2415–2421.

Wahl et al., 1990, "identification of Two Epidermal Growth Factor–Sensitive Tyrosine Phosphorylation Sites of Phospholipase–C–γ in Intact HSC–1 Cells", J. Biol. Chem. 265:3944–3948.

Whitman et al., 1985, "Association of Phosphatidylinositol Kinase Activity with Polyoma Middle–T Competent for Transformation", Nature 315:239–242.

Williams, 1989, "Signal Transduction by the Platelet–Derived Growth Factor Receptor", Science 243:1564–1570.

Woodgett et al., 1986, "Substrate Specificity of Protein Kinase C. Use of Synthetic Peptides Corresponding to Physiological Sites as Probes for Substrate Recognition Requirements", Eur. J. Biochem. 161:177–184.

```
       TACAACCAGGCTCAACTGTTGCATGGTAGCAGATTTGCAAACATGAGTGCTGAGGGGTAC
  1    ------+---------+---------+---------+---------+---------+     60
       ATGTTGGTCCGAGTTGACAACGTACCATCGTCTAAACGTTTGTACTCACGACTCCCCATG
                                                        M  S  A  E  G  Y

CAGTACAGAGCGCTGTATGATTATAAAAGGAAAGAGAAGATATTGACTGTGACTTG
 61    ------+---------+---------+---------+---------+---------+    120
       GTCATGTCTCGCGACATACTAATATTTTCCTTTCTCTTCTATAACTGAACGTGAAC
        Q  Y  R  A  L  Y  D  Y  K  K  E  R  E  E  D  I  D  L  H  L

GGTGACATATTGACTGTGAATAAGGGTCCTTAGTAGCTCTTGGATTCAGTGATGGACAG
121    ------+---------+---------+---------+---------+---------+    180
       CCACTGTATAACTGACACTTATTCCCAGGAATCATCGAGAACCTAAGTCACTACCTGTC
        G  D  I  L  T  V  N  K  G  S  L  V  A  L  G  F  S  D  G  Q

GAAGCCAGGCCTGAAGAAATTGGCTGGTTAAATGGCTATAATGAAACCACAGGGGAAAGG
181    ------+---------+---------+---------+---------+---------+    240
       CTTCGGTCCGGACTTCTTTAACCGACCAATTTACCGATATTACTTTGGTGTCCCCTTTCC
        E  A  R  P  E  E  I  G  W  L  N  G  Y  N  E  T  T  G  E  R

GGGGACTTTCCGGGAACTTACGTAGAATATATTGGAAGGAAAAAAATCTCGCCTCCCACA
241    ------+---------+---------+---------+---------+---------+    300
       CCCCTGAAAGGCCCTTGAATGCATCTTATATAACCTTCCTTTTTTTAGAGCGGAGGGTGT
        G  D  F  P  G  T  Y  V  E  Y  I  G  R  K  K  I  S  P  P  T

CCAAAGCCCCCGGCCACCTCGGCCCTCTTCCTGTTGCACCAGTTCTTCGAAAACTGAAGCA
301    ------+---------+---------+---------+---------+---------+    360
       GGTTTCGGGGGCCGGTGGAGCCGGGAGAAGGACAACGTGGTCCAAGAAGCTTTTGACTTCGT
        P  K  P  R  P  P  R  P  L  P  V  A  P  G  S  S  K  T  E  A
```

FIG. 4A

```
361 GATGTTGAACAACAAGCTTTGACTCTCCCGGATCTTGCAGAGCAGTTGCCCCTCCTGAC 420
    ----+----+----+----+----+----+----+----+----+----+----+----+
    CTACAACTTGTTGTTCGAAACTGAGAGGGCCTAGAACGTCTCGTCAACGGGGAGGACTG
     D  V  E  Q  Q  A  L  T  L  P  D  L  A  E  Q  F  A  P  P  D

421 ATTGCCCCGCCTCTTCTTATCAAGCTCGTGGAAGCCATTGAAAAGAAAGGTCTGGAATGT 480
    ----+----+----+----+----+----+----+----+----+----+----+----+
    TAACGGGGCGGAGAAGAATAGTTCGAGCACCTTCGGTAACTTTTCTTTCCAGACCTTACA
     I  A  P  P  L  L  I  K  L  V  E  A  I  E  K  K  G  L  E  C

481 TCAACTCTATACAGAACACAGAGCTCCAGCAACCTGGCAGAATTACGACAGCTTCTTGAT 540
    ----+----+----+----+----+----+----+----+----+----+----+----+
    AGTTGAGATATGTCTTGTGTCTCGAGGTCGTTGGACCGTCTTAATGCTGTCGAAGAACTA
     S  T  L  Y  R  T  Q  S  S  N  L  A  E  L  R  Q  L  L  D

541 TGTGATACACCCTCCGTGGACTTGGAAATGATCGATGTGCACGTTTTGGCTGACGCTTTC 600
    ----+----+----+----+----+----+----+----+----+----+----+----+
    ACACTATGTGGGAGGCACCTGAACCTTTACTAGCTACACGTGCAAAACCGACTGCGAAAG
     C  D  T  P  S  V  D  L  E  M  I  D  V  H  V  L  A  D  A  F

601 AAACGCTATCTCCTGGACTTACCAAATCCTGTCATTCCAGCAGCCGTTTACAGTGAAATG 660
    ----+----+----+----+----+----+----+----+----+----+----+----+
    TTTGCGATAGAGGACCTGAATGGTTTAGGACAGTAAGGTCGTCGGCAAATGTCACTTTAC
     K  R  Y  L  L  D  L  P  N  P  V  I  P  A  A  V  Y  S  E  M

661 ATTTCTTTAGCTCCAGAAGTACAAAGCTCCGAAGAATATATTCAGCTATTGAAGAAGCTT 720
    ----+----+----+----+----+----+----+----+----+----+----+----+
    TAAAGAAATCGAGGTCTTCATGTTTCGAGGCTTCTTATATAAGTCGATAACTTCTTCGAA
     I  S  L  A  P  E  V  Q  S  S  E  E  Y  I  Q  L  L  K  K  L
```

FIG. 4B

```
721  ATTAGGTCGCCTAGCATACCTCATCAGTATTGGCTTACGCTTCAGTATTTGTTAAAACAT
     ----+----|----+----|----+----|----+----|----+----|----+----| 780
     TAATCCAGCGGATCGTATGGAGTAGTCATAACCGAATGCGAAGTCATAAACAATTTGTA

I  R  S  P  S  I  P  H  Q  Y  W  L  T  L  Q  Y  L  L  K  H

781  TTCTTCAAGCTCTCTCAAACCTCCAGCAAAAATCTGTTGAATGCAAGAGTACTCTCTGAA
     ----+----|----+----|----+----|----+----|----+----|----+----| 840
     AAGAAGTTCGAGAGAGTTTGGAGGTCGTTTTTAGACAACTTACGTTCTCATGAGAGACTT

F  F  K  L  S  Q  T  S  S  K  N  L  L  N  A  R  V  L  S  E

841  ATTTTCAGCCCTATGCTTTTCAGATTCTCAGCAGCCAGCTCTGATAATACTGAAAACCTC
     ----+----|----+----|----+----|----+----|----+----|----+----| 900
     TAAAAGTCGGGATACGAAAAGTCTAAGAGTCGTCGGTCGAGACTATTATGACTTTTGGAG

I  F  S  P  M  L  F  R  F  S  A  A  S  S  D  N  T  E  N  L

901  ATAAAAGTTATAGAAATTTTAATCTCAACTGAATGAACAGCCTGCACCAGCA
     ----+----|----+----|----+----|----+----|----+----|----+----| 960
     TATTTTGAATATCTTTAAAATTAGAGTTGACTTACCTTGCTGTCGGACGTGGTCGT

I  K  V  I  E  I  L  I  S  T  E  W  N  E  R  Q  P  P  A

961  CTGCCTCCTAAACCACCAAAACCTACTGTAGCCAACAACGGTATGAATAACAATATG
     ----+----|----+----|----+----|----+----|----+----|----+----| 1020
     GACGGAGGATTTGGTGGTTTTGGATGATGACATCGGTTGTTGCCATACTTATTGTTATAC

L  P  P  K  P  P  K  P  T  T  V  A  N  N  G  M  N  N  M

1021 TCCTTACAAAATGCTGAATGGTACTGGGGAGATATCTCGAGGAAGAAGTGAATGAAAAA
     ----+----|----+----|----+----|----+----|----+----|----+----| 1080
     AGGAATGTTTTACGACTTACCATGACCCCTCTATAGAGCTCCTTCTTCACTTACTTTTT

```
       CTTCGAGATACAGCAGACGGGACCTTTTTGTGTACGAGATGGTCTACTAAAATGCATGGT
1081   ------+---------+---------+---------+---------+---------+ 1140
       GAAGCTCTATGTCGTCTGCCCTGGAAAAACCATGCTCTACGCAGATGATTTACGTACCA

L  R  D  T  A  D  G  T  F  L  V  R  D  A  S  T  K  M  H  G

GATTATACTCTTACACTAAGGAAAGGGGAAATAACAAATTAATCAAAATATTTCATCGA
1141   ------+---------+---------+---------+---------+---------+ 1200
       CTAATATGAGAATGTGATTCCTTTCCCCTTTATTGTTTAATTAGTTTTATAAAGTAGCT

D  Y  T  L  T  L  R  K  G  N  N  K  L  I  K  I  F  H  R

GATGGGAAATATGGCTTCTCTCTGACCCATTAACCTTCAGTTCTGTGGTTGAATTAATAAAC
1201   ------+---------+---------+---------+---------+---------+ 1260
       CTACCCTTTATACCGAAGAGACTGGGTAATTGGAAGTCAAGACACCAACTTAATTATTTG

D  G  K  Y  G  F  S  D  P  L  T  F  S  S  V  V  E  L  I  N

CACTACCGGAATGAATCTCTAGCTCAGTATAATCCCAAATTGGATGTGAAATTACTTTAT
1261   ------+---------+---------+---------+---------+---------+ 1320
       GTGATGGCCTTACTTAGAGATCGAGTCATATTAGGGTTTAACCTACACTTAATGAAATA

H  Y  R  N  E  S  L  A  Q  Y  N  P  K  L  D  V  K  L  L  Y

CCAGTATCCAAATACCAACAGGATCAAGTTGTCAAAGAAGATAATATTGAAGCTGTAGGG
1321   ------+---------+---------+---------+---------+---------+ 1380
       GGTCATAGGTTTATGGTTGTCCTAGTTCAACAGTTCTTCTATTATAACTTCGACATCCC

P  V  S  K  Y  Q  Q  D  Q  V  V  K  E  D  N  I  E  A  V  G

AAAAAATTACATGAATATAACACTCAGTTTCAAGAAAAAGTCGAGAATGATAGATTA
1381   ------+---------+---------+---------+---------+---------+ 1440
       TTTTTAATGTACTTATATTGTGAGTCAAAGTTCTTTTTTCAGCTCTTATACTATCTAAT

```
1441  TATGAAGAATATACCCGCACATCCCAGGAAATCCAAATGAAAAGGACAGCTATTGAAGCA
      ----+----+----+----+----+----+----+----+----+----+----+----+  1500
      ATACTTCTTATATGGGCGTGTAGGGTCCTTTAGGTTTACTTTTCCTGTCGATAACTTCGT
   a   Y  E  E  Y  T  R  T  S  Q  E  I  Q  M  K  R  T  A  I  E  A

1501  TTTAATGAAACCATAAAAATATTTGAAGAACAGTGCCAGAGCCAAGAGCGGTACAGCAAA
      ----+----+----+----+----+----+----+----+----+----+----+----+  1560
      AAATTACTTTGGTATTTTATAAACTTCTTGTCACGGTCTCGGTTCTCGCCATGTCGTTT
   a   F  N  E  T  I  K  I  F  E  E  Q  C  Q  T  Q  E  R  Y  S  K

1561  GAATACATAGAAAAGTTTAAACGTGAAGGCAATGAGAAAGAAATACAAAGGATTATGCAT
      ----+----+----+----+----+----+----+----+----+----+----+----+  1620
      CTTATGTATCTTTTCAAATTTGCACTTCCGTTACTCTTCTTTATGTTTCCTAATACGTA
   a   E  Y  I  E  K  F  K  R  E  G  N  E  K  E  I  Q  R  I  M  H

1621  AATTATGATAAGTTGAAGTCTCGAATCAGTGAAATTATTGACAGTAGAAGAAGATTGGAA
      ----+----+----+----+----+----+----+----+----+----+----+----+  1680
      TTAATACTATTCAACTTCAGAGCTTAGTCACTTTAATAACTGTCATCTTCTTCTAACCTT
   a   N  Y  D  K  L  K  S  R  I  S  E  I  I  D  S  R  R  R  L  E

1681  GAAGACTTGAAGAAGCAGGCAGCTGAGTATCGAGAAATTGACAAACGTATGAACAGCATT
      ----+----+----+----+----+----+----+----+----+----+----+----+  1740
      CTTCTGAACTTCTTCGTCCGTCGACTCATAGCTCTTTAACTGTTTGCATACTTGTCGTAA
   a   E  D  L  K  K  Q  A  A  E  Y  R  E  I  D  K  R  M  N  S  I

1741  AAACCAGACCTTATCCAGCTGAGAAAGACGAGAGACCAATACTTGATGTGGTTGACTCAA
      ----+----+----+----+----+----+----+----+----+----+----+----+  1800
      ATTGGTCTGGAATAGGTCGACTCTTTCTGCTCTCTGGTTATGAACTACACCAACTGAGTT
   a   K  P  D  L  I  Q  L  R  K  T  R  D  Q  Y  L  M  W  L  T  Q
```

FIG. 4E

```
1801 AAAGGTGTTCGGCAAAGAAGTTGAACGAGTGTTGGGCAATGAAAAACACTGAAGACCAA 1860
     ---------+---------+---------+---------+---------+---------+
     TTTCCACAAGCCGTTTCTTCAACTTGCTCACCAACCCGTTACTTTTTGTGACTTCTGGTT

K  G  V  R  Q  K  K  L  N  E  W  L  G  N  E  N  T  E  D  Q

1861 TATTCACTGGTGGAAGATGATGAAGATTTGCCCCATCATGATGAGAAGACATGGAATGTT 1920
     ---------+---------+---------+---------+---------+---------+
     ATAAGTGACCACCTTCTACTACTTCTAAACGGGGTAGTACTACTCTTCTGTACCTTACAA

Y  S  L  V  E  D  D  E  D  L  P  H  H  D  E  K  T  W  N  V

1921 GGAAGCAGCAACCGAAACAAAGCTGAAAACCTGTTGCGAGGAAGCGAGATGCACTTTT 1980
     ---------+---------+---------+---------+---------+---------+
     CCTTCGTCGTTGGCTTTGTTTCGACTTTTGGACAACGCTCCTTCGCTCTACCGTGAAAA

G  S  S  N  R  K  A  E  N  L  L  R  G  K  R  D  G  T  F

1981 CTTGTCCGGGAGAGCAGTAAACAGGGCTGCTATGCCTGCTCTGTAGTGGTGGACGGGGAA 2040
     ---------+---------+---------+---------+---------+---------+
     GAACAGGCCCTCTCGTCATTTGTCCCGACGATACGGACGAGACATCACCACCTGCCCGTT

L  V  R  E  S  S  K  Q  G  C  Y  A  C  S  V  V  V  D  G  E

2041 GTAAAGCATTGTGTCATAAACAAGACAGCAACTGGCTATGGCTTTGCCGAGCCCTATAAC 2100
     ---------+---------+---------+---------+---------+---------+
     CATTTCGTAACACAGTATTTGTTCTGTCGTTGACCGATACCGAAACGGCTCGGGATATTG

V  K  H  C  V  I  N  K  T  A  T  G  Y  G  F  A  E  P  Y  N

2101 TTGTACAGCTCTCTGAAAGAGCTTGTGCTACATTACCAACACCTCCCTTGTGCAGCAC 2160
     ---------+---------+---------+---------+---------+---------+
     AACATGTCGAGAGACTTTCTCGAACACGATGTAATGGTTGTGTGGAGGGAACACGTCGTG

```
        AACGACTCCCTCAATGTCACACTAGCCTACCCAGTATATGCACAGAGGCGATGAAGC
2161    ---------+---------+---------+---------+---------+---------+  2220
        TTGCTGAGGGAGTTACAGTGTGATCGGATGGGTCATATACGTGTCGTCCGCTACTTCG

N  D  S  L  N  V  T  L  A  Y  P  V  Y  A  Q  Q  R  R     a

GCTTACTCTCTTTGATCCTTCTCCTGAAGTTCAGCCACCCTGAGGCCTCTGGAAAGCAAAGG
2221    ---------+---------+---------+---------+---------+---------+  2280
        CGAATGAGAAACTAGGAAGAGGACTTCAAGTCGGTGGGACTCCGGAGACCTTTCGTTTCC
                                                                      a

GCTCCTCCTCCAGTCTGATCTGTGAATTGAGCTGCAGAAACGAAGCCATCTTTCTTTGGAT
2281    ---------+---------+---------+---------+---------+---------+  2340
        CGAGGAGAGGTCAGACTAGACACTTAACTCGACGTCTTTGCTTCGGTAGAAAGAAACCTA
                                                                      a

GGGACTAGAGCTTTCTTTCACAAAAAGAAGTAGGGGAAGACATGCAGCCTAAGGCTGTA
2341    ---------+---------+---------+---------+---------+---------+  2400
        CCCTGATCTCGAAAGAAAGTGTTTTTCTTCATCCCCTTCTGTACGTCGGATTCCGACAT
                                                                      a

TGATGACCACACGTTCCTAAGCTGGAGTGCTTATCCCTTCTTTTCTTTTTTCTTTGGT
2401    ---------+---------+---------+---------+---------+---------+  2460
        ACTACTGGTGTGCAAGGATTCGACCTCACGAATAGGGAAGAAAAAGAAAAAAGAAACCA
                                                                      a

TTAATTTAAAGCCACAACCACATACAACACAAAGAGAAAAAGAGAAAAATCAAAAATCTGC
2461    ---------+---------+---------+---------+---------+---------+  2520
        AATTAAATTTCGGTGTTGGTGTATGTTGTGTTTCTCTTTTTCTTTACGTTTTTAGAGACG
                                                                      a

GTGCAGGGACAAAGAGGCCTTTAACCATGGTGCTTGTTAATGCTTTCTGAAGCTTTACCA
2521    ---------+---------+---------+---------+---------+---------+  2580
        CACGTCCCCTGTTTCTCCGGAAATTGGTACCACGAACAATTACGAAAGACTTCGAAATGGT
```

FIG. 4G

```
2581  GCTGAAAGTTGGGACTCTGGAGAGCGGAGGAGAGAGGCAGAGAGAACCCTGCCTGAGA
      ---------+---------+---------+---------+---------+---------+ 2640
      CGACTTTCAACCCTGAGACCTCTCGCCTCCTCTCCGTCTTCTTGGACCGGACTCT

2641  AGGTTTGGTCCAGCCCTGGTTTAGCCCTGGATGTTGCTGTGCACGGTGGACCCAGACACATC
      ---------+---------+---------+---------+---------+---------+ 2700
      TCCAAACCAGGTCGGACCCAAATCGGACCTACAACGACACGTGCCACCTGGGTCTGTGTAG

2701  GCACTGTGGATTATTCATTTTGTAACAAATGAACGATATGTAGCAGAAAGGCACGTCCA
      ---------+---------+---------+---------+---------+---------+ 2760
      CGTGACACCTAATAAAGTAAAACATTGTTACTTGCTATACATCGTCTTTCCGTGCAGGT

2761  CTCACAAGGGACGCTTTGGGAGAATGTCAGTTCATGTATGTTCAGAAGAAATTCTGTCAT
      ---------+---------+---------+---------+---------+---------+ 2820
      GAGTGTTCCCTGCGAAACCCTCTTACAGTCAAGTACATACAAGTCTTCTTTAAGACAGTA

2821  AGAAAGTGCCAGAAAGTGTTTAACTTGTCAAAAACAAAAACCCAGCAACAGAAAAATGG
      ---------+---------+---------+---------+---------+---------+ 2880
      TCTTTCACGGTCTTTCACAAATGAACAGTTTTTTGTTTTTGGGTCGTTGTCTTTTTACC

2881  AGTTTGGAAAACAGGACTTAAAATGACATTCAGTATATAAAATATGTACATATAATTGGA
      ---------+---------+---------+---------+---------+---------+ 2940
      TCAAACCTTTTGTCCTGAATTTTACTGTAAGTCATATATTTTATACATGTATTATAACCT

2941  TGACTAACTATCAAATAGATGGATTTGTATCAATACCAAATAGCTTCTGTTTTGTTTTGC
      ---------+---------+---------+---------+---------+---------+ 3000
      ACTGATTGATAGTTTATCTACCTAAACATAGTTATGTTATCGAAGACAAAACAAAACG
```

FIG. 4H

```
3001  TGAAGGCTAAATTCACAGCGCTATGCAATTCTTAATTTTCATTAAGTTGTTATTTCAGTT
      ------------+---------+---------+---------+---------+---------+  3060
      ACTTCCGATTAAGTGTCGCGATACGTTAAGAATTAAAGTAATTCAACAATAAAGTCAA

3061  TTAAATGTACCTTCAGAATAAGCTTCCCCACCCCAGTTTTTGTTGCTTGAAAATATTGTT
      ------------+---------+---------+---------+---------+---------+  3120
      AATTTACATGGAAGTCTTATTCGAAGGGGGTGGGGTCAAAAACAACGAACTTTATAACAA

3121  GTCCCGGATTTTTGTTAATATATTCATTTTTGTTATCCTTTTTTAAAAATAAATGTACAGGA
      ------------+---------+---------+---------+---------+---------+  3180
      CAGGGCCTAAAAAGAATTATAAGTAAAACAATAGGAAAAATTTTATTACATGTCCT

3181  TGCCAGTAAAAAAAAAATGGCTTCAGAATTAAAACTATGAAATATTTTACAGTTTTCT
      ------------+---------+---------+---------+---------+---------+  3240
      ACGGTCATTTTTTTTTTTTACCGAAGTCTTAATTTTGATACTTTATAAAATGTCAAAAGA

3241  TGTACAGAGTACTTGCTGTTAGCCCAAGTTAAAAAAGTTCATAACAGATTTTTTGGAC
      ------------+---------+---------+---------+---------+---------+  3300
      ACATGTCTCATGAACGACAATCGGGTTCCAATTTTTCAAGTATTGTCTAAAAAAACCTG

3301  TGTTTTGTTGGGCAGTGCCTGATAAGCTTCAAAGCTGCTTTATTCAATAAAAAAAAACC
      ------------+---------+---------+---------+---------+---------+  3360
      ACAAAACAACCCGTCACGGACTATTCGAAGTTTCGACGAAATAAGTTATTTTTTTTGG

3361  CGAATTCACTGG
      ------+--  3372
      GCTTAAGTGACC
```

```
GRB-1 N 333  WYWGDIS --  R EE---- VN E- KL RDTAD------ GTFLVRDST KM HGDY T LT LRK------GG---NN LIKI
GRB-1 C 624  WNVGSSN --  R NK---- AE N-- LL RGKRD------ GTFLVRESS K-- QGCY A CS VVV------DG---EV KHCV c-src   150  WYFGKIT --  R RE---- SE RL LL NPENPR----- GTFLVRESE TT KGAY C LS VSDF-DNAKGLNVK HYKI
v-abl   248  WYHGPVS --  R NA---- AE YK KS SGIN------- GSFLVRESE SS PG-Q R -S ISLRYE---G-RVY HYRI
PLC N   550  WFHGKLG AG  R DGRHI AE R-- LL TEYCIETGAPD GSFLVRESE TF VGDY T LS F--WR-N--G-KVQ HCRI
PLC C   668  WYHASLT --  R AQ---- AE H-- ML MRVPRD----- GAFLVRKRN -E PNSY A IS F--RAE--G-KIK HCRV
GAP N   178  WYHGKLD --  R TI---- AE E-- RL RQAGKS----- GSYLIRESD RR PGSF V LS FRSQM-N-V---VN HPRI
GAP C   348  WYHGKIS --  K QE---- AY N-- LL MTVGQVC---- -SFLVRPSD NT PGDY S LY F-RTNENIQ--R-- -FKI
v-crk   248  WYWGRLS --  R GD---- AV S-- LL QGQRH------ GTFLVRDSG SI PGDF V LS VSES---S---RVS HYIV GRB-1 N 384  --FHRD G KYGFSDPLT-------------- F S SV V ELI N HY RNESLAQYNPKLDV- KL LY PVSK
GRB-1 C 672  INKTAT G -YGFAEPYNL-------------- Y S SL K ELV L HY QHTSLVQHNDSLNV- TL AY PVYA c-src   207  RKLDSG G FYITSRTQ--------------- F S SL Q QLV A YY SKHADGLCH------ RL TN -VCP
v-abl   298  -NTASD G KLYVSSESR-------------- F N TL A ELV H HH STVADGLITT----- LH YP --AP
PLC N   611  HSRQDA G TPKFFLTDNLV------------ F D SL Y DLI T HY QQVPLRCA-EFEM-- RL SL PV-P
PLC C   718  ---QQE G QTVMLGNSE------------- F D SL V DLI S YY EKHPLYRK----M-- KL RY PI--
GAP N   230  --IAMC G DYYIGGRR-------------- F S SL S DLI G YY SHVSCLLKGE------ KL LY PVAP
GAP C   399  -CPTPN N QFMMGGRY-------------- Y N SI G DII D HY RKEQIVEG-YY---- -L KE PV-P
v-crk   298  NSLGPA G GRRAGEGPFAPGLNPTRFLIGDNV F D SL P SLL E FY KIHYLDT--TT---- -L IE PV--

GRB-1   10  ALYDY KEREE D IDLHLGDI LT VNK G SLVALGFSDPEARPEDIG WL NGYNETTGER GDFP GT YVE YIGRK c-src   88  ALYDY ESRTET D --------  LA FKK G ERLQIV------MNTEGD WW LAHSLTTGQT GYIP SN YVA PS-DS
v-abl   68  ALYDF VASGDN T --------  LS ITK G EKLRVLG----YNHNGE WC EAQTK-NGQ- GWVP SN YIT PV-NS
PLC    148  ALFDY KAGRED E --------  LT FTK S AIIQNV------EKQEGG WW RGDYHHKKQ- LWFP SN YVE EMV-S
GAP    284  AILDY TKVPDT D --------  IS FLK G DMFIVN------NELEDG WM WVTNLRTDEQ GLIV ED LVE EV-GR
v-crk  375  ALFDF KGNDDG D --------  LP FKK G DILKIR------DKPEEQ WW NAEDMDGKR- GMIP VP YVE KCRPS
```

Imm.. Ab: 108
ATP  − + − +   − + − +

PLC-Ⓟ
PLC

|_____NO WASH_____|  |_____WASH_____|

Blt. Ab: PLC

FIG. 11

```
        GCCAGTGAATTCGGGCCCGAATTGGCAGAGCTTAATGGAAAAGACGGCTTCATTCCCAAG
  1     ------+---------+---------+---------+---------+---------+   60
        CGGTCACTTAAGCCCGGGCTTAACCGTCTCGAATTACCTTTTCTGCCGAAGTAAGGGTTC a    A  S  E  F  G  P  E  L  A  E  L  N  G  K  D  G  F  I  P  K  -

AACTACATAGAAATGAAACCACATCCGTGGTTTTTTGGCAAAATCCCCAGAGCCAAGGCA
  61    ------+---------+---------+---------+---------+---------+  120
        TTGATGTATCTTTACTTTGGTGTAGGCACCAAAAAACCGTTTTAGGGGTCTCGGTTCCGT
                                       SH2 DOMAIN
    a    N  Y  I  E  M  K  P  H  P  W  F  F  G  K  I  P  R  A  K  A  -

GAAGAAATGCTTAGCAAACAGCGGCACGATGGGGCCTTTCTTATCCGAGAGAGTGAGAGC
 121    ------+---------+---------+---------+---------+---------+  180
        CTTCTTTACGAATCGTTTGTCGCCGTGCTACCCCGGAAAGAATAGGCTCTCTCACTCTCG a    E  E  M  L  S  K  Q  R  H  D  G  A  F  L  I  R  E  S  E  S  -

GCTCCTGGGGACTTCTCCCTCTGTCAAGTTTGGAACGATGTGCAGCACTTTCAAGGTG
 181    ------+---------+---------+---------+---------+---------+  240
        CCACCACCCCTCAACACGGAGAGACAGTTCAAACCTTGCTACACGTCGTGAAAGTTCCAC a    A  P  G  D  F  S  L  S  V  K  F  G  T  M  C  S  T  F  K  V  -

CTCCCGAGATGGAGCCGGAAGTACTTCCTCTGGTGGTGAAGTTCAATTCTTTGAATGAG
 241    ------+---------+---------+---------+---------+---------+  300
        GAGGGCTCTACCTCGGCCTTCATGAAGGAGACCACCACTTCAAGTTAAGAAACTTACTC a    L  P  R  W  S  R  E  V  L  P  L  V  V  K  F  N  S  L  N  E  -
```

FIG. 16A

```
      CTGGTGGATTATCACAGATCTACATCTGTCTCCAGAAACCAGCAGATATTCCTGCGGGAC
301   ------+---------+---------+---------+---------+---------+ 360
      GACCACCTAATAGTGTCTAGATGTAGACAGAGTCTTTGGTCGTCTATAAGGACGCCCTG a   L  V  D  Y  H  R  S  T  S  V  S  R  N  Q  Q  I  F  L  R  D  -

ATAGAACAGGTGCCACAGCAGCCGACATACGTCCAGGCCCTCTTTGACTTTGATCCCCAG
361   ------+---------+---------+---------+---------+---------+ 420
      TATCTTGTCCACGGTGTCGTCGGCTGTATGCAGGTCCGGGAGAAACTGAAACTAGGGGTC
                                                     SH3 DOMAIN
    a   I  E  Q  V  P  Q  Q  P  T  Y  V  Q ┌→ A  L  F  D  F  D  P  Q  -

GAGGATGGAGAGCTGGGCTTCCGCCGGGAGATTTTATCCATGTCATGATAACTCAGAC
421   ------+---------+---------+---------+---------+---------+ 480
      CTCCTACCTCTCGACCCGAAGGCGCCCCTCTAAAATAGGTACAGTACCTATTGAGTCTG a   E  D  G  E  L  G  F  R  R  G  D  F  I  H  V  M  D  N  S  D  -

CCCAACTGGTGGAAAGGAGCTTGCCACGGGCAGACGGGCATGTTTCCCCGGAATTATGT
481   ------+---------+---------+---------+---------+---------+ 540
      GGGTTGACCACCTTTCCTCGAACGGTGCCCGTCTGCCCGTACAAAGGGGCGCTTAATACA a   P  N  W  K  G  A  C  H  G  Q  T  G  M  F  P  P  R  E  L  C  -

CTCCCCCXGTGAACCGGAACGTCTAAGAGTCAAGAAGCAATTATTTAAAGAAAGTGAAAA
541   ------+---------+---------+---------+---------+---------+ 600
      GAGGGGGXCACTTGGCCTTGCAGATTCTCAGTTCTTCGTTAATAAATTCTTTCACTTTT a   L  P  ?  *  T  G  T  S  K  S  Q  E  A  I  I  *  R  K  *  K  -
```

FIG. 16B

```
601  ATGTAAAACACATACAAAGAATTAAACCCACAAGCTGCCTCTGACAGCAGCCTGTGAGG
     ----+----|----+----|----+----|----+----|----+----|----+----| 660
     TACATTTTGTGTATGTTTCTTAATTTGGGTGTTCGACGGAGACTGTCGTCGGACACTCC

M  *  N  T  Y  K  R  I  K  P  T  S  C  L  *  Q  Q  P  V  R  -

661  GAGTGCAGAACACCTGGCCGGGTCACCCTGTGACCCTCACTTTGGTTGGAACTTTAGG
     ----+----|----+----|----+----|----+----|----+----|----+----| 720
     CTCACGTCTTGTGGACCGGCCCAGTGGGACACTGGGAGTGAAACCAACCTTGAAATCC

E  C  R  T  P  G  R  V  T  L  *  P  S  H  F  G  W  N  F  R  -

721  GGGTGGGAGGGGCGTTGGATTTAAAAATGCCAAAACTTACCTATAAATTAAGAAGAGTT
     ----+----|----+----|----+----|----+----|----+----|----+----| 780
     CCCACCCTCCCCGCAACCTAAATTTTTACGGTTTTGAATGGATATTTAATTCTTCTCAA

G  W  E  G  A  L  D  L  K  M  P  K  L  T  Y  K  L  R  R  V  -

781  TTTATTACAAATTTCACTGCTGCCTCCTCCTTTCCCCTCCTTTGTCTTTTTTTTCATCCT
     ----+----|----+----|----+----|----+----|----+----|----+----| 840
     AAATAATGTTTAAAAGTGACGACGGAGGAGGAAAGGGGAGGAAACAGAAAAAAAAGTAGGA

```
841  TTTTCTCTTCTGTCCATCAGTGCATGACGTTTAAGGCCACGTATAGTCCTAGCTGACGC
     ----------+---------+---------+---------+---------+---------+  900
     AAAAGAGAAGACAGGTAGTCACGTACTGCAAATTCCGGTGCATATCAGGATCGACTGCG a   F  F  S  S  V  H  Q  C  M  T  F  K  A  T  Y  S  P  S  *  R  -

901  CAATAATAAAAACCGAATTCGAGCTCGGGGATCCGGGGATCCTCTAGAGTC
     ----------+---------+---------+---------+---------+  949
     GTTATTATTTTTGGCTTAAGCTCGAGCCCCTAGGCCCCTAGGAGATCTCAG a   Q  *  *  K  P  N  S  S  S  D  P  G  I  L  *  S  ?  -
```

FIG. 16D

```
GRB-3    1  PDTGAGPLGAGARAGGARVPAAAQRESAEAAMAGNFDSEERSSWYWGRLSRQEAVALLQG   60
v-crk  205  QPRAGRGA.HRGLRRP.GRGQRVRPAGGA.I....Q....D.G.........GD..S....  264

GRB-3   61  QRDGVFLVRDSSTSPGDYVLSVSENSRVSHYIINSSGPRPPVPPSPAQP-PPGVSPSRLR  120
v-crk  265  ..H.T......GSI...F......S.......V..L..AGGRRAGGEG.GA..LN.T.FL  324

GRB-3  121  IGDQEFDSLPALLEFYKIHYLDTTTLIEPVARSRQCSGVILRQEEAEYVRALFDFNGNDE  180
v-crk  325  ....V.....S....................S....N.........V.........K...D  384

GRB-3  181  EDLPFKKGDILRIRDKPEEQWWNAEDSEGKRGMIPVPYVEKYRPASASVSALIGGNQEGS  240
v-crk  385  G..........K..............MD..............C..S.....T.T..R*   444
```

FIG.17

```
GRB-4    1  VIEKPENDPEWWKCKNARGQVGLVPKNYVVVLSDGP...ALHPAHTPQISYTGPSASGRF   60
nck    219  ..............RKIN.M.........T.MQNN.LTSG.E.S.P..CD.IR..LT.K.  278

GRB-4   61  AGREWYYGNVTRHQAECALNERGVEGDFLIRDSESSPSDFSVSLKASGRNKHFKVQLVDS  120
nck    279  ..NP....K.......M......H........N........Q.K........KET      338

GRB-4  121  VYCIGQRRFHSMDELVEHYKKAPIFTSEHGEKLYLVRALQ*                    161
nck    339  .......K.ST.E..............Q......KH.S*                     379
```

FIG.18

```
  1  MELDLSPTHLSSSPEDVCPTPATPPETPPPPDNPPPGDVKRSQPLPIPSSRKLREEFQA    60
 61  TSLPSIPNPFPELCSPPSQKPILGGSSGARGLLPRDSSRLCVVKVYSEDGACRSVEVAAG   120
121  ATARHVCEMLVQRAHALSDESWGLVESHPYLALERGLEDHEFVVEVQEAWPVGGDSRFIF   180
181  RKNFAKYELFKSPPHTLFPEKMVSSCLDAQTGISHEDLIQNFLNAGSFPEIQGFLQLRGS   240
241  GRGSGRKLWKRFFCFLRRSGLYYSTKGTSKDPRHLQYVADVNESNVYVVTQGRKLYGMPT   300
301  DFGFCVKPNKLRNGHKGLHIFCSEDEQSRTCWLAAFRLFKYGVQLYKNYQQAQSRHLRLS   360
361  YLGSPPLRSVSDNTLVAMDFSGHAGRVIDNPREALSAAMEEAQAWRKKTNHRLSLPTTCS   420
421  GSSLSAAIHRTQPWFHGRISREESQRLIGQQGLVDGVFLVRESQRNPQGFVLSLCHLQKV   480
481  KHYLILPSEDEGCLYFSMDEGQTRFTDLLQLVEFHQLNRGIIPCLLRHCCARVAL        535
```

FIG. 19

| | | | | | | |
|---|---|---|---|---|---|---|
| c-src | 148 | WYFGKITR | RE- SE | R- LLL | LNPENPR | GTFLVR | ESETTKGAYC— LSV SDFDNAKGLN— VKH -Y KI RKLDS——— |
| p85α-N | 333 | WYWGDISR | EE- VN | E-- KL | RDTA——D | GTFLVR | DASTKMHGDYT LTL RKGGNNKLIK— IFH —| RV QQE——— |
| PLCγ1-C | 668 | WYHASLTR | AQ- AE | H-- ML | MRVPR--D | GAFLVR | KRNEPNSYA—— ISF RAEGK——— IKH -C RD GKY——— |
| fyn | 149 | WYFGKLG | RKD AE | RQ LLL | SFGNPR- | GTFLIR | ESETTKGAYS— LSI RDMDMKGDH— VKH -Y KI RKLDN——— |
| GRB-3 | 44 | WYMGRLSR | QE- AV | A-- LLL | QCQR——— | GTFLVR | DSSTSPGDYV— LSV SENR——— VSH -Y II NSS——— |
| GRB-4 | 65 | WYYGNVTR | HQ- AE | C-- AL | NERGV-E | GDFLIR | DSESSPSDFS— VSL KASGR——— NKH -F KV QLVDSYYCI |
| GRB-7 | 434 | WFHGRISR | EE- SQ | R-- LI | GCQGLVD | GVFLVR | ESQRNPQGFV— LSL CHLQK——— VKH -Y II LPSEDE— |

| | | | | | | |
|---|---|---|---|---|---|---|
| c-src | 212 | G- F | YITSRTQ | FSSL QQ | LV A YY | SKHADG | L CH——— RL TNV |
| p85α-N | 387 | G- Q- | T VMLGNSE | FDSL VD | LI S YY | EKHP— | L YRKM——— KL RYPI |
| PLCγ1-C | 721 | G- | F SDPLT— | FSSV VE | LI N HY | RNES— | L AQYNPKLDV KL LYPV |
| fyn | 211 | G- Y | YITTRAQ | FETL QQ | LV Q HY | SERAAG | L CC——— RL W |
| GRB-3 | 98 | G- P- | R GPRPPVPPSPAQPPPGVSPSRLRIGDQE | FDSL PS | LL E FY | KIHY— | I DTT——— TL IEPV |
| GRB-4 | 125 | G- R- | R | FHSM DE | LV E HY | KKAP— | I FTSEHGE— KL YLV |
| GRB-7 | 492 | G- CL Y | FSMDEGQTR | FTDL LQ | LV E FH | QLNRG— | I LP——— LLL RHCCARV |

FIG. 21

```
GRB-7    242  RG S GRK L WK R FF CF L RR S G---LYY STKGTSKD PR H L QYVA DV NESN YYW TQGRK LYG M
Ras GAP  484  KG K GKR - WK N LY FI L EG S DAQL IYF KSEKRATK PK G L ---I DL SVCS VYW HDS-- LFG R

GRB-7    299  P TD F GFC V KPNK L RNG H KG L HIFCSKD EQ SRTC W LAA F RL F
Ras GAP  538  P NC F QIV V QH-- F SEE H YI F YFAGETP EQ AED- W MKG L QA F
```

FIG.22

```
GRB-7    19   P T PA TPPET PPPP DN PPPG DV K RSQP LP IPSSR KL RK EE - F QATS LP S I PNPFPK L C--SPP
P2B2     4    P E PA RAAPP PPPP PP PPPG AD R VVKA VP FPPTH RL TS EE V F DLDG IP R V DVLKNH L VKEGRV

GRB-7    78   SQKPI L GGSSGARG LL P RD SSRLCV V K V YSEDGA C RS V EVAAGATARH V C E MLVQR A HALSDESW
P2B2     66   DEEIA L RIINEGAA IL R RE KT--M I E V EAPITV C GD I H-GQFFDLMK L F E VGGSP A NT-RYLFL

GRB-7    143  G LVESHP YL A LE RG L EDHE F V V EVQEAWP V GGDSRF IFR K N F AK Y EL F FK SPPHTL F P EK
P2B2     126  G DYVDRG YF S IE CV L YLWV L K I LYPSTLF L LRGNHEC-- R H L TE Y FT FK QECKIK Y S ER

GRB-7    202  MVSS C L DA QTG I SHED LI - Q N FL --NA G SF PEI QC F LQ LR GSG R
P2B2     183  VTEA C M EA FDS L PLAA LL N Q FL CVHG G LS PEI HT L DD IR RLD R
```

FIG.23

```
  1 GCCAGTGAATTCGGGGCTCAGCCCTCCTCCCTTCCCCCTGCTTCAGGCTGCTGAG      60
    CGGTCACTTAAGCCCCCGAGTCGGGAGGAGGGAAGGGGACGAAGTCCGACGACTC

61 CACTGAGCAGCGCTCAGAATGGAAGCCATCGCCAAATATGACTTCAAAGCTACTGCAGAC     120
    GTGACTCGTCGCGAGTCTTACCTTCGGTAGCGGTTTATACTGAAGTTTCGATGACGTCTG
                  M  E  A  I  A  K  Y  D  F  K  A  T  A  D

121 GACGAGCTGAGCTTCAAAAGGGGACATCCTCAAGGTTTTGAACGAAGAATGTGATCAG      180
    CTGCTCGACTCGAAGTTTTCCCCCTGTAGGAGTTCCAAAACTTGCTTCTTACACTAGTC
     D  E  L  S  F  K  R  G  D  I  L  K  V  L  N  E  E  C  D  Q

181 AACTGGTACAAGGCAGAGCTTAATGGAAAAGACGGCTTCATTCCCAAGAACTACATAGAA     240
    TTGACCATGTTCCGTCTCGAATTACCTTTCTGCCGAAGTAAGGGTTCTTGATGTATCTT
     N  W  Y  K  A  E  L  N  G  K  D  G  F  I  P  K  N  Y  I  E

241 ATGAAACCACACATCCGTGGTTTTTTGGCAAAAAATCCCCGAAGGCAAGAAGAAATGCTT     300
    TACTTTGGTGTAGGCACCAAAAAACCGTTTTTTAGGGGCTTCCGTTCTTCTTTACGAA
     M  K  P  H  P  W  F  F  G  K  I  P  R  A  K  E  E  M  L

301 AGCAAACAGCGGCACGATGGGCCTTTCTTATCCGAGAGAGTGAGAGCGCTCCTGGGGAC     360
    TCGTTTGTCGCCGTGCTACCCGGAAAGAATAGGCTCTCTCACTCTCGCGAGGACCCCTG
     S  K  Q  R  H  D  G  A  F  L  I  R  E  S  E  S  A  P  G  D
```

FIG. 26A

```
361  TTCTCCCTCTCTGTCAAGTTTGGAAACGATGTGCAGCACTTCAAGGTGCTCCGAGATGGA
     ------+---------+---------+---------+---------+---------+   420
     AAGAGGGAGAGACAGTTCAAACCTTTGCTACACGTCGTGAAGTTCCACGAGGCTCTACCT
     F  S  L  S  V  K  F  G  N  D  V  Q  H  F  K  V  L  R  D  G   -

421  GCCGGGAAGTACTTCCTCTGGGTGGTGAAGTTCAATTCTTTGAATGAGCTGGTGGATTAT
     ------+---------+---------+---------+---------+---------+   480
     CGGCCCTTCATGAAGGAGACCCACCACTTCAAGTTAAGAAACTTACTCGACCACCTAATA
     A  G  K  Y  F  L  W  V  V  K  F  N  S  L  N  E  L  V  D  Y   -

481  CACAGATCTACATCTGTCTCCAGAAACCAGCAGATATTCCTGCGGGACATAGAACAGGTG
     ------+---------+---------+---------+---------+---------+   540
     GTGTCTAGATGTAGACAGAGGTCTTTGGTCGTCTATAAGGACGCCCTGTATCTTGTCCAC
     H  R  S  T  S  V  S  R  N  Q  Q  I  F  L  R  D  I  E  Q  V   -

541  CCACAGCAGCCGACATACGTCCAGGCCCTCTTTGACTTTGATCCCCAGGAGGATGGAGAG
     ------+---------+---------+---------+---------+---------+   600
     GGTGTCGTCGGCTGTATGCAGGTCCGGGAGAAACTGAAACTAGGGGTCCTCCTACCTCTC
     P  Q  Q  P  T  Y  V  Q  A  L  F  D  F  D  P  Q  E  D  G  E   -

601  CTGGGGCTTCCGCGCCGGAGATTTATCCATGTCATGGATAACTCAGACCCCAACTGGTGG
     ------+---------+---------+---------+---------+---------+   660
     GACCCCGAAGGCGCGGCCTCTAAATAGGTACAGTACCTATTGAGTCTGGGGTTGACCACC
     L  G  F  R  R  G  D  F  I  H  V  M  D  N  S  D  P  N  W  W   -
```

FIG. 26B

```
     AAAGGAGCTTGCCACGGGCAGACCGGCATGTTCCCCGCAATTATGTCACCCCGTGAAC
661  -------+---------+---------+---------+---------+---------+ 720
     TTCCTCGAACGGTGCCCGTCTGGCCGTCTGGCCGTAACAGGGGCGTTAATACAGTGGGGCACTTG
     K  G  A  C  H  G  Q  T  G  M  F  P  R  N  Y  V  T  P  V  N  .

CGGAACGTCTAAGAGTCAAGAAGCAATTATTAAAGAAGTAAAAATGTAAAACACATA
721  -------+---------+---------+---------+---------+---------+ 780
     GCCTTGCAGATTCTCAGTTCTTCGTTAATAAATTTCTTTCACTTTTTACATTTTGTGTAT
     R  N  V  *

CAAAAGAATTAAACCCACAAGCTGCCTCTGACAGCAGCCTGTGAGGAGTGCAGAACACC
781  -------+---------+---------+---------+---------+---------+ 840
     GTTTTCTTAATTTGGGTGTTCGACGGAGACTGTCGTGGACGACTCCCTCACGTCTTGTGG

TGGCCGGGTCACCCTGTGACCCTCTCACTTTGGTTGAACTTTAGGGGTGGGAGGGGC
841  -------+---------+---------+---------+---------+---------+ 900
     ACCGGCCCAGTGGGACACTGGGAGAGTGAAACAACCTTGAAATCCCCACCCTCCCCCG

GTTGGATTAAAAATGCCAAAACTTACCTATAAATTAAGAAGAGTTTTATTACAAATTT
901  -------+---------+---------+---------+---------+---------+ 960
     CAACCTAAATTTTACGGTTTGAATGGATATTTAATTCTTCTCAAAAATAATGTTTAAA

TCACTGCTGCTCCTCTTCCCCTTGTCTTTTTTTCATCCTTTTTCTCTGTC
961  -------+---------+---------+---------+---------+---------+ 1020
     AGTGACGACGAGGAGAAGGGGAGAAACAGAAAAAAAGTAGGAAAAAGAGAAGACAG

CATCAGTGCATGACGTTAAGGCCACGTATAGTCCTAGCTGACGCCAATAAT
1021 -------+---------+---------+---------+---- 1072
     GTAGTCACGTACTGCAATTCCGGTGCATATCAGGATCGACTGCGGTTATTA
```

FIG. 26C

```
GRB2      60  WFFGKIP-- R AK--- AE E- ML SKQRHD------ GAFLIRESE SA PGDF S LS VKF----- GNDVQ- HFKV

P85 N    333  WYWGDIS-- R EE--- VN E- KL RDTAD------ GTFLVRDST KM HGDY T LT LRK----- GG--NN- LIKI
P85 C    624  WNVGSSN-- R NK--- AE N- LL RGKRD------ GTFLVRESS K- QGCY A CS VVV----- DG-EV-- KHCV
c-src    150  WYFGKIT-- R RE--- SE RL LL NPENPR----- GTFLVRESE TT KGAY C LS VSDFDNAK-GLNVK- HYKI
v-abl    248  WEHGPVS-- R NA--- AE YK KS SGIN------- GSFLVRESE SS PG-Q R -S ISLRYE--G-RVY- HYRI
PLC N    550  WFHGKLG AG R DGRHI AE R- LL TEYCIETGAPD GSFLVRESE TF VGDY T LS --F--WRN-G-KVQ- HCRI
PLC C    668  WYHASLT-- R AQ--- AE H- ML MRVPRD----- GAFLVRKRN -E PNSY A IS --FRAE--G-KIK- HCRV
GAP N    178  WYHGKLD-- R TI--- AE E- RL RQAGKS----- GSYLIRESD RR PGSF V LS --FRSQMN-V--VN- HPRI
GAP C    348  WFHGKIS-- K QE--- AY N- LL MTVGQVC---- -SFLVRPSD NT PGDY S LY --FRTNENIQ-R--- -FKI
v-crk    248  WYWGRLS-- R GD--- AV S- LL QRERH------ GTFLVRDSG SI PGDF V LS VSES---S--- RVS- HYIV GRB2     111  LRDGA- G KY-FLWVVK------------- F N SL N ELV D YH RSTSVSRNQQIFLRD IE QV PQQP P85 N    384  --FHRD G KYGFSDPLT----------- F S SV V ELI N HY RNESLAQYNPKLDV- KL LY PVSK
P85 C    672  -YGFAEPY------NL- Y S SL K ELV L HY QHTSLVQHNDSLNV- TL AY PVYA
c-src    207  FYITSRTQ----------- F S SL Q QLV A YY SKHADGLCH------ RL TN -VCP
v-abl    611  HSRQDA G TPKF---------FLTDNLV F D SL Y DLI T HY QQVPLRCN-EFEM- RL SE PV-P
PLC C    718  ---QQE G QTVMLGNSE--------- F D SL V DLI S YY EKHPLYRK---M-- KL RY PI--
GAP N    230  --IAMC G DYYIGGRR---------- F S SL S DLI G YY SHVSCLLKGE---- KL LY PVAP
GAP C    399  -CPTPN N QFMMGGRY---------- Y N SI G DII D HY RKEQIVEG-YY---- -L KE PV-P
v-crk    298  NSLGPA G GRRAGGEGPFAPGLNPTRFLIGDNV F D SL P SLL E FY KIHYLDT--TT---- -L IE PV--
```

FIG. 26E

```
GRB2 N    5  AKYDF KATADD E----------- LS FKR G DILKVL------NEECDQN WY KAELN--GKD GFIP KN YIE
GRB2 C  163  ALFDF DPQEDG E----------- LG FRR G DFIKVM-------DNSDPN WW KGACH------ GQTG MF PRN

P85      10  ALYDY KKEREE D IDLHLGDI LT VNK G SLVALGFSDGQEARPEEIG WL NGYNETTGER GDFP GT YVE
c-src    88  ALYDY ESRTET D----------- LA FKK G ERLQIV-------MNTEGD WW LAHSLTTGQT GYIP SN YVA
v-abl    68  ALYDF VASGDN T----------- LS ITK G EKLRVLG------YNHNGE WC EAQTK-NGQ- GWVP SN YIT
PLC     148  ALFDY KAGRED E----------- LT FTK S AIIQNV-------EKQEGG WW RGDYHHKKQ- LWFP SN YVE
GAP     284  AILDY TKVPDT D E--------- IS FLK G DMFIVN-------NELEDG WM WVTNLRTDEQ GLIV ED LVE
v-crk   375  ALFDF KGNDDG D----------- LP FKK G DILKIR-------DKPEEQ WW NAEDMDGKR- GMIP VP YVE
```

FIG. 26F

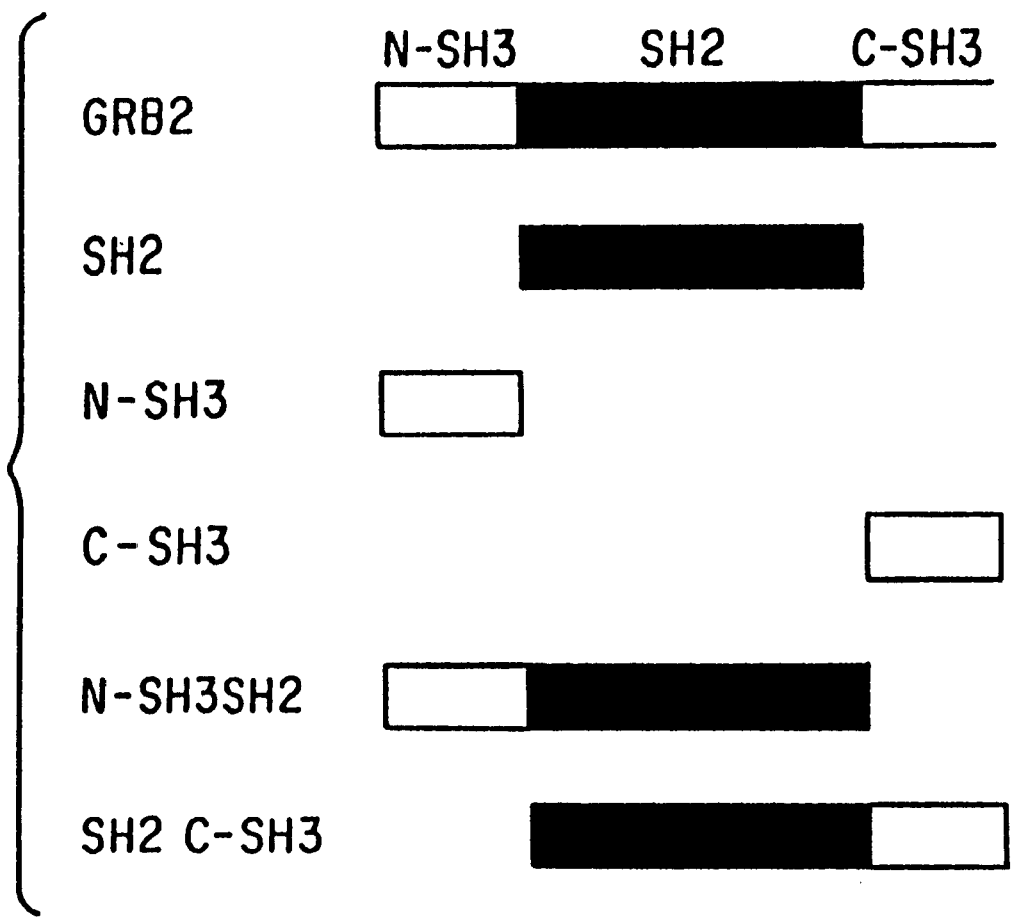
F I G. 29

| | | | |
|---|---|---|---|
| GRB2 | M E A I A k y D F k A t o d D E L S F K R G d i L | 25 | |
| SEM-5 | M E A V A e h D F q A g s p D E L S F K R G n t L | 25 | |
| GRB2 | K V L N e c D q n W Y K A E L n G k D G F I P k | 50 | |
| SEM-5 | K V L N k D e D p h W Y K A E L d G n E G F I P s | 50 | SH3 |
| GRB2 | N Y I e M k p h p W F f G K I p R o k A E e m L s | 75 | |
| SEM-5 | N Y I r M t e c n W Y I G K I t R n d A E v I L k | 75 | |
| GRB2 | K q r h - D G o F L I R e s E S o P G D F S L S V | 99 | |
| SEM-5 | K p t v r D G h F L V R q c E S s P G E F S I S V | 100 | |
| GRB2 | k F g n d V Q H F K V L R D g o G K Y F L W v V K | 124 | |
| SEM-5 | r F q d s V Q H F K V L R D q n G K Y Y L W o V K | 125 | SH2 |
| GRB2 | F N S L N E L V d Y H R s t S V S R n q q I f L r | 149 | |
| SEM-5 | F N S L N E L V o Y H R t o S V S R t h t I I L s | 150 | |
| GRB2 | D i e q v p q q p t Y V Q A L F D F d P Q E d G E | 174 | |
| SEM-5 | D m n v e t k - - - F V Q A L F D F n P Q E s G E | 172 | |
| GRB2 | L g F r R G D f I h V m d n s D P N W W k G o c h | 199 | |
| SEM-5 | L o F k R G D v I t L i n k d D P N W W e G q I n | 197 | SH3 |
| GRB2 | g q t G m F P r N Y V t P v N r N v | 217 | |
| SEM-5 | n r r G i F P s N Y V c P y N s N k s n s n v o p | 222 | |
| SEM-5 | g f n f g n | 228 | |

FIG. 32

```
  1   AGCCTGACACCGGAGCCGGTCCGCTGGGCCTGGGCCGGGGCTGGAGGGCGCGGTGC
      ----+----+----+----+----+----+----+----+----+----+----+  +60
      TCGGACTGTGGCCTCGGCCAGGCGACCCGGACCCGGTCCCCGACCTCCCCGCCACG
       P  D  T  G  A  G  P  L  G  A  G  A  R  A  G  G  A  R  V  P  -

61   CGGCGGCGGCCCAGCGTGAAAGCGCGGAGGCGGCCATGGCGGCAACTTCGACTCGGAGG
      ----+----+----+----+----+----+----+----+----+----+----+ +120
      GCCGCCGCCGGGTCGCACTTTCGCGCCTCCGCCGGTACCGCCGTTGAAGCTGAGCCTCC
       A  A  A  Q  R  E  S  A  E  A  A  M  A  G  N  F  D  S  E  E  -

121   AGCCGGAGTAGTCTGGTACTGGGGCCGCCTGAGCCGGCAGGAGGCGGTGGCGCTATTGCAGG
      ----+----+----+----+----+----+----+----+----+----+----+ +180
      TCGGCCTCATCGACCATGACCCCGGCGGACTCGGCCGTCCTCCGCCACCGCGATAACGTCC
       R  S  S  W  Y  W  G  R  L  S  R  Q  E  A  V  A  L  L  Q  G  -

181   GCCAGCGCGGACGGGGTGTTCCTGGTGCGCGGGGACTCGAGCACCAGCCCCGGGGACTATGTGC
      ----+----+----+----+----+----+----+----+----+----+----+ +240
      CGGTCGCGCCTGCCCCACAAGGACCACGCGCCCTGAGCTCGTGGTCGGGGCCCCTGATACACG
       Q  R  D  G  V  F  L  V  R  D  S  S  T  S  P  G  D  Y  V  L  -

241   TTAGCGTCTCCGAAAACTCGGCCGTCTCCCACTACATCAACAGCAGCGGCCCCGCC
      ----+----+----+----+----+----+----+----+----+----+----+ +300
      AATCGCAGAGGCTTTTGAGCGCGCAGAGGGTGATGTAGTAGTTGTCGTCGCCGGGGCGG
       S  V  S  E  N  S  R  V  S  H  Y  I  N  S  S  G  P  R  P  -

301   CTCCAGTGCCTCCGTCGCCCGCTCAGCCTCCGCCGGAGTCGAGTCCTCCAGGCTCCGAA
      ----+----+----+----+----+----+----+----+----+----+----+ +360
      GAGGTCACGGAGGCAGCAGGGCGAGTCGGAAGGCGGCCCTCACTCAGGAGGTCCGAGGCTT
       P  V  P  P  S  P  A  Q  P  P  P  G  V  S  P  S  R  R  L  R  I  -
```

FIG. 34A

```
361  TAGGAGATCAAGAATTTGATTCATTGCCTGCTTACTGGAATTCTACAAATACACTATT
     ----+----|----+----|----+----|----+----|----+----|----+----|  +420
     ATCCTCTAGTTCTTAAACTAAGTAACGGACGAAATGACCTTAAGATGTTTATGTGATAA
      G  D  Q  E  F  D  S  L  P  A  L  E  F  Y  K  I  H  Y  L  -

421  TGGACACTACAACATTGATAGAACCAGTGCCAGATCAAGGCAGGTAGTGGAGTGATTC
     ----+----|----+----|----+----|----+----|----+----|----+----|  +480
     ACCTGTGATGTTGTAACTATCTTGGTCACGGTCTAGTTCCGTCCCATCACCTCACTAAG
      D  T  T  T  L  I  E  P  V  A  R  S  R  Q  G  S  G  V  I  L  -

481  TCAGGCAGGAGGAGGCAGAGTATGTGCGGGCCCTCTTTGACTTTAATGGGAATGATGAAG
     ----+----|----+----|----+----|----+----|----+----|----+----|  +540
     AGTCCGTCCTCCTCCGTCTCATACACGCCCGGGAGAAACTGAAATTACCCTTACTACTTC
      R  Q  E  E  A  E  Y  V  R  A  L  F  D  F  N  G  N  D  E  E  -

541  AAGATCTTCCCTTTAAGAAAGGAGACATCCTGAGAATCCGGGATAAGCCTGAAGAGCAGT
     ----+----|----+----|----+----|----+----|----+----|----+----|  +600
     TTCTAGAAGGGAAATTCTTTCCTCTGTAGGACTCTTAGGCCCTATTCGGACTTCTCGTCA
      D  L  P  F  K  K  G  D  I  L  R  I  R  D  K  P  E  E  Q  W  -

601  GGTGGAATGCAGAGGACAGCGAAGGAAAGAGGGGATGATTCCTGTCCCTTACGTGGAGA
     ----+----|----+----|----+----|----+----|----+----|----+----|  +660
     CCACCTTACGTCTCCTGTCGCTTCCTTTCTCCCCTACTAAGGACAGGAATGCACCTCT
      W  N  A  E  D  S  E  G  K  R  G  M  I  P  V  P  Y  V  E  K  -

661  AGTATAGACCTGCCTCCGCCTCAGTATCGGCTCTGATTGGAGGTAACCAGGAGGGTTCCC
     ----+----|----+----|----+----|----+----|----+----|----+----|  +720
     TCATATCTGGACGGAGGCGGAGTCATAGCCGAGTACTAACCTCCATTGGTCCTCCCAAGGG
      Y  R  P  A  S  A  S  V  S  A  L  I  G  G  N  Q  E  G  S  H  -
```

FIG. 34B

```
721  ACCCACAGCCACTGGGTGGCCGGAGCCTGGGCCCTATGCCAACCCAGCGT  770
     ----+----+----+----+----+----+----+----+----+----+
     TGGGTGTCGGTGACCCACCGGCCTCGGACCCGGGATACGGTTGGGTCGCA

```
    GTGATTGAGAAGCCGGAGAATGACCCTGAATGGTGGAAAAATGCCCGAGGCCAA
1   ----------+---------+---------+---------+---------+---------+  60
    CACTAACTCTTCGGCCTCTTACTGGGACTTACCACCTTTTACGTTTTTACGGCTCCGGTT
    V  I  E  K  P  E  N  D  P  E  W  W  K  C  K  N  A  R  G  Q

GTGGGCCTGGTCCCCAAAAACTACGTGGTTGTCTCAGTGATGGGCCTGCTCTGCACCCC
61  ----------+---------+---------+---------+---------+---------+ 120
    CACCCGGACCAGGGGTTTTGATGCACCAACAGAGTACTACCCGGACGAGACGTGGGG
    V  G  L  V  P  K  N  Y  V  V  V  L  S  D  D  G  P  A  L  H  P

GCTCACACCCCCAGATCAGTCAGGGCCTTCAGCCAGGGCGCTTTGCTGGTCgg
121 ----------+---------+---------+---------+---------+---------+ 180
    CGAGTGTGGGGGTCTAGTCAGTCGATGTGGCCCGGAAGTCGGTCGCCGCGAAACGACCAGCC
    A  H  T  P  Q  I  S  Y  T  G  P  S  A  S  G  R  F  A  G  R

GAGTGGTACTATGGCAACGTGACACGGCACCAGGCCGAGTGTGCCCTCAATGAGCGGGGC
181 ----------+---------+---------+---------+---------+---------+ 240
    CTCACCATGATACCGTTGCACTGTGCCGTGGTCCGGCTCACACGCGAGTTACTCGCCCCG
    E  W  Y  Y  G  N  V  T  R  H  Q  A  E  C  A  L  N  E  R  G

GTCGAGGGGCGACTTCCTCATTAGGGACAGCGAGTCCTCGCCCAGTGACTTCTCCGTGTCT
241 ----------+---------+---------+---------+---------+---------+ 300
    CAGCTCCCGCTGAAGGAGTAATCCCTGTCGCTCAGGAGCGGGTCACTGAAGAGGCACAGA
    V  E  G  D  F  L  I  R  D  S  E  S  S  P  S  D  F  S  V  S

CTCAAAGCGTCAGGGAGAAACAGCACTTCAAGGTGCAGCTGGTGGACAGCGTCTACTGC
301 ----------+---------+---------+---------+---------+---------+ 360
    GAGTTTCGCAGTCCCTCTTTGTCGTGAAGTTCCACGTCGACCACCTGTCGCAGATGACG
    L  K  A  S  G  R  N  K  H  F  K  V  Q  L  V  D  S  V  Y  C
```

FIG. 35A

```
        ATTGGGCAGCGGCGTTCCACAGCATGGACGAGCTTGTGGAGCACTACAAGAAGGCCCC
361     ---------+---------+---------+---------+---------+---------+ 420
        TAACCCGTCGCCGCCAAGGTGTCGTACCTGCTCGAACACCTCGTGATGTTCTTCCGGGG
         I  G  Q  R  R  F  H  S  M  D  E  L  V  E  H  Y  K  K  A  P  -

ATCTTCACCAGCGAGCACGGGGAGAAGCTCTACCTTGTCCGAGCCCTACAGTGAAAGCAG
421     ---------+---------+---------+---------+---------+---------+ 480
        TAGAAGTGGTCGCTCGTGCCCCTCTTCGAGATGGAACAGGCTCGGGATGTCACTTTCGTC
         I  F  T  S  E  H  G  E  K  L  Y  L  V  R  A  L  Q  *

CCATTGCCCCTCATGCCCTGCCCACTGTGGGCTCGCTGCCACCTCTGCCTCCCAGAG
481     ---------+---------+---------+---------+---------+---------+ 540
        GGTAACCGGGGAGTACGGGACGGGTGACACCCGAGCGACGGTGGAGACGGAGGGTCTC

CCCAGCACTTCTGGCCACCTCCACCCATGTGGCTTGGATCACCTCTGTGGCCCAGTCTGT
541     ---------+---------+---------+---------+---------+---------+ 600
        GGGTCGTGAAGACCGGTGGAGGTGGGTACACCGAACCTAGTGGAGACACCGGGTCAGACA

CCTTTCTTTTTCAGCCCTGTTGGTCAACCGGCTACCTAGG
601     ---------+---------+---------+---------+-- 642
        GGAAAGAAAAAGTCGGGACAACCAGTTGGTGCCGATGGATCC
```

FIG. 35B

```
     CTCTCTCTCTCTCTCTCCCTCTCCTAGCACCTGCTGCTCAGTAGGAAGGCAAG
  1  ----+----+----+----+----+----+----+----+----+----+--  60
     GAGAGAGAGAGAGAGAGGAGAGAGGATCGTGACGACGAGTCATCCTTCCCGTTC

AGCAATTCGAGGCCGGTGCATTGTGAGGAGTCTCCACCCCTCCCTGCGCTTCTCTC
 61  ----+----+----+----+----+----+----+----+----+----+--- 120
     TCGTTAAGCTCCGGCCACGTAACACTCCTCAGAGGTGGGGAGGAGACGCGAAGAAGAG

CAGGGAGCCTCTCAGGCCGCCCTCACCTGCCCGAGATAATTTAGTTCCCTGGGCCTGG
121  ----+----+----+----+----+----+----+----+----+----+--- 180
     GTCCCTCGGAGAGTCCGGGCGGAGTGACGGGCTCTATTAAATCAAAGGACCCGGACC

AATCTGGATACGCAGGGCCTCGCTCTATATTCTCCGCCTCAACATTCCAAAGGCGGGAT
181  ----+----+----+----+----+----+----+----+----+----+--- 240
     TTAGACCTATGCGTCCCGGAGCGAGATATAGAGAGGGCGGAGTTGTAAGGTTCCGCCCTA

AGCCTTTCTACCATCTGTAGAGAAGAGAGAGAAAGGATTCGAAATCAAATCCAAGTGTCTGG
241  ----+----+----+----+----+----+----+----+----+----+--- 300
     TCGGAAAGATGGTAGACATCTCTCTTCTCTCCTAAGCTTTAGTTAGGTTCACAGACC

GATCTCTAGACAGAGCCCAGACTTTGGGCCGGTGTCCGGTCCCTTCGTTGGAGGTGCTC
301  ----+----+----+----+----+----+----+----+----+----+--- 360
     CTAGAGATCTGTCTCGGTCTGAAACCCGGCCACAGGCCGAGGAAGACAACCTCCACGAG

CAGGTGCCATGGAACTGGATCTGAGCCCGACTCATCTCAGCAGCTCCCCAGAAGATGTGT
361  ----+----+----+----+----+----+----+----+----+----+--- 420
     GTCCACGGTACCTTGACCTAGACTCGGGCTGAGTAGAGTCGTCGAGGGGTCTTCTACACA
      M  E  L  D  L  S  P  T  H  L  S  S  P  E  D  V  C  -
```

FIG. 36A

```
421  GCCCAACTCCTGTACCCCTCCTGAGACTCCTCCGCCCCCTGATAACCCTCCGCCAGGGG
     ------+---------+---------+---------+---------+---------+  480
     CGGGTTGAGGACGATGGGGAGGACTCTGAGGAGGCGGGGACTATTGGGAGGCGGTCCCC

P  T  P  A  T  P  P  E  T  P  P  P  P  D  N  P  P  P  G  D  -

481  ATGTGAAGCGGTCGCAGCCTTTGCCCATCCCCAGCAGGAAACTTGAGAAGAGGAGT
     ------+---------+---------+---------+---------+---------+  540
     TACACTTCGCCAGCGTCGGAAACGGGTAGGGGTCGTCCTTTGAACTCTTCTCCTCA

V  K  R  S  Q  P  L  P  I  P  S  R  K  L  R  E  E  F  -

541  TTCAGGCAACCCTCTGCCCTCCATCCCCGAGCTCTGCAGCCCCACCTT
     ------+---------+---------+---------+---------+---------+  600
     AAGTCCGTTGGGAGACGGGAGGTAGGGGCTCGAGACGTCGGGTGGAA

Q  A  T  S  L  P  S  I  P  N  P  F  P  E  L  C  S  P  P  S  -

601  CACAGAAACCCATTCTGGTGGTTCCTCCGGTGCAAGGGGTTGCTTCCTCGAGACTCCA
     ------+---------+---------+---------+---------+---------+  660
     GTGTCTTTGGGTAAGACCACCAAGGAGGCCACGTTCCCCAACGAAGAGCTCTGAGGT

Q  K  P  I  L  G  G  S  S  G  A  R  G  L  L  P  R  D  S  S  -

661  GCCGCCTCTGTGTGGTGAAGGTGTACAGTGAGGATGGGGCCTGCCGGTCTGTGAGGTGG
     ------+---------+---------+---------+---------+---------+  720
     CGGCGGAGACACACCACTTCCACATGTCACTCCTACCCCGGACGGCCAGACACTTCCACC

```
721  CAGCGGGCGCCACAGTCTCGTCAGTGTGTGAGATGCTGGTACAACGAGCTCACGCCCTGA
     ------+---------+---------+---------+---------+---------+  780
     GTCGCCCGCGGTGTCGAGCAGTGCAGCACTCTACGACCATGTTGCTCGAGTGCGGGACT
     A  G  A  T  A  R  H  V  C  E  M  L  V  Q  R  A  H  A  L  S  -

781  GCGACGAGAGCTGGGGACTAGTGGAATCCCACCTACCTGGCACTGGAGCGGGGTCTGG
     ------+---------+---------+---------+---------+---------+  840
     CGCTGCTCTCGACCCCTGATCACCTTAGGGTGGGATGGACCGTGACCTCGCCCCAGACC
     D  E  S  W  G  L  V  E  S  H  P  Y  L  A  L  E  R  G  L  E  -

841  AGGACCATGAATTTGTGGTGGAAGTGCAGGAGGCCTGGCCTGTGGGTGGAGATAGCCGCT
     ------+---------+---------+---------+---------+---------+  900
     TCCTGGTACTTAAACACCACCTTCACGTCCTCCGGACCGGACACCCACTCTATCGGCGA
     D  H  E  F  V  V  E  V  Q  E  A  W  P  V  G  G  D  S  R  F  -

901  TCATCTTCCGTAAAAACTTCGCCAAGTATGAACTATTCAAGAGCCCCACACACCCTGT
     ------+---------+---------+---------+---------+---------+  960
     AGTAGAAGGCATTTTTGAAGCGGTTCATACTTGATAAGTTCTCGGGGGTGTGTGGACA
     I  F  R  K  N  F  A  K  Y  E  L  F  K  S  P  P  H  T  L  F  -

961  TTCCAGAAAAGATGGTCTCCAGAGCTGTCTGAGCTGACTTGTCCGTATAGGGTACTTCTGG
     ------+---------+---------+---------+---------+---------+  1020
     AAGGTCTTTTCTACCAGAGGTCTCGACAGACTCTAGACCTAGCAAAGCCATATCCCATGAAGACC
     P  E  K  M  V  S  S  C  L  D  A  Q  T  G  I  S  H  E  D  L  -

1021 TCATCCAGAACTTCCTGAACGCTGGCAGCTTCCCTGAGATCCAGGGCTTCCTGCAGCTGC
     ------+---------+---------+---------+---------+---------+  1080
     AGTAGGTCTTGAAGGACTTGCGACCGTCGAAGGGACTCTAGGTCCCGAAGGACGTCGACG
     I  Q  N  F  L  N  A  G  S  F  P  E  I  Q  G  F  L  Q  L  R  -
```

FIG. 36C

```
1081  GGGGATCAGGCCGGGGGTCAGGTCGAAAGCTTTCTTCTGCTTTCTGCGTC
      ----+---------+---------+---------+---------+----  +1140
      CCCCTAGTCCGGCCCCCAGTCCAGTCCAGTTTCGAAAGAAGACGAAAGACGCAG
       G  S  G  R  G  S  G  R  K  L  W  K  R  F  F  C  F  L  R  R  -

1141  GATCTGGCCTCTACTACTCTACCAAGGGTACCTCCAAGGACCCCAGACACCTACAGTATG
      ----+---------+---------+---------+---------+----  +1200
      CTAGACCGGAGAGATGATGAGATGGTTCCCATGGAGGTTCCTGGGGTCTGTGGATGTCATAC
       S  G  L  Y  Y  S  T  K  G  T  S  K  D  D  P  R  H  L  Q  Y  V  -

1201  TGGCAGATGTGAATGAGTCCAATGTCTATGTGGTGACCCAGGGCCGCAAGCTGTATGGGA
      ----+---------+---------+---------+---------+----  +1260
      ACCGTCTACACTTACTCAGGTTACAGATACACCACTGGGTCCCGGCGTTCGACATACCCT
       A  D  V  N  E  S  N  V  Y  V  V  T  Q  G  R  K  L  Y  G  M  -

1261  TGCCCACTGACTTCGGCTTCTGTGTCAAGCCCAACAAGTTCGAAACGGCCACAAGGGGC
      ----+---------+---------+---------+---------+----  +1320
      ACGGGTGACTGAAGCCGAAGACACAGTTCGGGTTGTTCGAAGCTTTGCCGGTGTTCCCG
       P  T  D  F  G  F  C  V  K  P  N  K  L  R  N  G  H  K  G  L  -

1321  TCCACACATCTTCTGCAGTGAGGATGAGCAGAGTCGGACCTGCTGGCTGCCTTCCGGC
      ----+---------+---------+---------+---------+----  +1380
      AGGTGTAGAAGACGTCACTCCTACTCGTCTCAGCCTGGACGACCGACGGAAGGCCG
       H  I  F  C  S  E  D  E  Q  S  R  T  C  W  L  A  A  F  R  L  -

1381  TCTTTCAAGTACGGGGTACAGCTATATAAGAATTATCAGCAGGCCCAGTCTCGTCACCTGC
      ----+---------+---------+---------+---------+----  +1440
      AGAAGTTCATGCCCCATGTCGATATATTCTTAATAGTCGTCCGGTCAGAGCAGTGGACG
       F  K  Y  G  V  Q  L  Y  K  N  Y  Q  Q  A  Q  S  R  H  L  R  -

FIG. 36D
```

```
1441  GCCTATCCTATTTGGGGTCTCCACCCTTGAGGAGCGTCTCAGACAATACCCTAGTGGCTA
      ------+---------+---------+---------+---------+---------+  +1500
      CGGATAGGATAAACCCCAGAGGTGGAACTCCTCGCAGAGTCTGTTATGGGATCACCGAT
       L  S  Y  L  G  S  P  P  L  R  S  V  S  D  N  T  L  V  A  M  -

1501  TGGACTTCTCTGGCCATGCGGGGCGTGTCATTGATAACCCCCGGGAAGCTCTGAGTGCCG
      ------+---------+---------+---------+---------+---------+  +1560
      ACCTGAAGAGACCGGTACGCCCCGCACAGTAACTATTGGGGGCCCTTCGAGACTCACGGC
       D  F  S  G  H  A  G  R  V  I  D  N  P  R  E  A  L  S  A  A  -

1561  CCATGGAGGAGCCCAGCCTGGAGGAAGAAGACAAACCACCGTCTGAGCCTGCCCACCA
      ------+---------+---------+---------+---------+---------+  +1620
      GGTACCTCCTCGGGTCGGACCTCCTTCTTCTGTTTGGTGGCAGACTCGGACGGGTGT
       M  E  E  A  Q  A  W  R  K  K  T  N  H  R  L  S  L  P  T  T  -

1621  CATGCTCTCTGGCTCGAGCCTCAGCGCCTCAGCCATTCATCGCCAGCCCTGGTTCATGGAC
      ------+---------+---------+---------+---------+---------+  +1680
      GTACGAGAGACCGAGCTCGGAGTCGCGGAGTCGGTAAGTAGCGGTCGGGACCAAAGTACCTG
       C  S  G  S  S  L  S  A  A  I  H  R  T  Q  P  W  F  H  G  R  -

1681  GCATCTCTCGGGAGGAGAGCCAGAGGCTAATTGGACAGCAGGGCCTGGTGGATGGTGTGT
      ------+---------+---------+---------+---------+---------+  +1740
      CGTAGAGAGCCCTCCTCTCGGTCGCCGATTAACCTGTCGTCCCGGACCACTACCACACA
       I  S  R  E  E  S  Q  R  L  I  G  Q  Q  G  L  V  D  G  V  F  -

1741  TCCTGGTCCGGGAGAGCCAGAGGAACCCACAGGGCTTTGTCCTTGTCCTTGTGCCATCTGC
      ------+---------+---------+---------+---------+---------+  +1800
      AGGACCAGGCCCTCTCGGTCTCCTTGGGTGTCCCGAAACAGGAACAGGTAGACG
       L  V  R  E  S  Q  R  N  P  Q  G  F  V  L  S  L  C  H  L  Q  -
```

FIG. 36E

```
       AGAAAGTCAAGCATTATCTCATTTGCCAAGTGAAGATGAAGGTTGCCCTTTACTTCAGCA
1801   ------------+---------+---------+---------+---------+---------+  +1860
       TCTTTCAGTTCGTAATAGAGTAAACGGTTCACTTCTACTTCCAACGGAAATGAAGTCGT
        K  V  K  H  Y  L  I  L  P  S  E  D  E  G  C  L  Y  F  S  M  -

TGGATGAGGGCCAGACCCGTTTCACAGACCTGCTGCAGCTGGTAGAATTCCACCAGCTGA
1861   ------------+---------+---------+---------+---------+---------+  +1920
       ACCTACTCCCGGTCTGGGCAAAGTGTCTGGACGACGTCGACCATCTTAAGGTGGTCGACT
        D  E  G  Q  T  R  F  T  D  L  L  Q  L  V  E  F  H  Q  L  N  -

ACCGAGGCATCCTGCCCTGCCTGCTGCGCCACTGCTGTGCCCGTGTGGCCCTCTGAGGCC
1921   ------------+---------+---------+---------+---------+---------+  +1980
       TGGCTCCGTAGGACGGGACGGACGACGCGGTGACGACACGGGCACACCGGAGACTCCGG
        R  G  I  L  P  C  L  L  R  H  C  C  A  R  V  A  L  *

GCACAAGCTACTGCAGCCATGGGTTTGCCTACCACCCTTCTGTCCTGTGGACTCGGTGCA
1981   ------------+---------+---------+---------+---------+---------+  +2040
       CGTGTTCGATGACGTCGGTACCCAAACGGATGGTGGGAAGACAGGACACCTGAGCCACGT

GGTGGGTGGGGTGGTGTAAACAGTGGAAGAGCTCCCCCCCCAATTTTATCCCATTTTTTT
2041   ------------+---------+---------+---------+---------+---------+  +2100
       CCACCCACCCCACCACATTTGTCACCTTCTCGAGGGGGGGGTTAAAATAGGGTAAAAAAA

AACCTCTCTCAACCAGTGAAACATCCCTAACCCTGTCCATCCCTGACTCCCTGTCCCCAA
2101   ------------+---------+---------+---------+---------+---------+  +2160
       TTGGAGAGAGTTGGTCACTTTGTAGGGATTGGGACAGGTAGGGACTGAGGACAGGGGTT
```

FIG. 36F

```
2161  GGGAGGCATTGTGTCCTGTCCCTTGGTAGAGCTCCTGAGGTACTGTTCCAGTGAGGGG
      ----+----|----+----|----+----|----+----|----+----|----+----|  +2220
      CCCTCCGTAACACCAGGACAGGGAACCATCTCGAGGACTCCATGACAAGGTCACTCCCC

2221  CATTATGAGAGGAGCGGGGCAGCCCAGGAGGTCTCATACCCCACCCATAATCTGTACAGA
      ----+----|----+----|----+----|----+----|----+----|----+----|  +2280
      GTAATACTCTCCTCGCCCCGTCGGGTCCTCCAGAGTATGGGGTGGGTATTAGACATGTCT

2281  CTGAGAGGCCCAGTTGATCTGTCTGTTTTATACCAGTAACAATAAAGATTATTTTTGAT
      ----+----|----+----|----+----|----+----|----+----|----+----|  +2340
      GACTCTCCGGTCAACTAGACAGAACAAAATATGGTCATTGTTATTTCTAATAAAAACTA

2341  ACAAA
      -----  2345
```

FIG. 36G

```
   1  GGGGCCGGGG GAGGAGGAGG CGGAGGCGGC GGCGGAGGCT GGGAGGGCGG
  51  GCGGGGCCCG GAGAGTTTAA AGCCCATCGA GGGtGTGGGG TGCGGGGAGG
 101  CGGCAGGAAG GGAAGGGCGC TGCGACCAGT GGCGGGCGtG ATTCGCGTTC
 151  CGAGACCCAC GGGAGCACGA AGTTTCCGCG CACCGTCTCA CGCACGGCGA
 201  CTGGGACCGT CCAGTGTTCC GGCTTTGCCT TCGGTTTTTC TCCGTTGTGA
 251  CTCGTGCAAC GTGTGGCCAG CGGCCACGCG GAGGCGACGA GGAGCTGCAC
 301  GTCAGGACAA AGTGGGGCAG TCAACGTCCA AACCCGAAAA CCTAGCTAAG
 351  TCTGGGTTTT CGCCACAACA AAGAAGCCAA CCAGAGCATG GTCTTGGGCT
 401  TCAAGTACTA ATGAACAACG ATATTAACTC GTCCGTGGAA AGCCTTAACT
 451  CAGCTTGCAA CATGCAGTCT GATACTGATA CTGCACCACT TCTTGAGGAT
 501  GGCCAGCATG CCAGCAACCA GGGAGCAGCA TCTAGCTCCC GGGGACAGCC
 551  ACAGGCGTCC CCGAGGCAGA AAATGCAACG CTCGCAGCCT GTGCACATTC
 601  TCAGGCGCCT TCAGGAGGAA GACCAGCAGT TAAGAACTGC ATCTCTTCCG
 651  GCCATCCCCA ACCCATTTCC GGAGCTCACT GGTGCGGCCC CTGGGAGCCC
 701  TCCTTCGGTT GCTCCTAGCT CCTTACCTCC TCCTCCGAGC CAGCCACCTG
 751  CCAAGCATTG TGGCAGATGT GAGAAGTGGA TACCAGGGGA AAATACCCGG
 801  GGAAATGGGA AACGGAAGAT CTGGAGATGG CAGTTCCCTC CAGGCTTTCA
 851  GCTGTCGAAA CTCACCCGTC CAGGTCTGTG ACAAAGACC ACTGCGAGAT
 901  TTTCAAAGAA ACAACCTAAG AACCAGTGTC CAACCGACAC TGTGAATCCA
 951  GTGGCACGGA TGCCCACTTC ACAGATGGAG AAGCTGAGGC TCAGAAAGGA
1001  TGTCAAAGTC TTTAGTGAAG ATGGGACCAG CAAAGTGGTG GAGATTCTAA
```

FIG.37A

```
1051    CCGACATGAC AGCCAGGGAC CTGTGCCAGC TGCTGGTTTA CAAAAGTCAC

1101    TGTGTGGATG ACAACAGCTG GACTCTGGTG GAACACCACC CACAACTGGG

1151    ATTAGAGAGG TGCCTGGAGG ACCATGAGAT CGTGGTCCAA GTGGAGAGTA

1201    CCATGCCAAG TGAGAGCAAA TTCTTATTCA GAAAGAATTA TGCGAAGTAC

1251    GAGTTCTTTA AGAATCCAGT GAACTTCTTC CCGGATCAGA TGGTCAATTG

1301    GTGCCAGCAG TCCAACGGTG GCCAGGCGCA GCTTCTGCAG AATTTTCTGA

1351    ACACCAGCAG CTGCCCTGAG ATCCAGGGGT TCTTGCAGGT GAAAGAGGTA

1401    GGACGCAAGT CTTGGAAGAA GCTGTATGTG TGCCTGCGCA GATCTGGCCT

1451    CTATTACTCC ACCAAGGGGA CTTCAAAAGA ACCCAGACAC CTGCAGCTGC

1501    TGGCTGACCT GGAAGAAAGC AGCATCTTCT ACCTGATTGC TGGAAAGAAG

1551    CAGTACAACG CGCCGAATGA ACATGGGATG TGCATCAAGC CAAACAAAGC

1601    GAAGACCGAG ATGAAGGAGC TTCGTCTGCT CTGTGCCGAA GATGAGCAGA

1651    TCCGTACTTG CTGGATGACT GCCTTCAGAC TGCTCAAGTA CGGAATGCTC

1701    CTGTACCAAA ACTATCGCAT CCCACAGAGG AAGGGTCTGC CCCCTCCTTT

1751    CAACGCACCT ATGCGCAGTG TTTCTGAGAA TTCTCTTGTG GCCATGGATT

1801    TTTCTGGACA AATCGGAAGA GTGATCGATA ACCCGGCTGA AGCCCAGAGT

1851    GCTGCCCTGG AAGAGGGCCA TGCCTGGCGT AACGGGAGCA CACGGATGAA

1901    TATCCTAAGC AGCCAAAGCC CACTGCATCC TTCTACCCTG AATGCAGTGA

1951    TTCACAGGAC TCAGCATTGG TTCCATGGAC GTATCTCCCG CGAGGAGTCT

2001    CACAGGATCA TCAAGCAACA AGGTCTCGTG GACGGGCTGT TCCTCCTTCG

2051    TGACAGCCAG AGTAATCCAA AGGCGTTCGT ACTGACACTG TGCCATCACC

2101    AGAAGATTAA AAACTTCCAG ATCTTACCTT GCGAGGATGA TGGGCAGACC
```

FIG.37B

```
2151  TTCTTCACTC TGGATGATGG GAACACCAAG TTCTCCGATC TGATCCAGCT

2201  GGTCGACTTC TACCAGCTCA ACAAAGGTGT TCTGCCCTGC AAGCTGAAAC

2251  ACCACTGCAT CCGCGTGGCC TTATGACCTC CTTGCCCACT CACAGAGGCT

2301  GGAGGCAGCG ACACTGGAAC GGAGAAGAGA GATCTGCATG AGGCCGGAAT

2351  TCCGAAGACC AAGGAACCTT GAGAAGAAGA AGAAAAAAGA GAAGGTCCTT

2401  GCTACTGTCA CCAAAACAGT TGGTGGGGAC AAGAACGGTG GCACCCGGGT

2451  GGTGAAGCTT CGAAAAATGC CTTAGGTATT ATCCCACCGA AGATGTTCCT

2501  TCGGGAAGCT GCTGAGCCAC GGCAAGAAGC CCTTCAGCCA GCACGTGAGA

2551  AGGCTA
```

FIG.37C

```
  1  MNNDINSSVE  SLNSACNMQS  DTDTAPLLED  GQHASNQGAA  SSSRGQPQAS

51  PRQKMQRSQP  VHILRRLQEE  DQQLRTASLP  AIPNPFPELT  GAAPGSPPSV

101  APSSLPPPPS  QPPAKHCGRC  EKWIPGENTR  GNGKRKIWRW  QFPPGFQLSK

151  LTRPGLWTKT  TARFSKKQPK  NQCPTDTVNP  VARMPTSQME  KLRLRKDVKV

201  FSEDGTSKVV  EILTDMTARD  LCQLLVYKSH  CVDDNSWTLV  EHHPQLGLER

251  CLEDHEIVVQ  VESTMPSESK  FLFRKNYAKY  EFFKNPVNFF  PDQMVNWCQQ

301  SNGGQAQLLQ  NFLNTSSCPE  IQGFLQVKEV  GRKSWKKLYV  CLRRSGLYYS

351  TKGTSKEPRH  LQLLADLEES  SIFYLIAGKK  QYNAPNEHGM  CIKPNKAKTE

401  MKELRLLCAE  DEQIRTCWMT  AFRLLKYGML  LYQNYRIPQR  KGLPPPFNAP

451  MRSVSENSLV  AMDFSGQIGR  VIDNPAEAQS  AALEEGHAWR  NGSTRMNILS

501  SQSPLHPSTL  NAVIHRTQHW  FHGRISREES  HRIIKQQGLV  DGLFLLRDSQ

551  SNPKAFVLTL  CHHQKIKNFQ  ILPCEDDGQT  FFTLDDGNTK  FSDLIQLVDF

601  YQLNKGVLPC  KLKHHCIRVA  L
```

FIG. 38

```
      GGGGCCGGGGGAGGAGGAGGCGGAGGCGGCGGCGGAGGCTGGGAGGGCGGGCGGGGCCCG
   1  ------+---------+---------+---------+---------+---------+  60

GAGAGTTTAAAGCCCATCGAGGGtGTGGGGTGCGGGGAGGCGGCAGGAAGGGAAGGGCGC
  61  ------+---------+---------+---------+---------+---------+  120

TGCGACCAGTGGCGGGCGtGATTCGCGTTCCGAGACCCACGGGAGCACGAAGTTTCCGCG
 121  ------+---------+---------+---------+---------+---------+  180

CACCGTCTCACGCACGGCGACTGGGACCGTCCAGTGTTCCGGCTTTGCCTTCGGTTTTTC
 181  ------+---------+---------+---------+---------+---------+  240

TCCGTTGTGACTCGTGCAACGTGTGGCCAGCGGCCACGCGGAGGCGACGAGGAGCTGCAC
 241  ------+---------+---------+---------+---------+---------+  300

GTCAGGACAAAGTGGGGCAGTCAACGTCCAAACCCGAAAACCTAGCTAAGTCTGGGTTTT
 301  ------+---------+---------+---------+---------+---------+  360

CGCCACAACAAAGAAGCCAACCAGAGCATGGTCTTGGGCTTCAAGTACTAATGAACAACG
 361  ------+---------+---------+---------+---------+---------+  420
                                                      M  N  N  D

ATATTAACTCGTCCGTGGAAAGCCTTAACTCAGCTTGCAACATGCAGTCTGATACTGATA
 421  ------+---------+---------+---------+---------+---------+  480
       I  N  S  S  V  E  S  L  N  S  A  C  N  M  Q  S  D  T  D  T

CTGCACCACTTCTTGAGGATGGCCAGCATGCCAGCAACCAGGGAGCAGCATCTAGCTCCC
 481  ------+---------+---------+---------+---------+---------+  540
       A  P  L  L  E  D  G  Q  H  A  S  N  Q  G  A  A  S  S  R

GGGGACAGCCACAGGCGTCCCCGAGGCAGAAAATGCAACGCTCGCAGCCTGTGCACATTC
 541  ------+---------+---------+---------+---------+---------+  600
       G  Q  P  Q  A  S  P  R  Q  K  M  Q  R  S  Q  P  V  H  I  L

TCAGGCGCCTTCAGGAGGAAGACCAGCAGTTAAGAACTGCATCTCTTCCGGCCATCCCCA
 601  ------+---------+---------+---------+---------+---------+  660
```

FIG.39A

```
              R  R  L  Q  E  E  D  Q  Q  L  R  T  A  S  L  P  A  I  P  N
         ACCCATTTCCGGAGCTCACTGGTGCGGCCCCTGGGAGCCCTCCTTCGGTTGCTCCTAGCT
   661   ----------+---------+---------+---------+---------+---------+  720

P  F  P  E  L  T  G  A  A  P  G  S  P  P  S  V  A  P  S  S
         CCTTACCTCCTCCTCCGAGCCAGCCACCTGCCAAGCATTGTGGCAGATGTGAGAAGTGGA
   721   ----------+---------+---------+---------+---------+---------+  780

L  P  P  P  P  S  Q  P  P  A  K  H  C  G  R  C  E  K  W  I
         TACCAGGGGAAAATACCCGGGGAAATGGGAAACGGAAGATCTGGAGATGGCAGTTCCCTC
   781   ----------+---------+---------+---------+---------+---------+  840

P  G  E  N  T  R  G  N  G  K  R  K  I  W  R  W  Q  F  P  P
         CAGGCTTTCAGCTGTCGAAACTCACCCGTCCAGGTCTGTGGACAAAGACCACTGCGAGAT
   841   ----------+---------+---------+---------+---------+---------+  900

G  F  Q  L  S  K  L  T  R  P  G  L  W  T  K  T  T  A  R  F
         TTTCAAAGAAACAACCTAAGAACCAGTGTCCAACCGACACTGTGAATCCAGTGGCACGGA
   901   ----------+---------+---------+---------+---------+---------+  960

S  K  K  Q  P  K  N  Q  C  P  T  D  T  V  N  P  V  A  R  M
         TGCCCACTTCACAGATGGAGAAGCTGAGGCTCAGAAAGGATGTCAAAGTCTTTAGTGAAG
   961   ----------+---------+---------+---------+---------+---------+  1020

P  T  S  Q  M  E  K  L  R  L  R  K  D  V  K  V  F  S  E  D
         ATGGGACCAGCAAAGTGGTGGAGATTCTAACCGACATGACAGCCAGGGACCTGTGCCAGC
   1021  ----------+---------+---------+---------+---------+---------+  1080

G  T  S  K  V  V  E  I  L  T  D  M  T  A  R  D  L  C  Q  L
         TGCTGGTTTACAAAAGTCACTGTGTGGATGACAACAGCTGGACTCTGGTGGAACACCACC
   1081  ----------+---------+---------+---------+---------+---------+  1140

L  V  Y  K  S  H  C  V  D  D  N  S  W  T  L  V  E  H  H  P
         CACAACTGGGATTAGAGAGGTGCCTGGAGGACCATGAGATCGTGGTCCAAGTGGAGAGTA
   141   ----------+---------+---------+---------+---------+---------+  1200
```

CCATGCCAAGTGAGAGCAAATTCTTATTCAGAAAGAATTATGCGAAGTACGAGTTCTTTA
1201   ------+---------+---------+---------+---------+---------+ 1260

M  P  S  E  S  K  F  L  F  R  K  N  Y  A  K  Y  E  F  F  K

AGAATCCAGTGAACTTCTTCCCGGATCAGATGGTCAATTGCTGCCAGCAGTCCAACGGTG
1261   ------+---------+---------+---------+---------+---------+ 1320

N  P  V  N  F  F  P  D  Q  M  V  N  W  C  Q  Q  S  N  G  G

GCCAGGCGCAGCTTCTGCAGAATTTTCTGAACACCAGCAGCTGCCCTGAGATCCAGGGGT
1321   ------+---------+---------+---------+---------+---------+ 1380

Q  A  Q  L  L  Q  N  F  L  N  T  S  S  C  P  E  I  Q  G  F

TCTTGCAGGTGAAAGAGGTAGGACGCAAGTCTTGGAAGAAGCTGTATGTGTGCCTGCGCA
1381   ------+---------+---------+---------+---------+---------+ 1440

L  Q  V  K  E  V  G  R  K  S  W  K  K  L  Y  V  C  L  R  R

GATCTGGCCTCTATTACTCCACCAAGGGGACTTCAAAAGAACCCAGACACCTGCAGCTGC
1441   ------+---------+---------+---------+---------+---------+ 1500

S  G  L  Y  Y  S  T  K  G  T  S  K  E  P  R  H  L  Q  L  L

TGGCTGACCTGGAAGAAAGCAGCATCTTCTACCTGATTGCTGGAAAGAAGCAGTACAACG
1501   ------+---------+---------+---------+---------+---------+ 1560

A  D  L  E  E  S  S  I  F  Y  L  I  A  G  K  K  Q  Y  N  A

CGCCGAATGAACATGGGATGTGCATCAAGCCAAACAAAGCGAAGACCGAGATGAAGGAGC
1561   ------+---------+---------+---------+---------+---------+ 1620

P  N  E  H  G  M  C  I  K  P  N  K  A  K  T  E  M  K  E  L

TTCGTCTGCTCTGTGCCCGAAGATGAGCAGATCCGTACTTGCTGGATGACTGCCTTCAGAC
1621   ------+---------+---------+---------+---------+---------+ 1680
```

TGCTCAAGTACGGAATGCTCCTGTACCAAAACTATCGCATCCCACAGAGGAAGGGTCTGC
1681  ------+---------+---------+---------+---------+---------+   1740

L  K  Y  G  M  L  L  Y  Q  N  Y  R  I  P  Q  R  K  G  L  P

CCCCTCCTTTCAACGCACCTATGCGCAGTGTTTCTGAGAATTCTCTTGTGGCCATGGATT
1741  ------+---------+---------+---------+---------+---------+   1800

P  P  F  N  A  P  M  R  S  V  S  E  N  S  L  V  A  M  D  F

TTTCTGGACAAATCGGAAGAGTGATCGATAACCCGGCTGAAGCCCAGAGTGCTGCCCTGG
1801  ------+---------+---------+---------+---------+---------+   1860

S  G  Q  I  G  R  V  I  D  N  P  A  E  A  Q  S  A  A  L  E

AAGAGGGCCATGCCTGGCGTAACGGGAGCACACGGATGAATATCCTAAGCAGCCAAAGCC
1861  ------+---------+---------+---------+---------+---------+   1920

E  G  H  A  W  R  N  G  S  T  R  M  N  I  L  S  S  Q  S  P

CACTGCATCCTTCTACCCTGAATGCAGTGATTCACAGGACTCAGCATTGGTTCCATGGAC
1921  ------+---------+---------+---------+---------+---------+   1980

L  H  P  S  T  L  N  A  V  I  H  R  T  Q  H  W  F  H  G  R

GTATCTCCCGCGAGGAGTCTCACAGGATCATCAAGCAACAAGGTCTCGTGGACGGGCTGT
1981  ------+---------+---------+---------+---------+---------+   2040

I  S  R  E  E  S  H  R  I  I  K  Q  Q  G  L  V  D  G  L  F

TCCTCCTTCGTGACAGCCAGAGTAATCCAAAGGCGTTCGTACTGACACTGTGCCATCACC
2041  ------+---------+---------+---------+---------+---------+   2100

L  L  R  D  S  Q  S  N  P  K  A  F  V  L  T  L  C  H  H  Q

AGAAGATTAAAAACTTCCAGATCTTACCTTGCGAGGATGATGGGCAGACCTTCTTCACTC
2101  ------+---------+---------+---------+---------+---------+   2160
```

TGGATGATGGGAACACCAAGTTCTCCGATCTGATCCAGCTGGTCGACTTCTACCAGCTCA
2161   ------+---------+---------+---------+---------+---------+  2220

D  D  G  N  T  K  F  S  D  L  I  Q  L  V  D  F  Y  Q  L  N

ACAAAGGTGTTCTGCCCTGCAAGCTGAAACACCACTGCATCCGCGTGGCCTTATGACCTC
2221   ------+---------+---------+---------+---------+---------+  2280

K  G  V  L  P  C  K  L  K  H  H  C  I  R  V  A  L  *

CTTGCCCACTCACAGAGGCTGGAGGCAGCGACACTGGAACGGAGAAGAGAGATCTGCATG
2281   ------+---------+---------+---------+---------+---------+  2340
       GAACGGGTGAGTGTCTCCGACCTCCGTCGCTGTGACCTTGCCTCTTCTCTCTAGACGTAC

AGGCCGGAATTCCGAAGACCAAGGAACCTTGAGAAGAAGAAGAAAAAAGAGAAGGTCCTT
2341   ------+---------+---------+---------+---------+---------+  2400
       TCCGGCCTTAAGGCTTCTGGTTCCTTGGAACTCTTCTTCTTCTTTTTTCTCTTCCAGGAA

GCTACTGTCACCAAAACAGTTGGTGGGACAAGAACGGTGGCACCCGGGTGGTGAAGCTT
2401   ------+---------+---------+---------+---------+---------+  2460
       CGATGACAGTGGTTTTGTCAACCACCCCTGTTCTTGCCACCGTGGGCCCACCACTTCGAA

CGAAAAATGCCTTAGGTATTATCCCACCGAAGATGTTCCTTCGGGAAGCTGCTGAGCCAC
2461   ------+---------+---------+---------+---------+---------+  2520
       GCTTTTTACGGAATCCATAATAGGGTGGCTTCTACAAGGAAGCCCTTCGACGACTCGGTG

GGCAAGAAGCCCTTCAGCCAGCACGTGAGAAGGCTA
2521   ------+---------+---------+------  2556
       CCGTTCTTCGGGAAGTCGGTCGTGCACTCTTCCGAT
```

FIG.39E

```
GRB-7   (2)   ELDLSPTHLSSSPEDVCPTPATP..............PETPPPPDNPPPG
              | ||   |    |                        |    |   |
GRB-10  (4)   DINSSVESLNSACNMQSDTDTAPLLEDGQHASNQGAASSSRGQPQASPRQ

GRB-7   (38)  DVKRSQPLPIPSSRKLREEEFQATSLPSIPNPFPELCSPPSQKPILGGSS
              ||||   |            ||| ||||||||||      |       |
GRB-10  (54)  KMQRSQPVHILRRLQEEDQQLRTASLPAIPNPFPELTGAAPGSPPSVAPS

GRB-7   (88)  GA................................................

GRB-10  (104) SLPPPPSQPPAKHCGRCEKWIPGENTRGNGKRKIWRWQFPPGFQLSKLTR

GRB-7   (90)  RGLLPRDSSRLC...........................VVKVYSE
              ||    |                                 ||| ||
GRB-10  (154) PGLWTKTTARFSKKQPKNQCPTDTVNPVARMPTSQMEKLRLRKDVKVFSE

GRB-7   (109) DGACRSVEVAAGATARHVCEMLVQRAHALSDESWGLVESHPYLALERGLE
              ||   ||   |||    |  ||   |   |  ||| || | ||| ||
GRB-10  (204) DGTSKVVEILTDMTARDLCQLLVYKSHCVDDNSWTLVEHHPQLGLERCLE

GRB-7   (159) DHEFVVEVQEAWPVGGDSRFIFRKNFAKYELFKSPPHTLFPEKMVSSCLD
              ||| ||   |       |  | |||| |||| |||| ||   || ||  |
GRB-10  (254) DHEIVVQVESTMP..SESKFLFRKNYAKYEFFKNPVN.FFPDQMVNWCQQ

GRB-7   (209) AQTGISHEDLIQNFLNAGSFPEIQGFLQLRGSGRGSGRKLWKRFFCFLRR
                |       | ||||| | ||||||||||   ||    ||   |||
GRB-10  (301) SNGG..QAQLLQNFLNTSSCPEIQGFLQVKEVGRKS....WKKLYVCLRR

GRB-7   (259) SGLYYSTKGTSKDPRHLQYVADVNESNVYVVTQGRKLYGMPTDFGFCVKP
              ||||||||||| ||||| ||   ||  ||        |  |   | | ||
GRB-10  (345) SGLYYSTKGTSKEPRHLQLLADLEESSIFYLIAGKKQYNAPNEHGMCIKP

GRB-7   (309) NKLRNGHKGLHIFCSEDEQSRTCWLAAFRLFKYGVQLYKNYQQAQSRHLR
              ||     |    |||| |||| |||| ||| |||| || |         |
GRB-10  (395) NKAKTEMKELRLLCAEDEQIRTCWMTAFRLLKYGMLLYQNYRIPQRKGLP

GRB-7   (359) LSYLGSPPLRSVSDNTLVAMDFSGHAGRVIDNPREALSAAMEEAQAWRKK
              | |||| |||||||||| |||||||| ||||||| ||| || ||| |||
GRB-10  (445) PPF..NAPMRSVSENSLVAMDFSGQIGRVIDNPAEAQSAALEEGHAWRNG
```

FIG.40A

```
GRB-7   (409)  TNHRLSLPTTCS..GSSLSAAIHRTQPWFHGRISREESQRLIGQQGLVDG
                  |       |  | |||||  ||||||||||| | | |||||||
GRB-10  (493)  STRMNILSSQSPLHPSTLNAVIHRTQHWFHGRISREESHRIIKQQGLVDG

GRB-7   (457)  VFLVRESQRNPQGFVLSLCHLQKVKHYLILPSEDEGCLYFSMDEGQTRFT
               || | || ||   ||| ||| || |   ||| || |   | | ||
GRB-10  (543)  LFLLRDSQSNPKAFVLTLCHHQKIKNFQILPCEDDGQTFFTLDDGNTKFS

GRB-7   (507)  DLLQLVEFHQLNRGILPCLLRHCCARVAL
               || ||| | |||   ||| | | ||||
GRB-10  (593)  DLIQLVDFYQLNKGVLPCKLKHHCIRVAL
```

FIG.40B

```
GRB-7    (434)  WFhGRISREE  SqR.LIgQQG  LVDGvFLVRE  SqrNPggFVL  SLCHLQk...
GRB-10   (520)  WFhGRISREE  ShR.IIkQQG  LVDGIFLIRD  SqSNPkAFVL  TLCHhQk...
GRB2     (60)   WFfGKIpRak  aEe.MIskQr  .hDGaFLIRE  SeSaPGdFsL  SV.kFgn...
c-SRC    (148)  WYfGKITRrE  SERILInpen  .prGtFLVRE  SeTtkGAYcL  SVsdFdnakg GRB-7    (480)  ..VKHYIILP  sEDEGcLYFs  MDEgqTrFtd  LIQLVEFhQL  .....NrGIL
GRB-10   (566)  ..IKnFqILP  cEDDGqtFFT  LDDgnTKFSd  LiQLVDFyQL  .....NkGVL
GRB2     (104)  .dVqHFKVLr  .DgaGkYFL.  ...wvvKFns  LneLVDYhrs  tsvSrNqqIF
c-SRC    (197)  InVKHYKIrk  IDsgG.FYiT  ...sr.TqFSs  LqQLVaYy..  ...SkhadgL GRB-7    (523)  PCILrHcCaR  VAL....
GRB-10   (609)  PCkLkHhCiR  VAL....
GRB2     (148)  IrdieqVpqq  plyvqal
c-SRC    (238)  chrLtnV...  .......
```

FIG.42

```
GRB-7    (95)  pRDssRLc.v  VKVYSEDGoc  RsVEVaagaT  ARhVCeMLVq  RaHaLsDESW
GRB-10  (189)  .mEkIRLRkd  VKVFSEDGts  KvVEIItdmT  ARDLCqLLVy  KsHcVdDnSW
F10E9.6 (187)  .KEakvtKif  VKfFvEDGea  IqLIIderwT  vaDtIkqLae  KnHialmEdh
Consensus       ---e------  VK-f-EDG--  ---v-i----T  ----------L---  k-H-------

GRB-7   (143)  gLVEsHPyLa  LERgLEDHEf  VVEVqeaWPv  ggDSRFIFRK  NFAKYELFKs
GRB-10  (238)  tLVEhHPqLg  LERcLEDHEi  VVqVestmP.  .SESKFLFRK  NYAKYEFFKn
F10E9.6 (236)  cIVEeyPeLy  IkRvyEDHEk  VVEniqmWvq  dSpnKLyFmR  rpdKYafisr
Consensus      -IVE---P-L-  I-R---EDHE-  VV--------  ------f-F-k  ---KY-f---

GRB-7   (193)  PphtLFPEKM  VssCIdaqtG  isheDLIQNF  L......Nag  SfPEIQGFLQ
GRB-10  (286)  Pvn.FFPDqM  VnwCqqsnGG  ..qapVLQNF  L......Nts  ScPEIQFGLQ
F10E9.6 (286)  PelyLLtpKt  sdhmeipsGd  qwtiDVkQkF  Vseyfhrepv  vpPEmeGFLy
Consensus      P-----If---  ----------  -----I-Q-F  I---------  ---PE---GFL- GRB-7   (237)  LRgsGRgSgr  kIWKRFFcfL  RRSGLYYSTK  GTSKDPRHLQ  YVADVnESnV
GRB-10  (327)  VKevGRKS..  ..WKKLYvcL  RRSGLYYSTK  GTSKEPRHLQ  ILADLeESsI
F10E9.6 (336)  LKsdGRKS..  ..WKKhYfvL  RpSGLYYapK  skkpttKdLt  CLmnLhsnqV
Consensus      Ik---GR-S--  --WKk-y---L  R-SGLYY---K  -------r-L-  -I---I----v GRB-7   (287)  YvVtqGRKIY  gmPTDFGfCV  KPNKLRnghK  gL.hIFCsED  EQsRTCWLaA
GRB-10  (373)  FyLlaGKKqY  naPnEhGmCI  KPNKaKtemK  eL.RLLCAED  EQiRTCWMtA
F10E9.6 (382)  YtglgweKkY  ksPTpWcisI  KItaLqmkrs  qFiKyICAED  EmtFkkWLvA
Consensus      y---------K-Y  --P-------i  K---------  -I----IC-ED  E------W---A GRB-7   (336)  FRLFKYGvqL  YkNYqqA..Q  sRhLrIsYlg  spPLRSVSDN  tLVAMDFSGH
GRB-10  (422)  FRLLKYGmIL  YqNYrip..Q  RKgLppPF..  naPMRSVSEN  SLVAMDFSGq
F10E9.6 (432)  LRIaKnGaeL  IeNYerAcqi  RRetIgPass  msaasSstai  SeVphsLShH
Consensus      fRI-K-G---L  --NY------  --r-------  -------S----  --V----fS--

GRB-7   (384)  ..........  ...aGRVIDNP  rEALSAAMEE  aqAWRkktnh  rLSLpttcs.
GRB-10  (468)  ..........  ...iGRVIDNP  aEAqSAALEE  ghAWRNgStr  mniLsSqspl
F10E9.6 (482)  qrtpsvassi  qIsshmmnNP  thpLSvnV..  ....RNqSpa  sFSVnScqqs
Consensus      ----------  ---------NP  ----S-----  ------R----  ----I------

GRB-7   (421)  gSsLSAaI
GRB-10  (506)  HPStLnAvI
F10E9.6 (526)  HPSrtSAkL
Consensus      ---S----A-i
```

FIG.43

EXPRESSION-CLONING METHOD FOR IDENTIFYING TARGET PROTEINS FOR EUKARYOTIC TYROSINE KINASES AND NOVEL TARGET PROTEINS

This is a division of application Ser. No. 08/252,820, filed Jun. 2, 1994, the entire contents of which is incorporated herein by reference in its entirety.

This is a continuation-in-part of U.S. Ser. No. 08/208,227, filed Mar. 11, 1994, the entire contents of which is herein incorporated by reference. U.S. Ser. No. 08/208,227 is a continuation-in-part of each of U.S. Ser. No. 08/167,035, filed Dec. 16, 1993, and U.S. Ser. No. 07/906,349, filed Jun. 30, 1992. U.S. Ser. No. 08/167,035 is a divisional application of U.S. Ser. No. 07/906,349, which is a continuation-in-part of U.S. Ser. No. 07/643,237, filed Jan. 18, 1991, now abandoned.

BACKGROUND OF THE INVENTION

1. Field of the Invention

The invention, in the field of molecular and cell biology, relates to a novel method, based on direct expression cloning, for identifying target proteins capable of binding to and/or serving as substrates for receptor or cytoplasmic tyrosine kinases. The invention also relates to novel proteins identified using this method.

2. Description of the Background Art

A variety of polypeptide growth factors and hormones mediate their cellular effects by interacting with cell surface receptors and soluble or cytoplasmic polypeptide containing molecules having tyrosine kinase enzymatic activity (for review, see Williams, L. T. et al., Science 243:1564–1570 (1989); Ullrich, A. et al., Cell 61:203–212 (1990); Carpenter, G. et al. J. Biol. Chem. 265: 7709–7712 (1990)). The interaction of these ligands with their receptors induces a series of events which include receptor dimerization and stimulation of protein tyrosine kinase activity. For the epidermal growth factor receptor (EGFR) as well—as other receptors with tyrosine kinase activity, such as the platelet derived growth factor receptor (PDGFR), kinase activation and receptor autophosphorylation result in the physical association of the receptor with several cytoplasmic substrates (Ullrich et al., supra).

Two substrates for the EGFR kinase have now been definitively identified in living cells: (a) the phosphatidylinositol specific phospholipase C-γ (PLC-γ) and (b) the GTPase activating protein (GAP), a protein which may be in the effector loop of the ras protein (Margolis, B. et al. Cell 57: 1101–1107 (1989); Meisenhelder, J. et al. Cell 57: 1109–1122 (1989); Molloy, C. J. et al. Nature 342: 711–714 (1989); Wahl, M. I. et al. J. Biol. Chem. 265: 3944–3948 (1990); Ellis, C. et al. Nature 343: 377–381 (1990); Kaplan, D. R. et al. Cell 61: 121–133 (1990)).

Similarly, activated PDGFR was shown to tyrosine phosphorylate, and to become associated with PLC-γ, GAP, and cellular tyrosine kinases such as pp60$^{src}$ (Gould, K. L. et al., Molec. Cell. Biol. 8:3345–3356 (1988); Meisenhelder, J. et al., Cell 57:1109–1122 (1989); Molloy, C. J. et al., Nature 342:711–714 (1989); Kaplan, D. R. et al., Cell 61:121–133 (1990); Kazlauskas, A. et al., Science 247:1578–1581 (1990); Krypta, R. M. et al., Cell 62:481–492 (1990); Margolis, B. et al., Science 248:607–610 (1990)). While the exact sites responsible for the association of EGFR with either PLC-γ or GAP have not been completely clarified, recent work has begun to identify regions on both the substrate and receptor which contribute to the association.

SH2 (src homology 2) domains appear to be the regions responsible for the association of several tyrosine kinase substrates with activated growth factor receptors. SH2 domains are conserved sequences of about 100 amino acids found in cytoplasmic non-receptor tyrosine kinases such as pp6Osrc, PLC-γ, GAP and v-crk (Mayer, B. J. et al., Nature 332:272–275 (1988); Pawson, T. Oncogene 3:491–495 (1988)). While having distinct catalytic domains, all these molecules share conserved SH2 and SH3 (src homology 3) domains and the ability to associate with receptors with tyrosine kinase activity (Anderson, D. et al., Science 250:979–982 (1990)).

Tyrosine kinase activation and receptor autophosphorylation are prerequisites for the association between growth factor receptors and SH2 domain-containing proteins (Margolis, B. et al., Mol.

Cell. Biol. 10:435441 (1990); Kumjian et al., Proc. Natl. Acad. Sci. USA 86:8232–8239 (1989); Kazlauskas, A. et al., Science 247:1578–1581 (1990)). In particular, the carboxy-terminal (C-terminal) fragment of the EGFR, which contains all the known autophosphorylation sites, binds specifically to the SH2 domains of GAP and PLC-γ (see below). Hence, a major site of association exists between the SH2 domain of these substrate proteins and the tyrosine phosphorylated C-terminal tail of the EGFR.

With the recognition that binding to the activated tyrosine kinase receptor is conserved among several substrate proteins, efforts to identify additional substrates which share these properties have been undertaken. Target proteins which bind to activated receptors have been identified by analysis of proteins that co-immunoprecipitate with growth factor receptors, or that bind to receptors attached to immobilized matrices (Morrison, D. K. et al., Cell 58:649–657 (1989); Kazlauskas, A.-et al., EMBO J. 9:3279–3286 (1990)). While the identity of some of these proteins is known, several others detected utilizing these approaches have not been fully characterized. Moreover, it is possible that rare target molecules which interact with activated receptors have not been detected due to the limited sensitivity of these techniques; the actual stoichiometry of binding may be low, and the detergent solution necessary to solubilize proteins may disrupt binding.

Conventional approaches to isolate and clone these proteins have been arduous, requiring the use of large quantities of tissue or cells lines to purify sufficient amounts of protein for microsequence analysis and subsequent conventional CDNA cloning. Therefore, a need for new approaches for the cloning and subsequent isolation and identification of these proteins is recognized in the art.

SUMMARY OF THE INVENTION

It is an object of the present invention to overcome the deficiencies of the related art.

It is also an object of the present invention to understand and gain control over the regulation of cell growth and oncogenesis by providing the ability to identify target proteins for tyrosine kinases, including both receptor and cytoplasmic tyrosine kinases in eukaryotic organisms.

It is a further object of the present invention to provide a novel expression/cloning system for the rapid cloning of target proteins which bind tyrosine kinase proteins which are present intracellularly and in cell receptors of eukaryotes. The cloning method is based on the ability of a certain class of substrates to bind specifically to the tyrosine-phosphorylated carboxyterminus (C-terminus) of the proteins having tyrosine kinase activity. Non-limiting examples include proteins that bind at least one of cytoplasmic and receptor tyrosine kinases, such as a receptor tyrosine kinase found in epidermal growth factor receptor (EGFR) (see Example VI, below).

Another object of the present invention is to provide a method of cloning tyrosine kinase target proteins, which method important advantages over conventional cloning methods, including avoidance of the laborious and costly task of purifying potential target proteins for microsequencing analysis.

Another object of the present invention is to provide a method for identifying receptor target molecules having tyrosine kinase activity whose association with activation receptors could not otherwise be detected using conventional techniques.

Another object of the present invention is to provide for the identification of structurally or functionally related proteins which, though only weakly homologous at the nucleic acid level, are similar in their property of binding to activated receptors with tyrosine kinase activity, which latter ability is important since conventional screening methods used to identify related genes are typically based on low stringency nucleic acid hybridization. Conventional hybridization-based screening would not have been successful in cloning and identifying such tyrosine kinase target proteins of the present invention, exemplified as non limiting examples as GRB-1, GRB-2, GRB-3, GRB-4, GRB-7 or GRB-10, because of their lack of similarity at the DNA level.

Another object of the present invention is to provide a method for identifying compounds that disrupt or inhibit the interaction between activated tyrosine kinase molecules and those proteins (e. adaptor proteins) they bind.

The methods of the present invention take advantage of the discover that the C-terminus of the EGFR protein in which the tyrosine residues are phosphorylated can bind substrates as described herein. By creating a labelled polypeptide which substantially corresponds to at least a portion of phosphorylation domain of a tyrosine kinase, a probe is provided having at least one phosphorylated tyrosine. Such a probe can be used to detect, identify and/or purify target proteins from solutions or as part of screening of CDNA expression libraries from eukaryotic cells or tissues. Such tyrosine kinase target proteins, discovered according to the present invention, ar termed "GRB" (for Growth factor Receptor Bound) for the initial receptor tyrosine kinases used, but which target proteins are not limited to growth factor receptors. Accordingly, GRBs of the present invention include target proteins for any eukaryotic tyrosine kinase which are provided according to the present invention.

The novel cloning methodology of the present invention has been designated, "CORT" (for Cloning Of Receptor Targets), and may also be applied to detecting, identifying, cloning or purifying target proteins for any tyrosine kinase, such as a soluble, cytoplasmic or receptor tyrosine kinase.

The method of the present invention is proposed as a novel approach having both generality and rapidity for the identification and cloning of target molecules for tyrosine kinases.

The present invention is thus directed to a method for detecting a target protein in solution, which is a target of a receptor or cytoplasmic tyrosine kinase, the target protein being capable of binding to at least a portion of a tyrosine-phosphorylated polypeptide of the receptor or cytoplasmic tyrosine kinase, the method comprising:

(a) contacting the solution (as a cell, an extract thereof, a lysate thereof, or a supernatant thereof) with a solid phase carrier, causing the binding of the protein to the carrier to provide a carrier-bound target protein;

(b) incubating the carrier-bound target protein with the tyrosine-phosphorylated polypeptide, which has been detectably labeled, allowing the polypeptide to bind to the carrier-bound protein;

(c) removing materials not bound to the carrier-bound target protein;

(d) detecting the presence or measuring the amount of the tyrosine-phosphorylated polypeptide bound to the carrier, thereby quantitatively or qualitatively detecting the target protein in said solution.

In one embodiment, the receptor or cytoplasmic tyrosine kinase is any eukaryotic tyrosine kinase (e.g., epidermal growth factor receptor, a platelet-derived growth factor receptor, or a fibroblast growth factor receptor, $pp60^{v-src}$, $pp160^{gag-abl}$, $pp130^{gag-fps}$, $pp59^{c-fyn}$, PDGF receptor B, CSF-1 receptor, $pp150^{c-fms}$, $pp150^{v-fms}$, Insulin Receptor, IGF-1 receptor, $pp68^{gag-ros}$, PLC-γ, middle t-$pp60^{s-src}$ middle t-$pp62^{c-yes}$, and the consensus sequences EEEEEY($PO_4$)MPMXX (SEQ. ID No: 11), EEEEEY($PO_4$)VPMXX (SEQ ID NO:12), DDDDDY($PO_4$)MPMXX (SEQ ID NO:13), and DDDDDY($PO_4$)VPMXX (SEQ ID NO:14) or a phosphorylatable fragment thereof, preferably a polypeptide of about 10 to 250 amino acid residues, more preferably 10 to 40 or 15 to 50 residues, wherein the polypeptide is produced recombinantly, synthetically or by enzymatic digestion of a purified tyrosine kinase molecule.

This method is preferably performed using a prokaryotic cell, most preferably a bacterial cell such as *E. coli*. The cell may also be eukaryotic, such as a yeast or a mammalian cell.

Preferably, the phosphorylated polypeptide is detectably labeled.

The solid phase carrier can be any material which can be used to bind a target protein for a tyrosine kinase. The carrier may preferably be a nitrocellulose membrane, such as to which are transferred proteins released for lysed bacterial cells when a library is being screened.

The present invention also provides a method for mapping to a eukaryotic, such a mammalian, human, reurine, or other eukaryotic chromosome a gene encoding a protein which is capable of binding to a tyrosine phosphorylated polypeptide portion of a receptor or cytoplasmic tyrosine kinase molecule, the method comprising:

(a) infecting a host or host cells which a eukaryotic gene expression library;

(b) detecting a clone expressing the protein using a method as described above;

(c) sequencing the DNA of the clone; and (d) mapping the sequence to a eukaryotic chromosome.

The present invention is also directed to a polypeptide probe useful in the detection of the expression of a protein capable of binding to a tyrosine-phosphorylated polypeptide portion of a receptor or cytoplasmic tyrosine kinase. The probe comprises an amino acid sequence derived from the tyrosine-phosphorylated portion of the receptor or cytoplasmic molecule, or a functional derivative thereof, lacks the tyrosine kinase domain, and the sequence must contain at least one phosphotyrosine residue, such as 1, 2, 3, 4, 5, 6, 7, 8, 9, 10 or 11 phosphotyrosines. The probe should be detectably labeled with known labels. A preferred probe has between about 10 and 250 amino acid residues, preferably 10–35, 16–30, 21–35, 15–35, or 20–40 residues.

A probe of the present invention is useful for detecting target proteins for receptor or cytoplasmic tyrosine kinases including but not limited to, epidermal growth factor receptor (EGFR), platelet-derived growth factor receptor (PDGFR), fibroblast growth factor receptor (FGFR), colony stimulating factor-1, (CSF-1), insulin receptor, phospholipase C-γ (PLC-γ) and insulin like growth factor-1 (IGF-1), pp60$^{v-src}$, pp160$^{gag-abl}$, pp130$^{gag-fps}$, pp59$^{c-fyn}$, PDGF receptor B, CSF-1 receptor, pp150$^{c-fms}$, pp150$^{v-fms}$, EGF receptor, IGF-1 receptor, pp68$^{gag-ros}$, PLC, middle t-pp60$^{c-src}$ middle t-pp62$^{c-yes}$, and the consensus sequence EEEEY(PO$_4$)MPMX (SEQ. ID NO:11), EEEEEY(PO$_4$)VPMXX (SEQ ID NO:12), DDDDDY(PO$_4$)MPMXX (SEQ ID NO:13), and DDDDDY (PO$_4$)VPMXXX. (SEQ ID NO: 14) or a phosphorylatable fragment thereof, e.g., as described Cantley et al., Cell 64:281–302 (1991) or Ullrich and Schlessinger, Cell 61:203–312 (1990), which references are entirely herein incorporated by reference.

The present invention also includes a method for preparing the above probe, comprising (a) providing the receptor or cytoplasmic tyrosine kinase, or a recombinantly, enzymatically or synthetically produced fragment thereof wherein the receptor or cytoplasmic tyrosine kinase, or fragment thereof, has both a tyrosine kinase domain and a tyrosine-phosphorylated domain, the tyrosine-phosphorylated domain including at least one tyrosine residue capable of being phosphorylated by the tyrosine kinase;

(b) incubating the receptor or cytoplasmic tyrosine kinase, or fragment, with detectably labeled adenosine triphosphate under conditions permitting phosphorylation of the tyrosine residue, causing phosphorylation of the tyrosine residue thereby producing the probe. In a preferred embodiment, the method includes the step of:

(c) additionally treating the phosphorylated receptor or cytoplasmic tyrosine kinase molecule with an agent capable of cleaving the molecule between the tyrosine kinase domain and the tyrosine-phosphorylated domain.

A preferred cleaving agent is cyanogen bromide.

In another embodiment, the above method involves a genetically engineered receptor-like derivative which is a polypeptide encoded by a DNA molecule comprising a DNA sequence encoding tyrosine kinase, linked to a DNA sequence encoding a selective enzymatic cleavage site, linked to a DNA sequence encoding the tyrosine-phosphorylated domain, and wherein the agent is an enzyme capable of cleaving at this cleavage site. Preferred enzymes are Factor Xa and thrombin.

Also provided is a method for purifying from a complex mixture a protein which is capable of binding to a tyrosine-phosphorylated polypeptide portion of a receptor or cytoplasmic tyrosine kinase molecule, the method comprising:

(a) contacting the complex mixture with a solid phase carrier to which a probe is bound, allowing the protein to bind to the probe;

(b) removing materials not bound to the carrier; and (c) eluting the bound protein from the carrier, thereby purifying the protein.

The present invention is also directed to a GRB protein of at least 10 amino acids, including any range of value up to its entire native or mature length. The present invention, in one embodiment, provides a protein, GRB-1, having the amino acid sequence shown in FIG. 4 (SEQ ID NO:5). The invention also includes polypeptides having an amino acid sequence substantially corresponding to the amino acid sequence of a protein, GRB-2 which includes the amino acid sequence shown in FIGS. 26A–26C (SEQ ID NO:6). The invention also includes polypeptides having an amino acid sequence substantially corresponding to the amino acid sequence of a protein, GRB-3, which includes the amino acid sequence shown in FIGS. 34A–34C (SEQ ID NO:8). The invention also includes polypeptides having an amino acid sequence substantially corresponding to the amino acid sequence of a protein, GRB-4, which includes the amino acid sequence shown in FIGS. 35A–35B (SEQ ID NO:9). The invention also includes polypeptides having an amino acid sequence substantially corresponding to the amino acid sequence of a protein, GRB-7, which includes the amino acid sequence shown in FIGS. 36A–36G (SEQ ID NO:10). The invention also includes polypeptides having an amino acid sequence substantially corresponding to an amino acid sequence of a protein, GRB-10, which includes the amino acid sequence shown in FIG. 38 (SEQ ID NO:18).

The invention is also directed to a DNA or RNA molecule encoding a polypeptide having at least a 10 amino acid sequence substantially corresponding to the amino acid sequence of at least one of GRB-1, GRB-2, GRB-3, GRB-4, GRB-7 or GRB-10 proteins. Included are DNA molecules encoding functional derivatives of these proteins. When the DNA molecule naturally occurs, it is substantially free of the nucleotide sequences with which it is natively associated. The DNA molecules of this invention may be expression vehicles, such as plasmids.

Also provided is a host transformed with each of the above DNA molecules.

The present invention also includes a process for preparing a target protein substantially corresponding to the amino acid sequence GRB-1, GRB-2, GRB-3, GRB-4, GRB-7 or GRB-10 protein, comprising:

(a) culturing a host comprising a recombinant nucleic acid having a nucleotide sequence encoding the target protein under culturing conditions such that the target protein is expressed in recoverable amounts; and (b) recovering the protein from the culture.

BRIEF DESCRIPTION OF THE DRAWINGS

FIGS. 4A–4I shows the DNA sequence and predicted amino acid sequence of GRB-1 (SEQ ID NO:1). The protein has 724 amino acid residues.

FIG. 5 compares the sequences of the SH2 domains of GRB1 with other proteins with similar motifs. SH2 domains of GRB-1, c-src, v-abl, bovine PLC-γ, GAP, and V-crk. N and C refer to N-Terminal and C-terminal SH2 domains respectively. Conservation amino acid substitutions are as defined by Schwartz and Dayhoff: (A,G,P,S,T); (L,I,V,M); (D,E,N,Q); (K,R,H); (F,Y,W); and C. Bold letters identify those positions where the same or a conservative amino acid substitution is present at 5 or more positions. Boxes identify conserved motifs. A similar comparison of the SH3 domain of GRB-1.

FIG. 11 is a gel pattern showing that phosphorylation of PLC-γ reduces its binding to the EGF receptor. Full length EGFR was immunoprecipitated with Mab108, and allowed to autophosphorylate. Lysate from PLC-γ overexpressing 3T-P1 cells was added and mixed for 90 min at 4° C. After binding, ATP was added to one half of the samples allowing the PLC-γ molecules to be phosphorylated by the EGF receptor. SDS-PAGE sample buffer-was then added to one half of the EGFR-PLC-γ complexes (NO WASH, left panel) and directly loaded onto the 6% gel. The other half was washed three times with HNTG and then loaded on the gel (WASH, right panel. After running duplicate samples on SDS-PAGE, the proteins were transferred to nitrocellulose and probed with anti PLC-γ and ($^{125}$I)Protein A. The bands were subsequently cut from the nitrocellulose and quantitated in a γ counter. After three washes with HNTG, 50+/−5% (Mean+/−SEM, n=4) of the non-phosphorylated PLC-γ remained bound to the EGFR while only 22+/−4% of the phosphorylated PLC-γ remained (exposure time: 12 h).

In FIG. 12A, EGFR-C (0.5 μg) was immunoprecipitated with antibody C and washed. MnCl$_2$ alone or MnCl$_2$ and ATP were then added to facilitate autophosphorylation of TrpE or trpE/GAP SH2 (approximately 2 μg). The immunoprecipitates were separated on a 10% SDS-gel, transferred to nitrocellulose and immunoblotting was performed with anti-trpE. For comparison, about 0.1 μg of trpE or trpE/GAP SH2 lysate was loaded directly on to the gel (right panel of 12A). In FIG. 12B, trpE or trpE/GAP SH2 was immunoprecipitated with anti-trpE antibodies and washed. Phosphorylated or non-phosphorylated EGFR-C (0.5 μg) was then added and allowed to bind as above. After washing, samples were separated on a 10% gel, transferred to nitrocellulose and probed with antibody C. The two samples on the right represent 0.5 μg of phosphorylated and non-phosphorylated kinase loaded directly onto the gel (exposure time: 2 h).

In FIG. 13A, wild-type receptor (HER14) or the carboxy-terminal deletion CD126 receptor were immunoprecipitated with mAb 108. MnCl$_2$ alone or MnCl$_2$ and ATP were then added to the autophosphorylated half of the receptor-containing samples. One set of CD126 was also cross-phosphorylated with 0.5 μg of EGFR-C. TrpE/GAP SH2 was then added for 90 min at 4° C. and, after three more washes, loaded onto SDS-PAGE. After transfer to nitrocellulose, blots were probed with anti-trpE (left panel), anti-EGFR RK2 (center panel), or anti-PTyr (right panel). RK2 and anti-PTyr are both ⅛ of the total sample and were separated on 7k SDS-PAGE. The remaining sample was loaded on a 10% gel for the anti-trpE blot (exposure time 14 h).

In FIG. 13B, lysates from NIH3T3 2.2 cells containing no EGFR (3T3) or from cells with kinase-negative receptors (K21A) were immunoprecipitated with mAb108. To all immunoprecipitates, 0.5 μg of EGFR-C was added and then MnCl$_2$ alone or MnCl$_2$ and ATP. trpE/GAP SH2 was added and samples prepared and immunoblotted as in (13A) (exposure time 19 h).

FIGS. 16A–16D shows the partial nucleotide sequence and predicted amino acid sequence of GRB-2.

FIG. 17 is a comparison of sequence homology of avian crk to GRB-3 with dots indicating homologous amino acids.

FIG. 18 is a protein sequence of nck compared to that of GRB-4 for amino acid sequence homology.

FIG. 19 is a GRB-7 (SEQ ID NO:1) protein sequence.

FIG. 21 is a comparison of a GRB-7 amino acid sequences with SH2 domains from avian c-src, human PLC-γ, GRB-1/p85, mouse fyn, GRB-3 and GRB-4.

FIG. 22 is a comparison of a GRB-7 amino acid sequence with rasGAP.

FIG. 23 is a comparison of a GRB-7 amino acid sequence with P2B2.

FIGS. 26A–26A include a CDNA (SEQ ID NO:2) and protein sequence (SEQ ID NO:2) of GRB2 clone 10-53, with 5' and 3' untranslated flanking sequences; SH2 (thick line) and SH3 (thin lines) domains are indicated.

FIGS. 26E and 26F are sequence alignments of GRB2 SH2 and SH3 domains, respectively, with other proteins. N and C refer to N-terminal and C-terminal domains, respectively. The one letter code is used to indicate amino acid residues. Bold letters identify those positions where the same or a conservative amino acid substitution is present at that position. Compared are PLCγ1, GAP, v-src, v-abl, v-crk and p85. The SH2 domain of GRB2 is most similar to the SH2 domain of v-fgr (43% similarity) and the N-terminal SH3 domain is most similar to the SH3 domain of human vav (48% similarity).

FIG. 27B shows immunoprecipitation of GRB2 from ($^{35}$S) methionine labeled HER14 lysates with preimmune (lane 1) and immune GRB2 antiserum (Ab50) (lane 2). Immunoblot analysis of GRB2 from lysates of HER14 cells with Ab86 (lane 3). Molecular weight markers (sized in kDa) are indicated. Arrow indicates band corresponding to GRB2 protein. Exposure times are 24 hours.

FIG. 29 is a schematic representation of GRB2-GST fusion proteins. Gluthatione-S-transferase fusion proteins of full size GRB2 and various regions of GRB2 were generated and purified by affinity chromatography utilizing glutathione agarose beads, as described in methods. Shown are the SH2 domain of GRB2 (SH2), the amino terminal SH3 (N-SH3), carboxy terminal SH3 (C-SH3), the amino terminal SH3 and SH2 domains (NSH3 SH2), and the SH domain with the carboxy terminal SH3 domain (SH2 C-SH3). GST region of fusion proteins is not shown.

FIG. 32 presents the alignment of amino acid sequences of GRB2 and sem-5 (single letter code). Boxes surround the SH2 and SH3, domains, as indicated. Bold capital letters indicate identical amino acids, capital letter indicate conservative substitutions.

Ras (or let-60) acts downstream leading to either cell proliferation or vulval development.

FIGS. 34A–34C is a cDNA (SEQ ID NO:3) and protein sequence (SEQ ID NO:8) of GRB-3.

FIGS. 35A–35B is a cDNA (SEQ ID NO:4) and protein (SEQ ID NO:9) sequence of GRB-4.

FIGS. 36A–36G is a cDNA (SEQ ID NO:7) and protein (SEQ ID NO:10) sequence of GRB-7.

FIGS. 37A–37C. cDNA sequence including the coding sequence of GRB-10 (SEQ ID NO:17). A partial clone encompassing GRB-10 nucleotides 1950 to 2340 and encoding the GRB-10 SH2 domain was isolated by screening a randomly primed λEXlox library with the phosphorylated carboxyterminal tail of the EGF-Receptor. This probe was used to isolate the GRB-10 cDNA which encoded the full length protein using the CORT technique.

FIGS. 38 Deduced protein sequence of GRB-10 (SEQ ID NO:18).

FIGS. 39A–39E GRB-10 cDNA and protein sequence.

FIGS. 40A–40B Alignment of the protein sequence of GRB-7 and GRB-10. The GRB-7 and GRB-10 protein sequences were aligned using the BESTFIT program of the Wisconsin Genetics Group Sequence Analysis Software (GCG) (Deveraux et al., 1984, Nucleic Acids Res. 12:387–395). Identity is indicated by the vertical lines.

Figure 41:
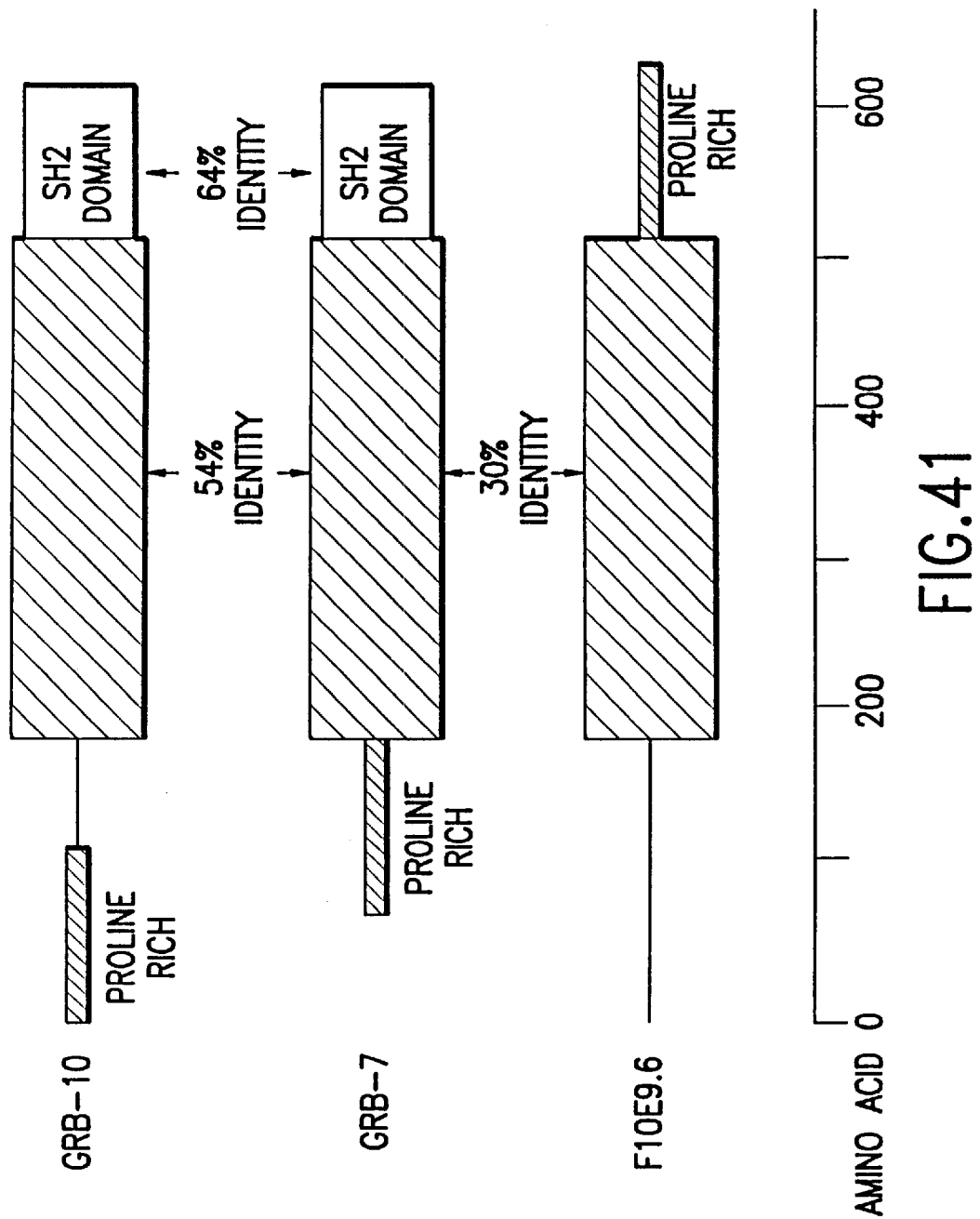

FIG. 41 Schematic representation of the alignment of GRB-7, GRB-10 and F10E9.6. GRB-7 and GRB-10 both display SH2 domains in their caboxyterminus.

FIG. 42 Alignment of the GRB-10 SH2 domain with those found in GRB-7, GRB-2 and c-Src. SH2 domains were aligned using the GCG programs LINEUP, PILEUP and PRETTY (Devereux et al., 1984, Nucleic Acids Res. 12:387–395).

FIG. 43 Alignment of the central domains of GRB-7, GRB-10 and F10E9.6. Alignment was performed using the GCG programs LINEUP, PILEUP and PRETTY with capital letters indicating identity or conservative substitution. F10E9.6 represents a putative gene derived from genomic sequence of *C. Elegans* using the program GENEFINDER. The F10E9.6 sequences were deposited into Genbank by the *C. Elegans* Sequencing Consortiun, Genbank accession number L10986 (Sulston et al., 1992, Nature 356:37–41).

Figure 44:
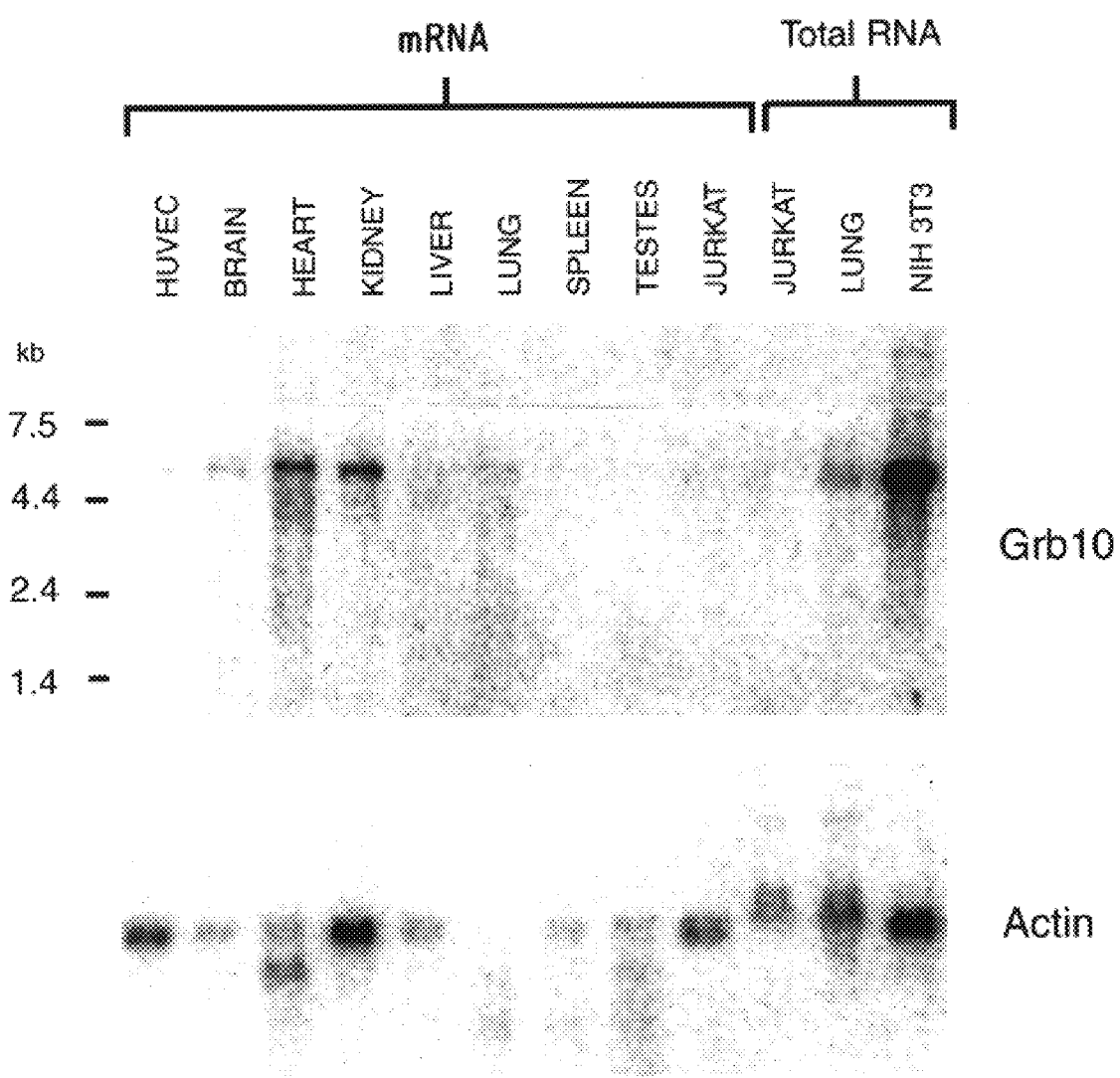

FIG. 44 Northern blot of GRB-10 Poly $(A)^+$ RNA. (Huvec: Human Umbilical Vein Endothelial Cells; Jurkat: human T cell leukemia cell line).

DETAILED DESCRIPTION OF THE PREFERRED EMBODIMENTS

Methods, compounds and compositions have now been discovered to provide a means to understand and gain control over the regulation of cell growth and oncogenesis by providing the ability to identify target proteins for tyrosine kinases, including both receptor and cytoplasmic tyrosine kinases in eukaryotic organisms.

One embodiment of the present invention is to provide a novel expression/cloning system for the rapid cloning of target proteins which bind tyrosine kinase proteins which are present intracellularly and in cell receptors of eukaryotes. The cloning method is based on the discovery that certain classes of substrates can bind specifically to the phosphorylated domains of proteins having tyrosine kinase activity.

According to another embodiment of the present invention, novel probes and methods using such probes for rapid expression cloning of DNA encoding proteins which have the characteristic of binding to the tyrosinephosphorylated portion, such as the C-terminus, of a receptor tyrosine kinase molecule, which molecule is present in the cytoplasm or in cell receptors of eukaryotic receptors.

By the term "eukaryote" or "eukaryotic" is intended any organism considered to have the attributes of a eukaryote, including a cell nucleus, mitochondria, chromosomes, etc., which are attributes which do not occur in bacteria, blue-green algae or viruses. Nonlimiting examples of eukaryotes include yeast, fungi, insects, plants, mammals, birds, reptiles, amphibians. Mammals include, but are not limited to, humans, mice, rats, rabbits, cows, pigs, goats, sheep, horses, cats, dogs, etc.

Expression cloning is a method wherein the DNA being cloned encodes a protein which is expressed from a cloned library from a cell known or expected to have the desired protein. The desired DNA, typically in the form of a cDNA library, is detected by means of its expression and/or direct detection of the protein which it encodes. Expression cloning systems and library cloning are well known in the art (see: Sambrook, J. et al. (Molecular Cloning: A Laboratory Manual, 2nd Edition, Cold Spring Harbor Press, Cold Spring Harbor, N.Y. (1989), and Ausubel et al, eds. (Current Protocols in Molecular Biology Wiley Interscience, NY (1987, 1992)), which references are hereby entirely incorporated by reference).

According to the present invention, the protein is expressed according to known method steps from a library and the expressed protein, released from the cell it is expressed in is transferred to a solid carrier or support, such as a nitrocellulose filter as a nonlimiting example, and detected using a detectable label for the expressed protein by known method steps.

One of the ways in which the polypeptide probe target protein can be detectably labeled is by providing peptide probes or anti-target protein antibodies and linking the peptide probes or antibodies to an enzyme for use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may additionally be accomplished using any of a variety of other immunoassays or detectably labeled peptide probes. For example, by radioactively labeling the peptide probes, anti-target protein antibodies or antibody fragments, such that the labeled target protein may also be detected through the use of a radioimmunoassay (RIA). A good description of RIA may be found in "Laboratory Techniques and Biochemistry in Molecular Biology", by Work, T. S., et al., North Holland Publishing Company, New York (1978) with particular reference to the chapter entitled "An Introduction to Radioimmune Assay and Related Techniques" by T. Chard, incorporated by reference herein. A radioactive isotope such as $^{32}P$, $^{35}S$, $^{12}C$ or $^3H$, can be detected by such means as the use of a gamma counter, a liquid scintillation counter or by autoradiography.

It is also possible to label the peptide probe or anti-target protein antibody with a fluorescent compound. When the fluorescently labeled peptide or antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, ophthaldehyde and fluorescamine. Suitable fluorescent probes are well known or commercially available, such as from Molecular Probes, Inc., Eugene Oreg.

The peptide probe or anti-target protein antibody an also be detectably labeled using fluorescence emitting metals such as $^{152}Eu$, or others of the lanthanide series. These metals can be attached to the peptide probe or anti-target protein antibody using such metal chelating groups as diethylenetriaminepentaacetic acid (DTPA) or ethylenediaminetetraacetic acid (EDTA).

The peptide probe or anti-target protein antibody also can be detectably labeled by coupling it to a chemiluminescent compound. The presence of the chemiluminescent-tagged peptide probe or anti-target protein antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the peptide probe or anti-target protein antibody of the present invention. Bioluminescence is a type of chemiluminescence found in biological systems in which a catalytic peptide probe or anti-target protein antibody increases the efficiency of the chemiluminescent reaction. The presence of a bioluminescent peptide probe or anti-target protein antibody is determined by detecting the presence of luminescence. Important bioluminescent compounds for purposes of labeling are luciferin, luciferase and aequorin.

The expression cloning method of the present invention for detecting and cloning a target protein for tyrosine kinase cytoplasmic or receptor protein may be used for detecting such target proteins from any eukaryotic cell source. For example, certain target molecules bind to the tyrosine phosphorylated portion of PDGFR and the colony stimulating factor 1 (CSF-1) (Coughlin, S. R. et al. , Science 243:1191–1194 (1989); Kazlauskas, A. et al., Cell 58:1121–1133 (1989); Shurtleff, S. A. et al., EMBO J. 2:2415–2421 (1990); and Reedjik, M. et al., Mol. Cell. Biol. 10:5601–5608 (1990)). In these receptors, the tyrosine phosphorylation occurs in a kinase insert domain, rather than in the C-terminal domain as is the case with the EGFR. Therefore, specific polypeptide probes in the range of 10–250, such as 10–20, 20–30, 40–50, 70–100, or 100–200, amino acids utilizing the kinase insert domain, or a portion thereof as defined herein, and cytoplasmic or receptor or PDGFR or CSF-1 receptor can be similarly used for expression cloning. Similar probes can also be constructed for the fibroblast growth factor (FGF) receptor (which is tyrosine phosphorylated in the (terminal domain) or the HER 2/neu receptor, both of the which are also able to interact with SH2 containing proteins such as PLC-γ. In other receptors, such as the insulin receptor, tyrosine phosphorylation occurs in the kinase domain itself.

Accordingly, any tyrosine kinase protein or fragment thereof of 10–250 amino acids, e.g., as described in Cantley et al. Cell 64:281–302 (1991) (the entire contents of which are herein incorporated by reference), can be used to bind a target protein in solution which is contacted to the tyrosine kinase protein bound or associated with a carrier or support. The carrier or support can be any known material that associates with a tyrosine kinase or fragment thereof, such that, once the target protein is bound, the non-bound material can be removed from the carrier without dissociated the tyrosine kinase bound to the target protein.

Thus the tyrosine kinase protein is used as a protein probe to bind target proteins. Alternatively, a polypeptide of 10–250 amino acids, corresponding to at least a phosphorylation domain of the tyrosine kinase; or corresponding to a consensus sequence of a class or group of tyrosine kinases, can be used as the protein or polypeptide probe and may be detectably labeled.

Thus, while it will be appreciated that different sites are tyrosine-phosphorylated in different proteins, e.g., the C-terminal domain in the EGFR, the kinase domain in insulin receptor, and a kinase domain insert in PDGFR, the present invention recognizes the common features of all these structures, the presence of one or more phosphotyrosine residues, and the ability of certain cellular proteins to bind on the basis of affinity to a polypeptide containing one or more phosphotyrosines. While reference will generally be made below to a probe which is a C-terminal domain, with reference to the EGFR, this language is not intended to be limiting and is intended to include all of the other alternative tyrosine-phosphorylated domains discussed above.

The methods and approach of the present invention can be applied to the cloning and identification of all target molecules which are capable of interacting in a specific manner with tyrosine phosphorylated polypeptides, such as cytoplasmic tyrosine kinases or the activated phosphorylated receptors described herein. Additional proteins which bind to tyrosine-phosphorylated sequences, such as the tyrosine-specific phosphatases, e.g., R-PTPases (Sap, J. et al., Proc. Natl. Acad. Sci. USA 87:6112–6116 (1990); Kaplan, R. et al., Proc. Natl. Acad. Sci. USA 87:7000–7004 (1990) may also be use according to a method of the present invention. The methods are also applicable in the cloning and identification of proteins which bind to phosphorylated serine/threonine residues, as with serine/threonine-specific phosphatases as a non-limiting example.

Use of a polypeptide or protein probe of the present invention allows the rapid cloning of DNA and identification of the encoded proteins from eukaryotic DNA or RNA libraries, such as a gene expression library. The method is particularly useful with a bacteriophage lambda gt11 library or a T7 library. As a non-limiting example of a eukaryotic library, screening a human fetal brain lambda gtll expression library has permitted the present inventors to clone several target protein genes and to characterize the proteins they encode. One, termed GRB-1, was fully DNA sequenced (SEQ ID NO:1) and found to encode novel human protein with an amino acid sequence as shown in FIG. 4 (SEQ ID NO:5) and a molecular weight of about 85 kDa which contained two SH2 domains and one SH3 domain (FIG. 4 and FIG. 5). GRB-2 DNA (FIGS. 26A–26C) (SEQ ID NO:2) also contains unique SH2 and SH3 domains in the amino acid sequence, (FIGS. 26A–26C) (SEQ ID NO:6). GRB-3 DNA (SEQ ID NO:3) was also sequenced (FIG. 34) and the GRB-3 amino acid sequence (SEQ ID NO:8). GRB-4 DNA (SEQ ID NO:4) (FIGS. 35A–35B) encoded a protein composed of three SH3 domains and one SH2 domain having the GRB-4 amino acid sequence (SEQ ID NO:9).

Several overlapping clones were identified which were used for DNA sequencing of GRB-7 (FIGS. 36A–36G)

Figure 20:
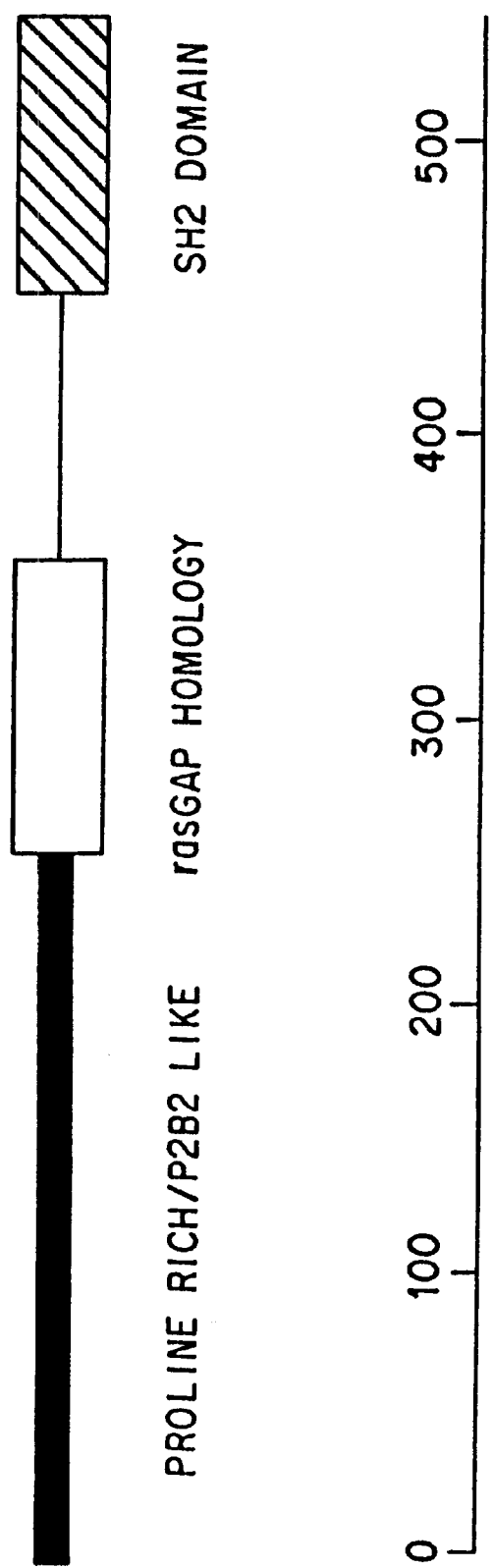
FIG. 20 is a schematic representation of GRB-7 to include the proline rich, P2B2, rasGAP and SH2 domain homology.

(SEQ ID NO:7) to obtain the full length GRB-7 amino acid sequence shown in FIGS. 36A–36G (SEQ ID NO: 10). A schematic representation of GRB-7 is displayed (NO:10). As in FIG. 20, depicting the regions of similarity to known proteins. The GRB-7 protein is 535 amino acids in length (FIGS. 36A–36G) (SEQ ID NO:7) and has one SH2 domain at its extreme carboxy-terminus. In FIG. 21, the SH2 domain of GRB-7 is compared to other SH2 domains including mouse fyn, human PLC-γ1 and the crk and nck-like proteins of the present invention. other protein motifs in GRB-7 were determined using Swissprot and GenEmbl databases, using software such as the University of Wisconsin Genetics Computer Group Sequence Analysis Software package (Devereaux et al Nucl. Acid Res. 12:387 (1984)). The Swissprot and GenEMBL database can be searched using known software, such as the FASTA and TFASTA respectively. Pearson and Lipman, Proc. Natl. Acad. Sci. USA 85:2444 (1988). Protein alignments can be performed using known software, such as BESTFIT, e.g., with conservative substitutions defined as a score of $\geq 0.8$ using the symbol comparison table for proteins. Gribskov and Burgess, Nucleic Acid Research 14:6745 (1984).

From such analysis, amino acids 242 to 339 of GRB-7 showed similarity to a sequence from the central region of ras GAP (FIG. 21). Over this region of 91 amino acids from ras GAP, GRB-7 has 26% identity and 42% similarity allowing for conservative substitutions (FIG. 22). This region of ras GAP lies between the SH2/SH3 domains and the GTPase activating carboxy terminal region and has not been assigned a specific function (Martin et al Science 255:192 (1992)). The amino-terminal sequence of GRB-7 was found to be proline rich and thus has similarity to many other proline rich-proteins. GRB-7 does have an extended region of limited similarity to the catalytic domain of protein phosphatase 2B (Guerini and Klee, Proc. Natl. Acad. Sci. USA 87:6112 (1990)) including this proline rich region (FIG. 23) but no significant similarity was found to other serine/threonine phosphatase such as protein phosphatase 1 or 2A.

A northern blot of GRB-7 in mouse tissues is presented in FIG. 25. Oligo dt selected mRNA was probed with GRB-7 CDNA using known methods. See Ausubel et al eds., Current protocols in molecular Biology, Wiley Interscience, New York, (1987, 1992) and Sap et al Proc. Natl. Acad. Sci. USA 87:6112 (1990), which are entirely incorporated herein by reference. The highest signal was detected in liver and kidney, but a signal was also detected in ovary and testes. On longer exposure, a weak signal was detectable in lung but not in heart, muscle, spleen or brain. The major transcript was seen at 2.4 kb which closely corresponds to the longest cDNA clone obtained.

GRB-7 represents another novel gene cloned using the CORT technology, according to the present invention. It belongs to a relatively rare group of proteins with SH2 domains but no SH3 domains including the fps tyrosine kinase, (I. Sadowski, J. C. Stone and T. Pawson, Mol. Cell. Biol. 6:4396 (1986)), protein tyrosine phosphatase 1C (Shen et al Nature (Lond.) 352:736 (1991)) and possibly tensin (Davis et al., Science 252:712 (1991)).

CORT methodology of the present invention provides proteins that interact with the EGFR and lie downstream of the EGFR signalling pathway. In general, in vitro associations between SH2 domain and tyrosine phosphorylated proteins correlate with interactions in living cells (McGlade et al., Mol. Cell. Biol. 12:991 (1992)). CORT methodology of the present invention is therefore expected to yield commercially important downstream signalling components of cytoplasmic tyrosine kinase target proteins, as well as growth factor receptors, as demonstrated by the finding that the C. elegans gene sem-5 is the homolog of human GRB-2. Sem-5 is crucial for vulval development, a process that requires the activity of let-23, an EGFR-like tyrosine kinase. Accordingly, it is expected that sem-5 lies downstream of the activated let-23, and that GRB-2 serves a similar crucial function in EGFR signalling.

CORT methodology of the present invention can also be used to identify new SH2 proteins that interact with the EGFR. Seven different exemplary SH2 domain proteins are expected to have important signalling functions. With the use of the T7 polymerase based library, this methodology may be more easily applied, due to relatively higher levels of expressions which increase detectability, to any eukaryotic cytoplasmic or receptor tyrosine kinase proteins, such as growth factor receptor systems. Hence such a method of the present invention can also be used to clone other novel SH2 domain proteins using other growth factor receptor tyrosine kinases, including the use of T7 polymerase based libraries, by performing expression/cloning techniques involving protein-protein interactions and DNA binding proteins.

SH2 domains, such as in the GAP and PLC-γ proteins, are responsible for the association of these proteins with the phosphorylated C-terminus of the EGFR (see Example VI, below). Thus, one function of SH2 domains is to juxtapose the intracellular portion of receptor tyrosine kinase molecules with their substrates to facilitate efficient tyrosine phosphorylation.

Detailed analysis of one of the CDNA clones of the present invention, GRB-1, identified using methods of the present invention, reveals a novel sequence containing two SH2 domains and one SH3 domain. This protein is expressed in various tissues and cell lines. Its predicted molecular weight, 85 kDa, is consistent with its migration on sodium dodecyl sulfate polyacrylamide gel electrophoresis (SDS-PAGE).

By the term "cytoplasmic tyrosine kinase" is meant a soluble form of protein or polypeptide having tyrosine kinase which can be found in the intracellular portion of a cell. By the term "receptor tyrosine kinase" is intended a transmembrane protein having an extracellular receptor domain, and one or more intracellular domains, including at least one extracellular or intracellular domain having tyrosine kinase enzymatic activity. Additional intracellular domains may have sequence homology to SH2. These molecules are well known in the art (Williams, L. T. et al., Science 243:1564–1570 (1989); Ullrich, A. et al., Cell 61:203–212 (1990); Carpenter, G. et al. J. Biol. Chem. 265: 7709–7712 (1990), which are entirely incorporated by reference).

The proteins which interact with, and which may be phosphorylated by, tyrosine kinases are referred to as "target" proteins for these kinases, as distinguished from the "ligands" for these receptors, which bind to the kinase.

According to the present invention, an expression cloning method is performed directly on a gene expression library, such as lambda gt11 or T7 expression library. In a preferred embodiment, the DNA is human cDNA. More preferably, the DNA is human fetal brain DNA. Using such a source as the starting material for the cloning of human genes has a great advantage over the alternative known means, in which a large amount of tissue is taken, and antibodies produced, or the protein purified and partially sequenced, and oligo-nucleotide probes are then prepared from this sequence and used to screen a genomic DNA or CDNA library. The advantage of bypassing these steps is of most relevance in the case of human genes, since tissue is generally not available in large quantities, with the exception of placenta.

The expression library may be screened in a single step. Preferably, the lambda plaques are blotted onto a solid carrier, preferably nitrocellulose, allowing the transfer of library DNA-encoded proteins which are expressed in the infected bacteria and transferred to the carrier. This carrier is then incubated with the probe of the present invention, as described herein. The probe is allowed to bind to proteins which have the capability of binding to the tyrosine-phosphorylated polypeptide. Based on the label used in the probe, such as an enzymatic, radioisotope or fluorescent label, an appropriate detection system is used to identify the plaques containing the protein of interest. The phage in these plaques are then selected, and the DNA inserts can then be re-cloned, excised and placed into other vectors, used for large scale expression of the protein, and the like, according to known method steps.

One of ordinary skill in the art will appreciate that the concentrations, times, temperatures can be varied depending on the precise nature of the system used, and will know how ovary the appropriate parameters without undue experimentation. Furthermore, general methods in this area are set forth in Sambrook et al. (supra).

Materials of which solid phase carrier can be made include, but are not limited to, nitrocellulose, cellulose, paper, substituted polystyrenes, acrylonitriles, polycarbonate, polypetene, or silicone oxide.

The probe of the present invention is a tyrosine-phosphorylated polypeptide molecule derived from the C-terminal domain of a cytoplasmic or receptor tyrosine kinase. The polypeptide can have between about 10 and about 250 amino acids in length. The probe can be a phosphorylated native sequence or a functional derivative thereof (defined below).

Highly efficient phosphorylation is obtained by using the tyrosine kinase domain present on the tyrosine kinase molecule to autophosphorylate the C-terminal region at between 1 and 5 tyrosine residues. Known methods and conditions (described in detail in Example I) are used to phosphorylate the tyrosine residues. A preferred substrate is detectably labeled substrate such as ($\gamma$-$^{32}$p-adenosine triphosphate). The source of tyrosine molecule used as the source material to make the probe can include molecules chemically purified from tissues or cells, or molecules produced recombinant DNA methods.

When using recombinant techniques, a native cytoplasmic or receptor tyrosine kinase may be produced, or alternatively, a tyrosine kinase derivative may be produced. A preferred tyrosine kinase derivative includes the tyrosine kinase domain linked to the Cterminal domain. In another embodiment, the two domains may be produced as separate molecules, and mixed together to achieve tyrosine phosphorylation of the C-terminus derived polypeptide.

The probe comprising a tyrosine-phosphorylated C-terminal portion of the tyrosine kinase, as described herein can be produced by recombinant means in the form of a fusion protein.

As used herein, a "fusion protein" may refer to a fused protein comprising a bacterial protein and a polypeptide of interest such as a protein having an SH2 domain. Alternatively, a fusion protein may also be an artificially constructed tyrosine kinase-like derivative, wherein a DNA sequence encoding the tyrosine kinase domain has been linked to a selective enzymatic cleavage site, which, in turn, is linked to a tyrosine kinase C-terminal domain having one or more tyrosine residues which can be phosphorylated by the kinase. Such a genetic construct encoding this type of "fusion protein" can be inserted into an expression. vehicle and expressed in a bacterial or eukaryotic host. Once expressed, such a fusion protein can be allowed to autophosphoxylate, wherein the kinase acts to phosphorylate the tyrosine residues in the C-terminal domain. Following this phosphorylation, use of the appropriate enzyme will cleave at the selective cleavage site, thus separating the N-terminal kinase from the C-terminal phosphorylated polypeptide, which can now serve as a probe.

Expression of fusion proteins and modifications to increase yields and to provide cleavage sites, etc., are well known. See, e.g., Ausubel, supra; Itakura et al. Science 198:1056–1063 (1977)) and Riggs (U.S. Pat. No. 4,366,246 (1982); Marston, Biochem. J. 240:1–12 (1986); Nagai et al. (Nature 309:810–812 (1984); (Germino et al., Proc. Natl. Acad. Sci. USA 81:692–4696 (1984); Scholtissek et al., Gene 62:55–64 (1988); Smith et al., Gene 67:31–40 (1988); Knott et al., Eur. J. Biochem. 174:405–410 (1988); and Dykes et al., Eur. J. Biochem. 174:411–416 (1988), which references are all entirely incorporated herein by reference.

The term "selective cleavage site" refers to an amino acid residue or residues which can be selectively cleaved with either chemicals or enzymes and where cleavage can be achieved in a predictable manner. A selective enzymatic cleavage site is an amino acid or a peptide sequence which is recognized and hydrolyzed by a proteolytic enzyme. Examples of such sites include trypsin or chymotrypsin cleavage sites. In a preferred embodiment of this invention, the, selective cleavage site is comprised of the sequence Ile-Glu-Gly-Arg (SEQ ID NO: 15), which is recognized and cleaved by blood coagulation factor Xa. In another embodiment, the selective cleavage site has the sequence Leu-Val-Pro-Arg (SEQ ID NO:16), which is recognized and cleaved by thrombin.

In constructing the tyrosine kinase-like derivative, an oligonucleotide sequence, 5' to the sequence coding for the enzyme recognition site can be included, and may vary in length. For example, in one embodiment, 13 nucleotides are situated between the codon for Ile (the start of the factor Xa recognition site) and the 3' end of the sequence encoding the tyrosine kinase domain.

Thus, in one embodiment of the present invention, the Ile-Glu-Gly-Arg (SEQ ID NO:15) sequence is introduced between the tyrosine kinase domain and the determinal domain. In another embodiment, the Leu-Val-Pro-Arg (SEQ ID NO:16) sequence is introduced. The proteins having this cleavage site are expressed in bacteria using standard methods. Thereafter, autophosphorylation of the C-terminal domain, preferably with ($\gamma^{32}$P) adenosine triphosphate, is allowed to occur, followed by selective cleavage of the tyrosine-phosphorylated C-terminal domain with the appropriate cleaving agent, e.g., factor Xa.

The present invention also provides a method for mapping a gene, preferably a human gene, which encodes a target protein for a tyrosine kinase (such as a GRB protein as defined herein), to a particular human chromosome. This method combines the new expression cloning method described herein with one of several known techniques for mapping a gene to a particular chromosome. Thus, according to the present invention, a clone, such as a lambda gt11 clone, containing a DNA insert encoding a GRB protein, is identified using the expression cloning methods disclosed herein. The insert may be further subcloned, if desired, using methods well-known in the art, and a probe constructed, either by direct labeling of the nucleic acid of the clone or by producing an oligonucleotide probe corresponding to a unique portion of the clone's sequence (see: Sambrook, J. et al. (Molecular Cloning: A Laboratory Manual, 2nd Edition, Cold Spring Harbor Press, Cold Spring Harbor, N.Y. (1989); and Ausubel, supra). This labeled probe can is then used in a hybridization assay with commercially available blots, such as Chromosome Blots from Bios Corporation (New Haven, Conn.) which contain DNA from a panel of human-hamster somatic cell hybrids (Kouri, R. E. et al., Cytogenet. Cell Genet. 51:1025 (1989)). By comparison of which human chromosomes remain in the human-hamster hybrid cell and the hybridization of the probe specific for the GRB gene of interest, the gene is mapped to a particular human chromosome. In this way, linkage is established to known human genes (or diseases caused by mutations therein) present on this chromosome. Using methods well-known in the art for finer mapping, e.g., using known human deletion mutations, the GRB gene can be mapped more precisely to other human genes.

The tyrosine-phosphorylated tyrosine kinase C-terminal probe polypeptide of the present invention, as well as the GRB proteins of the present invention, and additional yet unknown GRB proteins which are discovered using the methods of this invention, are useful in methods for screening drugs and other agents which are capable of modulating cell growth control that occurs via signal transduction through tyrosine kinases. By attaching a tyrosine-phosphorylated probe polypeptide or a GRB protein, or fragments thereof, to a solid phase carrier matrix, an affinity probe is created which can be used to isolate and purify molecules from complex mixtures which are capable of binding to the affinity probe. Furthermore, such an affinity probe is useful for detecting the presence in a biological fluid of a molecule capable of binding the tyrosine-phosphorylated probe or the GRB protein. Similarly, chemical agents can be tested for their capacity to interact with the probe or GRB.

Methods for coupling proteins and peptides to the solid phase, the solid phase substances useful in these methods, and means for elution, are well known to those of skill in the art.

In the case of growth factor receptors which are receptor tyrosine kinases (including as non-limiting examples EDGFR, PDGFR and FGFR), tyrosine phosphorylation is linked to cell growth and to oncogenic transformation. Disruption of the action of a GRB in the cell may prevent or inhibit growth, and might serve as means to counteract development of a tumor. Furthermore, a mutation in the C-terminal portion of the tyrosine kinase or the GRB, or a disregulation in their mutual interactions, may promote susceptibility to cancer.

The insulin receptor (InsR) is also a receptor tyrosine kinase, and tyrosine phosphorylation in cells bearing InsR is associated with normal physiological function. In contrast to the case of cell growth and cancer, disruption of normal interactions between of the tyrosine-phosphorylated portion of the receptor and the GRB would counteract insulin effects. Subnormal levels or activity of a GRB protein may act to remove a normal counterregulatory mechanisms. It is expected that overexpression or overactivity of a GRB protein could inhibit or totally prevent the action of insulin on cells, leading to diabetes (of an insulin-resistant variety). Thus susceptibility to diabetes may be associated with GRB protein dysregulation.

Therefore methods of the present invention for identifying normal or mutant GRB, protein genes, or for detecting the presence or the amount of GRB protein in a cell, can serve as methods for identifying susceptibility to cancer, diabetes, or other diseases associated with alterations in cellular metabolism mediated by tyrosine kinase pathways.

The present invention provides methods for evaluating the presence, and the level of normal or mutant GRB protein in a subject. Altered expression of these proteins, or presence of a mutant GRB protein, in an individual may serve as an important predictor of susceptibility to oncogenic transformation and the development of cancer. Alternatively, altered expression of GRB protein-may serve as an important predictor of susceptibility to diabetes.

Oligonucleotide probes encoding various portions of the GRB protein are used to test cells from a subject for the presence DNA or RNA sequences encoding the GRB protein. A preferred probe would be one directed to the nucleic acid sequence encoding at least 4 amino acid residues, and preferably at least 5 amino acid residues of the GRB-1, GRB-2, GRB-3, GRB-4, GRB-7 or GRB-10 protein of the present invention, such as 6, 7, 8, 9, 10, 11, 12, 13, 14, 15, 16, 17, 18, 19, 20, 25, 30, 35, 40, 45, or 50 amino acids. Qualitative or quantitative assays can be performed using such probes. For example, Northern analysis (see Example III, below) is used to measure expression of an GRB protein mRNA in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Sambrook et al. (supra), Ausubel et al, supra, etc.

Recently, an in vitro, enzymatic method has been described which is capable of increasing the concentration of such desired nucleic acid molecules. This method has been referred to as the "polymerase chain reaction or "PCR" (Mullis, K. et al., Cold Spring Harbor Symp. Quant. Biol. 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., Uq 4,582,788; and Saiki, R. et al., U.S. Pat. No. 4,683,194; Mullis, K. B. (Cold Spring Harbor Symp. Quant. Biol. 51:263–273 (1986)); Saiki, R. K., et al. (Bio/Technol 3-:1008–1012 (1985)); and Mullis, K. B., et al. (Meth. Enzymol. 155:335–350 (1987), which references are entirely incorporated herein by reference).

In one embodiment, the invention is directed to target proteins of eukaryotic tyrosine kinases, which include, as non-limiting examples, GRB proteins such as GRB-1, GRB-2, GRB-3, GRB-4, GRB-7 or GRB-10 proteins are included. In another embodiment, the invention is directed to recombinant eukaryotic GRB proteins. The invention provides the naturally occurring protein molecule substantially free of other proteins with which it is natively associated. "Substantially free of other proteins or glycoproteins" indicates that the protein has been purified away from at least 90 percent (on a weight basis), and from even at least 99 percent if desired, of other proteins and glycoproteins with which it is natively associated, and is therefore substantially free of them. That can be achieved by subjecting the cells, tissue or fluids containing the GRB-1, GRB-2, GRB-3, GRB4, GRB-7 or GRB-10 protein to standard protein purification techniques such as immunoadsorbent columns bearing monoclonal antibodies reactive against the protein.

The nucleotide sequence of the GRB-1 gene (SEQ ID NO:1), and the amino acid sequence of the GRB-1 protein (SEQ ID NO:5), are shown in FIG. 4 (SEQ ID NO:5). The partial nucleotide sequence of GRB-2 (1–949 of SEQ ID NO:2) and the partial amino acid sequence, are shown in FIGS. 16A–16D, and the complete amino acid sequence is shown in FIGS. 26A–26C (SEQ ID NO:6), as well as the complete nucleotide sequence. The nucleotide sequence of the GRB-10 gene is shown in FIGS. 37A–37C.

In a preferred embodiment, GRB-1, GRB-2, GRB-3, GRB-4, GRB-7 or GRB-10 or other eukaryotic GRB protein, can be isolated and purified using as an affinity probe, the probe of the present invention which is a tyrosinephosphorylated C-terminal domain of a tyrosine kinase, or a functional derivative thereof.

Alternatively, the purification can be achieved by a combination of standard methods, such as ammonium sulfate precipitation, molecular sieve chromatography, and ion exchange chromatography.

It will be understood that the GRB-1 proteins of the present invention can be biochemically purified from a variety of cell or tissue sources. For preparation of naturally occurring GRB protein, tissues such as mammalian placenta or brain are preferred.

The invention is also directed to a recombinant nucleic acid molecule having a nucleotide sequence that encodes at least one of the GRB proteins of the invention, including, but not limited to GRB-1, GRB-2, GRB-3, GRB-4, GRB-7 or GRB-10 proteins. Given their potential role in signal transduction, such GRB proteins may be referred to herein as "adaptor proteins". Further, the invention is directed to a recombinant nucleic acid molecule having a nucleotide sequence that selectively hybridizes to the complement of the recombinant nucleic acids which encode GRB proteins, as described above.

"Nucleic acids", as described herein, may refer, for example, to cDNA or to genomic DNA. Further, the recombinant nucleic acids described above may be contained within a recombinant vector, such as an expression vector containing a recombinant nucleic acid having a nucleotide sequence as described above, operatively associated with an element that controls expression of the nucleotide sequence in a host cell.

"Selective hybridization" refers to nucleic acid hybridization under standard stringency conditions, which are well known to those of skill in the art. (See, for example, Sambrook, supra, and Ausubel, supra.) For example, hybridization may be done under highly stringent conditions, e.g., washing in 0.1× SSC/0.1% SDS at 68° C. Alternatively, hybridization may be done under moderately stringent conditions, e.g., washing in $0.2^x$ SSC/0.1% SDS at 42° C.

The recombinant nucleic acids described above may also be contained within an engineered host cell, which may be of either eukaryotic or prokaryotic origin. Such an engineered host cell may further contain an element that controls the expression, in the host cell, of the nucleotide sequence of the above-described recombinant nucleic acids. Such an engineered host cell may be of prokaryotic or eukaryotic origin.

Alternatively, because the gene for GRB-1, GRB-2, GRB-3, GRB-4, GRB-7 or GRB-10 can be isolated or synthesized, the polypeptide can be synthesized substantially free of other proteins or glycoproteins of mammalian origin in a prokaryotic organism or in a nonmammalian eukaryotic organism, if desired. As intended by the present invention, a recombinant GRB-1, GRB-2, GRB-3, GRB-4, GRB-7 or GRB-10 molecule produced in mammalian cells, such as transfected COS, NIH-3T3, or CHO cells, for example, is either a naturally occurring protein-sequence or a functional derivative thereof. Where a naturally occurring protein or glycoprotein is produced by recombinant means, it is provided substantially free of the other proteins and glycoproteins with which it is natively associated.

Alternatively, methods are well known for the synthesis of polypeptides of desired sequence on solid phase supports and their subsequent separation from the support or carrier. In particular, the tyrosine-phosphorylated C-terminal domain probe of the present invention, or a functional derivative thereof, can be synthesized using a peptide synthesis method wherein phosphotyrosine is provided in place of tyrosine, resulting in direct synthesis of the phosphorylated form of the polypeptide. See, e.g., Staerkaer et al, Tetrahedron Letters 32:5289–5392 (1991); Shoelson et al Tetrahedron Letters 32:6061 (1991), which references are entirely incorporated herein by reference).

The present invention also provides "functional derivatives" of the tyrosine-phosphorylated C-terminal domain polypeptide and or the GRB-1, GRB-2, GRB-3, GRB-4, GRB-7 or GRB-10 proteins.

By "functional derivative" is meant a "fragment," "variant," "analog," or "chemical derivatives of the GRB protein, which terms are defined below. A functional derivative retains at least a portion of the function of the native protein which permits its utility in accordance with the present invention.

A "fragment" of any of the proteins or polypeptides of the present invention-refers to any subset of the molecule, that is, a shorter peptide.

A "variant" of the protein refers to a molecule substantially similar to either the entire peptide or a fragment thereof. Variant peptides may be conveniently prepared by direct chemical synthesis of the variant peptide, using methods well-known in the art.

The term "substantially corresponding to the amino acid sequence of" in the context of the present refers to a protein containing conservative amino acid substitutions, known in the art and as described herein, that would be expected to maintain the functional biological activity of the referenced sequence, and/or target protein binding characteristics.

Such substitutions can be readily determined without undue experimentation by using known conservative substitutions, as known in the art. Alternatively, known software can be used to provide such conservative substitutions according to the present invention. As a non-limiting example the program "BESTFIT" can be used to provide conservative amino acid substitutions of a define sequence, e.g., defined as having a score of $\geq 0.4$, 0.6, 0.8 or 1.0 depending on the type of protein used. See e.g., Gribskov and Burgess, Nucl. Acid. Res. 14:6745 (1984), which is entirely incorporated by reference. Variant peptides may be conveniently prepared by direct chemical synthesis of the variant peptide using methods well known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Mutations that will be made in the DNA encoding the variant peptide must not alter the reading frame and preferably will not create complementary regions that could produce secondary MRNA structure (see European Patent Publication No. EP 75,444).

At the genetic level, these variants ordinarily are prepared by site-directed mutagenesis (as exemplified by Adelman et al., DNA 2:183 (1983)) of nucleotides in the DNA encoding the peptide molecule, thereby producing DNA encoding the variant, and thereafter expressing the DNA in recombinant cell culture (see below). The variants typically exhibit the same qualitative biological activity as the nonvariant peptide.

Amino acid substitutions in the context of the present invention include substitutions wherein at least one amino acid residue in the peptide molecule, and preferably, only one, has been removed and a different residue inserted in its place. For a detailed description of protein chemistry and structure, see Schulz, G. E. et al., Principles of Protein Structure, Springer-Verlag, New York, 1978, and Creighton, T. E., Proteins: Structure and Molecule Properties, W. H. Freeman & Co., San Francisco, 1983, which are hereby incorporated by reference. The types of substitutions which may by made in the protein or peptide molecule of the present invention may be based on analysis of the frequencies of amino acid changes between a homologous protein of different species, such as those presented in Table 1–2 of Schultz et al, (supra) and FIGS. 3–9 of Creighton (supra). Base on such an analysis, conservative substitutions are defined herein as exchanges within one of the following five groups:

1. Small aliphatic, nonpolar or slightly polar residues: ala, ser, thr (pro, gly);
2. Polar, negatively charged residues and their amides: asp, asn, glu, gly;
3. Polar, positively charged residues: his, arg, lys;
4. Large aliphatic, nonpolar residues: met, leu, ile, val (cys); and
5. Large aromatic residues: phe, tyr, trp.

Accordingly, amino acid sequences substantially corresponding to a given sequence can be made without undue experimentation and then routinely screened for tyrosine kinase binding activity using known methods or those disclosed herein, such that one of ordinary skill in the art can determine which substitutions provide tyrosine kinase target proteins according to the present invention. For example, once target protein sequences are determined, such as for GRB-1, GRB-2, GRB-3, GRB-4, GRB-7 or GRB-10 conservative amino acid substitutions can be made to provide target proteins having amino acid sequences which substantially correspond to the determined target protein sequences.

The preferred bacterial host for this invention is *E. coli*. In other embodiments, other bacterial species can be used. In yet other embodiments, eukaryotic cells may be utilized, such as, for example, yeast, filamentous fungi, or the like. Use of these cell types are well known in the art. Any host may be used to express the protein which is compatible with replicon and control sequences in the expression plasmid. In general, vectors containing replicon and control sequences are derived from species compatible with a host cell are used in connection with the host. The vector ordinarily carries a replicon site, as well as specific genes which are capable of providing phenotypic selection in infected br in transformed cells. The expression of the fusion protein can also be placed under control with other regulatory sequences which may be homologous to the organism in its untransformed state. Preferred promoters can include a T7 promoter. Such preferred promoters express the human gene as a fusion protein such as the T7 capsid protein P10 under control of the T7 promoter. Such expression systems are commercially available, e.g., as the λEXlox vector from Novagen, Inc. (Madison, Wis.). In such fusion protein expression systems, the recombinant T7 vector containing a human gene, encoding such proteins obtainable by methods of the present invention, such as GRB-1, GRB-2, GRB-3, GRB-4, GRB-7 or GRB-10 as, e.g., a T10 fusion protein. The recombinant T7 vector can then be used to transform a bacteria, such as *E. coli*, by infection with a phage containing the recombinant T7 vector under lac control, such lacUV5 control. Induction of the infected, successfully transformed bacteria or other suitable host cell, by IPTG generates the T7 polymerase which then initiates transcription of the fusion protein encoded by the phage library. Because such resulting T7 vector infected bacteria provide human gene library plaques that have stronger signals than obtained by the use of bacterial RNA polymerases, such as *E. coli* RNA polymerase. According to the present invention, the use of a T7 polymerase expression system is particularly suitable for library screening when there as thousands of small plaques per plate. The major advantage of the use of a T7 expression system is the high level of protein expression due to the greater activity of the T7 polymerase versus *E. coli* RNA polymerase, and because fusion proteins using the smaller phage fusion protein gene, such as the TIO gene fragment (26 kd versus the 110 kd B-galactosidase of λgtll expression library) yields more stable expression and that its hydrophobic character promotes binding to nitrocellulose. In addition to directional cloning, the use of T7 phages also allow for automatic conversion to a PET plasmid (see, e.g., Palazzalo et al., Gene 88, 25 (1990)) which can be useful for expression of a fusion protein for antibody production.

This invention is also directed to an antibody specific for an epitope of the GRB-1, GRB-2, GRB-3, GRB-4, GRB-7 or GRB-10 protein and the use of such an antibody to detect the presence of, or measure the quantity or concentration of, the GRB protein in a cell, a cell or tissue extract, or a biological fluid.

The term "antibody" is meant to include polyclonal antibodies, monoclonal antibodies (mAbs), chimeric antibodies, and anti-idiotypic (anti-Id) antibodies.

Polyclonal antibodies are heterogeneous populations of antibody molecules, derived from the sera of animals immunized with an antigen.

Monoclonal antibodies are a substantially homogeneous population of antibodies to specific antigens. MAbs may be obtained by methods known to those skilled in the art. See, for example Kohler and Milstein, Nature 256:495–497 (1975) and U.S. Pat. No. 4,376,110. Such antibodies may be of any immunoglobulin class including IgG, IgM, IgE, IgA, GILD and any subclass thereof. The hybridoma producing the mabs of this invention may be cultivated in vitro or in vivo. Production of high titers of mAbs in vivo production makes this the presently preferred method of production. Briefly, cells from the individual hybridomas are injected intraperitoneally into pristane-primed BALB/C mice to produce ascites fluid containing high concentrations of the desired mabs. MAbs of isotype IgM or IgG may be purified from such ascites fluids, or from culture supernatants, using column chromatography methods well known to those of skill in the art.

Chimeric antibodies are molecules different portions of which are derived from different animal species, such as those having variable region derived from a murine mAb and a human immunoglobulin constant region. Chimeric antibodies and methods for their production are known in the art (Cabilly et al, Proc. Natl. Acad. Sci. USA 81:3273–3277 (1984); Morrison et al., Proc. Natl. Acad. Sci. USA 81:6851–6855 (1984); Boulianne et al., Nature 312:643–646 (1984); Cabilly et al., European Patent Application 125023 (published Nov. 14, 1984); Neuberger et al., Nature 314:268–270 (1985); Taniguchi et al., European Patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al., J. Immunol. 137:1066–1074 (1986); Robinson et al., International Patent Publication #PCT/US86/02269 (published 7 May 1987); Liu et al., Proc. Natl. Acad. Sci. USA 84:3439–3443 (1987); Sun et al., Proc. Natl. Acad. Sci. USA 84:214–218 (1987); Better et al., Science 240:1041–1043 (1988); and Harlow and Lane ANTIBODIES: A LABORATORY MANUAL Cold Spring Harbor Laboratory (1988)). These references are hereby entirely incorporated by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody).

The anti-Id antibody may also be used as an "Immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mabs generated against the GRB protein of the present invention may be used to induce anti-Id antibodies in suitable animals, such as BALB/C mice. Spleen cells from such immunized mice are used to produce anti-Id hybridomas secreting anti-Id mabs. Further, the anti-Id mabs can be coupled to a carrier such as keyhole limpet hemocyanin (KLH) and used to immunize additional BALB/C mice. Sera from these mice will contain anti-anti-Id antibodies that have the binding properties of the original mAb specific for a GRB protein epitope.

The anti-Id mAbs thus have their own idiotypic epitopes, or "idiotopes" structurally similar to the epitope being evaluated, such as GRB protein-a.

The term "antibody" is also meant to include both intact molecules as well as., fragments thereof, such as, for example, Fab and F(ab')$_2$ which are capable of binding antigen. Fab and F(ab')$_2$ fragments lack the Fc fragment of intact antibody, clear more rapidly from the circulation, and may have less non-specific tissue binding than an intact antibody (Wahl et al., J. Nucl. Med. 24:316–325 (1983)).

It will be appreciated that Fab and F(ab')$_2$ and other fragments of the antibodies useful in the present invention may be used for the detection and quantitation of GRB protein according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively or qualitatively detect the presence of cells which express the GRB protein. This can be accomplished b-immunofluorescence techniques employing. a fluorescently labeled antibody (see below) coupled with light microscopic, flow cytometric, or fluorometric detection.

The antibodies (of fragments thereof) useful in the present invention may be employed histologically, as in immunofluorescence or immunoelectron microscopy, for in situ detection of GRB proteins. In situ detection may be accomplished by removing a histological specimen form a patient, and providing the a labeled antibody of the present invention to such a specimen. The antibody (or fragment) is preferably provided by applying or by overlaying the labeled antibody (or fragment) to a biological sample. Through the use of such a procedure, it is possible to determine not only the presence of the GRB protein but also its distribution on the examined tissue. Using the present invention, those of ordinary skill will readily perceive that any of wide variety of histological methods (such as staining procedures) can be modified in order to achieve such in situ detection.

Such assays for GRB protein typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying GRB protein, and detecting the antibody by any of a number of techniques well-known in the art.

The biological sample may be treated with a solid phase support or carrier such as nitrocellulose, or other solid support or carrier which is capable of "immobilizing cells" cell particles or soluble proteins. The support or carrier may then be washed with suitable buffers followed by treatment with the detectably labeled GRB protein-specific antibody. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, or cylindrical, as in the inside surface of a test tube, or the external surface of a rod. Alternatively, the surface may be flat such as a sheet, test strip, etc. Preferred supports or carriers include polystyrene beads. Those skilled in the art will know many other suitable carriers for binding antibody or antigen, or will be able to ascertain the same by use of routine experimentation.

The binding activity of a given lot of anti-GRB-1, anti-GRB-2, anti-GRB-3, anti-GRB-4, anti-GRB-7 or anti-GRB-10 antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which a GRB-specific antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactivity labeling the antibodies or antibody fragments, it is possible to detect R-PTPase through the use of a radioimmunoassay (RIA). A good description of RIA maybe found in Laboratory Techniques and Biochemistry in molecular Biology, by Work, T. S. et al., North Holland Publishing company, NY (1978) with particular reference to the chapter entitled "An Introduction to Radioimmune Assay and Related Techniques" by Chard, T., incorporated by reference herein. The radioactive isotope can be detected by such means as the use of a γ counter or a scintillation counter or by autoradiography.

It is also possible to label the antibody with a fluorescent compound. When the fluorescently labeled antibody is exposed to light of the proper wave length, its presence can be then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as EU, or others of the lanthanide series. These metals can be attached to the antibody using such metal chelating groups as diethyletetriamine pentaacetic acid (EDTA).

The antibody also can be detectably labeled by. coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention.

Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in a immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid phase antibody, antigen, and labeled antibody.

Typical, and preferred, immunometric assays include "forward" assays in which the antibody bound to the solid phase is first contacted with the sample being tested to extract the antigen form the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncompleted labeled antibody. The presence of labeled antibody associated with the solid support or carrier is then determined as it would be in a conventional "forward" sandwich assay.

In the "reverse" assay, stepwise addition first of a solution of labeled antibody, to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

Any of a number of assay systems may be utilized to test compounds for their ability to interfere with (i.e., disrupt or inhibit) the interaction of the activated tyrosine kinase and the adaptor protein, which are sometimes referred to herein as "binding partners." However, rapid high throughput assays for screening large numbers of compounds, including but not limited to ligands (natural or synthetic), peptides, or small organic molecules are preferred. Compounds that are so identified to interfere with the interaction of the binding partners can be further evaluated for inhibitory activity as described herein.

The basic principle of the assay systems used to identify compounds that interfere with the interaction between the binding partners involves preparing a reaction mixture containing the activated tyrosine kinase protein and the adaptor protein under conditions and for a time sufficient to allow the two proteins to interact and bind, thus forming a complex. In order to test a compound for inhibitory activity, the reaction is conducted in the presence and absence of the test compound, i.e., the test compound may be initially included in the reaction mixture, or added at a time subsequent to the addition of the activated tyrosine kinase and the adaptor protein; controls are incubated without the test compound or with a placebo. The formation of any complexes between the binding partners protein is then detected. The formation of a complex in the control reaction, but not in the reaction mixture containing the test compound, or a decrease in the level of complex formation in the reaction mixture relative to the control reaction, indicates that the compound interferes with the interaction of the activated tyrosine kinase and the adaptor protein.

The assay components and various formats that may be utilized are described below.

The binding partners used as components in the assay may be derived from natural sources, e.g., purified from cells using protein separation techniques well known in the art; produced by recombinant DNA technology using techniques known in the art (see e.g., Sambrook et al., 1989, Molecular Cloning: A Laboratory Manual, Cold Spring Harbor Laboratories Press, Cold Spring Harbor, N.Y.); and/or chemically synthesized in whole or in part using techniques known in the art; e.g., peptides can be synthesized by solid phase techniques, cleaved from the resin and purified by preparative high performance liquid chromatography (see, e.g., Creighton, 1983, Proteins: Structures and Molecular Principles, W. H. Freeman & Co., N.Y., pp. 50–60). The composition of the synthetic peptides may be confirmed by amino acid analysis or sequencing; e.g., using the Edman degradation procedure (see e.g., Creighton, 1983, supra at pp. 34–49).

Peptide fragments may be produced to correspond to the binding domains of the respective proteins. For example, such fragments may include, but are not limited to SH2, SH3, SH2-binding, and/or SH3-binding peptide fragments. Any number of methods routinely practiced in the art can be used to identify and isolate the proteins' binding site. These methods include but are not limited to mutagenesis of one of the genes encoding the protein and screening for disruption of binding in a co-immunoprecipitation assay. Sequence analysis of the genes encoding the respective proteins will reveal the mutations that correspond to the region of the protein involved in interactive binding. Alternatively, one protein can be anchored to a solid surface and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene for the protein is obtained, short gene segments can be engineered to express peptide fragments of the protein, which can then be tested for binding activity and purified or synthesized.

Whether produced by molecular cloning methods or by chemical synthetic methods, the amino acid sequence of the binding partners which may be used in the assays of the invention need not be identical to the reported sequence of the genes encoding them. The binding partners may comprise altered sequences in which amino acid residues are deleted, added, or substituted resulting in a functionally equivalent product.

For example, functionally equivalent amino acid residues may be substituted for residues within the sequence resulting in a change of sequence. Such substitutes may be selected from other members of the class to which the amino acid belongs; e.g., the nonpolar (hydrophobic) amino acids include alanine, leucine, isoleucine, valine, proline, phenylalanine, tryptophan, and methionine; the polar neutral amino acids include glycine, serine, threonine, cysteine, tyrosine, asparagine, and glutamine; the positively charged (basic) amino acids include arginine, lysine, and histidine; the negatively charged (acidic) amino acids include aspartic and glutamic acid.

One of the binding partners used in the assay system should be labeled, either directly or indirectly, to facilitate detection of a complex formed between the activated tyrosine kinase and the adaptor proteins. Any of a variety of suitable labeling systems may be used including but not limited to radioisotopes such as $^{125}I$; enzyme labelling systems that generate a detectable colorimetric signal or light when exposed to substrate; and fluorescent labels.

Where recombinant DNA technology is used to produce the viral and host cell binding partners of the assay it may be advantageous to engineer fusion proteins that can facilitate labeling, immobilization and/or detection. For example, the coding sequence of the tyrosine kinase or adaptor protein can be fused to that of a heterologous protein that has enzyme activity or serves as an enzyme substrate in order to facilitate labeling and detection. The fusion constructs should be designed so that the heterologous component of the fusion product does not interfere with binding of the host cell and viral protein.

Indirect labeling involves the use of a third protein, such as a labeled antibody, which specifically binds to one of the binding partners. Such antibodies include but are not limited to polyclonal, monoclonal, chimeric, single chain, Fab fragments and fragments produced by an Fab expression library.

The assay can be conducted in a heterogeneous or homogeneous format. Heterogeneous assays involve anchoring one of the binding partners onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the binding partners, e.g., by competition, can be identified by conducting the reaction in the presence of the test substance; i.e., by adding the test substance to the reaction mixture prior to or simultaneously with the tyrosine kinase protein and adaptor protein. On the other hand, test compounds that disrupt preformed complexes, e.g. compounds with higher binding constants that displace one of the binding partners from the complex, can be tested by adding the test compound to the reaction mixture after complexes have been formed. The various formats are described briefly below.

In a heterogeneous assay system, one binding partner is anchored onto a solid surface, and its binding partner, which is not anchored, is labeled, either directly or indirectly. In practice, microtiter plates are conveniently utilized. The anchored species may be immobilized by non-covalent or covalent attachments. Non-covalent attachment may be accomplished simply by coating the solid surface with a solution of the protein and drying. Alternatively, an immobilized antibody specific for the protein may be used to anchor the protein to the solid surface. The surfaces may be prepared in advance and stored.

In order to conduct the assay, the binding partner of the immobilized species is added to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one binding partner to anchor any complexes formed in solution, and a labeled antibody specific for the other binding partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the host cell and viral protein is prepared in which one of the binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the binding partners from the preformed complex will result in the generation of a signal above background. In this way, test substances which disrupt the viral protein-host cell protein interaction can be identified.

The following examples are presented by way of further explanation of the present invention, and not by way of limitation.

EXAMPLE I

Figure 1:
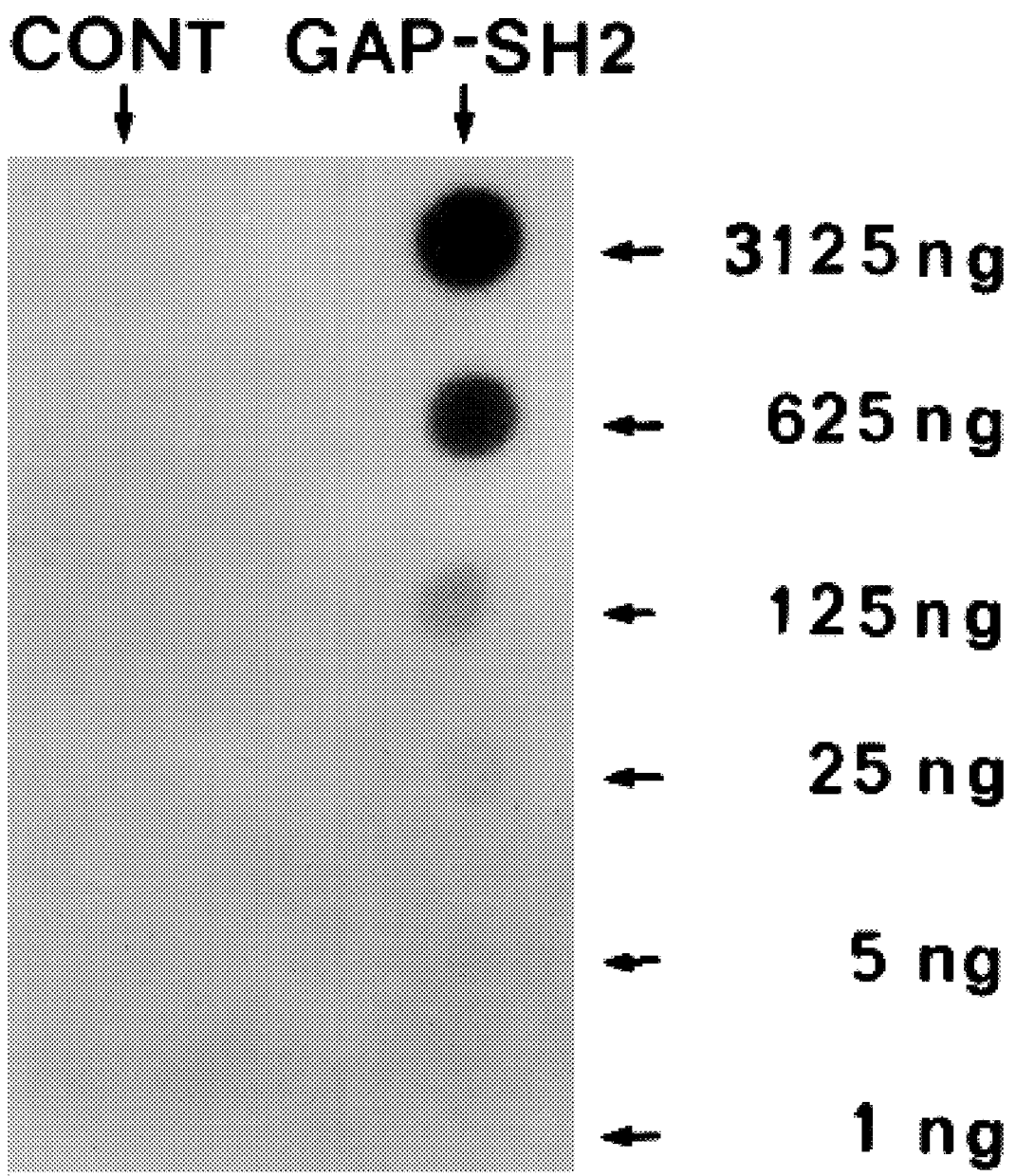
FIG. 1 is a filter blot pattern showing that the carboxy-terminus of the EGFR interacts with GAP-SH2 immobilized on nitrocellulose filters. Bacterially expressed trpE/GAP-SH2 fusion protein or trpe as a control was spotted at various concentrations onto nitrocellulose filters. The filters were hybridized overnight with ($^{32}$p)-labelled C-terminal domain of the EGFR. Autoradiography was for 2 hours.

A study was performed to determine the detectability of binding of the C-terminal domain of EGFR to a protein containing the SH2 domain immobilized on nitrocellulose filters. For this purpose, the binding of the C-terminal domain to a bacterially expressed fusion protein was assessed (see FIG. 1).

A. Isolation and Labelling of the Carboxyterminal Domain of the EGFR

The intracellular portion of the EGFR, which includes the tyrosine kinase domain and the carboxy terminal domain, was purified from recombinant baculovirus which expressed CDNA complementary to the intracellular domain of the human EGFR, as described previously (Hsu, C-Y. et al., Cell Growth and Differentiation 1:191–200 (1990)). The recombinant protein (2 μg) was then phosphorylated with ($\gamma$-$^{32}$P) ATP (200 μCi, 6000 Ci/Mmol), at 4° C. in HNTG (20 mM HEPES, pH 7.5, 150 mM NaCl, 0.1% Triton X-100, and 10% glycerol) buffer which contained 5 mM MnCl$_2$. In order to remove unincorporated ($\gamma$-$^{32}$P) ATP, the phosphorylated kinase was diluted to 1 ml with 20 mM HEPES, pH 7.5, containing 100 μg BSA and then concentrated in a Centricon-10 to a volume of 50 μl. This procedure was repeated 3 times resulting in the removal of >99% of the unincorporated ATP. To separate the C-terminal domain from the kinase domain, the concentrated protein was then digested with cyanogen bromide (CNBr) in 70% formic acid for 14 hours at room temperature (see also Example VI, below). Samples were then washed three times with water, dried and resuspended in binding buffer to a concentration of 2×10$^6$, cpm/ml.

B. Binding of the C-terminal Domain of the EGFR to Bacterially Expressed TrpE/GAP-SH2 Fusion Protein Immobilized on Nitrocellulose TrpE and TrpE/GAP-SH2 were obtained from the laboratory of Dr. Tony Pawson and/or prepared as previously described (Moran, M. F. et al., Proc. Natl. Acad. Sci. USA 87:8622–8626 (1990)). Filter binding studies were performed according to published methods (Schneider, W. J. et al., Proc. Natl. Acad. Sci. USA 76:5577–5581 (1979); Daniel, T. O. et al., J. Biol. Chem. 258:4606–4611 (1983)) with minor modifications. Various concentrations of either bacterially expressed TrpE fusion protein or bacterial protein alone were spotted onto nitrocellulose filters. After blocking the filters for 2 hour at 4° C. in PBS containing 5% Carnation dry milk, $^{32}$P-labelled C-terminal domain of the EGFR was added and incubation was continued overnight at 4° C. After 24 hours, the nitrocellulose filters were washed 3 times at room temperature with PBS containing 0.2% Triton X-100. The filters were dried and exposed to Kodak XAR-5 film at −80° C.

C. Results

The above method permitted detection of specific binding of the EGFR C-terminal domain to less than 5 ng of a bacterially expressed GAP-SH2 fusion protein. The binding was specific, since it required tyrosine phosphorylation of the probe and did not occur when irrelevant proteins were applied to nitrocellulose filters.

The demonstration that the EGFR C-terminal domain could bind specifically to an SH2-containing protein immobilized on nitrocellulose filters encouraged the present inventors to apply this approach to the screening of lambda gt11 expression libraries with the goal of identifying novel EGFR binding proteins.

EXAMPLE II

Figure 2:
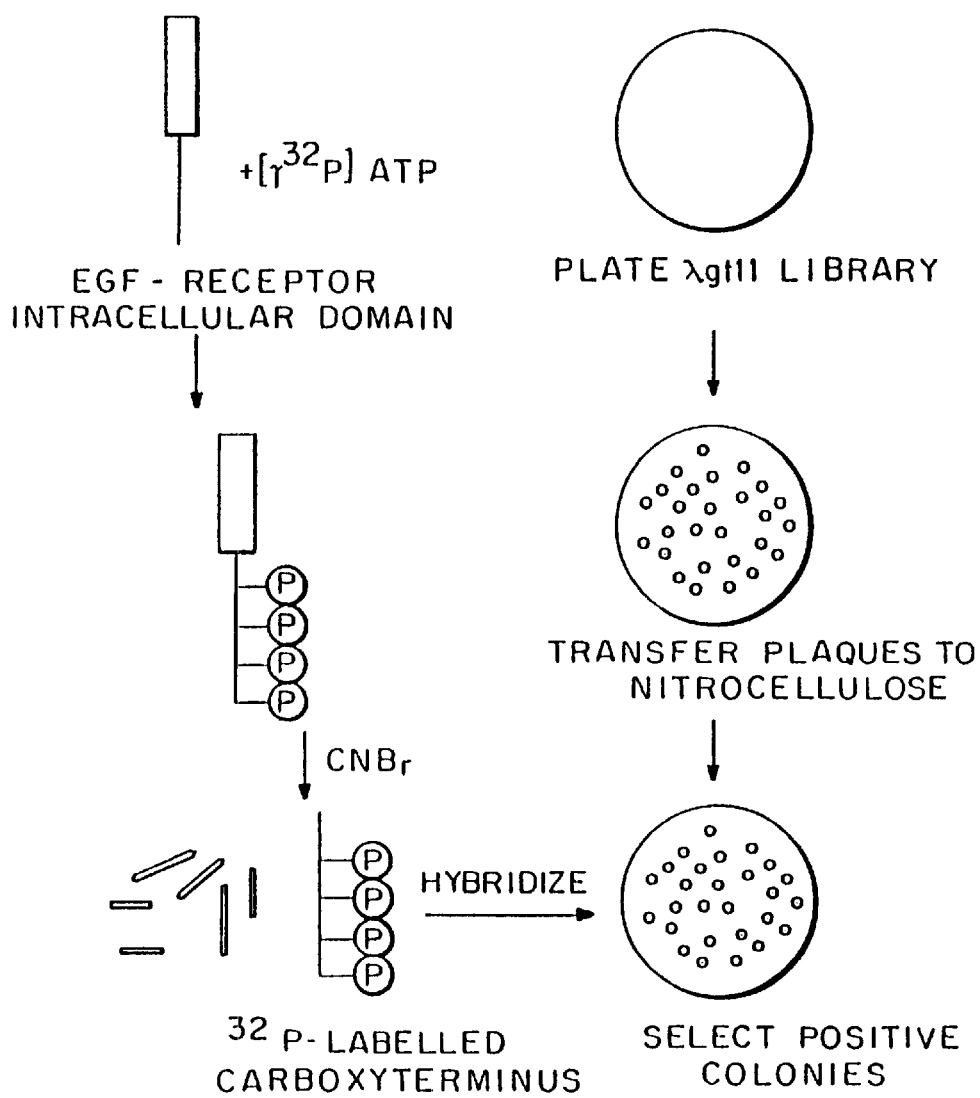
FIG. 2 is a schematic diagram depicting the method of cloning of receptor or cytoplasmic tyrosine kinase targets (CORT). C-terminal domain of the EGFR is phosphorylated with radiolabelled phosphorous. Lambda gt11 library was plated at a density of 4×10$^4$ plaques per 150 ml plate. The plaques were overlaid with IPTG-impregnated nitrocellulose filters for 12 hours, after which the plaques were transferred to nitrocellulose and incubated with the labelled probe. Positive colonies were then selected for further analysis.

Screening of Expression Libraries, and Isolation of a cDNA Clone Encoding a Novel SH2-Containing Protein The tyrosine phosphorylated C-terminal tail of the EGFR was used as a probe to screen expression libraries from several different human tissues as described above. The approach to screening is outlined in FIG. 2. Numerous positive clones have been identified so far using this approach, of which two have been analyzed in detail.

A. Screening of CDNA Library

A lambda gt11, library, constructed from mRNA isolated from human brain stem, was obtained from M. Jaye. To screen the library, lambda gt11 phage were plated at a density sufficient to produce 4×10$^4$ plaques per 150 mm agar plate. A total of six plates were initially screened. After incubation of the plates for 4 hours at 42° C., the plates were overlaid with nitrocellulose filters which had been impregnated with isopropyl-B-D-thiogalactopyranoside (IPTG), as previously described (MacGregor, P. F. et al., Oncogene 5:451–458 (1990)). Incubation was continued overnight at 37° C. The filters were then removed, washed with TBST (10 MM Tris-HCl pH 8, 150 mM NaCl, and 0.05% Triton X-100) at room temperature, and then blocked in HBB (20 mM HEPES, pH 7.5, 5 mM $MgCl_2$, 1 mM KCl) buffer containing 5% carnation dry milk for 1 hour at 4° C., as described (MacGregor et al., supra). Following blocking, labelled tyrosine phosphorylated carboxy-terminus (C-terminus) probe was added at a concentration of $1.6 \times 10^4$ μg/ml, and incubation was continued overnight. The filters were then washed 3 times at room temperature in PBS containing 0.2% Triton X-100. Filters were dried and exposed to Kodak XAR-5 film at −80° C.

Agar plugs, corresponding to the positive clones, were collect from the plates and placed in 1 ml of SM media. After allowing the phages to diffuse from the agar, the phages were replaced and rescreened as described above. Those phages that demonstrated enrichment on subsequent screening were isolated and sequence. Lambda gt11 phage DNA was isolated by the plate lysate method according to Maniatis et al., and subcloned into EcoRI-digested M13 MP19 (Maniatis et al., 1982). Single stranded DNA was isolated and sequenced by the dideoxy chain termination method using the Sequenase DNA sequencing kit (United States Biochemical).

Figure 3A:
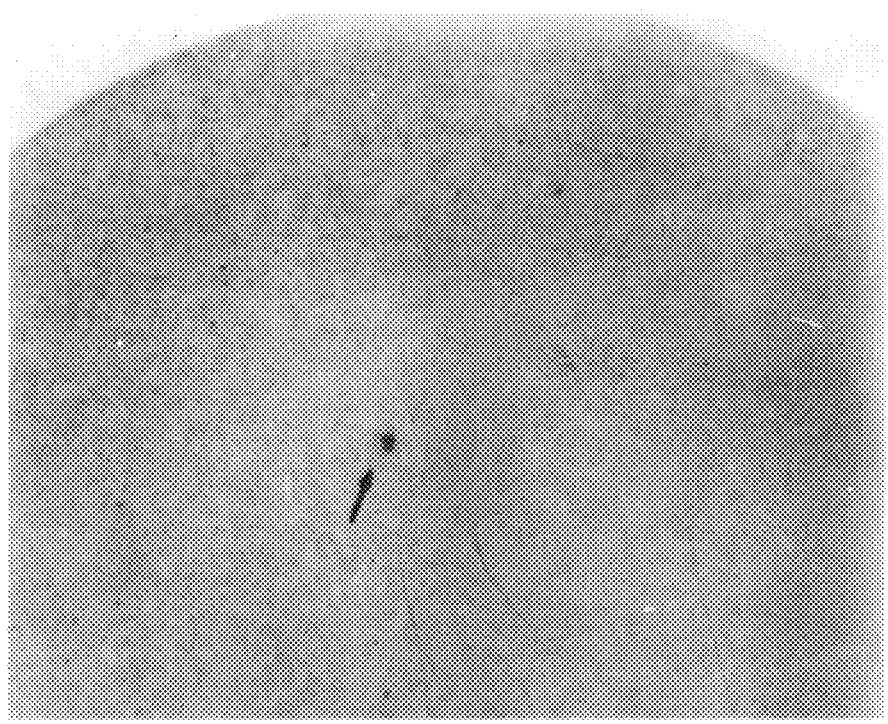
FIGS. 3A–B shows autoradiograms of phage expressing GRB-1 protein. 3A) Primary screen demonstrating one positive signal (arrow) out of 40,000 phage plated. 3B) Plaque purification of phage expressing GRB-1. All plaques bound to the ($^{32}$p)-labelled C-terminal domain of the EGFR.
Figure 3B:
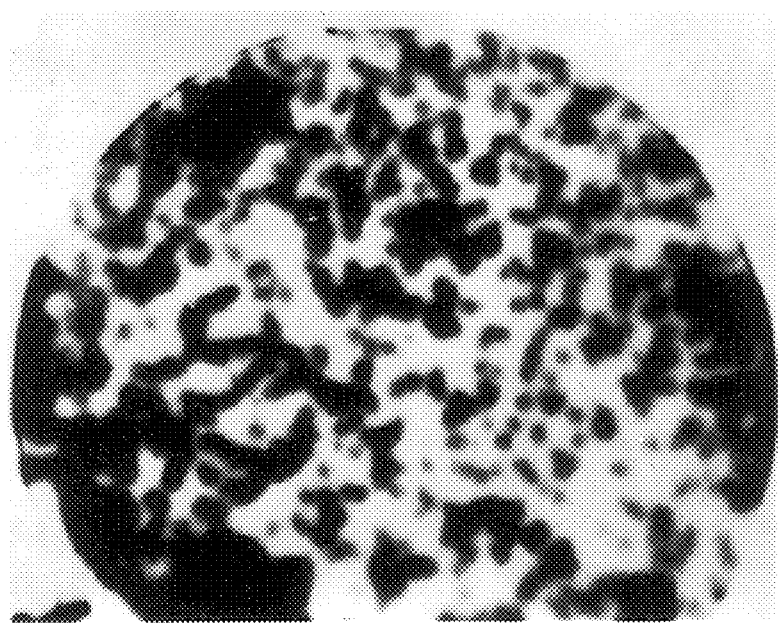

In one experiment, 240,000 pfu from a human brainstem lambda gt11 library were screened. A single plaque, clone ki4 (FIG. 3A) was isolated. On subsequent screening, this clone demonstrated enrichment, and on tertiary screening all plaques bound the probe (FIG. 3B). Clone ki4 contained an insert of about 900 nucleotides, which, upon induction of the lac promoter with IPTG, produced a fusion protein which could bind the EGFR. The size of the fusion protein predicted that the cDNA insert coded for a protein of about 300 amino acids, which was the size expected if the cDNA contained a single large open reading frame. To analyze clone ki4 in more detail, DNA was isolated and the EcoRI fragment, corresponding to the human cDNA insert, was subcloned into M13 and sequenced. Translation of the sequence from this insert demonstrated a single large open reading frame which, upon analysis using the Genbank database, was found to contain a single stretch of about 100 amino acids with sequence homology to SH2 domains of other known proteins (FIGS. 4 and 5A). However, in other regions, no sequence homology was noted. Thus, using this screening approach, a new SH2-containing protein which could bind to the EGFR was identified.

B. Isolated of Full Length cDNA

The initial clone isolated encoded for an SH2 domain, but did not contain the 3' or 5' ends of the gene. To isolated the full length cDNA, the library was rescreened using DNA isolated from the initial positive phage. DNA, from recombinant M13 bacteriophage which expressed the positive clone, was amplified using a thermal cycler, Taq1 polymerase and oligonucleotides complementary to the EcoR1 flanking regions of the M13 sequence in information, a second amplified DNA product, corresponding to the most 51 250 nucleotides of the initial isolated phage, was also generated by using oligonucleotides complementary to sequences at both ends of this region. ($^{32}p$) labelled DNA probes were then prepared by nick translation of the amplified products.

To rescreen the CDNA library, the library was replaced as described above. After incubation of the plates for 8 hours at 37° C., the plates were cooled for 1 hour at 4° C. following which the phage DNA was transferred to nitrocellulose filters. The filters were denatured in a solution of 0.2 N NAOH and 1.5 M NaCl and then baked in vacuo for 2 hours at 80° C. (Sambrook, J. et al., (Molecular Cloning: A Laboratory Manual, 2nd Edition, Cold Spring Harbor Press, Cold Spring Harbor, N.Y. (1989)). After prehybridization of the filters for 1 hour at 42° C., $^{32}$P-labelled DNA probe was added and hybridization was continued overnight at 42° C. in a solution containing 5× Denhardt's, 50% formamide, 5× SSC, 0.1% SDS, 200 mM TrisHCl, pH 7.6 and 100 μg/ml salmon sperm DNA. The filters were then washed in a solution containing 0.1× SSC and 0.1% SDS, dried and exposed to Kodak XAR-5 film at −70° C. Positive clones were then isolated and sequenced as described above.

Since the insert from clone ki4 lacked the 3' and 5' ends of the gene, the library was rescreened using two DNA probes which were generated by amplifying DNA from clone ki4. This approach enabled the identification of five additional clones. Three of the clones extended 3' from the initial clone ki4, two of which, clones, ki2.2 and ki2.4, contained a polyadenylation signal and a long 3' untranslated region (>1000 nucleotides). In addition, these clones encoded a protein which contained a second SH2 domain (FIGS. 4 and 5A).

The other two clones, ki3.0 and ki5.3, extended 5' from clone ki4. Both clones contained long open reading frames and an AUG codon which met the translation initiation criteria as defined by Kozak (Kozak, M. J. Cell. Biol. 108:229–241 (1989)). However, only clone ki3.0, when translated into protein and compared with known sequences in Genbank, was found to contain a domain of 50 amino acids which was homologous to SH3 domains present in other known proteins. The predicted molecular weight of the full length protein encoded by the overlapping clones, ki2.2 and ki3.0, was about 84 kDa. This new protein was termed GRB-1.

EXAMPLE III

GRB-1 Protein Contains SH2 and SH3 domains

Analysis of the GRB-1 protein sequence by comparison to sequences in the Genbank database revealed the presence of two stretches of about 100 amino acids, starting at amino acids 333 and 624, with sequence homology to SH2 domains of other proteins known to interact with the EGFR (FIG. 5A). While GRB-1 displayed striking homology to other SH2 domains at the protein level, it revealed no significant homology at the DNA level. GRB-1 also contained a segment of about 50 amino acids, located in the N-terminal region, which had sequence homology to SH3 domains (FIGS. 4 and 5B).

Figure 6:
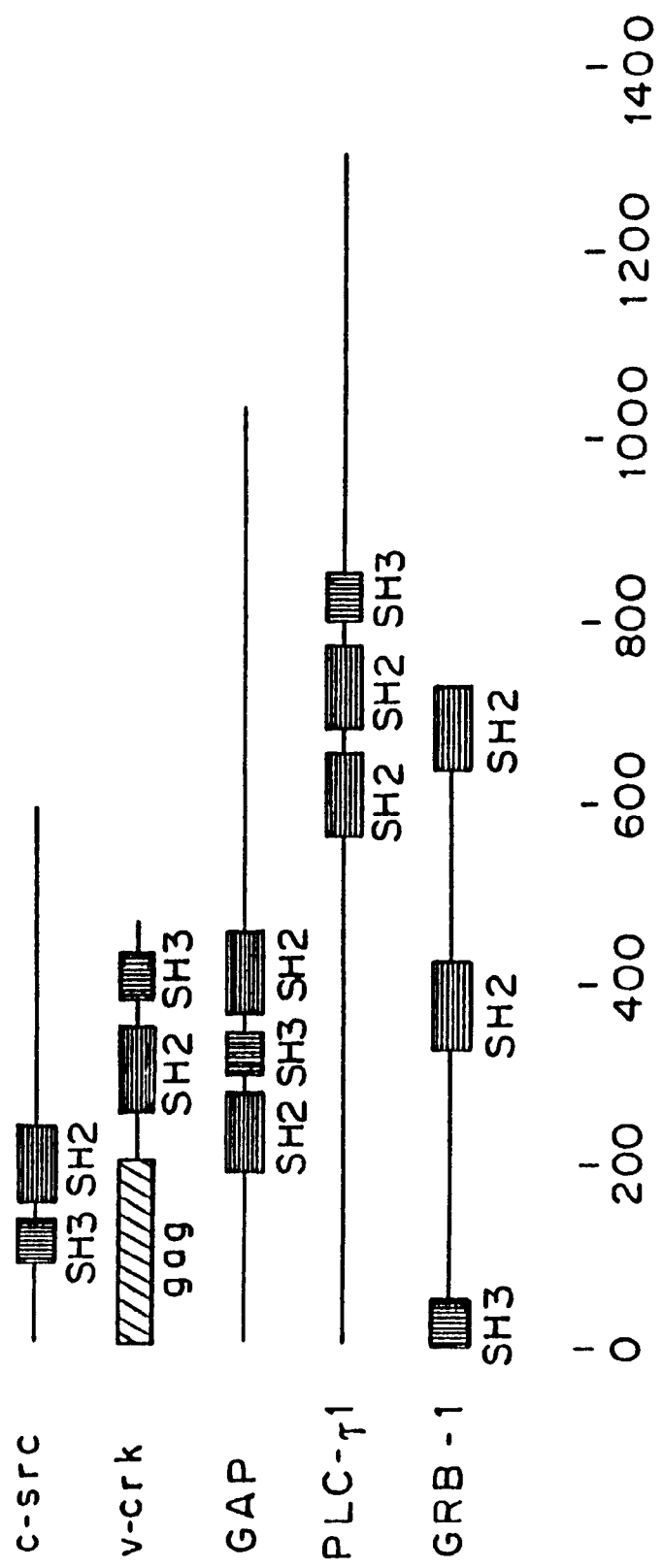
FIG. 6 is a schematic diagram comparing the structural organization of the SH2 and SH3 domains. The scheme-includes known proteins containing SH2 and SH3 domains, such as c-src, v-crk, PLC-γ, GAP1 and GRB-1.

A comparison of the structural organization of GRB-1 with several other SH2/SH3 containing proteins is shown in FIG. 6. It is apparent from this scheme that the localization of the SH2 and SH3 domains vary from protein to protein. Despite this there are certain similarities and differences among these SH2 containing proteins. GRB-1 is similar to some other substrates which have been found to interact with the EGFR, such as PLC-γ and GAP, in that GRB-1 contains two SH2 domains and a single SH3 domain. However, unlike these substrates, GRB-1 contains no homology to any known catalytic domain, and in this regard resembles the protein encoded by the avian sarcoma virus, v-crk.

Outside of these regions there was no sequence homology with other protein sequences present in Genbank. In particular, GRB-1 lacked a consensus ATP-binding domain, and did not display sequence homology with any serine/threonine kinase or tyrosine kinase.

The SH2 domain is thought to provide a common motif by which enzymatically distinct signalling molecules can be coupled to activated receptors with tyrosine kinase activity (Moran, M. F. et al., Proc. Natl. Acad. Sci. USA 87:8622–8626 (1990); Anderson, D. et al., Science 250:979–982 (1990)).

The presence of SH2 domains in GRB-1 (FIG. 4) and in GRB-2 further reinforces the importance of this domain in mediating the interaction of these proteins with the C-terminal tail of the EGFR. Moreover, since many proteins capable of interacting with cytoplasmic or receptor tyrosine kinases remain to be identified, this suggests that additional members of this protein family remain to be discovered.

In addition to containing two SH2 domains, GRB-1 also contains an SH3 domain. The SH3 domain is a non-catalytic domain of about 50 amino acid residues which is shared among many SH2-containing proteins. Since SH3 domains are also found in cytoskeletal proteins, such as spectrin and fodrin, the function of this domain could be to localize these proteins to the membrane or submembrane cytoskeleton where they would interact with other molecules.

Comparison of the deduced amino acid sequence of GRB-1 with the protein product encoded by the avian oncogene v-crk may shed light on GRB-1 function. The gene v-crk encodes a protein which is composed primarily of a viral gag protein fused to an SH2 and SH3 domain (Mayer, B. J. et al., Nature 332:272–275 (1988)). Both GRB-1 and the p47 $^{gag-crk}$ protein have no homology with any known catalytic domains. However, chicken embryo fibroblasts transformed with p47 $^{gag-crk}$ display elevated levels of phosphotyrosine-containing proteins (Mayer, B. J. et al., supra; Proc. Natl. Acad. Sci. USA 87:2638–2642 (1990); Matsuda, M. et al., Science 248:1537–1539 (1990)).

Since the v-crk product has been shown to bind several phosphotyrosine-containing proteins in v-crk transformed cells, it may be that the function of c-crk is to act as a bridge between kinases and substrates. In this regard, it is intriguing that GRB-1, like GAP and PLC-γ, contains two SH2 domains, the combination of which may be ideally suited for linking other proteins to activated tyrosine kinase molecules.

EXAMPLE IV

Northern Analysis of GRB-1 Expression

A. Methods

Total cellular RNA was prepared from monkey tissue by the guanidinium isothiocyanate/cesium chloride method described by Sambrook, J. et al., (supra). Poly (A)+ RNA was prepared by oligo(dT) cellulose chromatography. For Northern analysis, RNA was size fractionated by electrophoresis in a 1.2% agarose/2.2M formaldehyde gel, transferred onto a nylon membrane by capillary action and baked at 80° C. for 2 hours. Following prehybridization, the blot was hybridized with a ($^{32}$p) nick-translated DNA probe which was prepared as described above. Hybridization was carried out overnight at 42° C. in the presence of 50% formamide, 5× SSC, 0.1% SDS, and 5× Denhardt's. The membrane was then washed in 0.1× SSC, 0.1% SDS at 42° C., and exposed to Kodak XAR film at −70° C. for 12 hours using an intensifying screen.

B. Results

Figure 7:
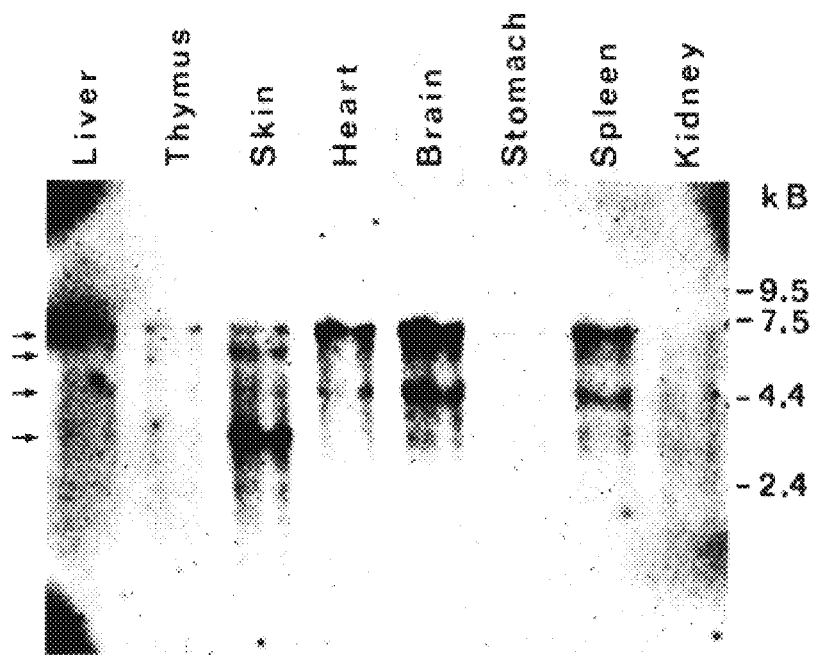
FIG. 7 is a Northern blot of monkey mRNA with GRB-1 probe. 5 μg of poly (A)+ mRNA, obtained from various monkey tissue, was electrophoresed on 1.2%/2.2M agarose-formaldehyde gel. The blot was hybridized with a ($^{32}$P)-nick translated DNA probe corresponding to the insert from clone ki4.

To test for the expression of MRNA corresponding to the newly isolated cDNA, Northern blot analysis of different monkey tissue MRNA, probed with DNA corresponding to the insert from clone ki4, demonstrated the presence of two major bands of 4.4 kb and 7.0 kb in most tissues examined (FIG. 7). Expression was highest in the brain, with heart, spleen, liver and thymus displaying decreasing levels of expression. The 4.4 kb message corresponds to the expected size of the transcript which would encode the isolated clones. In contrast to the 4.4 and 7.0 kb transcripts observed in most tissues, the skin contained two slightly smaller sized mRNAs of 3.6 and 6.6 kb.

The 3.6, 6.6 and 7.0 kb transcripts may represent alternatively spliced follow Of MRNA, or may encode distinct but related MRNA species.

EXAMPLE V

Production of anti-GRB-1 Antibodies and Analysis of GRB-1 Fusion Protein

A. Methods

Polyclonal antibodies were produced by immunizing rabbits with the β-galactosidase fusion protein expressed by the initial isolated phage clone, ki4. *coli* CAG 456 bacteria (obtained from—Dr. Michael Snyder, Yale University) were infected with recombinant phage ki4 at a multiplicity-of-infection of 10 and β-galactosidase fusion protein was recovered from the protein pellet after 1.5 hours. Protein extracts were prepared, separated on a 6% SDS-gel, and the band corresponding to the fusion protein excised from gel and used for immunization.

Human glioblastoma cell line U1242, rat bladder carcinoma cell line NBT II, and NIH3T3 cells were grown to confluence in DMEM medium supplemented with lot fetal bovine serum. Cells were labelled with ($^{35}$S)-methionine (50 μCi/ml) in 0.5% fetal bovine serum and lysed after 12 hours as previously described (Margolis, B. et al., Cell 57:1101–1107 (1989)). After immunoprecipitation with 10 μl of antibody coupled to protein A-Sepharose, the beads were washed three times with a solution containing 20 mm HEPES, pH 7.5, 300 mM NaCl, 10% glycerol, 1% Triton X-100, 0.1% SDS, and 1% sodium deoxycholate. After boiling in sample buffer proteins were separated on a 8t SDS-gel.

B. Results

Figure 8:
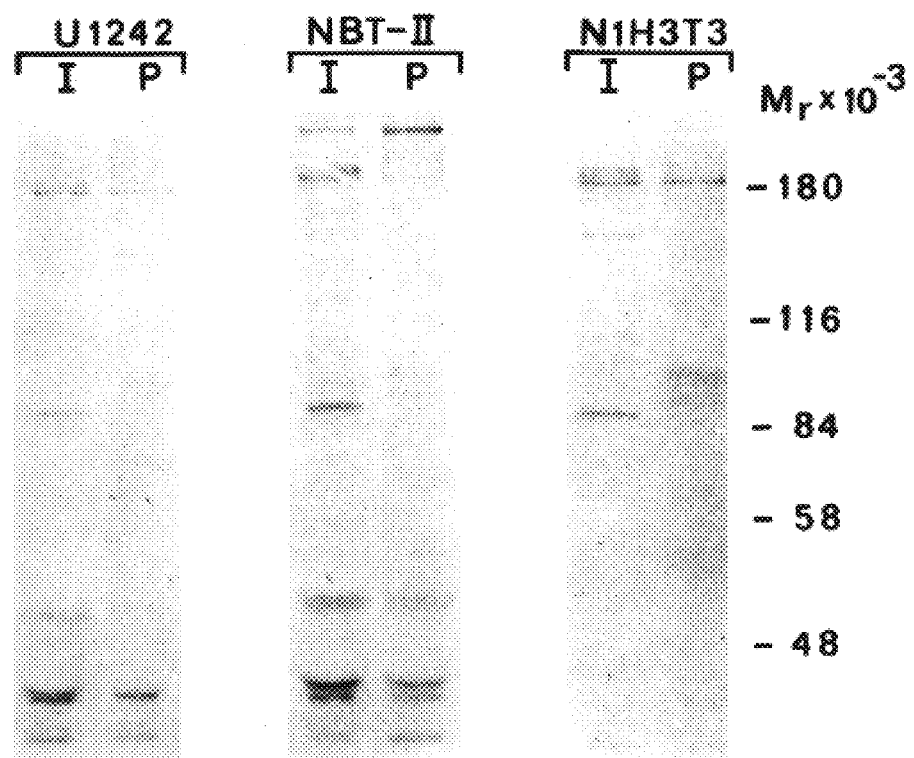
FIG. 8 is a gel pattern showing that antibodies to GRB-1 immunoprecipitate a protein of 85 kDa from biosynthetically labelled cells. Cells were metabolically labelled with ($^{35}$S) methionine, after which lysates were prepared and immunoprecipitated with either immune (I) or preimmune (P) serum. The immunoprecipitated protein was separated on a 8% SDS/PAGE. Autoradiography was performed overnight. Cell lines used include human glioblastoma cell line, U1242, rat bladder carcinoma cell line, NBT-II and NIH-3T3 cells.

Polyclonal antibodies were raised against the β-galactosidase fusion protein expressed by the initial isolated phage. Immunoprecipitation experiments, using biosynthetically labelled cells, demonstrated that these antibodies recognized an 85 kDa protein in three different cell lines (FIG. 8, lanes designated "I"). Recognition of the 85 kDa protein by this antiserum was specific since preimmune serum did not recognize this protein (lanes designated "P"). Th6@e results provided support for the predicted molecular weight based on the amino acid sequence of cloned GRB-1.

C. Discussion

The finding that the gene for GRB-1 encodes for a protein with an expected molecular weight of 85 kDa, together with the demonstration that antibodies to GRB-1 immunoprecipitated an 85 kDa protein from three different cell lines, suggest that GRB-1 may represent a particular protein which had previously been shown to associate with activated growth factor receptors, namely p85. While the exact function of p85 was unknown, it was presumed to be phosphatidylinositol (PI3)-kinase, since PI3-kinase activity copurified with an 85 kDa protein found in PDGF stimulated as well as middle T-antigen (MTAg)-transformed cells (Kaplan, D. R. Cell 50:1021–1029 (1987); Whitman, M. et al., Nature 315:239–242 (1985); Coughlin, S. R. et al., Science 243:1191–1194 (1989)). The absence of an ATP binding site argues that GRB-1 is most likely not a phospholipid kinase.

GRB-1 exhibits 97% sequence identity with murine and bovine p85. Hence, GRB-1 is the human counterpart of p85. Recombinant p85 is able to bind to the activated PDGFR or EGFR, but does not itself contain intrinsic PI3 kinase activity. p85, however, is found associated with a 110 kDa tyrosine phosphorylated protein which may be the catalytic subunit of the PI3 Kinase. While the exact relationship between PI3 kinase and p85 is not known, overexpression of p85 modulates the interaction between PI3 kinase and the PDGFR. p85 could function as a regulatory subunit or as a bridge between activated receptors and the PI3 kinase.

EXAMPLE VI

The Tyrosine Phosphorylated Carboxy-terminus of the EGF Receptor is a Binding Site for GAP and PLC-γ

The studies described below confirm that binding of PLC-γ and a fusion protein containing the SH2 and SH3 domains of GAP (trpE/GAP SH2) are specifically controlled by autophosphorylation of the EGFR. The results show that phosphorylation of PLC-γ actually reduces its association with the EGFR. Evidence is presented demonstrating that both PLC-γ and the trpE/GAP SH2 fusion protein bind specifically to the tyrosine phosphorylated C-terminus of the EGFR. In sum, these results indicate that the SH2/SH3 domains interact directly with phosphotyrosine containing regions of the EGF receptor.

A. Materials and Methods

1. Cell lines, mutant receptors and fusion proteins

The cell lines CD126 (Margolis, B. L. et al., J. Biol. Chem. 264: 10667–10671 (1989), HER14, K721. (Nonegger, A. M. et al., Cell 51: 199–209 (1987); Honegger, A. M. et al., Mol. Cell. Biol. 7:4567–4571 (1987)) were used as sources for wild-type EGF receptor, kinase-negative (kin7) EGF receptor and C-terminal (C-terminal) truncated EGF receptor, respectively. The intracellular domain of the EGF receptor (EGFR-C) was purified from a baculovirus expression system (Hsu, C-. J. et al., Cell Growth Differ 1: 191–200 (1990)) (FIG. 9A). 3TP1, a cell line which overexpresses transfected PLC-γ CDNA but has no EGF receptor was used as a source of PLC-γ (Margolis, B. et al., Science 248: 607–610 (1990)).

The preparation of trpE fusion proteins containing the GAP SH2 domain (GAP residues 171–448, 10 FIG. 9B) has been described by Moran, M. F. et al., Proc. Natl. Acad. Sci. USA 87: 8622–8626 (1990). Bacterial lysates containing trpE/GAP SH2 fusion proteins were prepared by resuspending 1 g of bacteria in 3 ml of 50 mM Tris pH 7.5, 0.5 mm EDTA, 0.1 mm PMSF. After incubation at 4° C. in 1 mg/ml lysozyme and 0.2% NP40, cells were sonicated 5 times for 5 seconds, and the lysate was clarified by centrifugation for 30 min at 10,000 g. Bacterial lysates were diluted 1:100 in the 1% Triton lysis buffer with proteinase and phosphatase inhibitors as described above and were precleared with protein A-Sepharose.

2. Antibodies, inmunoprecipitation and immunoblotting

The following anti-EGFR antibodies (FIG. 9A) were used: (a) mAb108, a monoclonal antibody directed against domain III of the extracellular domain (Lax, I. et al., EMBO J. 8: 421–427 (1989)); (b) antipeptide antibody RK2 specific for residues 984–996; (c) antipeptide antibody C specific for residues 1176–1186; and (d) antipeptide antibody F, specific for residues 656–676. For immunoprecipitating the trpE fusion proteins, a mouse monoclonal antibody against trpE (Oncogene Science) bound to agarose linked anti-mouse IgG (Sigma) was utilized. For immunoblotting, a polyclonal rabbit antibody against trpE was used (Moran, M. F. et al., Proc. Natl. Acad. Sci. USA 87: 8622–8626 (1990)). PLC-γ was immunoblotted and immunoprecipitated with a polyclonal rabbit anti-peptide antibody described previously (Margolis, B. et al., Cell 57: 1101–1107 (1989)).

The techniques used are described in several references from the present inventors, laboratory (Margolis, B. L. et al., J. Biol. Chem. 264: 10667–10671 (1989); Cell 57:1101–1107 (1989)). Unstimulated cells were grown to confluence in Dulbecco's Modified Eagle Medium with 10% calf serum and starved overnight in 1% fetal calf serum prior to lysis in a 1% Triton X-100 lysis buffer containing proteinase and phosphatase inhibitors. EGF receptors were immunoprecipitated utilizing antibodies bound to protein A-Sepharose. After washing the receptor material with HNTG (20 mM Hepes, pH 7.5 150 mM NaCl, 0.1% Triton X-100 and 10% glycerol), autophosphorylation was induced by the addition of 5 mm $MnCl_2$ and 30 μM ATP. Controls were incubated with $Mn^{2+}$ only. After further washes with HNTG, lysate containing either PLC-γ (from 3TP1 cells) or the bacterial fusion proteins was added. After allowing binding to proceed for 90 min, three further washes with HNTG were performed and samples were run on an SDS gel and inmunoblotted.

3. Cyanogen bromide (CNBr) cleavage

EGFR-C was phosphorylated at 4° C. with $MnCl_2$ and ATP sometimes in the presence of $(\gamma^{-32}p)ATP$ (NEN/Dupont, 6000 Ci/mmol). The-receptor preparation was then resuspended in 20 mM HEPES, pH 7.5, with 100 μg BSA and concentrated in a Centricon 10 (Amicon) to 50 μl. Then 240 μl 88% formic acid was added with two grains of CNBr and the samples were stored under nitrogen in the dark for 14 h at room temperature. Samples were dried and washed three times with water in a Speed-Vac (Savant) and then resuspended in 1% Triton lysis buffer.

B. Results

Figure 9A:
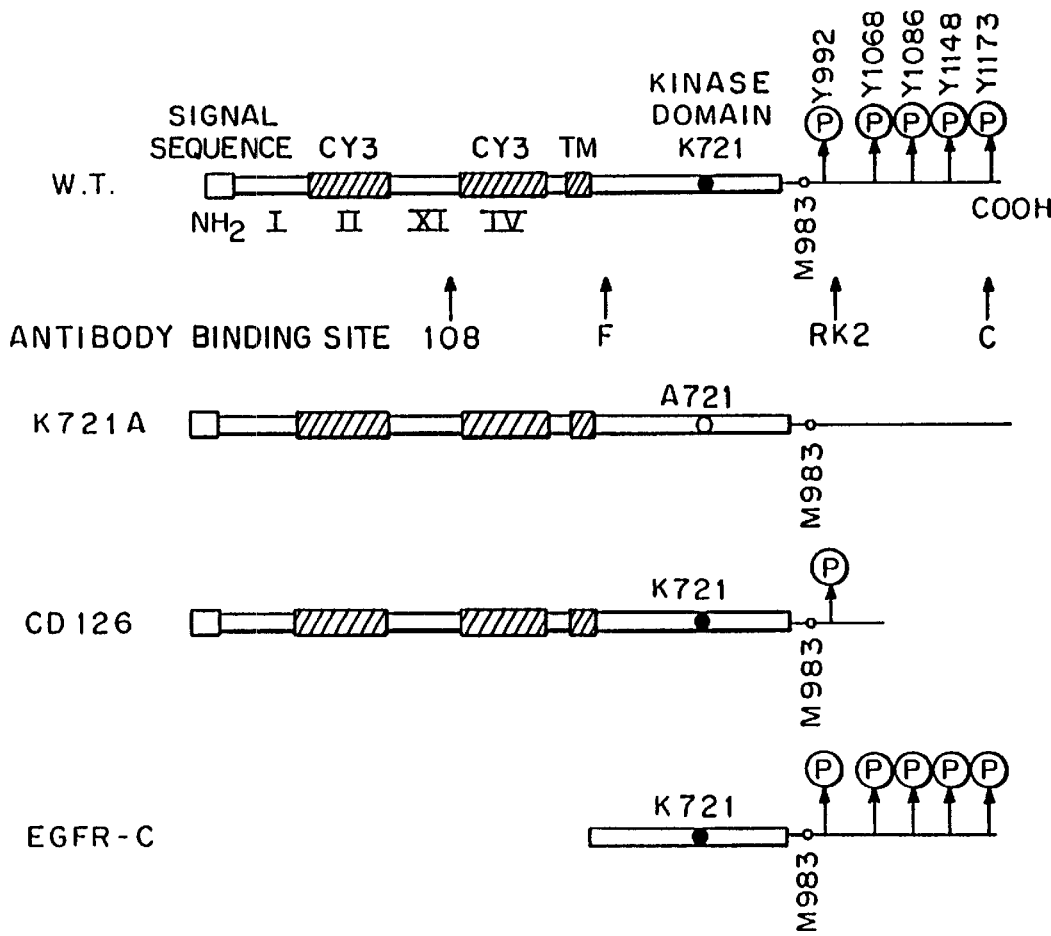
FIGS. 9A–B depicts several wild-type and mutant proteins used in the studies. (9A) EGF receptor constructs with their known or predicted autophosphorylation sites. Wild-type (W.T.), Kinase negative (K721A), and carboxyterminal deletion (CD126), were immunoprecipitated from previously described transfected NIH373 cells expressing approximately 300,000 EGF receptors. EGFR-C represents a deletion mutant containing the cytoplasmic domain of the EGF receptor produced by baculovirus-infected SF9 cells. (9B) Structure of PLC-γ and trpE/GAP SH2 proteins indicating location of the SH2 and SH3 domains and PLC-γ tyrosine phosphorylation sites.
Figure 9B:
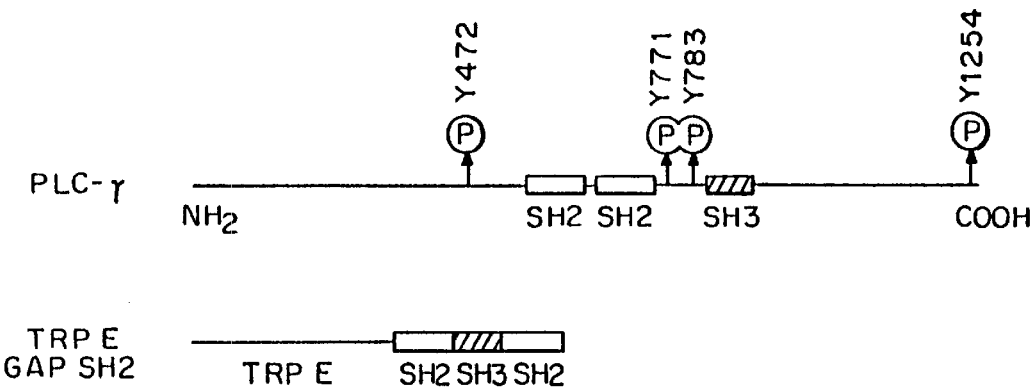
Figure 10A:
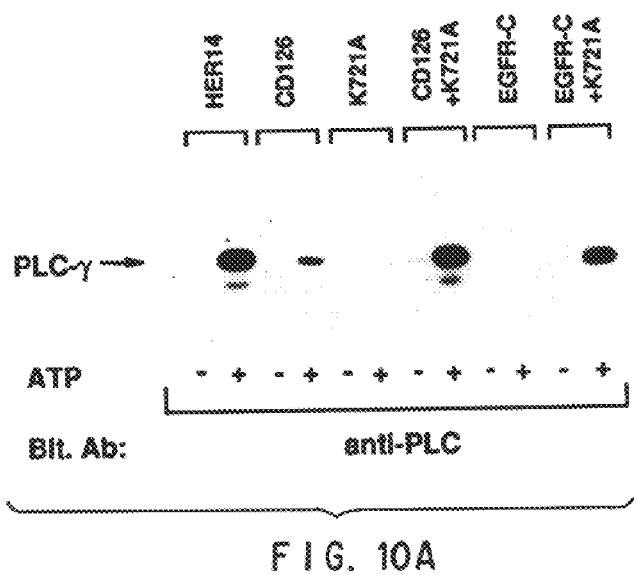
FIGS. 10A-10B is a gel pattern showing association of PLC-γ with EGFR mutants. Wild-type (HER14), carboxy-terminal deletion (DC126), or kinase-negative (K721A) EGFR were immunoprecipitated with anti-EGFR mAb108. Receptors were autophosphorylated with γ-$^{32}$P-ATP. Concomitantly EGFR-C was added to protein A-Sepharose beads alone or to immunoprecipitated K721A receptors either with or without ATP. After further washes to remove ATP, lysate from approximately 15×10$^6$ PLC-γ overexpressing 3T-P1 cells was added and mixed for 90 min. at 4° C. After washing to remove unbound PLC-γ proteins were separated on a 6% SDS-gel and transferred to nitrocellulose for immunoblotting. One eighth of the sample was utilized for anti-PTyr blotting, the remainder for anti-PLC-γ blotting (exposure time 14 h).
Figure 10B:
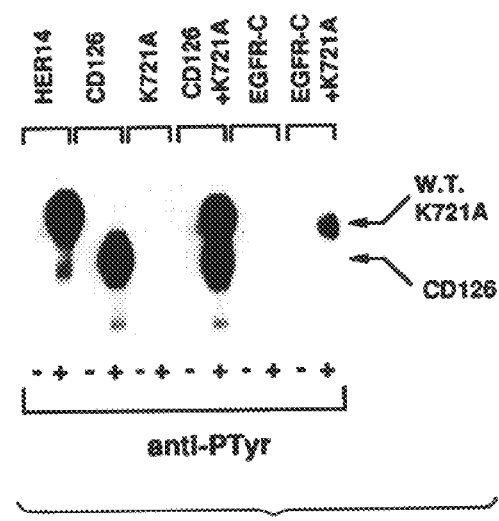

A comparison was performed of the binding of PLC-γ to wild-type and mutant EGFRs (FIG. 9A). First, wild-type and mutant receptors from transfected NIH-3T3 cells were immunoprecipitated and some of the receptor immunoprecipitates were allowed to undergo in vitro autophosphorylation with ATP and $Mn^{2+}$ (Margolis, B. et al., Mol. Cell. Biol. 10: 435–441 (1990)). Then, lysates from NIH-3T3 cells which overexpress PLC-γ (Margolis, B. et al., Science 248: 607–610 (1990)) were added and binding allowed to proceed for 90 min. at 4° C. After washing the immunoprecipitates with HNTG, the amount of PLC-γ bound was assessed by immunoblotting. As illustrated in FIGS. 10A-10B, PLC-γ bound only to the tyrosine phosphorylated wild-type receptor but not to the non-phosphorylated receptor. To assess the importance of autophosphorylation, two studies with mutant receptors were then undertaken. First to be examined was the binding of PLC-γ to a truncated EGF receptor missing 126 amino acids from the C-terminus (CD126, FIG. 9A) and devoid of four major autophosphorylation sites (Downward, J., et al., Nature 311: 483–485 (1984)). This truncated receptor was autophosphorylated, probably at tyrosine 992 (Walton, G. M. et al., J. Biol. Chem. 265: 1750–1754 (1990)). However, despite this level of tyrosine autophosphorylation, the binding of PLC-γ was markedly reduced compared to the full length receptor. Reduced association was also observed with CD63, a deletion mutant EGF receptor lacking 63 C-terminal residues containing two autophosphorylation sites. These results suggested a role for the receptor C-terminus in either binding or modulating the binding of PLC-γ to the EGF receptor.

FIGS. 10A-10B also demonstrates that PLC-γ cannot bind to the kin⁻ mutant receptor. To explore the importance of autophosphorylation in this effect, the kin⁻ receptor was cross-phosphorylated with the CD126 receptor (Nonegger, A. M. et al., Proc. Natl. Acad. Sci. USA 86:925–929 (1989)). This resulted in normalization of PLC-γ binding to wild-type levels. This suggested that phosphorylation of the kin⁻ receptor was sufficient to normalize binding to PLC-γ.

To confirm that the kin⁻ receptor alone could bind PLC-γ after phosphorylation, this receptor was cross-phosphorylated with a soluble, baculovirusexpressed EGFR cytoplasmic domain (EGFR-C) that does not bind to the mAb 108 (FIG. 9A).

Although cross-phosphorylation was not as strong as with the CD126 mutant, tyrosine phosphorylation of the K721A mutant and binding of PLC-γ were clearly detected. This finding confirms that tyrosine phosphorylation of the EGFR promotes binding of PLC-γ.

The role of PLC-γ tyrosine phosphorylation in the interaction between wild-type EGFR and PLC-γ was examined. Tyrosine phosphorylated PLC-γ could be dissociated from the EGFR more readily than non-phosphorylated PLC-γ (FIG. 11), suggesting a lower affinity of tyrosine phosphorylated PLC-γ for the EGFR.

Figure 12A:
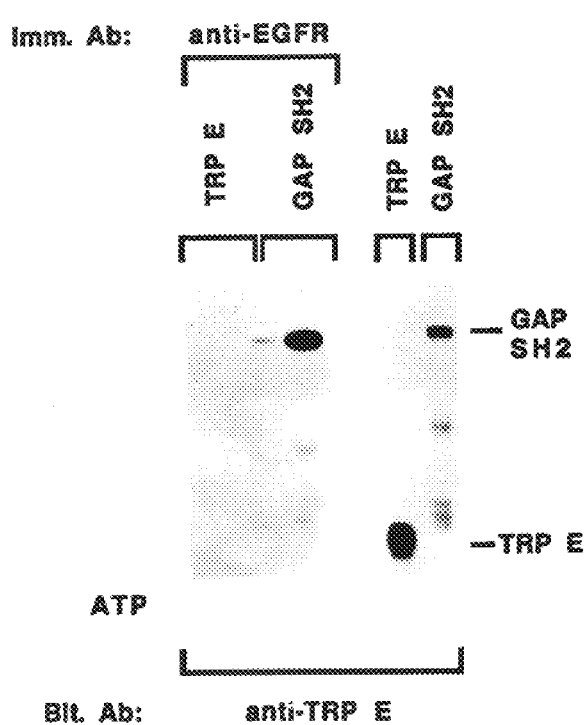
FIGS. 12A and 12B are representations of a gel pattern showing binding of EGFR-C to trpE proteins.
Figure 12B:
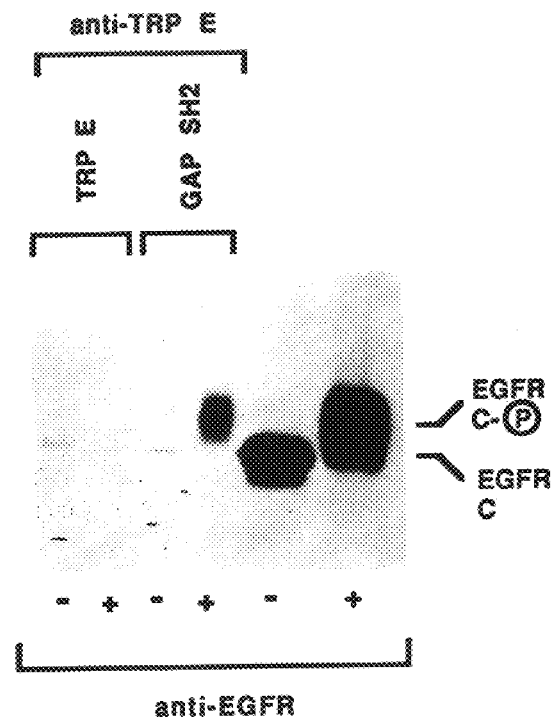

These findings were extended to examination of the binding of a fusion protein-containing trpE/GAP SH2 domain (FIG. 9B) to the baculovirus expressed EGFR-C, As with the full length EGFR and PLC-γ, the trpE/GAP SH2 fusion protein domain bound only to the tyrosine phosphorylated EGFR-C (FIG. 12A). The trpe protein alone did not bind to EGFR-C. Similarly, phosphorylated EGFR-C bound only to trpE/GAP SH2; however, non-specific binding of non-phosphorylated EGFR-C was high (FIG. 12B). These results demonstrated that the binding site of the EGFR is situated in its intracellular domain.

Figure 13A:
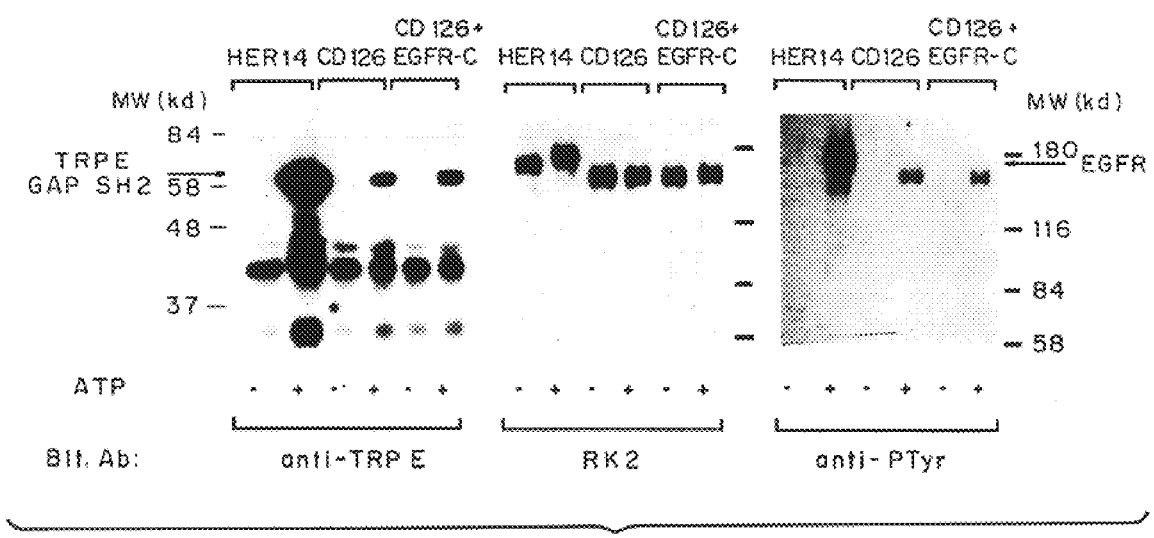
FIGS. 13A and 13B are representations of a gel pattern showing binding of trpE/GAP SH2 to wild-type and mutant EGFR.
Figure 13B:
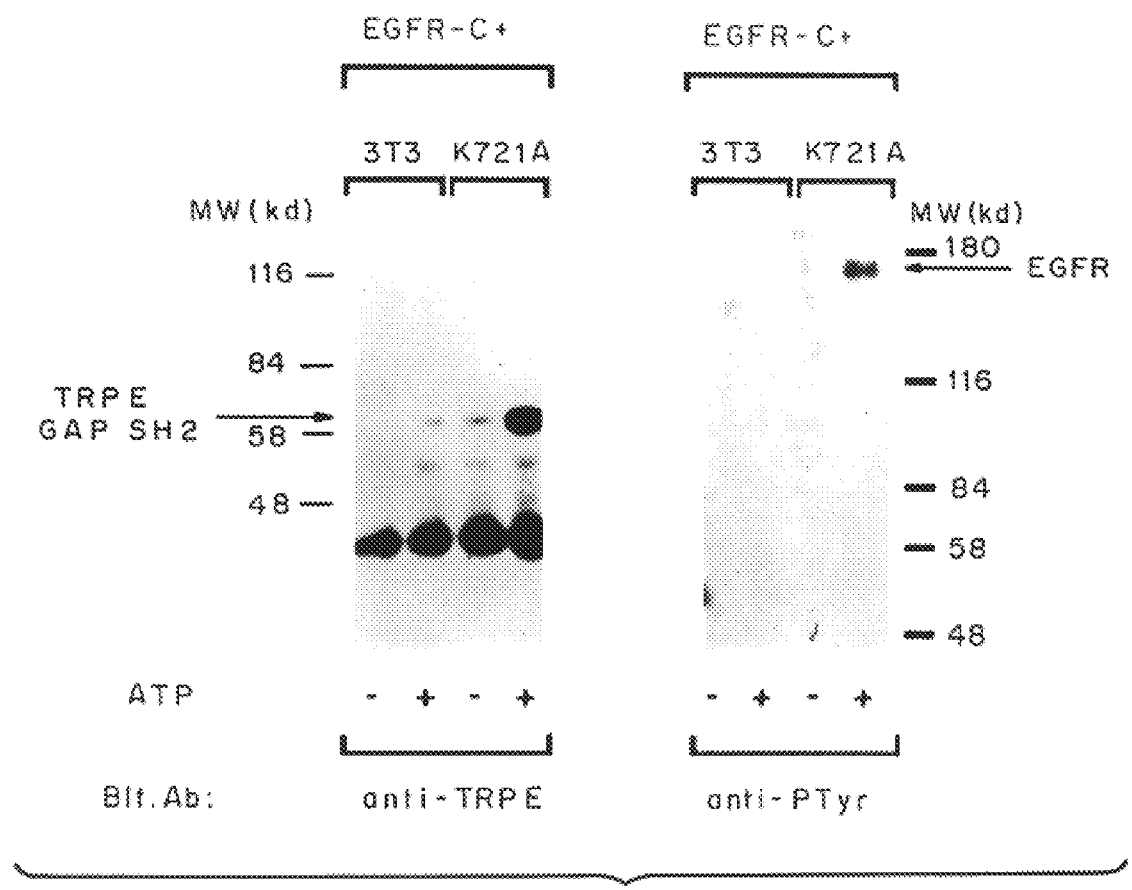

In general, the trpE/GAP SH2 fusion protein bound with a higher stoichiometry to full length EGFR than did PLC-γ. However, the fusion protein was not tyrosine phosphorylated by the EGFR. The trpE/GAP SH2 protein much better to the phosphorylated full length receptor compared to the CD126 deletion mutant (FIG. 13A). As shown in FIG. 13B, cross-phosphorylation of the kin full length EGF receptor by the EGFR-C allowed it to bind the trpE/GAP SH2 protein.

In control groups, the EGFR-C was shown not to enhance the binding to the CD126 receptor probably because this receptor was already maximally tyrosine phosphorylated (FIG. 13A). Also, no binding was observed when EGFR-C was tested in the presence of mAb 108 immunoprecipitate from cells containing no EGF receptor (FIG. 13B). This indicates that the effects of EGFR-C could not be attributed to non-specific binding of tyrosine phosphorylated EGFR-C to sepharose. These studies confirm the importance of autophosphorylation in mediating binding and show that for EGF receptor binding, the GAP SH2 domain behaves similarly to intact PLC-γ.

The poor binding to the CD126 deletion mutant suggested that at least part of the binding site for the molecule was in the C-terminus. Yet an effect, possibly allosteric, of this deletion on the overall conformation of the receptor could not be excluded. Therefore, the binding of PLC-γ and trpE/GAP SH2 to a C-terminal fragment of the EGFR was examined. In the EGFR, the most C-terminal methionine residue is found at position 983; CNBr cleavage therefore generates a 203 amino acid fragment which contains all the known autophosphorylation sites. This protein fragment is recognized by an antibody specific for the EGFR C-terminus, anti-C (FIG. 9A).

Figure 14:
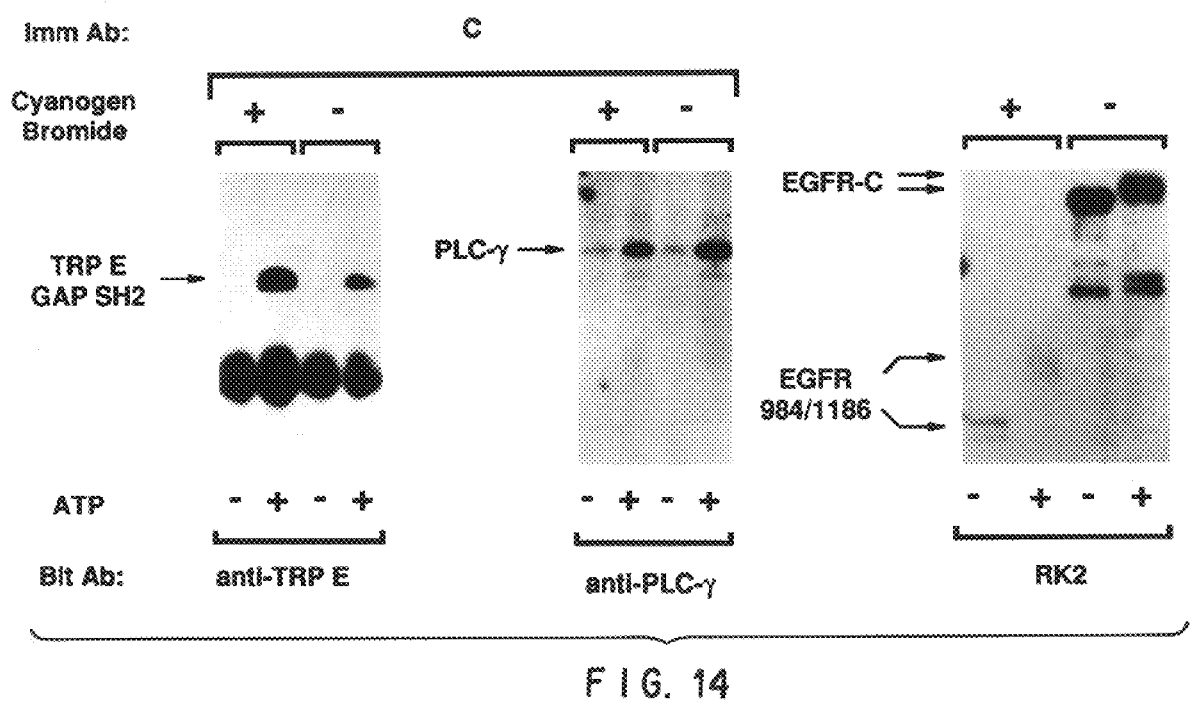
FIG. 14 is a gel pattern showing binding of PLC-γ and trpE/GAP SH2 to the CNBR cleaved C-terminal fragment of EGFR. EGFR-C (10 μg) was incubated in a Centricon 30 in 20 mm HEPES, pH 7.5 with 100 μg BSA as a carrier protein. The phosphorylated and non-phosphorylated EGFR-C were then each divided in two, with one half being stored in buffer while the other half was cleaved with CNBr. The four samples either with or without ATP, and with or without CNBr were then each brought up in 500 μl 1% Triton X-100 lysis buffer, split in two, and immunoprecipitated with anti-C antibody. After washing the immunoprecipitates, lysates containing PLC-γ or trpE/GAP SH2 were added. Immunoblotting was then performed on the samples as above with anti-trpE or anti-PLC-γ. For the right panel, a fraction of the cleaved and uncleaved EGFR-C (0.1 μg) was loaded directly on the gel without immunoprecipitation and immunoblotted with RK2 (exposure time 14 h). The dark band seen in all lines of the anti-trpE blot runs at about 40 kDa (also seen in FIG. 13) and represents ($^{125}$I) protein A binding to the heavy chain of the immunoprecipitating antibody.
Figure 15:
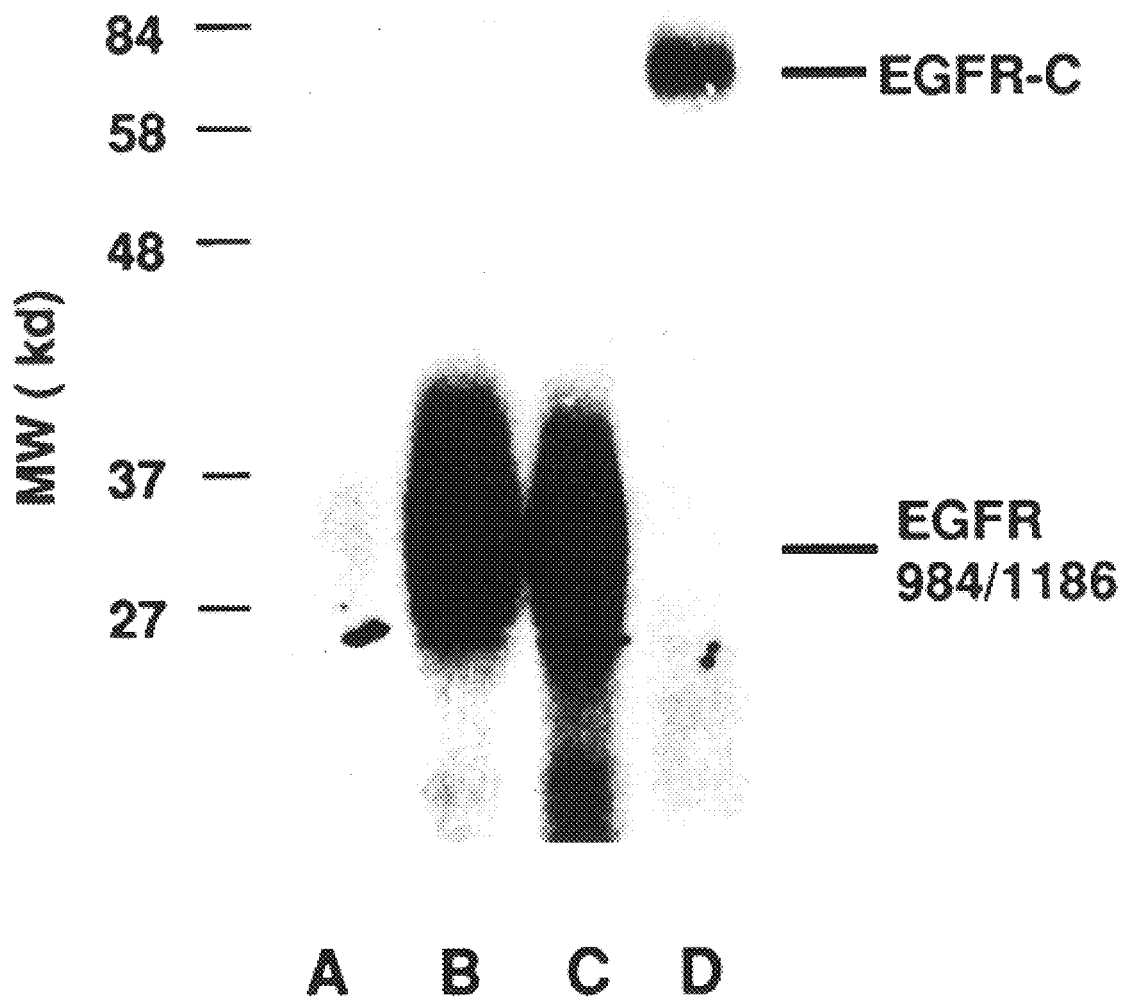
FIG. 15 is a gel pattern showing binding of the tyrosine phosphorylated C-terminal EGFR fragment to trpE/GAP SH2 but not to trpE. EGFR-C (5 μg) was autophosphorylated by the addition of ($\gamma^{32}$p)ATP. The phosphorylated EGFR-C was concentrated in a Centricon 30, and then cleaved with CNBr in 70% formic acid. one half of the sample (350,000 c.p.m.) was allowed to bind to trpE or trpE/GAP SH2 as in FIG. 12B, washed and run on a 10% SDS-gel. (15A) Binding of phosphorylated CNBR cleaved EGFR-C to trpE (15B) Binding of phosphorylated CNBr cleaved EGFR-C to trpE GAP SH2 (15C) 3000 c.p.m. of CNBr cleaved EGFR-C (15D) for comparison 3000 c.p.m. of cleaved EGFR-C (exposure time 20 h). EGFR 984/1186 indicates the sequence of the tyrosine autophosphorylated fragment generated by CNBr.

When this C-terminal fragment was specifically immunoprecipitated and tyrosine phosphorylated, it bound PLC-γ and the trpE/GAP SH2 fusion protein (FIG. 14). CNBr cleavage was complete; no full-length EGFR-C could be detected after proteolysis that could account for the binding. Again, no binding was seen to the nonphosphorylated C-terminal CNBR fragment. CNBR cleavage of EGFR-C also generated a 97 amino acid N-terminal peptide identified by antibody F (FIG. 9A, EGFR residues 645–742). This fragment, immunoprecipitated by antibody F, did not bind trpE/GAP SH2. Additionally, EGFR-C was autophosphorylated with ($^{32}$p)ATP and a $^{32}$p-labeled CNBr C-terminal fragment was generated. As shown in FIG. 15, this fragment bound to the trpE/GAP SH2 fusion protein but not to trpE. In total, these findings demonstrate that direct binding to the tyrosine phosphorylated C-terminus contributes, at least in part, to the specific binding of SH2 and SH3 domain proteins to the EGFR.

C. Discussion

When taken together, the above findings and several additional lines of evidence argue strongly that the phosphotyrosine residues are part of the actual binding site of the EGFR for SH2 domains. First, p47 $^{gag-crk}$ was found to bind to nearly all phosphotyrosine containing proteins in v-crk transformed cells (Matsuda, M. et al., Science 248: 1537–1539 (1990)). Second, mutations of two autophosphorylation sites on the PDGF receptor greatly decreased the binding of GAP (Kazlauskas, A. et al., Science 247: 1578–1581 (1990)). Finally, the results presented above demonstrate specific binding to the C-terminus of the EGFR only when phosphotyrosine is present. Thus, it is concluded that the phosphotyrosine residues either comprise a part of the binding site or locally alter the conformation of this region, allowing binding. It is unlikely that phosphotyrosine alone constitutes the binding site. For example, phosphotyrosine alone cannot interfere with the binding of p47 $^{gag-crk}$ to phosphotyrosine-containing proteins (Matsuda et al., supra). Additionally, PLC-γ does not bind to activated all molecules that contain phosphotyrosine residues, such as the CSF-1 receptor (Downing, J. R. et al., EMBO J. 8:3345–3350 (1989)). Similarly, the binding of PLC-γ to PDGFR does not appear to be identical to GAP binding; different SH2 and SH3 domain-containing proteins may have different binding specificities (Kazlauskas et al., supra).

EXAMPLE VII

Cloning, Isolation & Characterization of a Target Protein for Receptor Tyrosine Kinase Methods: The intracellular domain of the EGFR, which includes the tyrosine kinase and carboxy terminal domain, was purified from a recombinant baculovirus expression system as described (Margolis, Mol. Cell. Biol. 10:435–441 (1990) and EMBO J. 2:4375–4390 (1990); Skolnik et al. Cell 65:83–90 (1991). The recombinant protein was phosphorylated with ($^{32}$p) γ-ATP, washed, and cyanogen bromide digested to yield a 204 residue carboxyterminal tail containing all five phosphorylated tyrosine residues (Margolis, Mol. Cell. Biol. 10:435–441 (1990) and EMBO J. 9:4375–4390 (1990). The ($^{32}$p) carboxyterminal tail was then used as probe to screen a λgt11 human brainstem expression library, as previously described (Skolnik et al. Cell 65:83–90 (1991)).

An oligo (dT) λgt11, constructed from mRNA isolated from human brain stem, was obtained from M. Jaye (Rhone Poulenic-Rorer Pharmaceuticals) and is readily available from commercial sources. Screening of the library was performed as previously described (Skolnik et al. Cell 65:83–90 (1991)). cDNA inserts isolated from positive recombinant phage that bound the EGFR were subcloned into M13 and sequenced by the dideoxy chain termination method, using the Sequenase 2.0 kit (U.S.B). Since the initial clone isolated by expression/cloning did not contain the 5' ends of the gene, the library was rescreened, using the clone 2-4 insert as a DNA probe.

Total cellular RNA was prepared with the Stratagene RNA isolation kit. For Northern analysis, RNA was size fractionated on a 1.2% agarose-2.2M formaldehyde gel, transferred by capillary action to a Nytran membrane (Schleicher and Schuell), and prehybridized and hybridized at 65° C. in 0.5M sodium phosphate pH 7.2, 7% SDS, 1 mM EDTA, 100 µg/ml salmon sperm DNA. The membrane was then washed 1× at room temp and then 2× at 65° C. in 40 mM sodium phosphate pH 7.2, 1% SDS, 1 mM EDTA.

HER14 are NIH 3T3 cells (clone 2.2) which express approximately 400,000 wild type human EGF receptors per cell (Honeggar et al. Cell 51:199–209 (1987)). HER14 cells were maintained in Dulbecco's modified Eagles medium (DMEM) containing 10% calf serum (CS). Prior to stimulation, cells were cultured for 18 hours in DMEM/1% CS. Cells were then stimulated with either EGF (275 ng/ml) or PDGF-BB (50-ng/ml) Intergen, Purchase, N.Y.) for 2 minutes in DMEM containing 1 mg/ml BSA and 20 mM HEPES pH 7.5, following which the cells were immediately washed and lysed. Lysate protein content was normalized as described (Bradford, 1976). Cell lysis, immunoprecipitation, and immunoblotting were performed as previously described (Margolis et al. Cell 57:1101–1107 (1989)). 293 cells were transfected using a modification of the calcium phosphate precipitation method (Chen and (Okayama Mol. Cell. Biol. 7:2745–272 (1987).

Several polyclonal antibodies were generated against GRB2. A synthetic peptide derived from the N-terminal SH3 domain (residues 36–50) and the full length GRB2-GST (glutathione-S-transferase) fusion protein were used to produce rabbit polyclonal antisera called Ab 86 and Ab 55, respectively. Both of these antisera are effective at recognizing denatured GRB2 in immunoblots. A third polyclonal rabbit antisera called Ab50 was generated against the GRB2-GST fusion protein containing the C-terminal SH3 domain of GRB2 (residues 167–221), and is capable of immunoprecipitating GRB2 from solubilized cells. Monoclonal antiphosphotyrosine antibodies (lG2) covalently coupled to agarose were purchased from oncogene Science (Manhasset, N.Y.). Anti-P-Tyr inmunoblots were performed with a rabbit polyclonal antibody. Anti-EGF receptor immunoprecipitates were performed with monoclonal antibody mAb m108 (Bellot et al. J. Cell Biol. 110:491–502 (1990).

Anti-EGF receptor immunoblots were performed with anti-C terminus peptide (residues 1176–1186) antisera (Margolis et al. Cell 57:1101–1107 (1989)).

Using the CDNA of GRB2 as a template, DNA fragments corresponding to the various GRB2 domains were synthesized using PCR and oligonucleotides which contained appropriate restriction sites and bordered the domains of interest. The amplified DNA was isolated, digested with BamHI and EcoRI and cloned into pGEX3X (Pharmacia), which was then used to transform *E. coli* HB 101 to ampicillin resistance. Large scale cultures were then grown, induced with IPTG, and the glutathione Stransferase (GST) fusion proteins purified on glutathione agarose beads as previously described (Smith and Johnson Gene 67:31–40 (1988)).

The following fusion proteins were prepared: GST-GRB2 full length (FL) (amino acids AA 2–217); GSTSH2 (AA 50–161); GST-N-terminal SH3 (AA 2–59); GST-C-terminal SH3 (AA 156–217); GST-N-terminal SH3-SH2 (AA-161); GST-SH22-C-terminal SH3 (AA 50–217).

To assay the binding of native growth factor receptors to GST-fusion proteins 500 µl of HER14 cell lysate was incubated for 90 min at 4° C. with approximately 5 µg of fusion protein coupled to glutathione agarose beads. The beads were then washed three times with HNTG, and after boiling in sample buffer, the proteins were separated on 8% SDS-PAGE. Bound proteins were transferred to nitrocellulose and blotted with antibodies as described (Margolis et al. Mol. Cell. Biol. 10:435–411 (1990), Margolis et al. EMBO J. 2:4375–4380 (1990); Margolis, Cell Growth and Differentiation 3:73–80 (1992); and Margolis et al. Nature 35:71–74 (1992).

Labeling cells with ($^{32}$P)-orthophosphate were carried out as previously described (Li et al., Mol. Biol. Cell 2:641–649, 1991). Briefly, confluent HER14 cells starved for 16 hrs in 1% FCS/DMEM were incubated for two hours in $P_i$-free media, and labeled for two hours in $P_i$-free media, dialyzed FBS, 1 mCi/ml orthophosphate (carrier free, 314.5–337.5 TBq/mmole, purchased form NEN, Wilmington, Del.) at 37° C. Where appropriate, cells were incubated with vanadate (200 µM) at 37° C. for the last 20 minutes of cell labeling. Cells were then stimulated for two minutes with EGF (250 ng/ml) or PDGF (50 ng/ml), rapidly washed 2 times with ice cold phosphate-buffered saline (PBS), and solubilized immediately in lysis buffer (10 mM Tris-Cl pH 7.6, 50 mM NaCl, 30 nM sodium pyrophosphate, 50 mM sodium fluoride, 100 µM sodium orthovanadate, 5 µM $ZnCl_2$, 1 mM PMSF and 0.5% Triton-X-100). After nuclei were removed by centrifugation, the lysates where precleared for 1 hour with 50 µl Sepharose G25, and then incubated overnight with anti-GRB2 antiserum (Ab5O) at 4° C. The immune complexes were then precipitated with protein A-Sepharose for 45 min at 4° C., washed 8–15 times with RIPA buffer (20 MM Tris-Cl pH 7.6, 300 mM NaCl, 2 mM EDTA, 2% Triton-X-100, 2% sodium deoxycholate and 0.1% SDS), heated in Laemmli sample buffer containing 0.2 M β-mercaptoethanol and 1% SDS at 95° C. for 5 min, resolved by SDS PAGE (8–15% gradient), and visualized by autoradiography of dried gels. To isolate tyrosine phosphorylated proteins, the cell lysates were incubated with anti-PY antibody (Oncogene Science) beads for 2 hours at 4° C. The anti-PY beads were washed 5 times with lysis buffer, followed by elution with phenylphosphate (2 mM) in the presence of ovalbumin.

Results: Isolation of a cDNA clone encoding a protein with novel SH2 and SH3 domains.

Figure 26D:
FIG. 26D is a schematic representation of the overall domain structure of GRB2.

The carboxyterminal tail of the EGFR was used as a probe to screen a human brain stem λgtll protein expression library as previously described (Skolnik et al. Cell 6:4396–4408, 1991). One of the clones isolated utilizing this technique, clone 2-4, contained an insert of 1100 nucleotides found to contain a reading frame encoding novel SH2 and SH3 domains. The insert from clone 2-4 contained a 3' stop codon followed by a polyadenylation signal, but did not contain the 5' start site. To isolate the 5' end of the gene, the library was rescreened using DNA probes generated by amplifying DNA from clone 2-4. This approach enabled identification of clone 10-53, which was found to encode the full length protein. Clone 10-53, while overlapping with clone 2-4 at the 3' end contained a 5' ATG codon meeting Kozak translation initiation criteria (Kozak J. Cell. Biol. 108:229–241 (1989)), giving a 660 bp open reading frame from the initiating methionine (Ficket el. Nucleic Acids Research 10:5303–5318 (1982)) (FIGS. 26A–26C). Analysis of the protein sequence of clone 10–53 using Genbank revealed that the full length protein contained a single SH2 domain flanked by two SH3 domains, and that these three domains comprise the bulk of the protein (FIG. 26D). The SH2 and SH3 domains of GRB2 are compared to those in other proteins in FIGS. 26E and 26F. The full length protein encoded by clone 10-53 was named GRB2 (for the second growth factor receptor binding protein identified by the CORT method), and encoded a protein with a predicted molecular weight of about 24.5 kDa. The sequence also contains two potential protein kinase C phosphorylation sites (aa 22 and 102), two potential casein kinase 2 phosphorylation consensus sequences (aa 16 and 131) (Woodget et al., Eur. J. Biochem. 161:177–184, 1986; Kishimoto et al. J. Biol. Chem. 260:12492–12499, 1985; Marin et al. Eur. T. Biochem. 160:239–244 1986; Kuenzel et al. J. Biol. Chem. 262:9136–9140, 1987) and two RGD motifs.

Northern Analysis and Protein Expression

Figure 27A:
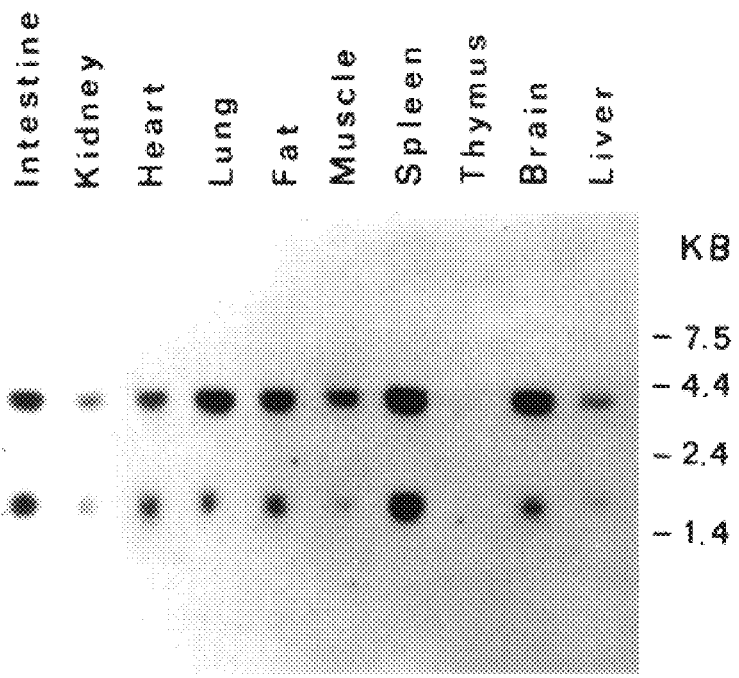
FIGS. 27A–27B show the analysis of expression of GRB2 in various murine tissues and cell lines. 27A shows a Northern analysis in murine tissues, with tissue of origin as indicated, with 20 μg total RNA loaded per lane. The sizes of the GRB2 transcripts (relative to BRL size markers indicated) are 3.8 kb and 1.5 kb.

To determine tissue distribution of GRB2, Northern hybridization analysis of various mouse tissue RNAs was performed, using as a probe the insert from clone 10-53. This analysis demonstrated GRB2 expression in every tissue examined, with the highest expression in the brain, spleen, lung, and intestine (FIG. 27A). GRB2 transcripts were visible in the thymus upon longer exposure. We have thus far been unable to identify a tissue or cell line which does not express GRB2, further demonstrating the ubiquitous nature of GRB2 expression. GRB2 hybridized to two transcripts of 1.5 and 3.8 kb. The 1.5 kb transcript corresponds to the expected size of clone 10-53.

Figure 27B:
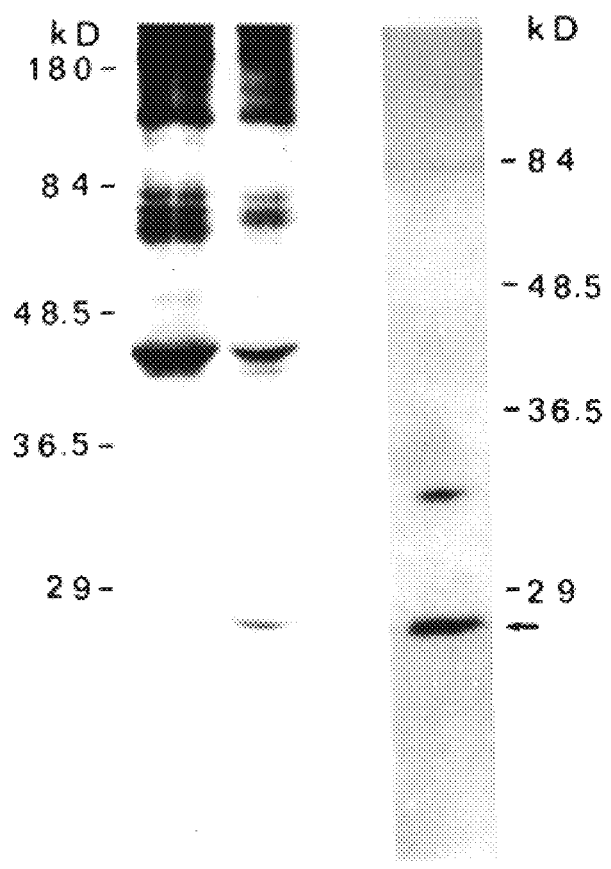

Several polyclonal rabbit antisera against GRB2 were generated (see methods section) and used to analyze the GRB2 protein by immunoblotting or immunoprecipitation experiments. FIG. 27B shows that a protein of 25 kDa is recognized by the immune, but not by the preimmune antiserum utilizing either immunoprecipitation analysis of ($^{35}$S) methionine labelled cells or an immunoblotting approach. The various antisera recognized a 25 kDa protein in every cell line and tissue examined, consistent with the distribution of the GRB2 transcript found in Northern analysis.

GRB2 associates with growth factor receptors in living cells. Receptor substrates, which contain SH2 domains are endowed with the ability to physically associate with certain activated growth factor receptors. Since the goal of the CORT cloning technique is to identify target proteins for particular growth factor receptors, we assessed whether GRB2 associates with the EGF receptor. HER 14 cells were treated with or without EGF, lysed, and subjected to immunoprecipitation analysis, according to published procedures (Margolis et al. 1990, 1991, supra).

Figure 28:
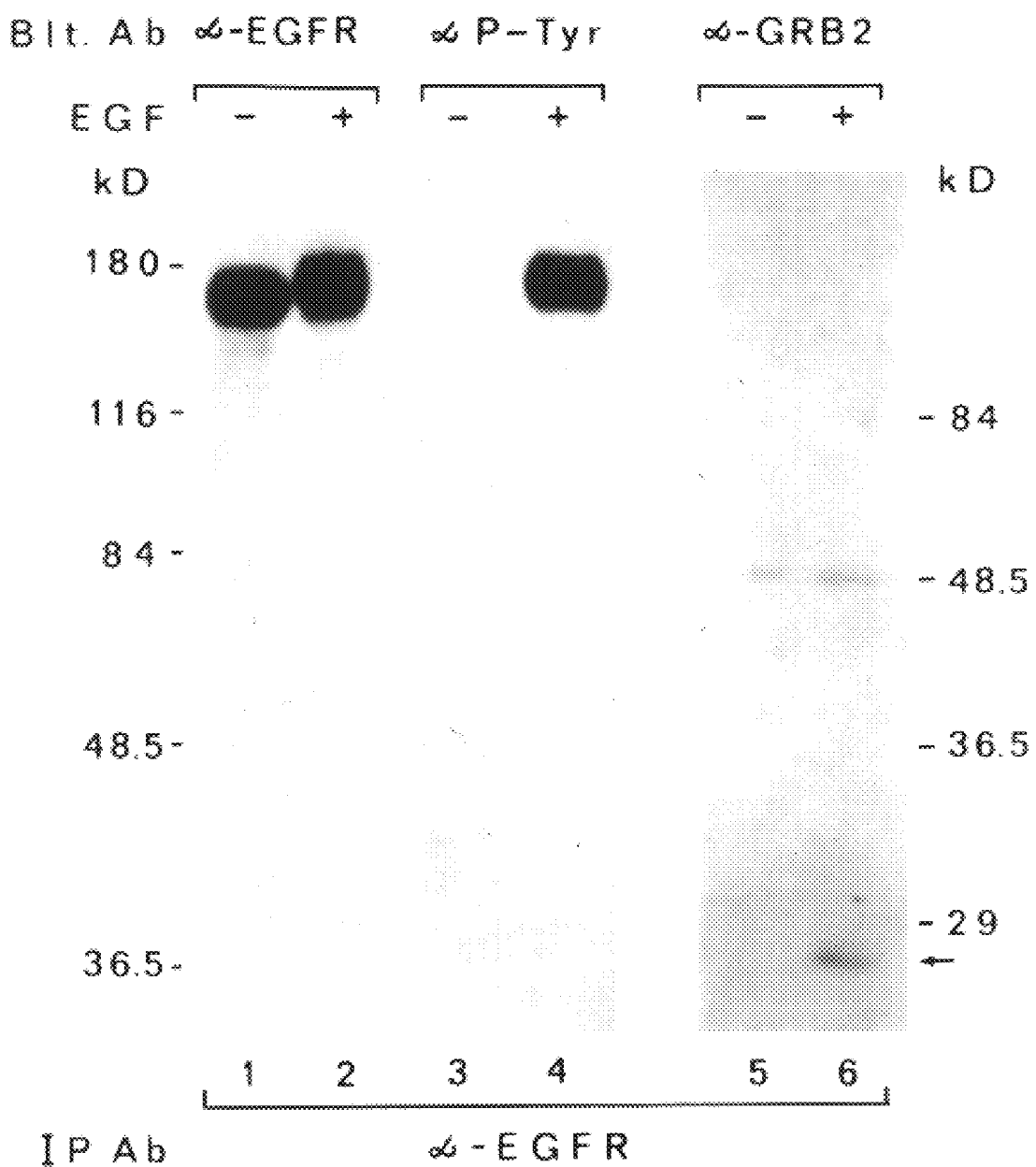
FIG. 28 shows the association of endogenous GRB2 with EGFR in HER14 cells. HER14 cells mock treated lanes 1, 3, 5) or EGF treated (lanes 2, 4, 6) were lysed and immunoprecipitated with anti-EGF receptor antibodies (mAb 108), subjected to SDS-PAGE, and after transfer to nitrocellulose, blotted with polyclonal anti-EGFR antibodies (Anti-C) lanes 1 and 2), anti-phosphotyrosine antibodies (lanes 3 and 4), or anti-GRB2 antibodies (Ab86) (lanes 5 and 6). The immunoblots were labeled with $^{125}$I-protein A followed by autoradiography at –70° C. Anti-GRB2 blot were exposed for 24 hrs. Anti-EGFR and antiP-tyr blots were exposed for 16 hrs. The positions of molecular weight markers (sized in kDa) are indicated.

Immunoblotting of anti-EGFR immunoprecipitates with antibodies to GRB-2 demonstrated association of the 25 kDa (GRB-2 protein with activated EGFR (FIG. 28, lane 6). As shown for PLC-$\gamma$, the association between EGFR and GRB2 was strictly dependent upon ligand activation and tyrosine autophosphorylation (FIG. 28, lanes 5 and 6) (Anderson et al. Science 250:979–982 (1990); Margolis et al. Cell 57:1101–1107. 1989, Mol. Cell. Biol. 10:435–441 1990a, EMBO J. 9:4375–4380 1990b; Wahl et al. Proc. Natl. Acad. Sci. USA 86:1568–1572 1989, Meisenhelder Cell 57:1109–1122 1989). Thus, GRB2 associates only with the activated tyrosine phosphorylated EGFR. GRB2 was also demonstrated to have an association with EGFR by inmunoprecipitation of GRB2 followed by immunoblotting with anti EGF-receptor antibodies (data not shown). Similar results were obtained with PDGF receptor; activated PDGF receptor associated with GRB2 in HER14 cells in a growth factor dependent manner.

However, no association between GRB2 and the FGF receptor was detected when similar experiments, using anti GRB2 for immunoprecipitation and anti FGF receptor antibodies for immunoblotting, were performed with cell lines expressing FGF-receptor (Mohammadi et al. Mol. Cell. Biol. 11:5068–5078, 1991).

Interaction of GRB2 with growth factor receptors is mediated via the SH2 domain

It has been shown that SH2 domains mediate the interaction of signalling molecules, such as PLC$\gamma$ or GAP, with tyrosine phosphorylated growth factor receptors (Koch et al. Science 252:668–674 (1991); Heldin et al. Trends in Biol. Sci. 16:450–452 (1991); Margolis et al., Cell Growth and Differentiation 3:73–80 (1992), Margolis et al. Nature 356:71–74,1992). In order to determine whether the interaction between GRB2 and growth factor receptors is mediated via the SH2 domain of GRB2, we constructed bacterial expression vectors which were designed to express GRB2 as well as the various domains of GRB2 as GST-fusion protein (FIG. 4). These fusion proteins were purified by affinity chromatography on glutathione agarose beads (Smith et al. Gene 67:31–40 1988), and subsequently incubated with lysates from EGF- or PDGFtreated HER 14 cells. The ability of the fusion proteins to bind the activated EGF or PDGF receptors was assessed by immunoblotting the washed complexes with either antiphosphotyrosine or anti-receptor antibodies.

Figure 30:
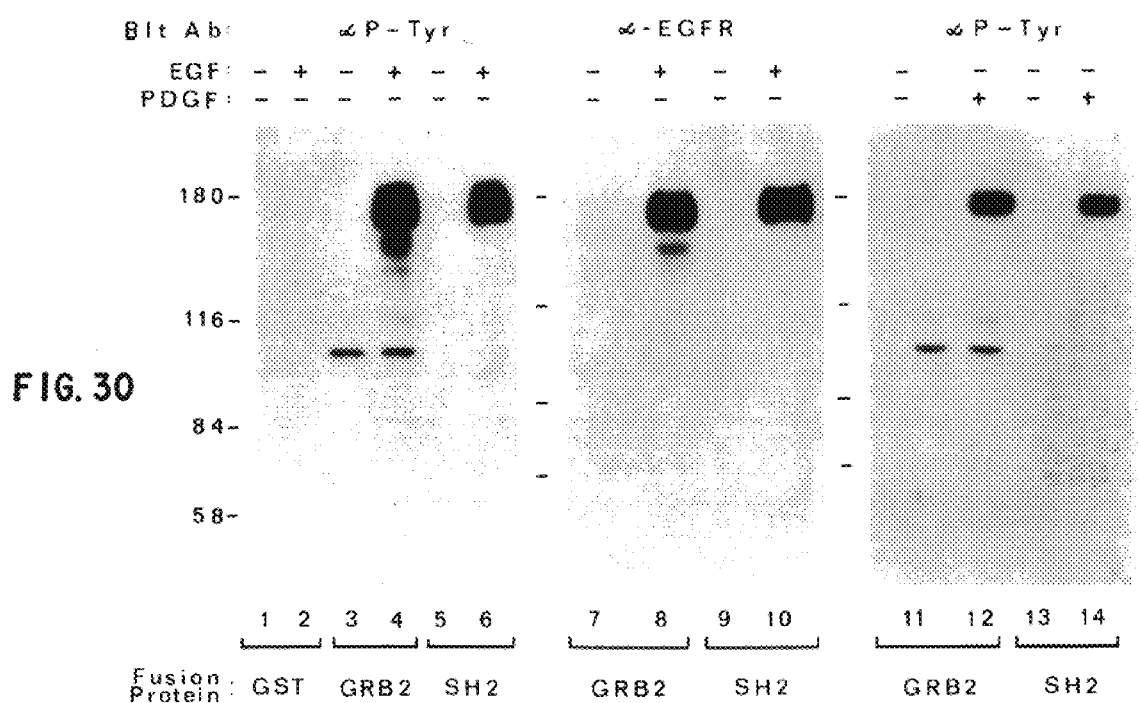
FIG. 30 represents the binding of GST-GRB2 fusion proteins to activated growth factor receptors in vitro. Binding of fusion proteins to the tyrosine phosphorylated proteins (lanes 1 through 6) and EGFR (lanes 7 through 10) in control and EGF stimulated HER14 cell lysates, and tyrosine phosphorylated proteins in control and PDGF stimulated lysates (lanes 11 through 14). Lysates were incubated with equal amounts of fusion proteins immobilized on glutathione-agarose beads. Bound proteins were washed, subjected to SDS-PAGE and immunoblotted with antiphosphotyrosine (lanes 1 through 6, 11 through 14)) or anti EGF-receptor (lanes 7 through 10) antibodies. The immunoblots were labelled with $^{125}$I proteins a followed by autoradiography at –70° C. exposure time 16 hrs. The positions of the molecular weight markers are indicated (sizes in kDA).

Both the full length GRB2 fusion protein and a fusion protein containing only the SH2 domain of GRB2 were each capable of binding tyrosine phosphorylated proteins which comigrated with the activated EGF or PDGF receptors (FIG. 30, lanes 4, 6, 12 and 14). In contrast, neither receptor bound GST alone (FIG. 30, lane 2) nor a GST-fusion protein containing either the amino or carboxy terminal SH3 domains could bind to activated receptors. Binding was ligand dependent, since immunoblotting with anti-EGFR antibodies revealed association of the EGFR with the fusion proteins only when incubated with lysates from growth factor stimulated cells (FIG. 30, lanes 7 through 10). Thus, in agreement with data about other SH2 domain containing proteins, the association between GRB2 and growth factor receptors is mediated by the SH2 domain (Koch et al. Science 252:668–674 1991); Heldin et al., Trends in Biol. Sci. 16:450–452 (1991); Margolis et al., Cell Growth and Differentiation 3:73–80 (1992) and Nature 356:71–74 (1992).

It is noteworthy that the full length GRB2 fusion protein bound several other tyrosine phosphorylated proteins in EGF- and PDGF-stimulated cell lysates (FIG. 30, lanes 3, 4, 11 and 12). While these bound proteins failed to interact with the SH2-GST fusion protein (FIG. 30, lane 6) or either SH3 domain of GRB2 expressed independently, they did interact with a fusion protein containing both the N-terminal SH3 and SH2 domains. The ability of SH3 domain of GRB2 to. enhance the binding activity of the SH2 domain suggests that the N-terminal SH3 domain is important for binding to various cellular proteins and that binding to these proteins may require the concerted action of both SH2 and SH3 domains. GRB2 binds to activated growth factor receptors without being phosphorylated in living cells.

After demonstrating that GRB2 was able to bind to activated EGF and PDGF receptors, we were next interested in determining if GRB2 was a substrate for receptor tyrosine kinases. We examined the capacity of EGF to stimulate phosphorylation of GRB2 in HER14 labelled with ($^{32}$P)-orthophosphate. These cells were treated with EGF, lysed and immunoprecipitated with antibodies to GRB2. While anti-GRB2 antibodies immunoprecipitated GRB2 from ($^{35}$S) methionine labeled cell lysates (FIG. 31, lanes 6 and 8), phosphorylated GRB2 was not detected in the anti-GRB2 immunoprecipitates from orthophosphate labelled cells. Despite marked overexposure of this gel, no detectable band corresponding to GRB2 was evident in the orthophosphate labelled immunoprecipitates. In similar experiments, stimulation of HER14 cells with PDGF also did not result in detectable phosphorylation of GRB2. The failure of detect-phosphorylated GRB2 was not due to poor stimulation of the cells by EGF, since anti-P-Tyr immunoprecipitation of the ($^{32}$Pi)-labeled lysates demonstrated a marked increase in tyrosine phosphorylation of numerous cellular substrates following EGF stimulation. Similarly anti-phosphotyrosine immunoblotting of GRB2 immunoprecipitated from EGF- or PDGF-stimulated HER14 cell lysates, did not reveal tyrosine phosphorylated GRB2 (data not shown).

To determine if the failure to detect tyrosine phosphorylated GRB2 was due to the rapid dephosphorylation by a protein tyrosine phosphatase, a potent tyrosine phosphatase inhibitor, vanadate, was tested for its effects upon GRB2 phosphorylation. ($^{32}$p) orthophosphate-labelled cells were incubated with or without vanadate at 37° C. for 20 min prior to the addition of EGF, and GRB2 phosphorylation was assessed as described above. Vanadate treatment of EGF stimulated cells similarly did not result in detectable GRB2 phosphorylation.

The inability to demonstrate GRB2 phosphorylation was further corroborated in a double immunoprecipitation experiment. ($^{32}$p)-labeled HER 14 lysates were immunoprecipitated with anti-P-Tyr antibodies bound to beads, eluted and the eluates subjected to a second immunoprecipitation with anti-GRB2 antibodies. While clear stimulation of tyrosine phosphorylation was demonstrated in these lysates no significant phosphorylation of the anti-P-Tyr-associated GRB2 fraction was detected. Thus, our data demonstrates that while GRB2 associates with the EGF and PDGF-receptors it is not a good substrate for either receptors, and that GRB2 is not phosphorylated by a tyrosine or serine/threonine kinase acting later in the signaling pathway induced by ligand binding. This data suggests that growth factor regulation of GRB2 is not mediated through GRB2 phosphorylation.

GRB2 tyrosine phosphorylation was detected in 293 cells transiently overexpressing PDGFR and GRB2 as determined by anti-PTyr and anti-GRB2 blotting (data not shown). A shift in the mobility of GRB2 was detected on anti-GRB2 (Ab86) blots, in the presence of activated PDGF receptor and the lower mobility form was shown to be tyrosine phosphorylated by anti-PTyr blotting. Similar experiments have confirmed that the immunoprecipitating antibody (Ab50) will recognize tyrosine phosphorylated GRB2. These data suggest that it is possible to tyrosine phosphorylate GRB2 under conditions of overexpression of both receptor and GRB2 protein.

Figure 31:
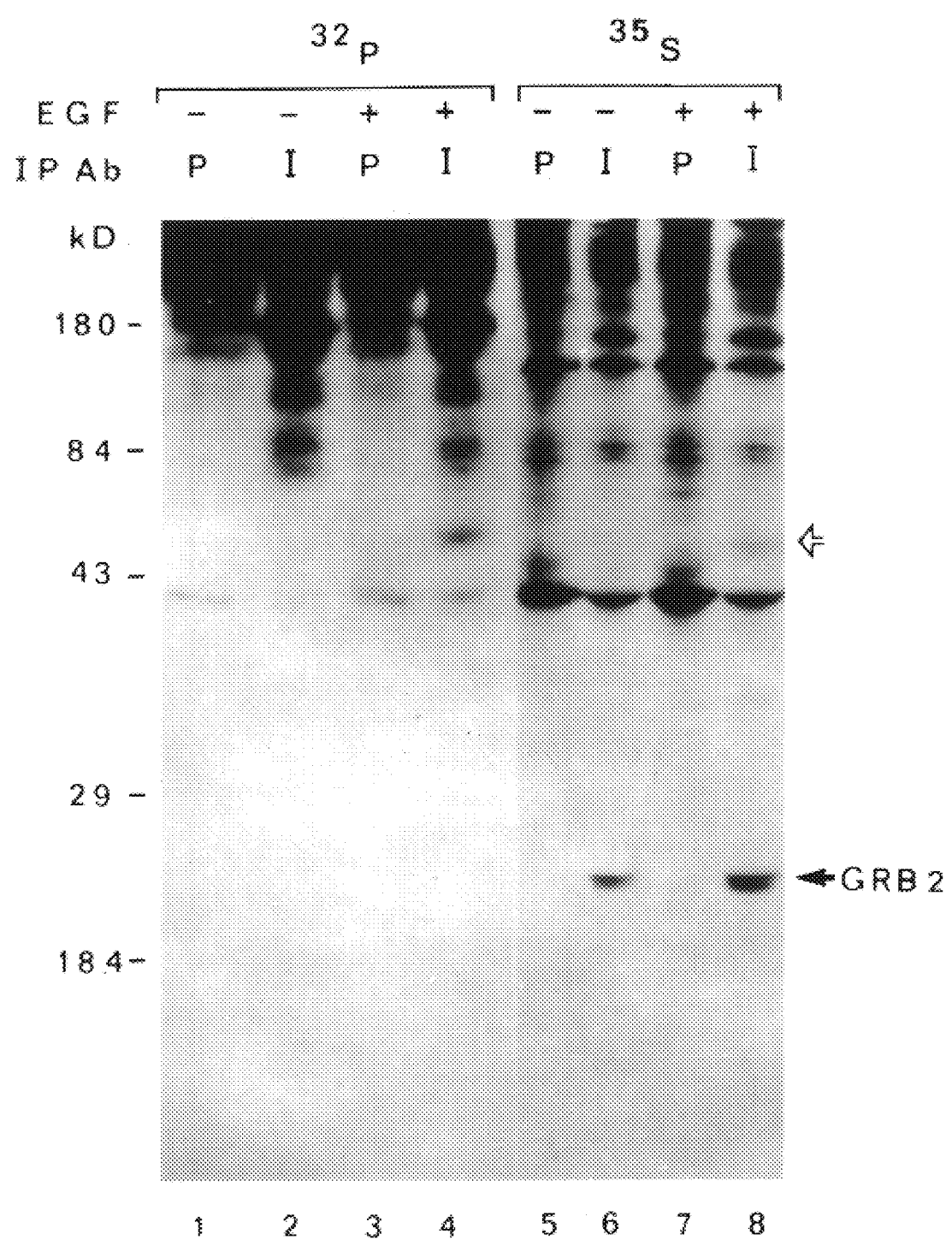
FIG. 31 shows data representing the lack of significant phosphorylation of GRB2 in HER14 cells following stimulation with EGF. ($^{32}$p) orthophosphate (lanes 1 through 4) or ($^{35}$S) methionine (lanes 5 through 8) metabolically labeled HER14 cells were lysed following mocked EGF treatment. The precleared lysates were immunoprecipitated with either preimmune or anti-GRB2 antibodies (Ab50), and subjected to SDS-PAGE and autoradiography. Two hour ($^{32}$P) and two day ($^{35}$S) exposure times are shown. The position of GRB2 and the co-immunoprecipitating 55 kDa phosphoprotein are marked with arrows.

Interestingly, a phosphoprotein of approximately 55 kDa was found to co-immunoprecipitate with GRB2 using immune, but not preimmune sera, in lysates from EGF or PDGF stimulated HER14 cells (FIG. 31, lanes 3, 4 and 7, 8). The association of the 55 kDa protein with GRB2 immunoprecipitates was dependent upon growth factor stimulation, since this interaction was not observed in GRB2 immunoprecipitates from unstimulated cell lysates. The identity of this protein is unknown. GRB2 represents the human homologue of the C. elegans gene product sem-5.

As mentioned earlier, GRB2 is composed of one SH2 domain flanked by two SH3 domains in the order of SH3, SH2, SH3. A C. elegans gene encoding for a protein with similar size and domain order has been cloned in the laboratory of R. Horvitz (Clark et al., 1992). This gene, called sem-5, plays a crucial role in C. elegans development as mutations in sem-5 impair both vulval development and sex myoblast migration. FIG. 32 shows a comparison of the amino acid sequences of GRB2 and sem-5. The N-SH3 domains are 58% (63%) and the C-terminal SH3 domains are 58% identical (60%), respectively. The overall sequence identity (similarity) is 58% (63%). Considering the evolutionary distance between human and nematode, these two genes are very similar suggesting the sem-5 represents the C. elegans homologue of GRB2.

Discussion

A novel EGF receptor binding protein of the present invention was cloned by the CORT expression cloning method of the present invention, designated as GRB2. This 25 kDa protein contains on SH2 domain and two SH3 domains. GRB2 is widely expressed, as determined by Northern analysis in ten different murine tissues. It is also expressed in every human, monkey and murine cell line tested, as revealed by Northern blotting, immunoprecipitation and immunoblotting experiments. Also shown is that GRB2 associates with EGF and PDGF receptors in a ligand-dependent manner, both in vitro and in living cells. Like other SH2-domain containing proteins, the association between GRB2 and growth factor receptors is mediated by the SH2 domain, can be dependent upon receptor tyrosine autophosphorylation, and involves a direct interaction between GRB2 and the tyrosine phosphorylated receptors.

Despite the fact that GRB2 forms stable complexes with tyrosine phosphorylated, on tyrosine, serine, or threonine residues at physiologic levels of expression to any significant extent. The fact that pretreatment of cells with vanadate did not increase GRB2 phosphorylation indicates that GRB2 is not rapidly dephosphorylated by tyrosine phosphatases.

The extent of sequence homology between GRB2 and sem-5 is striking considering the evolutionary distance between nematode and man. The 58% sequence identity (63% similarity) and the conserved overall architecture of these two proteins suggest that sem-5 and C. elegans homologue of GRB2 or a closely related member of the same gene family. The similarity between GRB2 and sem-5 is higher than the similarity between let-23 and EGFR; approximately 44% and 28.7% sequence similarities in the catalytic kinase and ligand binding domain, respectively (Aroian et al. Nature 348:693–699 1990).

Figure 33:
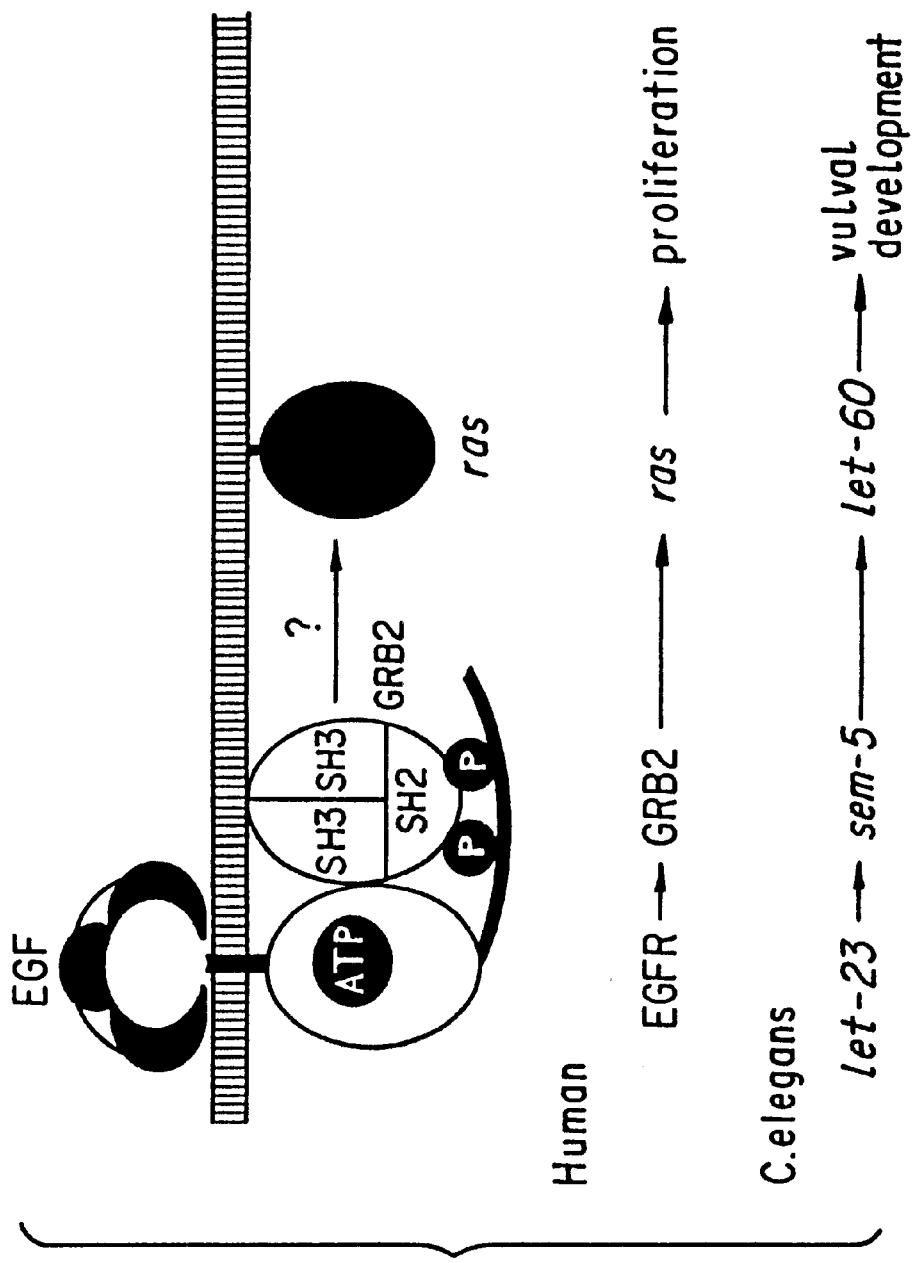
FIG. 33 is a representation showing a model for the interaction between EGF receptor and GRB2 and their *C. elegans* counterparts. Tyrosine autophosphorylated EGFR (or let-23) binds to the SH2 domain of GRB2 (or sem-5).

By detailed genetic studies, the laboratories of Horvitz and Sternberg have identified gene crucial for C. elegans vulval development and sex myoblast migration (Horvitz and Sternberg Nature 351:535–341, 1991; Aroian et al. Nature 348:693–699, 1990). It was shown that mutation sin let-23 (EGFR like), sem-5 (GRB2) or let-60 (ras like) lead to defects in vulval development, while sem-5 also functions in sex myoblast migration. It was therefore proposed that the products of these genes lie along the same signal transduction pathway crucial for normal vulval development. Hence, on the basis of genetic studies of C. elegans (Horvitz and Sternberg Nature 351:535–541; Aroian et al. Nature 348:693–699), previous studies on growth factor receptors (Ullrich and Schlessinger Cell 61:203–211 (1990)) and the results presented in this report it is possible to propose a model for the information flow and interaction among these proteins in *C. elegans* and mammalian cells (FIG. 33). Because of the similarity of sem-5 with GRB2 and let-23 with the EGFR it is likely that sem-5 with GRB2 35 and let-23 with the EGFR it is likely that sem-5 will bind tyrosine phosphorylated let-23 via its SH2 domain according to the scheme presented in FIG. 8. Since situations in let-60 cause a similar phenotype as mutations in either let-23 and Sem-5, and since activated ras can rescue let-23 and sem-5 mutations, it is reasonable to assume the let-60/ras functions downstream from EGFR and GRB2 and that GRB2 is somehow involved in regulation of ras activity. In this regard, the 55 kDa phosphoprotein which binds to GRB2 in response to growth factor stimulation is expected to be a downstream signaling molecule regulated upon GRB2 binding to activated growth factor receptors.

EXAMPLE VIII

Utilization of an Alternative Phage Library Expression System For Detecting Proteins of the Present Invention A T7 phage library expression system, used an alternative to the phage λgtil system described in Example II above, was used to express tyrosine kinase target proteins, as presented in the above Examples, with modifications as described below. A T7 polymerase system (Palazzalo et al., Gene 88, 25 (1990); λEXlox vector, Novagen, Inc.), based on the PET expression systems of Studier and coworkers (Studier et al Meth. Enzymol. 185:60 (1990)) fusing CDNA clones to a fragment of the T7 capsid protein T10 under the control of the T7 promoter. These phages were then used to infect *E. coli* harboring the T7 polymerase under lacUV5 control. Induction with IPTG generated the T7 polymerase which then initiated transcription of the fusion protein encoded by the phage library. The SH2 domain fragment of PLC-γ was incorporated into this phage and analyzed the binding of the phosphorylated EGFR, as described in the above Examples. The DNA fragment containing the human PLC-γ1 (Burgess et al., Mol. Cell. Biol. 10, 4770 (1990)) was amplified by PCT with primers that incorporated EcoRl sites such that the PLC-γ1 fragment would be in the correct reading frame for λgtll. The amplified DNA was cut with EcoRl and ligated into EcoRl digested λgtll DNA (Promega). After packaging (Gigapack, Stragene), the phages were plated and screened with PLC-γ1 antibody using known techniques (Huynh, T. V. et al. In: DNA CLONING, ed. Glover, IRL Press, Oxford, 1:49–78 (1985)). This phage was then tested for binding to a cyanogen bromide generated fragment from $^{32}$-ATP labelled EGFR as described in the above Examples. An identical approach was taken to clone the two SH2 domains into λgtll or λEXlox vectors.

Figure 25A:
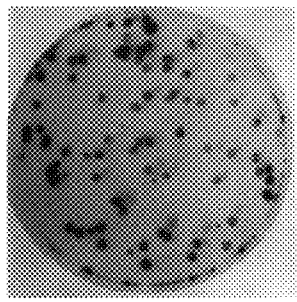
FIGS. 25A–25C is a comparison of binding of the phosphorylated EGFR carboxy-terminus to PLC-g fragments expressed in a λ.gtll or T7 polymerase based library.
Figure 25B:
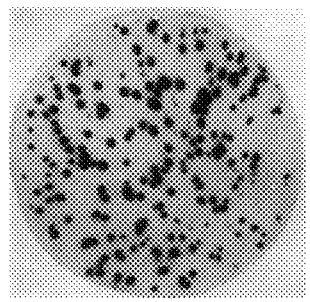
Figure 25C:
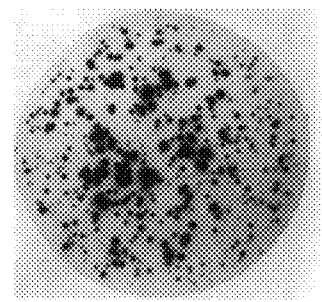

As can be seen in FIGS. 25A–C, uniform binding of the EGFR was seen in the that appeared stronger than was seen with the λgtll system (compare FIGS. 25A and 25B). We also cloned in a longer fragment which ran from 532–1290 of PLCγ1 and this was also easily seen in the T7 system (FIG. 25C). The T7 plaques although mostly smaller than the λgtll plaques gave stronger signals. This makes this system particularly suitable for library screening when there as thousands of small plaques per plate. The major advantage of this system is the high level of protein expression due to the greater activity of the T7 polymerase versus *E. coli* RNA polymerase. It may also be that the fusion proteins using the smaller T10 gene fragment (26 kd versus the 110 kd β-galactosidase of λgtll) yields more stable expression and that its hydrophobic character promotes binding to nitrocellulose. In addition to directional cloning, the λEXlox phages also allow for automatic conversion to a PET plasmid (Palazzalo et al., Gene 88, 25 (1990)) which can be useful for expression of a fusion protein for antibody production. Accordingly, screening an T7 expression library is expected to give superior results than for λ.gt11 for such a cloning strategy of the present invention.

Of 1.6 million clones of a directional oligo dT primed mouse T7 (λEXlox) library screened, nine positive clones were obtained. The library from a 16 day mouse embryo was obtained from Novagen. The library was plated at 40,000 phages per plate in *E. coli* pLysS according to known methods. After growth for 8 hours, plates were covered with-nitrocellulose impregnated with 1 mM IPTG. Plates were grown overnight and the filters probed as described in the above Examples. Positive clones were selected and reprobed until plaques were purified. Phages were then converted to plasmids utilizing the bacterial strain Bm25.5 per manufacturer's instruction. These plasmids were used to transform bacterial strain DH5α and the resultant plasmids subjected to double stranded sequencing using known techniques (Sequenase Version 2.0, U.S. Biochemical). Six of nine clones encoded proteins that were similar or identical to other known genes which contained SH2 domains TABLE I, below. The comparison of two of these protein sequences of the present invention, GRB-3 and GRB-4, to their known counterparts is displayed in FIGS. 17 and 18. Partial sequence of three clones revealed that they were closely related to the avian oncogene v-crk. GRB-3 has a high degree of identity with v-crk beginning with the methionine at residue 32 and this methionine has been found to be the start site of avian c-crk. In the sequence carboxy-terminus to this methionine, there is 77% amino acid homology (FIG. 17) and 80% DNA similarity between v-crk and GRB-3. GRB-4, was similar to nck (FIG. 18), a human protein composed of three SH3 domains and one SH2 domain. Our clone contained one SH3 domain and one SH2 domain and was 74% identical at the protein level and 66% similar at the DNA level in the open reading frame. We also cloned two SH2 domain proteins with intrinsic enzymatic activity.

TABLE I

| SH2 DOMAIN PROTEIN | CLONES ISOLATED | DESCRIPTION |
| --- | --- | --- |
| GRB-3 | #19, #76, #80 | crk-like |
| GRB-4 | #64 | nck-like |
| GRB-5 | #63B | fyn |
| GRB-6 | #88 | PLC-γ1 |
| GRB-7 | #63A, #66, #88 | novel protein |

A remaining clone encoded a new protein with a unique SH2 domain as GRB-7. To obtain a full length DNA clone, the T7 (λEXlox) library was plated in an *E. coli* strain without T7 polymerase gene and routine DNA hybridization performed with a 700 base pair EcoRl fragment from the GRB-7 clone using standard published techniques (Ausubel et al eds., Current Protocols in molecular Biology, Wiley Interscience, New York, (1987, 1992)). Several overlapping clones were identified which were used for DNA sequencing to obtain the full length GRB-7 protein sequence shown in FIG. 19. A schematic representation of GRB-7 is displayed in FIG. 20 depicting the regions of similarity to known proteins as discussed below. The protein is 535 amino acids in length and has one SH2 domain at its extreme carboxy-terminus. In FIG. 21, the SH2 domain of GRB-7 is compared to other SH2 domains including mouse fyn, human PLC-γ1 and the crk and nck-like proteins we cloned in this project. One interesting aspect is that GRB-1 has an isoleucine at amino acid 448, whereas other SH2 domains have a leucine at this position. To look for other protein motifs in GRB-7, a sequence of 433 amino acids from GRB-7 which excluded the SH2 domain was used to scan the Swissprot and GenEmbl databases, as described herein. Amino acids 242 to 339 of GRB-7, showed similarity to a sequence from the central region of ras GAP. Over this region of 91 amino acids from ras GAP, GRB-7 has 26%, identity and 42% similarity allowing for conservative substitutions (FIG. 22). This region of ras GAP lies between the SH2/SH3 domains and he GTPase activating carboxyterminal region and has not been assigned a specific function. The amino-terminal sequence of GRB-7 was found to be proline rich and thus has similarity to many other proline rich proteins. GRB-7 does have an extended region of limited similarity to the catalytic domain of protein phosphatase 2B including this proline rich region (FIG. 23) but no significant similarity was found to other serine/threonine phosphatase such as protein phosphatase 1 or 2A.

Figure 24:
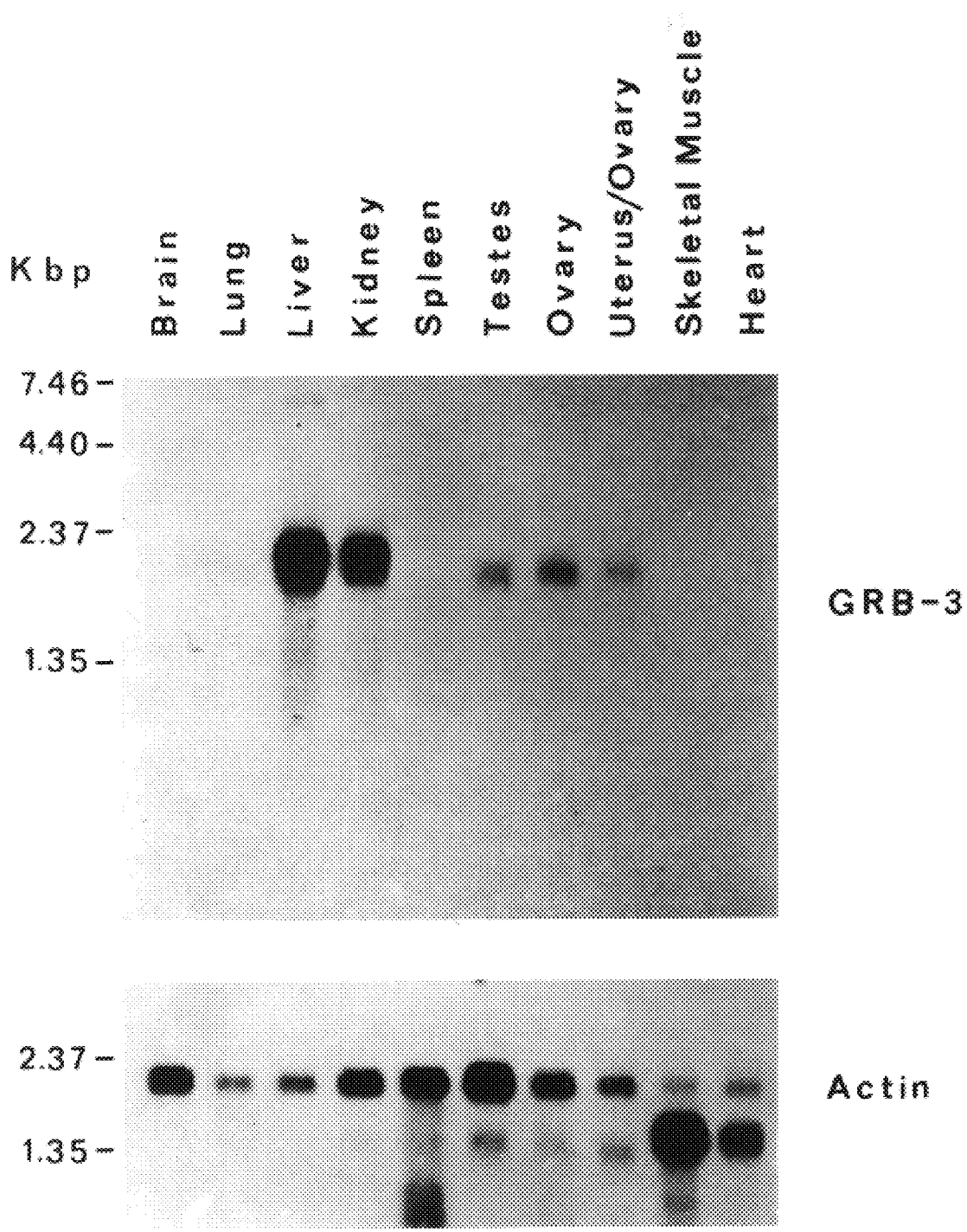
FIG. 24 is a representation of a Northern blot analysis of GRB-7 mRNA.

A northern blot of GRB-7 in mouse tissues is presented in FIG. 24. Oligo dt selected mRNA was probed with the same EcoR1 fragment used to isolate full length GRB-7. See Ausubel et al eds., Current Protocols in Molecular Wiley Interscience, New York, (1987, 1992) and Sap et al Proc. Natl. Acad. Sci. USA 87:6112 (1990). The mRNA was extracted from six week old mice tissues by known methods, e.g., as described by Sap et al., Proc. Natl. Acad. Sci. USA 87:6112 (1990). Approximately 3 μg was run on a 1.2%, agarose formaldehyde gel and blotted to nytran (Schleicher and Scheull). The blot was probed with a DNA fragment that encodes amino acids 297 to 515 and labelled with $^{32}$p-dCTP using a random priming labeling kit (U.S. Biochemical). Blots were probed in 0.5 M sodium phosphate, pH 7.2, 7% sodium dodecyl sulfate and 1 mM EDTA at 65° C. overnight. Blots were washed in 40 mM sodium phosphate, pH 7.2, 1% SDS and 1 mM EDTA at 65° C. After exposure of the GRB-7 blot for 4 days, blots were stripped and reprobed with actin (exposure 36 hours). The highest signal was detected in liver and kidney, but was also detected in ovary and testes. On longer exposure, a weak signal was detected in lung.

EXAMPLE IX

Cloning of the GRB-10 gene via the CORT method

The following Example IX presents the cloning, via the CORT method, and characterization of the GRB- gene. As demonstrated herein, the GRB-10 gene exhibits a high level of homology to the GRB-7 gene. Such homology indicates that GRB-10 and GRB-7 represent a family of genes likely to have overlapping functions.

GRB-10 was cloned from a λlEXlox NIH 3T3 (mouse fibroblast cell line) using the CORT technique, as described in the Detailed Description of the Preferred Embodiments, above. The probe utiized was the EGF-Receptor carboxyterminus. The randomly primed NIH 3T3 library was generated using standard techniques (Sambrook et al. 1989, Molecular Cloning: A Laboratory Manual, Cold Spring Harbor Laboratory Press, Cold Spring Harbor). After the initial clone was isolated, GRB-10 cDNA encoding the full length GRB-10 protein was cloned from the same library using DNA hybridization as described, above, in the Detailed Description of the Preferred Embodiments. The cDNA sequence is presented in FIGS. 37A–37C and the protein sequence in FIG. 38. FIG. 39 combines protein and cDNA data. The GRB-10 protein is highly related to the GRB-7 protein with an overall amino acid identity of 51% (FIGS. 40A-40B).

The major regions of similarity are schematically depicted in FIG. 41 and primarily consist of the carboxyterminal SH2 domain and a larger central domain. They also share a common central domain of approximately 330 amino acids with an identity of 54%. The central domain is also found in one other protein in the Genbank database. This gene, know as F10E9.6, was identified by the *Caenorhabditis Elegans* genome sequencing project during sequencing of *C. Elegans* chromosome III. It is noteworthy that F10E9.6 does not contain an SH2 domain but does not contain a proline rich domain as do GRB-7 and GRB-10.

The amino acid alingnment of the GRB-10 SH2 domain with SH2 domains from GRB-7, GRB-2 and c-SRC is show in FIG. 42. FIG. 43 displays the amino acid alignment of the central domains and includes a domain found in the *Caenorhabditis Elegans* gene, F10E9.6, a gene identified by the *C. Elegans* genome sequencing project (Sulston et al. 1992, Nature 356: 37–41). This *C. Elegans* gene is also schematically depicted in FIG. 41. The central domains of GRB-7 and F10E9.6. This region spans approximately 330 amino acids, with an identity of 28% and similarity of 38%, and covers a region that includes a puntative pleckstrin domain (Mayer, B. J. et al., 1993, Cell 73:629–630), which it has been suggested, may function as a protein binding domain.

Northern analysis of RNA from mouse tissues reveal mRNA for GRB-10 in brain, heart, kidney, and lung (FIG. 44). Three cell lines were tested for GRB-10 messenger RNA but GRB-10 mRNA was found only in NIH 3T3 cells. Poly (A)$^+$ RNA was extracted from tissues and cells with SDS and proteinase K and directly purified by oligo (dT)-cellulose chromatography as described (Vennstrom et al., 1982, Cell 28:135–143). Two micrograms of mRNA was electrophoresed on a 1% formaldehyde/agarose gel and transferred to Nytran overnight in 10× SSC. As indicated, certain lanes contain total RNA rather than mRNA. The blot was probed with a $^{32}$P-dCTP labeled fragment of GRB-10. The membrane was subject to prehybridization (4 hours) and hybridizaton (overnight) in the Church buffer (7% SDS, 1% BSA, 1 mM EDTA, 250 mM Na$_2$HPO$_4$, pH 7.2) at 60° C. The next day, the blots were washed with high stringency buffer (40 mM sodium phosphate, pH 7.2, 1% SDS, 1 mM EDTA) at 60° C. To control for RNA quantity, the blot was stripped and reprobed with actin (bottom). The mRNA from lung was degraded but GRB-10 message could be detected in total RNA. Using antibodies, the GRB-10 protein is also detected in NIH 3T3 fibroblast cells, rat L6 skeletal muscle cells, rate mesangial cells and dog kidney MDCK eithelial cells.

The spatial expression pattern of GRB-10 contrasts with that seen for GRB-7, with GRB-7 found only in liver, kidney and testes. The results indicate that GRB-7 and GRB-10 represent a family of genes that are likely to have overlapping functions but individual patterns of expression.

EXAMPLE X

Screening assay for the identification of Compounds that disrupt protein/tyrosine kinase interactions The Example presented herein describes a means for assessing the potential of a test substance to inhibit the interaction between an adaptor protein and an activated tyrosine kinase molecule. Compounds identified herein may be capable of modulating cell growth control, and may also be capable of regulating oncogenesis. "Adaptor protein", as described herein, refers to a protein comprising one or more SH2 and/or one or more SH3 non-catalytic peptide domains. Such adaptor proteins include, for example, SHC, ISGF3α, and members of the GRB subfamily of proteins, such as those described herein.

In this assay, an adaptor-GST fusion protein capable of binding to a phosphorylated tyrosine kinase protein is incubated with the phosphorylated tyrosine kinase protein, which has been immobilized on a solid phase, in the presence of a test substance. When the test substance is capable of inhibiting the interaction between the adaptor protein-GST fusion protein and the tyrosine kinase molecule, it causes a detectable decrease in the amount of adaptor-GST fusion protein bound to the immobilized tyrosine kinase molecule, relative to the amount of adaptor-GST fusion protein bound to the tyrosine kinase molecule in the absence of the test substance.

This example is illustrated in detail for the screening of inhibitors of the interaction between GRB-2 and EGF-R. The same principles can be applied, however, to the detection of inhibitors of the interaction between any tyrosine kinase protein or tyrosine phosphorylated substrates of tyrosine kinases (e.g., SHC, Phosphatase 1D) and any adaptor protein with which it interacts.

Adaptor-GST fusion protein

The adaptor-GST (glutathione-S-transferase) fusion proteins used herein were GRB-2-GST fusion proteins prepared by expression in $E.\ coli$ transformed with GRB-2/pGEX constructs. The GRB-2 portions of these fusion proteins consisted of only the SH2 domain of the GRB-2 protein. Transformed cells are grown in Luria broth (LB) supplemented with ampicillin. After reaching an optical density (OD) at 600 nm of 0.3, the cells are induced for 6 hours with isopropyl β-D-thiogalactopyranoside (IPTG) in order to express the fusion protein.

After the 6 hour expression period, the cells are precipitated, pelleted at 10,000× g for 10 minutes at 4° C., washed, and resuspended in phosphate buffered saline (PBS). Next, the cells are lysed by sonication (6 strokes, 5 seconds per stroke). Insoluble material is removed by centrifugation at 10,000× g for 10 minutes at 4° C., and the supernatant is passed over a Glutathion-Sepharose column. Bound GRB-2-GST fusion protein is eluted off the column with 5 mM reduced glutathion, then dialyzed against PBS.

Immobilized tyrosine kinase molecule

The tyrosine kinase molecule used herein is the epidermal growth factor receptor tyrosine kinase (EGF-R). EGF-R is isolated from cells overexpressing EGF-R, such as the A431 (ATCC CRL 1551), cell line. The cells are lysed in HNTG buffer (20 mM Hepes/HCl, pH 7.4, 150 mM NaCl, 1.0% Triton X-100, 5% glycerol, 1 mM phenylmethylsulfonyl fluoride (PMSF), 1 mg/L aprotonin, 1 mg/L leupeptin, 10 mg/L benzamidine).

EGF-R protein is isolated from the cell lysates by immobilization onto microtiter plates, as described below. EGF-R is subsequently phosphorylated in vitro as explained below.

The EGF-R molecule is immobilized onto microtiter plates. Microtiter plates are prepared by first coating the wells of the plate, overnight at 4° C., with an anti-EGF-R monoclonal antibody directed against the extracellular domain of EGFR (UBI, #05-101) at a concentration of 0.5 μg (in PBS) per microtiter well, at a final volume of 150 μl per well.

After overnight coating, the coating solution is removed from the microtiter wells, and replaced with blocking buffer (5% dry milk in PBS) for 30 minutes at room temperature, after which the blocking buffer is removed and the wells are washed 4 times with TBST buffer (150 mM NaCl, 50 mM Tris-HCl, pH 7.2, 0.1% Triton X-100).

Cell lysate from EGF-R-expressing cells is added to each well, in 150 μl of PBS, incubated 30 minutes at room temperature, with shaking. Unbound EGF-R is removed by washing wells 5 times with TBST buffer. Approximately 50–100 ng of EGF-R protein is bound per well.

It is important to use an EGF-R overexpressing cell line which exhibits a high endogenous phosphatase activity, such as, for example, the A431 cell line. This is because during lysis and incubation with the immobilized antibody, the phosphatases remove phosphate groups from the EGF-R molecules, thus prohibiting endogenous adaptor proteins, such as GRB proteins, to bind EGFR, which could potentially lead to artifactual results. Alternatively, cells may be starved before lysis, if the cell line utilized may be readily starved.

Preparation of autophophorylated EGF-R

The following in vitro kinase reaction yielded autophosphorylated EGF-R. The kinase reaction was initiated by the addition of 15 μl of ATP/Mn$^2$+ mix (in 50 mM MnCl$_2$, final concentration of 10 μM ATP, for a total volume of 150 μl. The plate was incubated for 5 minutes at room temperature, shaking, the supernatent was aspirated, and the plates were then washed 5 times with TBST.

Assay procedure

Either 30 ng GRB-2-GST fusion proteins (i.e. a 1:1 ratio of EGF-R:GRB-2 proteins) or 5 ng GRB-2-GST fusion proteins (i.e. a 4:1 ratio of EGF-R:GRB-2 proteins) are added to the phosphorylated EGF-R coated microtiter wells in incubation buffer (0.1 M potassium phosphate buffer, pH 6.5) for 30 minutes, at room temperature, in the presence of a test substance dissolved in dimethyl sulfoxide (DMSO). Control wells are incubated with GRB-2-GST fusion proteins in the absence of test substance.

After incubation, wells are washed extensively with TBST. The amount of GRB-2-GST fusion protein bound to the immobilized EGF-R is then preferably determined by with a purified rabbit antiserum against the GST-moiety of the fusion protein (AMRAD, New Victoria, Australia; Catalog No. 00001605). Incubations are for 30 minutes at room temperature. After incubation, antibody is removed and the wells are washed extensively with TBST. For visualization, wells are next incubated with a TAGO goat-anti-rabbit peroxidase antibody at room temperature for 30 minutes. After incubation, the antibody is removed, the wells are washed with tap water, and then with TBST. Substrate solution, ABTS (2,2'-Azinobis(3-ethylbenzthiazolinesulfonic acid)/H$_2$O$_2$ (1.2 μl H$_2$O$_2$ to 10 ml ABTS) is applied to the wells, and incubated for 20 minutes at room temperature. The reaction is stopped by addition of 5NH$_2$SO$_4$. The O.D. at 410 nm is determined for each well. Utilizing this technique, it is possible to detect as little as 2 ng GRB-2-GST over background.

Alternatively, after incubation of the test substance and the GRB-2-GST fusion protein on the EGF-R wells, biotinylated monoclonal antibodies e.g., L-6 or EL-12, may be utilized to assay fusion protein binding. The epitopes recognized by such antibodies map on the SH2 domain of GRB-2, but do not interfere with GRB-2 binding to phosphorylated EGFR. Binding of these antibodies is then determined by using a streptavidin-biotinylated horseradish peroxidase reactant.

Additionally, after incubation of the test substance and the GRB-2-GST fusion protein on the EGF-R wells, binding of the fusion protein to the immobilized EGFR may be assayed by incubating with 1 mM 1-chloro-2,4 dinitrobenzene (CDNB) and 1.54 mg/ml reduced glutathion in incubation buffer. The OD is then measured at 340 nm. This reaction is linear up to OD 1.0, and can be stopped with competitive GST inhibitors, as described in Mannervik and Danielson (Mannervik, B. and Danielson, U. H., 1988, CRC Critical Reviews in Biochemistry 23:238).

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the generic concept of the present invention. Therefore, such adaptations and modifications are intended to be comprehended within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein.

SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
        (A) LENGTH: 3372 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:1:

```
TACAACCAGG CTCAACTGTT GCATGGTAGC AGATTTGCAA ACATGAGTGC TGAGGGGTAC      60

CAGTACAGAG CGCTGTATGA TTATAAAAAG GAAAGAGAAG AAGATATTGA CTTGCACTTG     120

GGTGACATAT TGACTGTGAA TAAAGGGTCC TTAGTAGCTC TTGGATTCAG TGATGGACAG     180

GAAGCCAGGC CTGAAGAAAT TGGCTGGTTA AATGGCTATA ATGAAACCAC AGGGGAAAGG     240

GGGGACTTTC CGGGAACTTA CGTAGAATAT ATTGGAAGGA AAAAAATCTC GCCTCCCACA     300

CCAAAGCCCC GGCCACCTCG GCCTCTTCCT GTTGCACCAG GTTCTTCGAA AACTGAAGCA     360

GATGTTGAAC AACAAGCTTT GACTCTCCCG GATCTTGCAG AGCAGTTTGC CCCTCCTGAC     420

ATTGCCCCGC CTCTTCTTAT CAAGCTCGTG GAAGCCATTG AAAAGAAAGG TCTGGAATGT     480

TCAACTCTAT ACAGAACACA GAGCTCCAGC AACCTGGCAG AATTACGACA GCTTCTTGAT     540

TGTGATACAC CCTCCGTGGA CTTGGAAATG ATCGATGTGC ACGTTTTGGC TGACGCTTTC     600

AAACGCTATC TCCTGGACTT ACCAAATCCT GTCATTCCAG CAGCCGTTTA CAGTGAAATG     660

ATTTCTTTAG CTCCAGAAGT ACAAAGCTCC GAAGAATATA TTCAGCTATT GAAGAAGCTT     720

ATTAGGTCGC CTAGCATACC TCATCAGTAT TGGCTTACGC TTCAGTATTT GTTAAAACAT     780

TTCTTCAAGC TCTCTCAAAC GTCCAGCAAA AATCTGTTGA ATGCAAGAGT ACTCTCTGAA     840

ATTTTCAGCC CTATGCTTTT CAGATTCTCA GCAGCCAGCT CTGATAATAC TGAAAACCTC     900

ATAAAAGTTA TAGAAATTTT AATCTCAACT GAATGGAATG AACGACAGCC TGCACCAGCA     960

CTGCCTCCTA AACCACCAAA ACCTACTACT GTAGCCAACA ACGGTATGAA TAACAATATG    1020

TCCTTACAAA ATGCTGAATG GTACTGGGGA GATATCTCGA GGGAAGAAGT GAATGAAAAA    1080
```

```
CTTCGAGATA CAGCAGACGG GACCTTTTTG GTACGAGATG CGTCTACTAA AATGCATGGT    1140

GATTATACTC TTACACTAAG GAAAGGGGGA AATAACAAAT TAATCAAAAT ATTTCATCGA    1200

GATGGGAAAT ATGGCTTCTC TGACCCATTA ACCTTCAGTT CTGTGGTTGA ATTAATAAAC    1260

CACTACCGGA ATGAATCTCT AGCTCAGTAT AATCCCAAAT TGGATGTGAA ATTACTTTAT    1320

CCAGTATCCA AATACCAACA GGATCAAGTT GTCAAAGAAG ATAATATTGA AGCTGTAGGG    1380

AAAAAATTAC ATGAATATAA CACTCAGTTT CAAGAAAAAA GTCGAGAATA TGATAGATTA    1440

TATGAAGAAT ATACCCGCAC ATCCCAGGAA ATCCAAATGA AAGGACAGC TATTGAAGCA     1500

TTTAATGAAA CCATAAAAAT ATTTGAAGAA CAGTGCCAGA CCCAAGAGCG GTACAGCAAA    1560

GAATACATAG AAAAGTTTAA ACGTGAAGGC AATGAGAAAG AAATACAAAG GATTATGCAT    1620

AATTATGATA AGTTGAAGTC TCGAATCAGT GAAATTATTG ACAGTAGAAG AAGATTGGAA    1680

GAAGACTTGA AGAAGCAGGC AGCTGAGTAT CGAGAAATTG ACAAACGTAT GAACAGCATT    1740

AAACCAGACC TTATCCAGCT GAGAAAGACG AGAGACCAAT ACTTGATGTG GTTGACTCAA    1800

AAAGGTGTTC GGCAAAAGAA GTTGAACGAG TGGTTGGGCA ATGAAAACAC TGAAGACCAA    1860

TATTCACTGG TGGAAGATGA TGAAGATTTG CCCCATCATG ATGAGAAGAC ATGGAATGTT    1920

GGAAGCAGCA ACCGAAACAA AGCTGAAAAC CTGTTGCGAG GGAAGCGAGA TGGCACTTTT    1980

CTTGTCCGGG AGAGCAGTAA ACAGGGCTGC TATGCCTGCT CTGTAGTGGT GGACGGCGAA    2040

GTAAAGCATT GTGTCATAAA CAAAACAGCA ACTGGCTATG GCTTTGCCGA GCCCTATAAC    2100

TTGTACAGCT CTCTGAAAGA ACTGGTGCTA CATTACCAAC ACACCTCCCT TGTGCAGCAC    2160

AACGACTCCC TCAATGTCAC ACTAGCCTAC CCAGTATATG CACAGCAGAG GCGATGAAGC    2220

GCTTACTCTT TGATCCTTCT CCTGAAGTTC AGCCACCCTG AGGCCTCTGG AAAGCAAGG     2280

GCTCCTCTCC AGTCTGATCT GTGAATTGAG CTGCAGAAAC GAAGCCATCT TTCTTTGGAT    2340

GGGACTAGAG CTTTCTTTGA CAAAAAAGAA GTAGGGAAG ACATGCAGCC TAAGGCTGTA     2400

TGATGACCAC ACGTTCCTAA GCTGGAGTGC TTATCCCTTC TTTTTCTTTT TTCTTTGGT     2460

TTAATTTAAA GCCACAACCA CATACAACAC AAAGAGAAAA AGAAATGCAA AAATCTCTGC    2520

GTGCAGGGAC AAAGAGGCCT TTAACCATGG TGCTTGTTAA TGCTTTCTGA AGCTTTACCA    2580

GCTGAAAGTT GGGACTCTGG AGAGCGGAGG AGAGAGAGGC AGAAGAACCC TGGCCTGAGA    2640

AGGTTTGGTC CAGCCTGGTT TAGCCTGGAT GTTGCTGTGC ACGGTGGACC CAGACACATC    2700

GCACTGTGGA TTATTTCATT TTGTAACAAA TGAACGATAT GTAGCAGAAA GGCACGTCCA    2760

CTCACAAGGG ACGCTTTGGG AGAATGTCAG TTCATGTATG TTCAGAAGAA ATTCTGTCAT    2820

AGAAAGTGCC AGAAAGTGTT TAACTTGTCA AAAAACAAAA ACCCAGCAAC AGAAAAATGG    2880

AGTTTGGAAA ACAGGACTTA AAATGACATT CAGTATATAA AATATGTACA TAATATTGGA    2940

TGACTAACTA TCAAATAGAT GGATTTGTAT CAATACCAAA TAGCTTCTGT TTTGTTTGC     3000

TGAAGGCTAA ATTCACAGCG CTATGCAATT CTTAATTTTC ATTAAGTTGT TATTTCAGTT    3060

TTAAATGTAC CTTCAGAATA AGCTTCCCCA CCCCAGTTTT TGTTGCTTGA AAATATTGTT    3120

GTCCCGGATT TTTGTTAATA TTCATTTTTG TTATCCTTTT TTAAAAATAA ATGTACAGGA    3180

TGCCAGTAAA AAAAAAAATG GCTTCAGAAT TAAAACTATG AAATATTTTA CAGTTTTTCT    3240

TGTACAGAGT ACTTGCTGTT AGCCCAAGGT TAAAAAGTTC ATAACAGATT TTTTTGGAC     3300

TGTTTTGTTG GGCAGTGCCT GATAAGCTTC AAAGCTGCTT TATTCAATAA AAAAAAACC    3360

CGAATTCACT GG                                                        3372
```

(2) INFORMATION FOR SEQ ID NO:2:

(i) SEQUENCE CHARACTERISTICS:
        (A) LENGTH: 1072 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:2:

```
GCCAGTGAAT TCGGGGCTC  AGCCCTCCTC  CCTCCCTTCC  CCCTGCTTCA  GGCTGCTGAG     60
CACTGAGCAG CGCTCAGAAT GGAAGCCATC  GCCAAATATG  ACTTCAAAGC  TACTGCAGAC    120
GACGAGCTGA GCTTCAAAAG GGGGGACATC  CTCAAGGTTT  TGAACGAAGA  ATGTGATCAG    180
AACTGGTACA AGGCAGAGCT TAATGGAAAA  GACGGCTTCA  TTCCCAAGAA  CTACATAGAA    240
ATGAAACCAC ATCCGTGGTT TTTTGGCAAA  ATCCCCAGAG  CCAAGGCAGA  AGAAATGCTT    300
AGCAAACAGC GGCACGATGG GGCCTTTCTT  ATCCGAGAGA  GTGAGAGCGC  TCCTGGGGAC    360
TTCTCCCTCT CTGTCAAGTT TGGAAACGAT  GTGCAGCACT  TCAAGGTGCT  CCGAGATGGA    420
GCCGGGAAGT ACTTCCTCTG GGTGGTGAAG  TTCAATTCTT  TGAATGAGCT  GGTGGATTAT    480
CACAGATCTA CATCTGTCTC CAGAAACCAG  CAGATATTCC  TGCGGGACAT  AGAACAGGTG    540
CCACAGCAGC CGACATACGT CCAGGCCCTC  TTTGACTTTG  ATCCCCAGGA  GGATGGAGAG    600
CTGGGCTTCC GCCGGGGAGA TTTTATCCAT  GTCATGGATA  ACTCAGACCC  CAACTGGTGG    660
AAAGGAGCTT GCCACGGGCA GACCGGCATG  TTTCCCCGCA  ATTATGTCAC  CCCCGTGAAC    720
CGGAACGTCT AAGAGTCAAG AAGCAATTAT  TTAAAGAAAG  TGAAAAATGT  AAAACACATA    780
CAAAAGAATT AAACCCACAA GCTGCCTCTG  ACAGCAGCCT  GTGAGGGAGT  GCAGAACACC    840
TGGCCGGGTC ACCCTGTGAC CCTCTCACTT  TGGTTGGAAC  TTTAGGGGGT  GGGAGGGGGC    900
GTTGGATTTA AAAATGCCAA AACTTACCTA  TAAATTAAGA  AGAGTTTTTA  TTACAAATTT    960
TCACTGCTGC TCCTCTTTCC CCTCCTTTGT  CTTTTTTTTC  ATCCTTTTTT  CTCTTCTGTC   1020
CATCAGTGCA TGACGTTTAA GGCCACGTAT  AGTCCTAGCT  GACGCCAATA  AT           1072
```

(2) INFORMATION FOR SEQ ID NO:3:

(i) SEQUENCE CHARACTERISTICS:
        (A) LENGTH: 770 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:3:

```
AGCCTGACAC CGGAGCCGGT  CCGCTGGGCG  CGGGCGCCAG  GGCTGGAGGG  GCGCGCGTGC     60
CGGCGGCGGC CCAGCGTGAA  AGCGCGGAGG  CGGCCATGGC  GGGCAACTTC  GACTCGGAGG    120
AGCGGAGTAG CTGGTACTGG  GGCCGCCTGA  GCCGGCAGGA  GGCGGTGGCG  CTATTGCAGG    180
GCCAGCGCGA CGGGGTGTTC  CTGGTGCGGG  ACTCGAGCAC  CAGCCCCGGG  GACTATGTGC    240
TTAGCGTCTC CGAAAACTCG  CGCGTCTCCC  ACTACATCAT  CAACAGCAGC  GGCCCGCGCC    300
CTCCAGTGCC TCCGTCGCCC  GCTCAGCCTC  CGCCGGGAGT  GAGTCCCTCC  AGGCTCCGAA    360
TAGGAGATCA AGAATTTGAT  TCATTGCCTG  CTTTACTGGA  ATTCTACAAA  ATACACTATT    420
TGGACACTAC AACATTGATA  GAACCAGTGG  CCAGATCAAG  GCAGGGTAGT  GGAGTGATTC    480
TCAGGCAGGA GGAGGCAGAG  TATGTGCGGG  CCCTCTTTGA  CTTTAATGGG  AATGATGAAG    540
```

```
AAGATCTTCC CTTTAAGAAA GGAGACATCC TGAGAATCCG GGATAAGCCT GAAGAGCAGT        600

GGTGGAATGC AGAGGACAGC GAAGGAAAGA GGGGGATGAT TCCTGTCCCT TACGTGGAGA        660

AGTATAGACC TGCCTCCGCC TCAGTATCGG CTCTGATTGG AGGTAACCAG GAGGGTTCCC        720

ACCCACAGCC ACTGGGTGGC CGGAGCCTGG GCCCTATGCC AACCCAGCGT                   770

(2) INFORMATION FOR SEQ ID NO:4:

(i) SEQUENCE CHARACTERISTICS:
        (A) LENGTH: 642 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:4:

GTGATTGAGA AGCCGGAGAA TGACCCTGAA TGGTGGAAAT GCAAAAATGC CCGAGGCCAA         60

GTGGGCCTGG TCCCCAAAAA CTACGTGGTT GTTCTCAGTG ATGGGCCTGC TCTGCACCCC        120

GCTCACACCC CCCAGATCAG CTACACCGGG CCTTCAGCCA GCGGGCGCTT TGCTGGTCGG        180

GAGTGGTACT ATGGCAACGT GACACGGCAC CAGGCCGAGT GTGCGCTCAA TGAGCGGGGC        240

GTCGAGGGCG ACTTCCTCAT TAGGGACAGC GAGTCCTCGC CCAGTGACTT CTCCGTGTCT        300

CTCAAAGCGT CAGGGAGAAA CAAGCACTTC AAGGTGCAGC TGGTGGACAG CGTCTACTGC        360

ATTGGGCAGC GGCGGTTCCA CAGCATGGAC GAGCTTGTGG AGCACTACAA GAAGGCCCCC        420

ATCTTCACCA GCGAGCACGG GGAGAAGCTC TACCTTGTCC GAGCCCTACA GTGAAAGCAG        480

CCATTGGCCC CCTCATGCCC TGCCCACTGT GGGCCTCGCT GCCACCTCTG CCTCCCAGAG        540

CCCAGCACTT CTGGCCACCT CCACCCATGT GGCTTGGATC ACCTCTGTGG CCCAGTCTGT        600

CCTTTCTTTT TCAGCCCTGT TGGTCAACCA CGGCTACCTA GG                           642

(2) INFORMATION FOR SEQ ID NO:5:

(i) SEQUENCE CHARACTERISTICS:
        (A) LENGTH: 724 amino acids
        (B) TYPE: amino acid
        (D) TOPOLOGY: unknown (ii) MOLECULE TYPE: protein (xi) SEQUENCE DESCRIPTION: SEQ ID NO:5:
```

Met Ser Ala Glu Gly Tyr Gln Tyr Arg Ala Leu Tyr Asp Tyr Lys Lys
1               5                   10                  15

Glu Arg Glu Glu Asp Ile Asp Leu His Leu Gly Asp Ile Leu Thr Val
            20                  25                  30

Asn Lys Gly Ser Leu Val Ala Leu Gly Phe Ser Asp Gly Gln Glu Ala
        35                  40                  45

Arg Pro Glu Glu Ile Gly Trp Leu Asn Gly Tyr Asn Glu Thr Thr Gly
    50                  55                  60

Glu Arg Gly Asp Phe Pro Gly Thr Tyr Val Glu Tyr Ile Gly Arg Lys
65                  70                  75                  80

Lys Ile Ser Pro Pro Thr Pro Lys Pro Arg Pro Pro Arg Pro Leu Pro
                85                  90                  95

Val Ala Pro Gly Ser Ser Lys Thr Glu Ala Asp Val Glu Gln Gln Ala
            100                 105                 110

Leu Thr Leu Pro Asp Leu Ala Glu Gln Phe Ala Pro Pro Asp Ile Ala
        115                 120                 125

-continued

```
Pro Pro Leu Leu Ile Lys Leu Val Glu Ala Ile Glu Lys Lys Gly Leu
    130                 135                 140
Glu Cys Ser Thr Leu Tyr Arg Thr Gln Ser Ser Asn Leu Ala Glu
145                 150                 155                 160
Leu Arg Gln Leu Leu Asp Cys Asp Thr Pro Ser Val Asp Leu Glu Met
                165                 170                 175
Ile Asp Val His Val Leu Ala Asp Ala Phe Lys Arg Tyr Leu Leu Asp
            180                 185                 190
Leu Pro Asn Pro Val Ile Pro Ala Ala Val Tyr Ser Glu Met Ile Ser
        195                 200                 205
Leu Ala Pro Glu Val Gln Ser Ser Glu Glu Tyr Ile Gln Leu Leu Lys
    210                 215                 220
Lys Leu Ile Arg Ser Pro Ser Ile Pro His Gln Tyr Trp Leu Thr Leu
225                 230                 235                 240
Gln Tyr Leu Leu Lys His Phe Phe Lys Leu Ser Gln Thr Ser Ser Lys
                245                 250                 255
Asn Leu Leu Asn Ala Arg Val Leu Ser Glu Ile Phe Ser Pro Met Leu
            260                 265                 270
Phe Arg Phe Ser Ala Ala Ser Ser Asp Asn Thr Glu Asn Leu Ile Lys
        275                 280                 285
Val Ile Glu Ile Leu Ile Ser Thr Glu Trp Asn Glu Arg Gln Pro Ala
    290                 295                 300
Pro Ala Leu Pro Pro Lys Pro Pro Lys Pro Thr Thr Val Ala Asn Asn
305                 310                 315                 320
Gly Met Asn Asn Asn Met Ser Leu Gln Asn Ala Glu Trp Tyr Trp Gly
                325                 330                 335
Asp Ile Ser Arg Glu Glu Val Asn Glu Lys Leu Arg Asp Thr Ala Asp
            340                 345                 350
Gly Thr Phe Leu Val Arg Asp Ala Ser Thr Lys Met His Gly Asp Tyr
        355                 360                 365
Thr Leu Thr Leu Arg Lys Gly Gly Asn Asn Lys Leu Ile Lys Ile Phe
    370                 375                 380
His Arg Asp Gly Lys Tyr Gly Phe Ser Asp Pro Leu Thr Phe Ser Ser
385                 390                 395                 400
Val Val Glu Leu Ile Asn His Tyr Arg Asn Glu Ser Leu Ala Gln Tyr
                405                 410                 415
Asn Pro Lys Leu Asp Val Lys Leu Leu Tyr Pro Val Ser Lys Tyr Gln
            420                 425                 430
Gln Asp Gln Val Val Lys Glu Asp Asn Ile Glu Ala Val Gly Lys Lys
        435                 440                 445
Leu His Glu Tyr Asn Thr Gln Phe Gln Glu Lys Ser Arg Glu Tyr Asp
    450                 455                 460
Arg Leu Tyr Glu Glu Tyr Thr Arg Thr Ser Gln Glu Ile Gln Met Lys
465                 470                 475                 480
Arg Thr Ala Ile Glu Ala Phe Asn Glu Thr Ile Lys Ile Phe Glu Glu
                485                 490                 495
Gln Cys Gln Thr Gln Glu Arg Tyr Ser Lys Glu Tyr Ile Glu Lys Phe
            500                 505                 510
Lys Arg Glu Gly Asn Glu Lys Glu Ile Gln Arg Ile Met His Asn Tyr
        515                 520                 525
Asp Lys Leu Lys Ser Arg Ile Ser Glu Ile Ile Asp Ser Arg Arg Arg
    530                 535                 540
```

—continued

```
Leu Glu Glu Asp Leu Lys Lys Gln Ala Ala Glu Tyr Arg Glu Ile Asp
545                 550                 555                 560

Lys Arg Met Asn Ser Ile Lys Pro Asp Leu Ile Gln Leu Arg Lys Thr
                565                 570                 575

Arg Asp Gln Tyr Leu Met Trp Leu Thr Gln Lys Gly Val Arg Gln Lys
                580                 585                 590

Lys Leu Asn Glu Trp Leu Gly Asn Glu Asn Thr Glu Asp Gln Tyr Ser
                595                 600                 605

Leu Val Glu Asp Glu Asp Leu Pro His His Asp Glu Lys Thr Trp
610                 615                 620

Asn Val Gly Ser Ser Asn Arg Asn Lys Ala Glu Asn Leu Leu Arg Gly
625                 630                 635                 640

Lys Arg Asp Gly Thr Phe Leu Val Arg Glu Ser Ser Lys Gln Gly Cys
                645                 650                 655

Tyr Ala Cys Ser Val Val Val Asp Gly Glu Val Lys His Cys Val Ile
                660                 665                 670

Asn Lys Thr Ala Thr Gly Tyr Gly Phe Ala Glu Pro Tyr Asn Leu Tyr
                675                 680                 685

Ser Ser Leu Lys Glu Leu Val Leu His Tyr Gln His Thr Ser Leu Val
690                 695                 700

Gln His Asn Asp Ser Leu Asn Val Thr Leu Ala Tyr Pro Val Tyr Ala
705                 710                 715                 720

Gln Gln Arg Arg (2) INFORMATION FOR SEQ ID NO:6:

(i) SEQUENCE CHARACTERISTICS:
        (A) LENGTH: 217 amino acids
        (B) TYPE: amino acid
        (D) TOPOLOGY: unknown (ii) MOLECULE TYPE: protein (xi) SEQUENCE DESCRIPTION: SEQ ID NO:6:

Met Glu Ala Ile Ala Lys Tyr Asp Phe Lys Ala Thr Ala Asp Asp Glu
1               5                   10                  15

Leu Ser Phe Lys Arg Gly Asp Ile Leu Lys Val Leu Asn Glu Glu Cys
                20                  25                  30

Asp Gln Asn Trp Tyr Lys Ala Glu Leu Asn Gly Lys Asp Gly Phe Ile
                35                  40                  45

Pro Lys Asn Tyr Ile Glu Met Lys Pro His Pro Trp Phe Phe Gly Lys
                50                  55                  60

Ile Pro Arg Ala Lys Ala Glu Glu Met Leu Ser Lys Gln Arg His Asp
65                  70                  75                  80

Gly Ala Phe Leu Ile Arg Glu Ser Glu Ser Ala Pro Gly Asp Phe Ser
                85                  90                  95

Leu Ser Val Lys Phe Gly Asn Asp Val Gln His Phe Lys Val Leu Arg
                100                 105                 110

Asp Gly Ala Gly Lys Tyr Phe Leu Trp Val Val Lys Phe Asn Ser Leu
                115                 120                 125

Asn Glu Leu Val Asp Tyr His Arg Ser Thr Ser Val Ser Arg Asn Gln
                130                 135                 140

Gln Ile Phe Leu Arg Asp Ile Glu Gln Val Pro Gln Gln Pro Thr Tyr
145                 150                 155                 160

Val Gln Ala Leu Phe Asp Phe Asp Pro Gln Glu Asp Gly Glu Leu Gly
                165                 170                 175
```

```
Phe Arg Arg Gly Asp Phe Ile His Val Met Asp Asn Ser Asp Pro Asn
        180                 185                 190

Trp Trp Lys Gly Ala Cys His Gly Gln Thr Gly Met Phe Pro Arg Asn
    195                 200                 205

Tyr Val Thr Pro Val Asn Arg Asn Val
    210                 215
```

(2) INFORMATION FOR SEQ ID NO:7:

(i) SEQUENCE CHARACTERISTICS:
        (A) LENGTH: 2345 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:7:

```
CTCTCTCTCT CTCTCTCTCT CCCTCTCTCC TAGCACCTGC TGCTCAGTAG GAAGGGCAAG      60

AGCAATTCGA GGCCGGTGCA TTGTGAGGAG TCTCCACCCC TCCTCCTGCG CTTCCTTCTC     120

CAGGGAGCCT CTCAGGCCGC CCTCACCTGC CCAGATAAT TTTAGTTTCC CTGGGCCTGG      180

AATCTGGATA CGCAGGGCCT CGCTCTATAT TCTCCCGCCT CAACATTCCA AAGGCGGGAT     240

AGCCTTTCTA CCATCTGTAG AGAAGAGAGA AAGGATTCGA AATCAAATCC AAGTGTCTGG     300

GATCTCTAGA CAGAGCCAGA CTTTGGGCCG GGTGTCCGGC TCCTTCTGTT GGAGGTGCTC     360

CAGGTGCCAT GGAACTGGAT CTGAGCCCGA CTCATCTCAG CAGCTCCCCA GAAGATGTGT     420

GCCCAACTCC TGCTACCCCT CCTGAGACTC CTCCGCCCCC TGATAACCCT CCGCCAGGGG     480

ATGTGAAGCG GTCGCAGCCT TTGCCCATCC CCAGCAGCAG GAAACTTCGA GAAGAGGAGT     540

TTCAGGCAAC CTCTCTGCCC TCCATCCCCA ACCCCTTCCC TGAGCTCTGC AGCCCACCTT     600

CACAGAAACC CATTCTTGGT GGTTCCTCCG GTGCAAGGGG GTTGCTTCCT CGAGACTCCA     660

GCCGCCTCTG TGTGGTGAAG GTGTACAGTG AGGATGGGGC CTGCCGGTCT GTGGAGGTGG     720

CAGCGGGCGC CACAGCTCGT CACGTGTGTG AGATGCTGGT ACAACGAGCT CACGCCCTGA     780

GCGACGAGAG CTGGGGACTA GTGGAATCCC ACCCCTACCT GGCACTGGAG CGGGGTCTGG     840

AGGACCATGA ATTTGTGGTG GAAGTGCAGG AGGCCTGGCC TGTGGGTGGA GATAGCCGCT     900

TCATCTTCCG TAAAAACTTC GCCAAGTATG AACTATTCAA GAGCCCCCCA CACACCCTGT     960

TTCCAGAAAA GATGGTCTCG AGCTGTCTGG ATGCACAAAC AGGCATATCC CATGAAGACC    1020

TCATCCAGAA CTTCCTGAAC GCTGGCAGCT TCCCTGAGAT CCAGGGCTTC CTGCAGCTGC    1080

GGGGATCAGG CCGGGGGTCA GGTCGAAAGC TTTGGAAACG TTTCTTCTGC TTTCTGCGTC    1140

GATCTGGCCT CTACTACTCT ACCAAGGGTA CCTCCAAGGA CCCCAGACAC CTACAGTATG    1200

TGGCAGATGT GAATGAGTCC AATGTCTATG TGGTGACCCA GGGCCGCAAG CTGTATGGGA    1260

TGCCCACTGA CTTCGGCTTC TGTGTCAAGC CCAACAAGCT TCGAAACGGC CACAAGGGGC    1320

TCCACATCTT CTGCAGTGAG GATGAGCAGA CTCGGACCTG CTGGCTGGCT GCCTTCCGGC    1380

TCTTCAAGTA CGGGGTACAG CTATATAAGA ATTATCAGCA GGCCCAGTCT CGTCACCTGC    1440

GCCTATCCTA TTTGGGGTCT CCACCCTTGA GGAGCGTCTC AGACAATACC CTAGTGGCTA    1500

TGGACTTCTC TGGCCATGCG GGGCGTGTCA TTGATAACCC CCGGGAAGCT CTGAGTGCCG    1560

CCATGGAGGA GGCCCAGGCC TGGAGGAAGA AGACAAACCA CCGTCTGAGC CTGCCCACCA    1620

CATGCTCTGG CTCGAGCCTC AGCGCAGCCA TTCATCGCAC CCAGCCCTGG TTTCATGGAC    1680
```

-continued

```
GCATCTCTCG GGAGGAGAGC CAGCGGCTAA TTGGACAGCA GGGCCTGGTG GATGGTGTGT    1740

TCCTGGTCCG GGAGAGCCAG AGGAACCCAC AGGGCTTTGT CCTGTCCTTG TGCCATCTGC    1800

AGAAAGTCAA GCATTATCTC ATTTTGCCAA GTGAAGATGA AGGTTGCCTT TACTTCAGCA    1860

TGGATGAGGG CCAGACCCGT TTCACAGACC TGCTGCAGCT GGTATAATTC CACCAGCTGA    1920

ACCGAGGCAT CCTGCCCTGC CTGCTGCGCC ACTGCTGTGC CCGTGTGGCC CTCTGAGGCC    1980

GCACAAGCTA CTGCAGCCAT GGGTTTGCCT ACCACCCTTC TGTCCTGTGG ACTCGGTGCA    2040

GGTGGGTGGG GTGGTAAACA GTGGAAGAGC TCCCCCCCCC AATTTTATCC CATTTTTTTT    2100

AACCTCTCTC AACCAGTGAA ACATCCCCTA ACCCTGTCCA TCCCTGACTC CTGTCCCCAA    2160

GGGAGGCATT GTGGTCCTGT CCCCTTGGTA GAGCTCCTGA GGTACTGTTC CAGTGAGGGG    2220

CATTATGAGA GGAGCGGGGC AGCCCAGGAG GTCTCATACC CCACCCATAA TCTGTACAGA    2280

CTGAGAGGCC AGTTGATCTG CTCTGTTTTA TACCAGTAAC AATAAAGATT ATTTTTTGAT    2340

ACAAA                                                                2345
```

(2) INFORMATION FOR SEQ ID NO:8:

(i) SEQUENCE CHARACTERISTICS:
        (A) LENGTH: 256 amino acids
        (B) TYPE: amino acid
        (D) TOPOLOGY: unknown (ii) MOLECULE TYPE: protein (xi) SEQUENCE DESCRIPTION: SEQ ID NO:8:

```
Pro Asp Thr Gly Ala Gly Pro Leu Gly Ala Gly Ala Arg Ala Gly Gly
1               5                   10                  15

Ala Arg Val Pro Ala Ala Ala Gln Arg Glu Ser Ala Glu Ala Ala Met
            20                  25                  30

Ala Gly Asn Phe Asp Ser Glu Glu Arg Ser Ser Trp Tyr Trp Gly Arg
        35                  40                  45

Leu Ser Arg Gln Glu Ala Val Ala Leu Leu Gln Gly Gln Arg Asp Gly
    50                  55                  60

Val Phe Leu Val Arg Asp Ser Ser Thr Ser Pro Gly Asp Tyr Val Leu
65                  70                  75                  80

Ser Val Ser Glu Asn Ser Arg Val Ser His Tyr Ile Ile Asn Ser Ser
                85                  90                  95

Gly Pro Arg Pro Pro Val Pro Pro Ser Pro Ala Gln Pro Pro Pro Gly
            100                 105                 110

Val Ser Pro Ser Arg Leu Arg Ile Gly Asp Gln Glu Phe Asp Ser Leu
        115                 120                 125

Pro Ala Leu Leu Glu Phe Tyr Lys Ile His Tyr Leu Asp Thr Thr Thr
    130                 135                 140

Leu Ile Glu Pro Val Ala Arg Ser Arg Gln Gly Ser Gly Val Ile Leu
145                 150                 155                 160

Arg Gln Glu Glu Ala Glu Tyr Val Arg Ala Leu Phe Asp Phe Asn Gly
                165                 170                 175

Asn Asp Glu Glu Asp Leu Pro Phe Lys Lys Gly Asp Ile Leu Arg Ile
            180                 185                 190

Arg Asp Lys Pro Glu Glu Gln Trp Trp Asn Ala Glu Asp Ser Glu Gly
        195                 200                 205

Lys Arg Gly Met Ile Pro Val Pro Tyr Val Glu Lys Tyr Arg Pro Ala
    210                 215                 220

Ser Ala Ser Val Ser Ala Leu Ile Gly Gly Asn Gln Glu Gly Ser His
```

```
                225                 230                 235                 240
Pro Gln Pro Leu Gly Gly Arg Ser Leu Gly Pro Met Pro Thr Gln Arg
                    245                 250                 255

(2) INFORMATION FOR SEQ ID NO:9:

(i) SEQUENCE CHARACTERISTICS:
        (A) LENGTH: 157 amino acids
        (B) TYPE: amino acid
        (D) TOPOLOGY: unknown (ii) MOLECULE TYPE: protein (xi) SEQUENCE DESCRIPTION: SEQ ID NO:9:

Val Ile Glu Lys Pro Glu Asn Asp Pro Glu Trp Trp Lys Cys Lys Asn
1               5                   10                  15

Ala Arg Gly Gln Val Gly Leu Val Pro Lys Asn Tyr Val Val Val Leu
                20                  25                  30

Ser Asp Gly Pro Ala Leu His Pro Ala His Thr Pro Gln Ile Ser Tyr
            35                  40                  45

Thr Gly Pro Ser Ala Ser Gly Arg Phe Ala Gly Arg Glu Trp Tyr Tyr
        50                  55                  60

Gly Asn Val Thr Arg His Gln Ala Glu Cys Ala Leu Asn Glu Arg Gly
65                  70                  75                  80

Val Glu Gly Asp Phe Leu Ile Arg Asp Ser Glu Ser Ser Pro Ser Asp
                85                  90                  95

Phe Ser Val Ser Leu Lys Ala Ser Gly Arg Asn Lys His Phe Lys Val
                100                 105                 110

Gln Leu Val Asp Ser Val Tyr Cys Ile Gly Gln Arg Arg Phe His Ser
            115                 120                 125

Met Asp Glu Leu Val Glu His Tyr Lys Lys Ala Pro Ile Phe Thr Ser
        130                 135                 140

Glu His Gly Glu Lys Leu Tyr Leu Val Arg Ala Leu Gln
145                 150                 155

(2) INFORMATION FOR SEQ ID NO:10:

(i) SEQUENCE CHARACTERISTICS:
        (A) LENGTH: 535 amino acids
        (B) TYPE: amino acid
        (D) TOPOLOGY: unknown (ii) MOLECULE TYPE: protein (xi) SEQUENCE DESCRIPTION: SEQ ID NO:10:

Met Glu Leu Asp Leu Ser Pro Thr His Leu Ser Ser Ser Pro Glu Asp
1               5                   10                  15

Val Cys Pro Thr Pro Ala Thr Pro Pro Glu Thr Pro Pro Pro Asp
                20                  25                  30

Asn Pro Pro Pro Gly Asp Val Lys Arg Ser Gln Pro Leu Pro Ile Pro
            35                  40                  45

Ser Ser Arg Lys Leu Arg Glu Glu Glu Phe Gln Ala Thr Ser Leu Pro
        50                  55                  60

Ser Ile Pro Asn Pro Phe Pro Glu Leu Cys Ser Pro Ser Gln Lys
65                  70                  75                  80

Pro Ile Leu Gly Gly Ser Ser Gly Ala Arg Gly Leu Leu Pro Arg Asp
                85                  90                  95

Ser Ser Arg Leu Cys Val Val Lys Val Tyr Ser Glu Asp Gly Ala Cys
                100                 105                 110
```

-continued

```
Arg Ser Val Glu Val Ala Ala Gly Ala Thr Ala Arg His Val Cys Glu
        115                 120                 125
Met Leu Val Gln Arg Ala His Ala Leu Ser Asp Glu Ser Trp Gly Leu
        130                 135                 140
Val Glu Ser His Pro Tyr Leu Ala Leu Glu Arg Gly Leu Glu Asp His
145                 150                 155                 160
Glu Phe Val Val Glu Val Gln Glu Ala Trp Pro Val Gly Gly Asp Ser
                165                 170                 175
Arg Phe Ile Phe Arg Lys Asn Phe Ala Lys Tyr Glu Leu Phe Lys Ser
                180                 185                 190
Pro Pro His Thr Leu Phe Pro Glu Lys Met Val Ser Ser Cys Leu Asp
                195                 200                 205
Ala Gln Thr Gly Ile Ser His Glu Asp Leu Ile Gln Asn Phe Leu Asn
        210                 215                 220
Ala Gly Ser Phe Pro Glu Ile Gln Gly Phe Leu Gln Leu Arg Gly Ser
225                 230                 235                 240
Gly Arg Gly Ser Gly Arg Lys Leu Trp Lys Arg Phe Phe Cys Phe Leu
                245                 250                 255
Arg Arg Ser Gly Leu Tyr Tyr Ser Thr Lys Gly Thr Ser Lys Asp Pro
                260                 265                 270
Arg His Leu Gln Tyr Val Ala Asp Val Asn Glu Ser Asn Val Tyr Val
        275                 280                 285
Val Thr Gln Gly Arg Lys Leu Tyr Gly Met Pro Thr Asp Phe Gly Phe
        290                 295                 300
Cys Val Lys Pro Asn Lys Leu Arg Asn Gly His Lys Gly Leu His Ile
305                 310                 315                 320
Phe Cys Ser Glu Asp Glu Gln Ser Arg Thr Cys Trp Leu Ala Ala Phe
                325                 330                 335
Arg Leu Phe Lys Tyr Gly Val Gln Leu Tyr Lys Asn Tyr Gln Gln Ala
                340                 345                 350
Gln Ser Arg His Leu Arg Leu Ser Tyr Leu Gly Ser Pro Pro Leu Arg
        355                 360                 365
Ser Val Ser Asp Asn Thr Leu Val Ala Met Asp Phe Ser Gly His Ala
370                 375                 380
Gly Arg Val Ile Asp Asn Pro Arg Glu Ala Leu Ser Ala Ala Met Glu
385                 390                 395                 400
Glu Ala Gln Ala Trp Arg Lys Lys Thr Asn His Arg Leu Ser Leu Pro
                405                 410                 415
Thr Thr Cys Ser Gly Ser Ser Leu Ser Ala Ala Ile His Arg Thr Gln
                420                 425                 430
Pro Trp Phe His Gly Arg Ile Ser Arg Glu Glu Ser Gln Arg Leu Ile
        435                 440                 445
Gly Gln Gln Gly Leu Val Asp Gly Val Phe Leu Val Arg Glu Ser Gln
        450                 455                 460
Arg Asn Pro Gln Gly Phe Val Leu Ser Leu Cys His Leu Gln Lys Val
465                 470                 475                 480
Lys His Tyr Leu Ile Leu Pro Ser Glu Asp Glu Gly Cys Leu Tyr Phe
                485                 490                 495
Ser Met Asp Glu Gly Gln Thr Arg Phe Thr Asp Leu Leu Gln Leu Val
                500                 505                 510
Glu Phe His Gln Leu Asn Arg Gly Ile Leu Pro Cys Leu Leu Arg His
        515                 520                 525
```

```
Cys Cys Ala Arg Val Ala Leu
    530                 535

(2) INFORMATION FOR SEQ ID NO:11:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 6
        (D) OTHER INFORMATION: /label= A
            /note= "The tyrosine is phosphorylated."

(xi) SEQUENCE DESCRIPTION: SEQ ID NO:11:

Glu Glu Glu Glu Glu Tyr Met Pro Met Xaa Xaa
1               5                   10

(2) INFORMATION FOR SEQ ID NO:12:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 6
        (D) OTHER INFORMATION: /label= A
            /note= "The tyrosine is phosphorylated."

(xi) SEQUENCE DESCRIPTION: SEQ ID NO:12:

Glu Glu Glu Glu Glu Tyr Val Pro Met Xaa Xaa
1               5                   10

(2) INFORMATION FOR SEQ ID NO:13:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 6
        (D) OTHER INFORMATION: /label= A
            /note= "The tyrosine is phosphorylated."

(xi) SEQUENCE DESCRIPTION: SEQ ID NO:13:

Asp Asp Asp Asp Asp Tyr Met Pro Met Xaa Xaa
1               5                   10

(2) INFORMATION FOR SEQ ID NO:14:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 6
```

(D) OTHER INFORMATION: /label= A
                /note= "The tyrosine is phosphorylated."

(xi) SEQUENCE DESCRIPTION: SEQ ID NO:14:

Asp Asp Asp Asp Asp Tyr Val Pro Met Xaa Xaa
1               5                   10

(2) INFORMATION FOR SEQ ID NO:15:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (xi) SEQUENCE DESCRIPTION: SEQ ID NO:15:

Ile Glu Gly Arg
1

(2) INFORMATION FOR SEQ ID NO:16:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (xi) SEQUENCE DESCRIPTION: SEQ ID NO:16:

Leu Val Pro Arg
1

(2) INFORMATION FOR SEQ ID NO:17:

(i) SEQUENCE CHARACTERISTICS:
        (A) LENGTH: 2556 base pairs
        (B) TYPE: nucleic acid
        (C) STRANDEDNESS: single
        (D) TOPOLOGY: unknown (ii) MOLECULE TYPE: DNA (genomic)

(ix) FEATURE:
        (A) NAME/KEY: CDS
        (B) LOCATION: 411..2273

(xi) SEQUENCE DESCRIPTION: SEQ ID NO:17:

GGGGCCGGGG GAGGAGGAGG CGGAGGCGGC GGCGGAGGCT GGGAGGGCGG GCGGGGCCCG      60

GAGAGTTTAA AGCCCATCGA GGGTGTGGGG TGCGGGGAGG CGGCAGGAAG GGAAGGGCGC     120

TGCGACCAGT GGCGGGCGTG ATTCGCGTTC CGAGACCCAC GGGAGCACGA AGTTTCCGCG     180

CACCGTCTCA CGCACGGCGA CTGGGACCGT CCAGTGTTCC GGCTTTGCCT TCGGTTTTTC     240

TCCGTTGTGA CTCGTGCAAC GTGTGGCCAG CGGCCACGCG GAGGCGACGA GGAGCTGCAC     300

GTCAGGACAA AGTGGGGCAG TCAACGTCCA AACCCGAAAA CCTAGCTAAG TCTGGGTTTT     360

CGCCACAACA AAGAAGCCAA CCAGAGCATG GTCTTGGGCT TCAAGTACTA ATG AAC        416
                                                        Met Asn
                                                           1

AAC GAT ATT AAC TCG TCC GTG GAA AGC CTT AAC TCA GCT TGC AAC ATG       464
Asn Asp Ile Asn Ser Ser Val Glu Ser Leu Asn Ser Ala Cys Asn Met
             5                  10                  15

CAG TCT GAT ACT GAT ACT GCA CCA CTT CTT GAG GAT GGC CAG CAT GCC       512
Gln Ser Asp Thr Asp Thr Ala Pro Leu Leu Glu Asp Gly Gln His Ala
     20                  25                  30

```
AGC AAC CAG GGA GCA GCA TCT AGC TCC CGG GGA CAG CCA CAG GCG TCC      560
Ser Asn Gln Gly Ala Ala Ser Ser Ser Arg Gly Gln Pro Gln Ala Ser
 35              40                  45                  50

CCG AGG CAG AAA ATG CAA CGC TCG CAG CCT GTG CAC ATT CTC AGG CGC      608
Pro Arg Gln Lys Met Gln Arg Ser Gln Pro Val His Ile Leu Arg Arg
                 55                  60                  65

CTT CAG GAG GAA GAC CAG CAG TTA AGA ACT GCA TCT CTT CCG GCC ATC      656
Leu Gln Glu Glu Asp Gln Gln Leu Arg Thr Ala Ser Leu Pro Ala Ile
             70                  75                  80

CCC AAC CCA TTT CCG GAG CTC ACT GGT GCG GCC CCT GGG AGC CCT CCT      704
Pro Asn Pro Phe Pro Glu Leu Thr Gly Ala Ala Pro Gly Ser Pro Pro
         85                  90                  95

TCG GTT GCT CCT AGC TCC TTA CCT CCT CCT CCG AGC CAG CCA CCT GCC      752
Ser Val Ala Pro Ser Ser Leu Pro Pro Pro Pro Ser Gln Pro Pro Ala
     100                 105                 110

AAG CAT TGT GGC AGA TGT GAG AAG TGG ATA CCA GGG GAA AAT ACC CGG      800
Lys His Cys Gly Arg Cys Glu Lys Trp Ile Pro Gly Glu Asn Thr Arg
115                 120                 125                 130

GGA AAT GGG AAA CGG AAG ATC TGG AGA TGG CAG TTC CCT CCA GGC TTT      848
Gly Asn Gly Lys Arg Lys Ile Trp Arg Trp Gln Phe Pro Pro Gly Phe
                 135                 140                 145

CAG CTG TCG AAA CTC ACC CGT CCA GGT CTG TGG ACA AAG ACC ACT GCG      896
Gln Leu Ser Lys Leu Thr Arg Pro Gly Leu Trp Thr Lys Thr Thr Ala
             150                 155                 160

AGA TTT TCA AAG AAA CAA CCT AAG AAC CAG TGT CCA ACC GAC ACT GTG      944
Arg Phe Ser Lys Lys Gln Pro Lys Asn Gln Cys Pro Thr Asp Thr Val
         165                 170                 175

AAT CCA GTG GCA CGG ATG CCC ACT TCA CAG ATG GAG AAG CTG AGG CTC      992
Asn Pro Val Ala Arg Met Pro Thr Ser Gln Met Glu Lys Leu Arg Leu
     180                 185                 190

AGA AAG GAT GTC AAA GTC TTT AGT GAA GAT GGG ACC AGC AAA GTG GTG     1040
Arg Lys Asp Val Lys Val Phe Ser Glu Asp Gly Thr Ser Lys Val Val
195                 200                 205                 210

GAG ATT CTA ACC GAC ATG ACA GCC AGG GAC CTG TGC CAG CTG CTG GTT     1088
Glu Ile Leu Thr Asp Met Thr Ala Arg Asp Leu Cys Gln Leu Leu Val
                 215                 220                 225

TAC AAA AGT CAC TGT GTG GAT GAC AAC AGC TGG ACT CTG GTG GAA CAC     1136
Tyr Lys Ser His Cys Val Asp Asp Asn Ser Trp Thr Leu Val Glu His
             230                 235                 240

CAC CCA CAA CTG GGA TTA GAG AGG TGC CTG GAG GAC CAT GAG ATC GTG     1184
His Pro Gln Leu Gly Leu Glu Arg Cys Leu Glu Asp His Glu Ile Val
         245                 250                 255

GTC CAA GTG GAG AGT ACC ATG CCA AGT GAG AGC AAA TTC TTA TTC AGA     1232
Val Gln Val Glu Ser Thr Met Pro Ser Glu Ser Lys Phe Leu Phe Arg
     260                 265                 270

AAG AAT TAT GCG AAG TAC GAG TTC TTT AAG AAT CCA GTG AAC TTC TTC     1280
Lys Asn Tyr Ala Lys Tyr Glu Phe Phe Lys Asn Pro Val Asn Phe Phe
275                 280                 285                 290

CCG GAT CAG ATG GTC AAT TGG TGC CAG CAG TCC AAC GGT GGC CAG GCG     1328
Pro Asp Gln Met Val Asn Trp Cys Gln Gln Ser Asn Gly Gly Gln Ala
                 295                 300                 305

CAG CTT CTG CAG AAT TTT CTG AAC ACC AGC AGC TGC CCT GAG ATC CAG     1376
Gln Leu Leu Gln Asn Phe Leu Asn Thr Ser Ser Cys Pro Glu Ile Gln
             310                 315                 320

GGG TTC TTG CAG GTG AAA GAG GTA GGA CGC AAG TCT TGG AAG AAG CTG     1424
Gly Phe Leu Gln Val Lys Glu Val Gly Arg Lys Ser Trp Lys Lys Leu
         325                 330                 335

TAT GTG TGC CTG CGC AGA TCT GGC CTC TAT TAC TCC ACC AAG GGG ACT     1472
Tyr Val Cys Leu Arg Arg Ser Gly Leu Tyr Tyr Ser Thr Lys Gly Thr
     340                 345                 350
```

```
TCA AAA GAA CCC AGA CAC CTG CAG CTG CTG GCT GAC CTG GAA GAA AGC        1520
Ser Lys Glu Pro Arg His Leu Gln Leu Leu Ala Asp Leu Glu Glu Ser
355                 360                 365                 370

AGC ATC TTC TAC CTG ATT GCT GGA AAG AAG CAG TAC AAC GCG CCG AAT        1568
Ser Ile Phe Tyr Leu Ile Ala Gly Lys Lys Gln Tyr Asn Ala Pro Asn
                375                 380                 385

GAA CAT GGG ATG TGC ATC AAG CCA AAC AAA GCG AAG ACC GAG ATG AAG        1616
Glu His Gly Met Cys Ile Lys Pro Asn Lys Ala Lys Thr Glu Met Lys
            390                 395                 400

GAG CTT CGT CTG CTC TGT GCC GAA GAT GAG CAG ATC CGT ACT TGC TGG        1664
Glu Leu Arg Leu Leu Cys Ala Glu Asp Glu Gln Ile Arg Thr Cys Trp
        405                 410                 415

ATG ACT GCC TTC AGA CTG CTC AAG TAC GGA ATG CTC CTG TAC CAA AAC        1712
Met Thr Ala Phe Arg Leu Leu Lys Tyr Gly Met Leu Leu Tyr Gln Asn
    420                 425                 430

TAT CGC ATC CCA CAG AGG AAG GGT CTG CCC CCT CCT TTC AAC GCA CCT        1760
Tyr Arg Ile Pro Gln Arg Lys Gly Leu Pro Pro Pro Phe Asn Ala Pro
435                 440                 445                 450

ATG CGC AGT GTT TCT GAG AAT TCT CTT GTG GCC ATG GAT TTT TCT GGA        1808
Met Arg Ser Val Ser Glu Asn Ser Leu Val Ala Met Asp Phe Ser Gly
                455                 460                 465

CAA ATC GGA AGA GTG ATC GAT AAC CCG GCT GAA GCC CAG AGT GCT GCC        1856
Gln Ile Gly Arg Val Ile Asp Asn Pro Ala Glu Ala Gln Ser Ala Ala
            470                 475                 480

CTG GAA GAG GGC CAT GCC TGG CGT AAC GGG AGC ACA CGG ATG AAT ATC        1904
Leu Glu Glu Gly His Ala Trp Arg Asn Gly Ser Thr Arg Met Asn Ile
        485                 490                 495

CTA AGC AGC CAA AGC CCA CTG CAT CCT TCT ACC CTG AAT GCA GTG ATT        1952
Leu Ser Ser Gln Ser Pro Leu His Pro Ser Thr Leu Asn Ala Val Ile
    500                 505                 510

CAC AGG ACT CAG CAT TGG TTC CAT GGA CGT ATC TCC CGG GAG GAG TCT        2000
His Arg Thr Gln His Trp Phe His Gly Arg Ile Ser Arg Glu Glu Ser
515                 520                 525                 530

CAC AGG ATC ATC AAG CAA CAA GGT CTC GTG GAC GGG CTG TTC CTC CTT        2048
His Arg Ile Ile Lys Gln Gln Gly Leu Val Asp Gly Leu Phe Leu Leu
                535                 540                 545

CGT GAC AGC CAG AGT AAT CCA AAG GCG TTC GTA CTG ACA CTG TGC CAT        2096
Arg Asp Ser Gln Ser Asn Pro Lys Ala Phe Val Leu Thr Leu Cys His
            550                 555                 560

CAC CAG AAG ATT AAA AAC TTC CAG ATC TTA CCT TGC GAG GAT GAT GGG        2144
His Gln Lys Ile Lys Asn Phe Gln Ile Leu Pro Cys Glu Asp Asp Gly
        565                 570                 575

CAG ACC TTC TTC ACT CTG GAT GAT GGG AAC ACC AAG TTC TCC GAT CTG        2192
Gln Thr Phe Phe Thr Leu Asp Asp Gly Asn Thr Lys Phe Ser Asp Leu
    580                 585                 590

ATC CAG CTG GTC GAC TTC TAC CAG CTC AAC AAA GGT GTT CTG CCC TGC        2240
Ile Gln Leu Val Asp Phe Tyr Gln Leu Asn Lys Gly Val Leu Pro Cys
595                 600                 605                 610

AAG CTG AAA CAC CAC TGC ATC CGC GTG GCC TTA TGACCTCCTT GCCCACTCAC      2293
Lys Leu Lys His His Cys Ile Arg Val Ala Leu
                615                 620

AGAGGCTGGA GGCAGCGACA CTGGAACGGA GAAGAGAGAT CTGCATGAGG CCGGAATTCC      2353

GAAGACCAAG GAACCTTGAG AAGAAGAAGA AAAAAGAGAA GGTCCTTGCT ACTGTCACCA      2413

AAACAGTTGG TGGGACAAG AACGGTGGCA CCCGGGTGGT GAAGCTTCGA AAAATGCCTT       2473

AGGTATTATC CCACCGAAGA TGTTCCTTCG GGAAGCTGCT GAGCCACGGC AAGAAGCCCT      2533

TCAGCCAGCA CGTGAGAAGG CTA                                              2556
```

(2) INFORMATION FOR SEQ ID NO:18:

(i) SEQUENCE CHARACTERISTICS:
        (A) LENGTH: 621 amino acids
        (B) TYPE: amino acid
        (D) TOPOLOGY: unknown (ii) MOLECULE TYPE: protein (xi) SEQUENCE DESCRIPTION: SEQ ID NO:18:

```
Met Asn Asp Ile Asn Ser Ser Val Glu Ser Leu Asn Ser Ala Cys
  1               5                  10                  15

Asn Met Gln Ser Asp Thr Asp Thr Ala Pro Leu Leu Glu Asp Gly Gln
                 20                  25                  30

His Ala Ser Asn Gln Gly Ala Ala Ser Ser Arg Gly Gln Pro Gln
             35                  40                  45

Ala Ser Pro Arg Gln Lys Met Gln Arg Ser Gln Pro Val His Ile Leu
     50                  55                  60

Arg Arg Leu Gln Glu Glu Asp Gln Gln Leu Arg Thr Ala Ser Leu Pro
 65              70                  75                  80

Ala Ile Pro Asn Pro Phe Pro Glu Leu Thr Gly Ala Ala Pro Gly Ser
                 85                  90                  95

Pro Pro Ser Val Ala Pro Ser Ser Leu Pro Pro Pro Ser Gln Pro
            100                 105                 110

Pro Ala Lys His Cys Gly Arg Cys Glu Lys Trp Ile Pro Gly Glu Asn
            115                 120                 125

Thr Arg Gly Asn Gly Lys Arg Lys Ile Trp Arg Trp Gln Phe Pro Pro
    130                 135                 140

Gly Phe Gln Leu Ser Lys Leu Thr Arg Pro Gly Leu Trp Thr Lys Thr
145                 150                 155                 160

Thr Ala Arg Phe Ser Lys Lys Gln Pro Lys Asn Gln Cys Pro Thr Asp
                165                 170                 175

Thr Val Asn Pro Val Ala Arg Met Pro Thr Ser Gln Met Glu Lys Leu
            180                 185                 190

Arg Leu Arg Lys Asp Val Lys Val Phe Ser Glu Asp Gly Thr Ser Lys
    195                 200                 205

Val Val Glu Ile Leu Thr Asp Met Thr Ala Arg Asp Leu Cys Gln Leu
    210                 215                 220

Leu Val Tyr Lys Ser His Cys Val Asp Asp Asn Ser Trp Thr Leu Val
225                 230                 235                 240

Glu His His Pro Gln Leu Gly Leu Glu Arg Cys Leu Glu Asp His Glu
                245                 250                 255

Ile Val Val Gln Val Glu Ser Thr Met Pro Ser Glu Ser Lys Phe Leu
            260                 265                 270

Phe Arg Lys Asn Tyr Ala Lys Tyr Glu Phe Phe Lys Asn Pro Val Asn
    275                 280                 285

Phe Phe Pro Asp Gln Met Val Asn Trp Cys Gln Gln Ser Asn Gly Gly
    290                 295                 300

Gln Ala Gln Leu Leu Gln Asn Phe Leu Asn Thr Ser Ser Cys Pro Glu
305                 310                 315                 320

Ile Gln Gly Phe Leu Gln Val Lys Glu Val Gly Arg Lys Ser Trp Lys
                325                 330                 335

Lys Leu Tyr Val Cys Leu Arg Arg Ser Gly Leu Tyr Tyr Ser Thr Lys
            340                 345                 350

Gly Thr Ser Lys Glu Pro Arg His Leu Gln Leu Leu Ala Asp Leu Glu
```

-continued

```
                355                 360                 365
Glu Ser Ser Ile Phe Tyr Leu Ile Ala Gly Lys Lys Gln Tyr Asn Ala
    370                 375                 380
Pro Asn Glu His Gly Met Cys Ile Lys Pro Asn Lys Ala Lys Thr Glu
385                 390                 395                 400
Met Lys Glu Leu Arg Leu Leu Cys Ala Glu Asp Glu Gln Ile Arg Thr
                405                 410                 415
Cys Trp Met Thr Ala Phe Arg Leu Leu Lys Tyr Gly Met Leu Leu Tyr
                420                 425                 430
Gln Asn Tyr Arg Ile Pro Gln Arg Lys Gly Leu Pro Pro Phe Asn
                435                 440                 445
Ala Pro Met Arg Ser Val Ser Glu Asn Ser Leu Val Ala Met Asp Phe
450                 455                 460
Ser Gly Gln Ile Gly Arg Val Ile Asp Asn Pro Ala Glu Ala Gln Ser
465                 470                 475                 480
Ala Ala Leu Glu Glu Gly His Ala Trp Arg Asn Gly Ser Thr Arg Met
                485                 490                 495
Asn Ile Leu Ser Ser Gln Ser Pro Leu His Pro Ser Thr Leu Asn Ala
                500                 505                 510
Val Ile His Arg Thr Gln His Trp Phe His Gly Arg Ile Ser Arg Glu
                515                 520                 525
Glu Ser His Arg Ile Ile Lys Gln Gln Gly Leu Val Asp Gly Leu Phe
                530                 535                 540
Leu Leu Arg Asp Ser Gln Ser Asn Pro Lys Ala Phe Val Leu Thr Leu
545                 550                 555                 560
Cys His His Gln Lys Ile Lys Asn Phe Gln Ile Leu Pro Cys Glu Asp
                565                 570                 575
Asp Gly Gln Thr Phe Phe Thr Leu Asp Asp Gly Asn Thr Lys Phe Ser
                580                 585                 590
Asp Leu Ile Gln Leu Val Asp Phe Tyr Gln Leu Asn Lys Gly Val Leu
                595                 600                 605
Pro Cys Lys Leu Lys His His Cys Ile Arg Val Ala Leu
    610                 615                 620

(2) INFORMATION FOR SEQ ID NO:19:

(i) SEQUENCE CHARACTERISTICS:
        (A) LENGTH: 96 amino acids
        (B) TYPE: amino acid
        (D) TOPOLOGY: unknown (ii) MOLECULE TYPE: protein (xi) SEQUENCE DESCRIPTION: SEQ ID NO:19:

Trp Tyr Trp Gly Asp Ile Ser Arg Glu Glu Val Asn Glu Lys Leu Arg
1                   5                   10                  15
Asp Thr Ala Asp Gly Thr Phe Leu Val Arg Asp Ser Thr Lys Met His
                20                  25                  30
Gly Asp Tyr Thr Leu Thr Leu Arg Lys Gly Gly Asn Asn Leu Ile Lys
            35                  40                  45
Ile Phe His Arg Asp Gly Lys Tyr Gly Phe Ser Asp Pro Leu Thr Phe
        50                  55                  60
Ser Ser Val Val Glu Leu Ile Asn His Tyr Arg Asn Glu Ser Leu Ala
65                  70                  75                  80
Gln Tyr Asn Pro Lys Leu Asp Val Lys Leu Leu Tyr Pro Val Ser Lys
                85                  90                  95
```

(2) INFORMATION FOR SEQ ID NO:20:

(i) SEQUENCE CHARACTERISTICS:
        (A) LENGTH: 97 amino acids
        (B) TYPE: amino acid
        (D) TOPOLOGY: unknown (ii) MOLECULE TYPE: protein (xi) SEQUENCE DESCRIPTION: SEQ ID NO:20:

```
Trp Asn Val Gly Ser Ser Asn Arg Asn Lys Ala Glu Asn Leu Leu Arg
1               5                   10                  15
Gly Lys Arg Asp Gly Thr Phe Leu Val Arg Glu Ser Ser Lys Gln Gly
                20                  25                  30
Cys Tyr Ala Cys Ser Val Val Val Asp Gly Glu Val Lys His Cys Val
            35                  40                  45
Ile Asn Lys Thr Ala Thr Gly Tyr Gly Phe Ala Glu Pro Tyr Asn Leu
        50                  55                  60
Tyr Ser Ser Leu Lys Glu Leu Val Leu His Tyr Gln His Thr Ser Leu
65                  70                  75                  80
Val Gln His Asn Asp Ser Leu Asn Val Thr Leu Ala Tyr Pro Val Tyr
                85                  90                  95
Ala
```

(2) INFORMATION FOR SEQ ID NO:21:

(i) SEQUENCE CHARACTERISTICS:
        (A) LENGTH: 99 amino acids
        (B) TYPE: amino acid
        (D) TOPOLOGY: unknown (ii) MOLECULE TYPE: protein (xi) SEQUENCE DESCRIPTION: SEQ ID NO:21:

```
Trp Tyr Phe Gly Lys Ile Thr Arg Arg Glu Ser Glu Arg Leu Leu Leu
1               5                   10                  15
Asn Pro Glu Asn Pro Arg Gly Thr Phe Leu Val Arg Glu Ser Glu Thr
                20                  25                  30
Thr Lys Gly Ala Tyr Cys Leu Ser Val Ser Asp Phe Asp Asn Ala Lys
            35                  40                  45
Gly Leu Asn Val Lys His Tyr Lys Ile Arg Lys Leu Asp Ser Gly Gly
        50                  55                  60
Phe Tyr Ile Thr Ser Arg Thr Gln Phe Ser Ser Leu Gln Gln Leu Val
65                  70                  75                  80
Ala Tyr Tyr Ser Lys His Ala Asp Gly Leu Cys His Arg Leu Thr Asn
                85                  90                  95
Val Cys Pro
```

(2) INFORMATION FOR SEQ ID NO:22:

(i) SEQUENCE CHARACTERISTICS:
        (A) LENGTH: 92 amino acids
        (B) TYPE: amino acid
        (D) TOPOLOGY: unknown (ii) MOLECULE TYPE: protein (xi) SEQUENCE DESCRIPTION: SEQ ID NO:22:

```
Trp Tyr His Gly Pro Val Ser Arg Asn Ala Ala Glu Tyr Lys Lys Ser
1               5                   10                  15
```

```
Ser Gly Ile Asn Gly Ser Phe Leu Val Arg Glu Ser Glu Ser Ser Pro
             20                  25                  30

Gly Gln Arg Ser Ile Ser Leu Arg Tyr Glu Gly Arg Val Tyr His Tyr
         35                  40                  45

Arg Ile Asn Thr Ala Ser Asp Gly Lys Leu Tyr Val Ser Ser Glu Ser
     50                  55                  60

Arg Phe Asn Thr Leu Ala Glu Leu Val His His Ser Thr Val Ala
65                  70                  75                  80

Asp Gly Leu Ile Thr Thr Leu His Tyr Pro Ala Pro
                 85                  90
```

(2) INFORMATION FOR SEQ ID NO:23:

(i) SEQUENCE CHARACTERISTICS:
        (A) LENGTH: 109 amino acids
        (B) TYPE: amino acid
        (D) TOPOLOGY: unknown (ii) MOLECULE TYPE: protein (xi) SEQUENCE DESCRIPTION: SEQ ID NO:23:

```
Trp Phe His Gly Lys Leu Gly Ala Gly Arg Asp Gly Arg His Ile Ala
1                5                  10                  15

Glu Arg Leu Leu Thr Glu Tyr Cys Ile Glu Thr Gly Ala Pro Asp Gly
             20                  25                  30

Ser Phe Leu Val Arg Glu Ser Glu Thr Phe Val Gly Asp Tyr Thr Leu
         35                  40                  45

Ser Phe Trp Arg Asn Gly Lys Val Gln His Cys Arg Ile His Ser Arg
     50                  55                  60

Gln Asp Ala Gly Thr Pro Lys Phe Phe Leu Thr Asp Asn Leu Val Phe
65                  70                  75                  80

Asp Ser Leu Tyr Asp Leu Ile Thr His Tyr Gln Gln Val Pro Leu Arg
                 85                  90                  95

Cys Ala Glu Phe Glu Met Arg Leu Ser Leu Pro Val Pro
                100                 105
```

(2) INFORMATION FOR SEQ ID NO:24:

(i) SEQUENCE CHARACTERISTICS:
        (A) LENGTH: 89 amino acids
        (B) TYPE: amino acid
        (D) TOPOLOGY: unknown (ii) MOLECULE TYPE: protein (xi) SEQUENCE DESCRIPTION: SEQ ID NO:24:

```
Trp Tyr His Ala Ser Leu Thr Arg Ala Gln Ala Glu His Met Leu Met
1                5                  10                  15

Arg Val Pro Arg Asp Gly Ala Phe Leu Val Arg Lys Arg Asn Glu Pro
             20                  25                  30

Asn Ser Tyr Ala Ile Ser Phe Arg Ala Glu Gly Lys Ile Lys His Cys
         35                  40                  45

Arg Val Gln Gln Glu Gly Gln Thr Val Met Leu Gly Asn Ser Glu Phe
     50                  55                  60

Asp Ser Leu Val Asp Leu Ile Ser Tyr Tyr Glu Lys His Pro Leu Tyr
65                  70                  75                  80

Arg Lys Met Lys Leu Arg Tyr Pro Ile
                 85
```

(2) INFORMATION FOR SEQ ID NO:25:

(i) SEQUENCE CHARACTERISTICS:
        (A) LENGTH: 94 amino acids
        (B) TYPE: amino acid
        (D) TOPOLOGY: unknown (ii) MOLECULE TYPE: protein (xi) SEQUENCE DESCRIPTION: SEQ ID NO:25:

```
Trp Tyr His Gly Lys Leu Asp Arg Thr Ile Ala Glu Glu Arg Leu Arg
 1               5                  10                  15

Gln Ala Gly Lys Ser Gly Ser Tyr Leu Ile Arg Glu Ser Asp Arg Arg
                20                  25                  30

Pro Gly Ser Phe Val Leu Ser Phe Arg Ser Gln Met Asn Val Val Asn
            35                  40                  45

His Pro Arg Ile Ile Ala Met Cys Gly Asp Tyr Tyr Ile Gly Gly Arg
        50                  55                  60

Arg Phe Ser Ser Leu Ser Asp Leu Ile Gly Tyr Tyr Ser His Val Ser
65                  70                  75                  80

Cys Leu Leu Lys Gly Glu Lys Leu Leu Tyr Pro Val Ala Pro
                85                  90
```

(2) INFORMATION FOR SEQ ID NO:26:

(i) SEQUENCE CHARACTERISTICS:
        (A) LENGTH: 92 amino acids
        (B) TYPE: amino acid
        (D) TOPOLOGY: unknown (ii) MOLECULE TYPE: protein (xi) SEQUENCE DESCRIPTION: SEQ ID NO:26:

```
Trp Tyr His Gly Lys Ile Ser Lys Gln Glu Ala Tyr Asn Leu Leu Met
 1               5                  10                  15

Thr Val Gly Gln Val Cys Ser Phe Leu Val Arg Pro Ser Asp Asn Thr
                20                  25                  30

Pro Gly Asp Tyr Ser Leu Tyr Phe Arg Thr Asn Glu Asn Ile Gln Arg
            35                  40                  45

Phe Lys Ile Cys Pro Thr Pro Asn Asn Gln Phe Met Met Gly Gly Arg
        50                  55                  60

Tyr Tyr Asn Ser Ile Gly Asp Ile Ile Asp His Tyr Arg Lys Glu Gln
65                  70                  75                  80

Ile Val Glu Gly Tyr Tyr Leu Lys Glu Pro Val Pro
                85                  90
```

(2) INFORMATION FOR SEQ ID NO:27:

(i) SEQUENCE CHARACTERISTICS:
        (A) LENGTH: 107 amino acids
        (B) TYPE: amino acid
        (D) TOPOLOGY: unknown (ii) MOLECULE TYPE: protein (xi) SEQUENCE DESCRIPTION: SEQ ID NO:27:

```
Trp Tyr Trp Gly Arg Leu Ser Arg Gly Asp Ala Val Ser Leu Leu Gln
 1               5                  10                  15

Gly Gln Arg His Gly Thr Phe Leu Val Arg Asp Ser Gly Ser Ile Pro
                20                  25                  30

Gly Asp Phe Val Leu Ser Val Ser Glu Ser Ser Arg Val Ser His Tyr
```

```
                35                  40                  45
Ile Val Asn Ser Leu Gly Pro Ala Gly Gly Arg Arg Ala Gly Gly Glu
    50                  55                  60

Gly Pro Phe Ala Pro Gly Leu Asn Pro Thr Arg Phe Leu Ile Gly Asp
65                  70                  75                  80

Asn Val Phe Asp Ser Leu Pro Ser Leu Leu Glu Phe Tyr Lys Ile His
                85                  90                  95

Tyr Leu Asp Thr Thr Thr Leu Ile Glu Pro Val
                100                 105
```

(2) INFORMATION FOR SEQ ID NO:28:

(i) SEQUENCE CHARACTERISTICS:
        (A) LENGTH: 70 amino acids
        (B) TYPE: amino acid
        (D) TOPOLOGY: unknown (ii) MOLECULE TYPE: protein (xi) SEQUENCE DESCRIPTION: SEQ ID NO:28:

```
Ala Leu Tyr Asp Tyr Lys Lys Glu Arg Glu Asp Ile Asp Leu His
1               5                   10                  15

Leu Gly Asp Ile Leu Thr Val Asn Lys Gly Ser Leu Val Ala Leu Gly
                20                  25                  30

Phe Ser Asp Pro Glu Ala Arg Pro Glu Asp Ile Gly Trp Leu Asn Gly
                35                  40                  45

Tyr Asn Glu Thr Thr Gly Glu Arg Gly Asp Phe Pro Gly Thr Tyr Val
    50                  55                  60

Glu Tyr Ile Gly Arg Lys
65                  70
```

(2) INFORMATION FOR SEQ ID NO:29:

(i) SEQUENCE CHARACTERISTICS:
        (A) LENGTH: 55 amino acids
        (B) TYPE: amino acid
        (D) TOPOLOGY: unknown (ii) MOLECULE TYPE: protein (xi) SEQUENCE DESCRIPTION: SEQ ID NO:29:

```
Ala Leu Tyr Asp Tyr Glu Ser Arg Thr Glu Thr Asp Leu Ala Phe Lys
1               5                   10                  15

Lys Gly Glu Arg Leu Gln Ile Val Met Asn Thr Glu Gly Asp Trp Trp
                20                  25                  30

Leu Ala His Ser Leu Thr Thr Gly Gln Thr Gly Tyr Ile Pro Ser Asn
                35                  40                  45

Tyr Val Ala Pro Ser Asp Ser
    50                  55
```

(2) INFORMATION FOR SEQ ID NO:30:

(i) SEQUENCE CHARACTERISTICS:
        (A) LENGTH: 54 amino acids
        (B) TYPE: amino acid
        (D) TOPOLOGY: unknown (ii) MOLECULE TYPE: protein (xi) SEQUENCE DESCRIPTION: SEQ ID NO:30:

```
Ala Leu Tyr Asp Phe Val Ala Ser Gly Asp Asn Thr Leu Ser Ile Thr
1               5                   10                  15
```

```
Lys Gly Glu Lys Leu Arg Val Leu Gly Tyr Asn His Asn Gly Glu Trp
            20                  25                  30

Cys Glu Ala Gln Thr Lys Asn Gly Gln Gly Trp Val Pro Ser Asn Tyr
        35                  40                  45

Ile Thr Pro Val Asn Ser
        50
```

(2) INFORMATION FOR SEQ ID NO:31:

(i) SEQUENCE CHARACTERISTICS:
        (A) LENGTH: 54 amino acids
        (B) TYPE: amino acid
        (D) TOPOLOGY: unknown (ii) MOLECULE TYPE: protein (xi) SEQUENCE DESCRIPTION: SEQ ID NO:31:

```
Ala Leu Phe Asp Tyr Lys Ala Gly Arg Glu Asp Glu Leu Thr Phe Thr
1               5                   10                  15

Lys Ser Ala Ile Ile Gln Asn Val Glu Lys Gln Glu Gly Gly Trp Trp
            20                  25                  30

Arg Gly Asp Tyr His His Lys Lys Gln Leu Trp Phe Pro Ser Asn Tyr
        35                  40                  45

Val Glu Glu Met Val Ser
        50
```

(2) INFORMATION FOR SEQ ID NO:32:

(i) SEQUENCE CHARACTERISTICS:
        (A) LENGTH: 56 amino acids
        (B) TYPE: amino acid
        (D) TOPOLOGY: unknown (ii) MOLECULE TYPE: protein (xi) SEQUENCE DESCRIPTION: SEQ ID NO:32:

```
Ala Ile Leu Asp Tyr Thr Lys Val Pro Asp Thr Asp Glu Ile Ser Phe
1               5                   10                  15

Leu Lys Gly Asp Met Phe Ile Val Asn Asn Glu Leu Glu Asp Gly Trp
            20                  25                  30

Met Trp Val Thr Asn Leu Arg Thr Asp Glu Gln Gly Leu Ile Val Glu
        35                  40                  45

Asp Leu Val Glu Glu Val Gly Arg
        50                  55
```

(2) INFORMATION FOR SEQ ID NO:33:

(i) SEQUENCE CHARACTERISTICS:
        (A) LENGTH: 55 amino acids
        (B) TYPE: amino acid
        (D) TOPOLOGY: unknown (ii) MOLECULE TYPE: protein (xi) SEQUENCE DESCRIPTION: SEQ ID NO:33:

```
Ala Leu Phe Asp Phe Lys Gly Asn Asp Asp Gly Asp Leu Pro Phe Lys
1               5                   10                  15

Lys Gly Asp Ile Leu Lys Ile Arg Asp Lys Pro Glu Glu Gln Trp Trp
            20                  25                  30

Asn Ala Glu Asp Met Asp Gly Lys Arg Gly Met Ile Pro Val Pro Tyr
        35                  40                  45
```

```
Val Glu Lys Cys Arg Pro Ser
    50              55
```

(2) INFORMATION FOR SEQ ID NO:34:

(i) SEQUENCE CHARACTERISTICS:
        (A) LENGTH: 949 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 1..949

(xi) SEQUENCE DESCRIPTION: SEQ ID NO:34:

```
GCCAGTGAAT TCGGGCCCGA ATTGGCAGAG CTTAATGGAA AAGACGGCTT CATTCCCAAG      60
AACTACATAG AAATGAAACC ACATCCGTGG TTTTTTGGCA AAATCCCCAG AGCCAAGGCA     120
GAAGAAATGC TTAGCAAACA GCGGCACGAT GGGGCCTTTC TTATCCGAGA GAGTGAGAGC     180
GCTCCTGGGG ACTTCTCCCT CTCTGTCAAG TTTGGAACGA TGTGCAGCAC TTTCAAGGTG     240
CTCCCGAGAT GGAGCCGGGA AGTACTTCCT CTGGTGGTGA AGTTCAATTC TTTGAATGAG     300
CTGGTGGATT ATCACAGATC TACATCTGTC TCCAGAAACC AGCAGATATT CCTGCGGGAC     360
ATAGAACAGG TGCCACAGCA GCCGACATAC GTCCAGGCCC TCTTTGACTT TGATCCCCAG     420
GAGGATGGAG AGCTGGGCTT CCGCCGGGGA GATTTTATCC ATGTCATGGA TAACTCAGAC     480
CCCAACTGGT GGAAAGGAGC TTGCCACGGG CAGACCGGCA TGTTTCCCCG CGAATTATGT     540
CTCCCCCNGT GAACCGGAAC GTCTAAGAGT CAAGAAGCAA TTATTTAAAG AAAGTGAAAA     600
ATGTAAAACA CATACAAAAG AATTAAACCC ACAAGCTGCC TCTGACAGCA GCCTGTGAGG     660
GAGTGCAGAA CACCTGGCCG GGTCACCCTG TGACCCTCTC ACTTTGGTTG GAACTTTAGG     720
GGGTGGGAGG GGGCGTTGGA TTTAAAAATG CCAAAACTTA CCTATAAATT AAGAAGAGTT     780
TTTATTACAA ATTTTCACTG CTGCTCCTCT TTCCCCTCCT TTGTCTTTTT TTTTCATCCT     840
TTTTTCTCTT CTGTCCATCA GTGCATGACG TTTAAGGCCA CGTATAGTCC TAGCTGACGC     900
CAATAATAAA AACCGAATTC GAGCTCGGAT CCGGGGATCC TCTAGAGTC                 949
```

(2) INFORMATION FOR SEQ ID NO:35:

(i) SEQUENCE CHARACTERISTICS:
        (A) LENGTH: 183 amino acids
        (B) TYPE: amino acid
        (D) TOPOLOGY: unknown (ii) MOLECULE TYPE: protein (xi) SEQUENCE DESCRIPTION: SEQ ID NO:35:

```
Ala Ser Glu Phe Gly Pro Glu Leu Ala Glu Leu Asn Gly Lys Asp Gly
1               5                  10                  15

Phe Ile Pro Lys Asn Tyr Ile Glu Met Lys Pro His Pro Trp Phe Phe
            20                  25                  30

Gly Lys Ile Pro Arg Ala Lys Ala Glu Glu Met Leu Ser Lys Gln Arg
        35                  40                  45

His Asp Gly Ala Phe Leu Ile Arg Glu Ser Glu Ser Ala Pro Gly Asp
    50                  55                  60

Phe Ser Leu Ser Val Lys Phe Gly Thr Met Cys Ser Thr Phe Lys Val
65                  70                  75                  80
```

```
Leu Pro Arg Trp Ser Arg Glu Val Leu Pro Leu Val Val Lys Phe Asn
                85                  90                  95

Ser Leu Asn Glu Leu Val Asp Tyr His Arg Ser Thr Ser Val Ser Arg
            100                 105                 110

Asn Gln Gln Ile Phe Leu Arg Asp Ile Glu Gln Val Pro Gln Gln Pro
        115                 120                 125

Thr Tyr Val Gln Ala Leu Phe Asp Phe Asp Pro Gln Glu Asp Gly Glu
    130                 135                 140

Leu Gly Phe Arg Arg Gly Asp Phe Ile His Val Met Asp Asn Ser Asp
145                 150                 155                 160

Pro Asn Trp Trp Lys Gly Ala Cys His Gly Gln Thr Gly Met Phe Pro
                165                 170                 175

Arg Glu Leu Cys Leu Pro Xaa
            180
```

(2) INFORMATION FOR SEQ ID NO:36:

(i) SEQUENCE CHARACTERISTICS:
        (A) LENGTH: 236 amino acids
        (B) TYPE: amino acid
        (D) TOPOLOGY: unknown (ii) MOLECULE TYPE: protein (xi) SEQUENCE DESCRIPTION: SEQ ID NO:36:

```
Gln Pro Arg Ala Gly Arg Gly Ala Gly His Arg Gly Leu Arg Arg Pro
1               5                   10                  15

Ala Gly Arg Gly Gln Arg Val Arg Pro Ala Gly Gly Ala Ala Leu Met
            20                  25                  30

Ala Gly Gln Glu Asp Ser Glu Asp Arg Gly Ser Trp Tyr Trp Gly Arg
        35                  40                  45

Leu Ser Arg Gly Asp Ala Val Ser Leu Ile Gln Gly Gln Arg His Gly
    50                  55                  60

Thr Phe Leu Val Arg Asp Ser Gly Ser Ile Pro Gly Asp Phe Val Leu
65                  70                  75                  80

Ser Val Ser Glu Ser Ser Arg Val Ser His Tyr Ile Val Asn Ser Leu
                85                  90                  95

Gly Pro Ala Gly Gly Arg Arg Ala Gly Gly Glu Gly Pro Gly Ala Pro
            100                 105                 110

Gly Leu Asn Pro Thr Arg Phe Leu Ile Gly Asp Gln Val Phe Asp Ser
        115                 120                 125

Leu Pro Ser Leu Leu Glu Phe Tyr Lys Ile His Tyr Leu Asp Thr Thr
    130                 135                 140

Thr Leu Ile Glu Pro Val Ser Arg Ser Arg Gln Asn Ser Gly Val Ile
145                 150                 155                 160

Leu Arg Gln Glu Glu Val Glu Tyr Val Arg Ala Leu Phe Asp Phe Lys
                165                 170                 175

Gly Asn Asp Asp Gly Asp Leu Pro Phe Lys Lys Gly Asp Ile Leu Lys
            180                 185                 190

Ile Arg Asp Lys Pro Glu Glu Gln Trp Trp Asn Ala Glu Asp Met Asp
        195                 200                 205

Gly Lys Arg Gly Met Ile Pro Val Pro Tyr Val Glu Lys Cys Arg Pro
    210                 215                 220

Ser Ser Ala Ser Val Ser Thr Leu Thr Gly Gly Arg
225                 230                 235
```

(2) INFORMATION FOR SEQ ID NO:37:

(i) SEQUENCE CHARACTERISTICS:
        (A) LENGTH: 160 amino acids
        (B) TYPE: amino acid
        (D) TOPOLOGY: unknown (ii) MOLECULE TYPE: protein (xi) SEQUENCE DESCRIPTION: SEQ ID NO:37:

```
Val Ile Glu Lys Pro Glu Asn Asp Pro Glu Trp Trp Lys Cys Arg Lys
 1               5                  10                  15

Ile Asn Gly Met Val Gly Leu Val Pro Lys Asn Tyr Val Thr Val Met
            20                  25                  30

Gln Asn Asn Pro Leu Thr Ser Gly Leu Glu Pro Ser His Pro Pro Gln
         35                  40                  45

Cys Asp Tyr Ile Arg Pro Ser Leu Thr Gly Lys Phe Ala Gly Asn Pro
 50                  55                  60

Trp Tyr Tyr Gly Lys Val Thr Arg His Gln Ala Glu Met Ala Leu Asn
 65                  70                  75                  80

Glu Arg Gly His Glu Gly Asp Phe Leu Ile Arg Asp Ser Glu Ser Ser
                 85                  90                  95

Pro Asn Asp Phe Ser Val Ser Leu Lys Ala Gln Gly Lys Asn Lys His
                100                 105                 110

Phe Lys Val Gln Leu Lys Glu Thr Val Tyr Cys Ile Gly Gln Arg Lys
            115                 120                 125

Phe Ser Thr Met Glu Glu Leu Val Glu His Tyr Lys Lys Ala Pro Ile
130                 135                 140

Phe Thr Ser Glu Gln Gly Glu Lys Leu Tyr Leu Val Lys His Leu Ser
145                 150                 155                 160
```

(2) INFORMATION FOR SEQ ID NO:38:

(i) SEQUENCE CHARACTERISTICS:
        (A) LENGTH: 96 amino acids
        (B) TYPE: amino acid
        (D) TOPOLOGY: unknown (ii) MOLECULE TYPE: protein (xi) SEQUENCE DESCRIPTION: SEQ ID NO:38:

```
Trp Tyr Phe Gly Lys Leu Gly Arg Lys Asp Ala Glu Arg Gln Leu Leu
 1               5                  10                  15

Ser Phe Gly Asn Pro Arg Gly Thr Phe Leu Ile Arg Glu Ser Glu Thr
            20                  25                  30

Thr Lys Gly Ala Tyr Ser Leu Ser Ile Arg Asp Trp Asp Asp Met Lys
         35                  40                  45

Gly Asp His Val Lys His Tyr Lys Ile Arg Lys Leu Asp Asn Gly Gly
 50                  55                  60

Tyr Tyr Ile Thr Thr Arg Ala Gln Phe Glu Thr Leu Gln Gln Leu Val
 65                  70                  75                  80

Gln His Tyr Ser Glu Arg Ala Ala Gly Leu Cys Cys Arg Leu Val Val
                 85                  90                  95
```

(2) INFORMATION FOR SEQ ID NO:39:

(i) SEQUENCE CHARACTERISTICS:
        (A) LENGTH: 92 amino acids
        (B) TYPE: amino acid
        (D) TOPOLOGY: unknown (ii) MOLECULE TYPE: protein (xi) SEQUENCE DESCRIPTION: SEQ ID NO:39:

Lys Gly Lys Gly Lys Arg Trp Lys Asn Leu Tyr Phe Ile Leu Glu Gly
1               5                   10                  15

Ser Asp Ala Gln Leu Ile Tyr Phe Glu Ser Glu Lys Arg Ala Thr Lys
                20                  25                  30

Pro Lys Gly Leu Ile Asp Leu Ser Val Cys Ser Val Tyr Val Val His
            35                  40                  45

Asp Ser Leu Phe Gly Arg Pro Asn Cys Phe Gln Ile Val Val Gln His
    50                  55                  60

Phe Ser Glu Glu His Tyr Ile Phe Tyr Phe Ala Gly Glu Thr Pro Glu
65                  70                  75                  80

Gln Ala Glu Asp Trp Met Lys Gly Leu Gln Ala Phe
                85                  90

(2) INFORMATION FOR SEQ ID NO:40:

(i) SEQUENCE CHARACTERISTICS:
        (A) LENGTH: 223 amino acids
        (B) TYPE: amino acid
        (D) TOPOLOGY: unknown (ii) MOLECULE TYPE: protein (xi) SEQUENCE DESCRIPTION: SEQ ID NO:40:

Pro Lys Pro Ala Arg Ala Ala Pro Pro Pro Pro Pro Pro Pro Pro Pro
1               5                   10                  15

Pro Pro Gly Ala Asp Arg Val Val Lys Ala Val Pro Phe Pro Pro Thr
                20                  25                  30

His Arg Leu Thr Ser Glu Glu Val Phe Asp Leu Asp Gly Ile Pro Arg
            35                  40                  45

Val Asp Val Leu Lys Asn His Leu Val Lys Glu Gly Arg Val Asp Glu
    50                  55                  60

Glu Ile Ala Leu Arg Ile Ile Asn Glu Gly Ala Ala Ile Leu Arg Arg
65                  70                  75                  80

Glu Lys Thr Met Ile Glu Val Glu Ala Pro Ile Thr Val Cys Gly Asp
                85                  90                  95

Ile His Gly Gln Phe Phe Asp Leu Met Lys Leu Phe Lys Val Gly Gly
            100                 105                 110

Ser Pro Ala Asn Thr Arg Tyr Leu Phe Leu Gly Asp Tyr Val Asp Arg
        115                 120                 125

Gly Tyr Phe Ser Ile Glu Cys Val Leu Tyr Leu Trp Val Leu Lys Ile
    130                 135                 140

Leu Tyr Pro Ser Thr Leu Phe Leu Leu Arg Gly Asn His Glu Cys Arg
145                 150                 155                 160

His Leu Thr Glu Tyr Phe Thr Phe Lys Gln Glu Cys Lys Ile Lys Tyr
                165                 170                 175

Ser Glu Arg Val Tyr Glu Ala Cys Met Glu Ala Phe Asp Ser Leu Pro
            180                 185                 190

Leu Ala Ala Leu Leu Asn Gln Gln Phe Leu Cys Val His Gly Gly Leu
        195                 200                 205

Ser Pro Glu Ile His Thr Leu Asp Asp Ile Arg Arg Leu Asp Arg
    210                 215                 220

(2) INFORMATION FOR SEQ ID NO:41:

```
    (i) SEQUENCE CHARACTERISTICS:
        (A) LENGTH: 99 amino acids
        (B) TYPE: amino acid
        (D) TOPOLOGY: unknown (ii) MOLECULE TYPE: protein (xi) SEQUENCE DESCRIPTION: SEQ ID NO:41:

Trp Phe Phe Gly Lys Ile Pro Arg Ala Lys Ala Glu Glu Met Leu Ser
1               5                   10                  15

Lys Gln Arg His Asp Gly Ala Phe Leu Ile Arg Glu Ser Glu Ser Ala
            20                  25                  30

Pro Gly Asp Phe Ser Leu Ser Val Lys Phe Gly Asn Asp Val Gln His
        35                  40                  45

Phe Lys Val Leu Arg Asp Gly Ala Gly Lys Tyr Phe Leu Trp Val Val
    50                  55                  60

Lys Phe Asn Ser Leu Asn Glu Leu Val Asp Tyr His Arg Ser Thr Ser
65                  70                  75                  80

Val Ser Arg Asn Gln Gln Ile Phe Leu Arg Asp Ile Glu Gln Val Pro
                85                  90                  95

Gln Gln Pro (2) INFORMATION FOR SEQ ID NO:42:

(i) SEQUENCE CHARACTERISTICS:
        (A) LENGTH: 50 amino acids
        (B) TYPE: amino acid
        (D) TOPOLOGY: unknown (ii) MOLECULE TYPE: protein (xi) SEQUENCE DESCRIPTION: SEQ ID NO:42:

Ala Lys Tyr Asp Phe Lys Ala Thr Ala Asp Asp Glu Leu Ser Phe Lys
1               5                   10                  15

Arg Gly Asp Ile Leu Lys Val Leu Asn Glu Glu Cys Asp Gln Asn Trp
            20                  25                  30

Tyr Lys Ala Glu Leu Asn Gly Lys Asp Gly Phe Ile Pro Lys Asn Tyr
        35                  40                  45

Ile Glu
    50

(2) INFORMATION FOR SEQ ID NO:43:

(i) SEQUENCE CHARACTERISTICS:
        (A) LENGTH: 46 amino acids
        (B) TYPE: amino acid
        (D) TOPOLOGY: unknown (ii) MOLECULE TYPE: protein (xi) SEQUENCE DESCRIPTION: SEQ ID NO:43:

Ala Leu Phe Asp Phe Asp Pro Gln Glu Asp Gly Glu Leu Gly Phe Arg
1               5                   10                  15

Arg Gly Asp Phe Ile His Val Met Asp Asn Ser Asp Pro Asn Trp Trp
            20                  25                  30

Lys Gly Ala Cys His Gly Gln Thr Gly Met Phe Pro Arg Asn
        35                  40                  45

(2) INFORMATION FOR SEQ ID NO:44:

(i) SEQUENCE CHARACTERISTICS:
        (A) LENGTH: 228 amino acids
```

(B) TYPE: amino acid
            (D) TOPOLOGY: unknown (ii) MOLECULE TYPE: protein (xi) SEQUENCE DESCRIPTION: SEQ ID NO:44:

Met Glu Ala Val Ala Glu His Asp Phe Gln Ala Gly Ser Pro Asp Glu
1               5                   10                  15

Leu Ser Phe Lys Arg Gly Asn Thr Leu Lys Val Leu Asn Lys Asp Glu
            20                  25                  30

Asp Pro His Trp Tyr Lys Ala Glu Leu Asp Gly Asn Glu Gly Phe Ile
        35                  40                  45

Pro Ser Asn Tyr Ile Arg Met Thr Glu Cys Asn Trp Tyr Leu Gly Lys
    50                  55                  60

Ile Thr Arg Asn Asp Ala Glu Val Leu Leu Lys Lys Pro Thr Val Arg
65                  70                  75                  80

Asp Gly His Phe Leu Val Arg Gln Cys Glu Ser Ser Pro Gly Glu Phe
                85                  90                  95

Ser Ile Ser Val Arg Phe Gln Asp Ser Val Gln His Phe Lys Val Leu
                100                 105                 110

Arg Asp Gln Asn Gly Lys Tyr Tyr Leu Trp Ala Val Lys Phe Asn Ser
            115                 120                 125

Leu Asn Glu Leu Val Ala Tyr His Arg Thr Ala Ser Val Ser Arg Thr
130                 135                 140

His Thr Ile Leu Leu Ser Asp Met Asn Val Glu Thr Lys Phe Val Gln
145                 150                 155                 160

Ala Leu Phe Asp Phe Asn Pro Gln Glu Ser Gly Glu Leu Ala Phe Lys
                165                 170                 175

Arg Gly Asp Val Ile Thr Leu Ile Asn Lys Asp Asp Pro Asn Trp Trp
            180                 185                 190

Glu Gly Gln Leu Asn Asn Arg Arg Gly Ile Phe Pro Ser Asn Tyr Val
            195                 200                 205

Cys Pro Tyr Asn Ser Asn Lys Ser Asn Ser Asn Val Ala Pro Gly Phe
        210                 215                 220

Asn Phe Gly Asn
225

(2) INFORMATION FOR SEQ ID NO:45:

(i) SEQUENCE CHARACTERISTICS:
            (A) LENGTH: 106 amino acids
            (B) TYPE: amino acid
            (D) TOPOLOGY: unknown (ii) MOLECULE TYPE: protein (xi) SEQUENCE DESCRIPTION: SEQ ID NO:45:

Trp Tyr Trp Gly Arg Leu Ser Arg Gln Glu Ala Val Ala Leu Leu Gln
1               5                   10                  15

Gly Gln Arg Asp Gly Val Phe Leu Val Arg Asp Ser Ser Thr Ser Pro
            20                  25                  30

Gly Asp Tyr Val Leu Ser Val Ser Glu Asn Ser Arg Val Ser His Tyr
        35                  40                  45

Ile Ile Asn Ser Ser Gly Pro Arg Pro Pro Val Pro Pro Ser Pro Ala
    50                  55                  60

Gln Pro Pro Pro Gly Val Ser Pro Ser Arg Leu Arg Ile Gly Asp Gln
65                  70                  75                  80

```
Glu Phe Asp Ser Leu Pro Ala Leu Leu Glu Phe Tyr Lys Ile His Tyr
                85                  90                  95
Leu Asp Thr Thr Thr Leu Ile Glu Pro Val
               100             105
```

(2) INFORMATION FOR SEQ ID NO:46:

(i) SEQUENCE CHARACTERISTICS:
        (A) LENGTH: 92 amino acids
        (B) TYPE: amino acid
        (D) TOPOLOGY: unknown (ii) MOLECULE TYPE: protein (xi) SEQUENCE DESCRIPTION: SEQ ID NO:46:

```
Trp Tyr Tyr Gly Asn Val Thr Arg His Gln Ala Glu Cys Ala Leu Asn
1               5                   10                  15
Glu Arg Gly Val Glu Gly Asp Phe Leu Ile Arg Asp Ser Glu Ser Ser
                20                  25                  30
Pro Ser Asp Phe Ser Val Ser Leu Lys Ala Ser Gly Arg Asn Lys His
                35                  40                  45
Phe Lys Val Gln Leu Val Asp Ser Val Tyr Cys Ile Gly Gln Arg Arg
50                  55                  60
Phe His Ser Met Asp Glu Leu Val Glu His Tyr Lys Lys Ala Pro Ile
65                  70                  75                  80
Phe Thr Ser Glu His Gly Glu Lys Leu Tyr Leu Val
                85                  90
```

(2) INFORMATION FOR SEQ ID NO:47:

(i) SEQUENCE CHARACTERISTICS:
        (A) LENGTH: 100 amino acids
        (B) TYPE: amino acid
        (D) TOPOLOGY: unknown (ii) MOLECULE TYPE: protein (xi) SEQUENCE DESCRIPTION: SEQ ID NO:47:

```
Trp Phe His Gly Arg Ile Ser Arg Glu Glu Ser Gln Arg Leu Ile Gly
1               5                   10                  15
Gln Gln Gly Leu Val Asp Gly Val Phe Leu Val Arg Glu Ser Gln Arg
                20                  25                  30
Asn Pro Gln Gly Phe Val Leu Ser Leu Cys His Leu Gln Lys Val Lys
                35                  40                  45
His Tyr Leu Ile Leu Pro Ser Glu Asp Glu Gly Cys Leu Tyr Phe Ser
50                  55                  60
Met Asp Glu Gly Gln Thr Arg Phe Thr Asp Leu Leu Gln Leu Val Glu
65                  70                  75                  80
Phe His Gln Leu Asn Arg Gly Ile Leu Pro Cys Leu Leu Arg His Cys
                85                  90                  95
Cys Ala Arg Val
            100
```

(2) INFORMATION FOR SEQ ID NO:48:

(i) SEQUENCE CHARACTERISTICS:
        (A) LENGTH: 98 amino acids
        (B) TYPE: amino acid
        (D) TOPOLOGY: unknown (ii) MOLECULE TYPE: protein (xi) SEQUENCE DESCRIPTION: SEQ ID NO:48:

```
Arg Gly Ser Gly Arg Lys Leu Trp Lys Arg Phe Phe Cys Phe Leu Arg
 1               5                  10                  15

Arg Ser Gly Leu Tyr Tyr Ser Thr Lys Gly Thr Ser Lys Asp Pro Arg
                20                  25                  30

His Leu Gln Tyr Val Ala Asp Val Asn Glu Ser Asn Val Tyr Val Val
            35                  40                  45

Thr Gln Gly Arg Lys Leu Tyr Gly Met Pro Thr Asp Phe Gly Phe Cys
        50                  55                  60

Val Lys Pro Asn Lys Leu Arg Asn Gly His Lys Gly Leu His Ile Phe
65                  70                  75                  80

Cys Ser Glu Asp Glu Gln Ser Arg Thr Cys Trp Leu Ala Ala Phe Arg
                85                  90                  95

Leu Phe
```

(2) INFORMATION FOR SEQ ID NO:49:

(i) SEQUENCE CHARACTERISTICS:
        (A) LENGTH: 224 amino acids
        (B) TYPE: amino acid
        (D) TOPOLOGY: unknown (ii) MOLECULE TYPE: protein (xi) SEQUENCE DESCRIPTION: SEQ ID NO:49:

```
Pro Thr Pro Ala Thr Pro Pro Glu Thr Pro Pro Pro Asp Asn Pro
 1               5                  10                  15

Pro Pro Gly Asp Val Lys Arg Ser Gln Pro Leu Pro Ile Pro Ser Ser
                20                  25                  30

Arg Lys Leu Arg Glu Glu Glu Phe Gln Ala Thr Ser Leu Pro Ser Ile
            35                  40                  45

Pro Asn Pro Phe Pro Glu Leu Cys Ser Pro Pro Ser Gln Lys Pro Ile
        50                  55                  60

Leu Gly Gly Ser Ser Gly Ala Arg Gly Leu Leu Pro Arg Asp Ser Ser
65                  70                  75                  80

Arg Leu Cys Val Val Lys Val Tyr Ser Glu Asp Gly Ala Cys Arg Ser
                85                  90                  95

Val Glu Val Ala Ala Gly Ala Thr Ala Arg His Val Cys Glu Met Leu
                100                 105                 110

Val Gln Arg Ala His Ala Leu Ser Asp Glu Ser Trp Gly Leu Val Glu
            115                 120                 125

Ser His Pro Tyr Leu Ala Leu Glu Arg Gly Leu Glu Asp His Glu Phe
        130                 135                 140

Val Val Glu Val Gln Glu Ala Trp Pro Val Gly Gly Asp Ser Arg Phe
145                 150                 155                 160

Ile Phe Arg Lys Asn Phe Ala Lys Tyr Glu Leu Phe Lys Ser Pro Pro
                165                 170                 175

His Thr Leu Phe Pro Glu Lys Met Val Ser Ser Cys Leu Asp Ala Gln
            180                 185                 190

Thr Gly Ile Ser His Glu Asp Leu Ile Gln Asn Phe Leu Asn Ala Gly
        195                 200                 205

Ser Phe Pro Glu Ile Gln Gly Phe Leu Gln Leu Arg Gly Ser Gly Arg
    210                 215                 220
```

(2) INFORMATION FOR SEQ ID NO:50:

(i) SEQUENCE CHARACTERISTICS:
        (A) LENGTH: 102 amino acids
        (B) TYPE: amino acid
        (D) TOPOLOGY: unknown (ii) MOLECULE TYPE: protein (xi) SEQUENCE DESCRIPTION: SEQ ID NO:50:

Trp Phe His Gly Arg Ile Ser Arg Glu Glu Ser His Arg Ile Ile Lys
1               5                   10                  15

Gln Gln Gly Leu Val Asp Gly Leu Phe Leu Leu Arg Asp Ser Gln Ser
            20                  25                  30

Asn Pro Lys Ala Phe Val Leu Thr Leu Cys His His Gln Lys Ile Lys
        35                  40                  45

Asn Phe Gln Ile Leu Pro Cys Glu Asp Asp Gly Gln Thr Phe Phe Thr
    50                  55                  60

Leu Asp Asp Gly Asn Thr Lys Phe Ser Asp Leu Ile Gln Leu Val Asp
65                  70                  75                  80

Phe Tyr Gln Leu Asn Lys Gly Val Leu Pro Cys Lys Leu Lys His His
                85                  90                  95

Cys Ile Arg Val Ala Leu
            100

(2) INFORMATION FOR SEQ ID NO:51:

(i) SEQUENCE CHARACTERISTICS:
        (A) LENGTH: 335 amino acids
        (B) TYPE: amino acid
        (D) TOPOLOGY: unknown (ii) MOLECULE TYPE: protein (xi) SEQUENCE DESCRIPTION: SEQ ID NO:51:

Pro Arg Asp Ser Ser Arg Leu Cys Val Val Lys Val Tyr Ser Glu Asp
1               5                   10                  15

Gly Ala Cys Arg Ser Val Glu Val Ala Ala Gly Ala Thr Ala Arg His
            20                  25                  30

Val Cys Glu Met Leu Val Gln Arg Ala His Ala Leu Ser Asp Glu Ser
            35                  40                  45

Trp Gly Leu Val Glu Ser His Pro Tyr Leu Ala Leu Glu Arg Gly Leu
    50                  55                  60

Glu Asp His Glu Phe Val Val Glu Val Gln Glu Ala Trp Pro Val Gly
65                  70                  75                  80

Gly Asp Ser Arg Phe Ile Phe Arg Lys Asn Phe Ala Lys Tyr Glu Leu
            85                  90                  95

Phe Lys Ser Pro Pro His Thr Leu Phe Pro Glu Lys Met Val Ser Ser
            100                 105                 110

Cys Leu Asp Ala Gln Thr Gly Ile Ser His Glu Asp Leu Ile Gln Asn
            115                 120                 125

Phe Leu Asn Ala Gly Ser Phe Pro Glu Ile Gln Gly Phe Leu Gln Leu
    130                 135                 140

Arg Gly Ser Gly Arg Gly Ser Gly Arg Lys Leu Trp Lys Arg Phe Phe
145                 150                 155                 160

Cys Phe Leu Arg Arg Ser Gly Leu Tyr Tyr Ser Thr Lys Gly Thr Ser
                165                 170                 175

Lys Asp Pro Arg His Leu Gln Tyr Val Ala Asp Val Asn Glu Ser Asn
            180                 185                 190

Val Tyr Val Val Thr Gln Gly Arg Lys Leu Tyr Gly Met Pro Thr Asp

-continued

```
            195                 200                 205
Phe Gly Phe Cys Val Lys Pro Asn Lys Leu Arg Asn Gly His Lys Gly
            210                 215                 220

Leu His Ile Phe Cys Ser Glu Asp Glu Gln Ser Arg Thr Cys Trp Leu
225                 230                 235                 240

Ala Ala Phe Arg Leu Phe Lys Tyr Gly Val Gln Leu Tyr Lys Asn Tyr
                245                 250                 255

Gln Gln Ala Gln Ser Arg His Leu Arg Leu Ser Tyr Leu Gly Ser Pro
            260                 265                 270

Pro Leu Arg Ser Val Ser Asp Asn Thr Leu Val Ala Met Asp Phe Ser
            275                 280                 285

Gly His Ala Gly Arg Val Ile Asp Asn Pro Arg Glu Ala Leu Ser Ala
            290                 295                 300

Ala Met Glu Glu Ala Gln Ala Trp Arg Lys Lys Thr Asn His Arg Leu
305                 310                 315                 320

Ser Leu Pro Thr Thr Cys Ser Gly Ser Ser Leu Ser Ala Ala Ile
                        325                 330                 335
```

(2) INFORMATION FOR SEQ ID NO:52:

(i) SEQUENCE CHARACTERISTICS:
        (A) LENGTH: 326 amino acids
        (B) TYPE: amino acid
        (D) TOPOLOGY: unknown (ii) MOLECULE TYPE: protein (xi) SEQUENCE DESCRIPTION: SEQ ID NO:52:

```
Met Glu Lys Leu Arg Leu Arg Lys Asp Val Lys Val Phe Ser Glu Asp
1               5                   10                  15

Gly Thr Ser Lys Val Val Glu Ile Leu Thr Asp Met Thr Ala Arg Asp
                20                  25                  30

Leu Cys Gln Leu Leu Val Tyr Lys Ser His Cys Val Asp Asp Asn Ser
                35                  40                  45

Trp Thr Leu Val Glu His His Pro Gln Leu Gly Leu Glu Arg Cys Leu
    50                  55                  60

Glu Asp His Glu Ile Val Val Gln Val Glu Ser Thr Met Pro Ser Glu
65                  70                  75                  80

Ser Lys Phe Leu Phe Arg Lys Asn Tyr Ala Lys Tyr Glu Phe Phe Lys
                85                  90                  95

Asn Pro Val Asn Phe Phe Pro Asp Gln Met Val Asn Trp Cys Gln Gln
                100                 105                 110

Ser Asn Gly Gly Gln Ala Gln Leu Leu Gln Asn Phe Leu Asn Thr Ser
                115                 120                 125

Ser Cys Pro Glu Ile Gln Gly Phe Leu Gln Val Lys Glu Val Gly Arg
                130                 135                 140

Lys Ser Trp Lys Lys Leu Tyr Val Cys Leu Arg Arg Ser Gly Leu Tyr
145                 150                 155                 160

Tyr Ser Thr Lys Gly Thr Ser Lys Glu Pro Arg His Leu Gln Leu Leu
                165                 170                 175

Ala Asp Leu Glu Glu Ser Ser Ile Phe Tyr Leu Ile Ala Gly Lys Lys
                180                 185                 190

Gln Tyr Asn Ala Pro Asn Glu His Gly Met Cys Ile Lys Pro Asn Lys
                195                 200                 205

Ala Lys Thr Glu Met Lys Glu Leu Arg Leu Leu Cys Ala Glu Asp Glu
                210                 215                 220
```

```
Gln Ile Arg Thr Cys Trp Met Thr Ala Phe Arg Leu Leu Lys Tyr Gly
225                 230                 235                 240

Met Leu Leu Tyr Gln Asn Tyr Arg Ile Pro Gln Arg Lys Gly Leu Pro
                245                 250                 255

Pro Pro Phe Asn Ala Pro Met Arg Ser Val Ser Glu Asn Ser Leu Val
                260                 265                 270

Ala Met Asp Phe Ser Gly Gln Ile Gly Arg Val Ile Asp Asn Pro Ala
                275                 280                 285

Glu Ala Gln Ser Ala Ala Leu Glu Glu Gly His Ala Trp Arg Asn Gly
                290                 295                 300

Ser Thr Arg Met Asn Ile Leu Ser Ser Gln Ser Pro Leu His Pro Ser
305                 310                 315                 320

Thr Leu Asn Ala Val Ile
                325

(2) INFORMATION FOR SEQ ID NO:53:

(i) SEQUENCE CHARACTERISTICS:
        (A) LENGTH: 348 amino acids
        (B) TYPE: amino acid
        (D) TOPOLOGY: unknown (ii) MOLECULE TYPE: protein (xi) SEQUENCE DESCRIPTION: SEQ ID NO:53:

Lys Glu Ala Lys Val Thr Lys Ile Phe Val Lys Phe Val Glu Asp
1               5                   10                  15

Gly Glu Ala Leu Gln Leu Leu Ile Asp Glu Arg Trp Thr Val Ala Asp
                20                  25                  30

Thr Leu Lys Gln Leu Ala Glu Lys Asn His Ile Ala Leu Met Glu Asp
                35                  40                  45

His Cys Ile Val Glu Glu Tyr Pro Glu Leu Tyr Ile Lys Arg Val Tyr
            50                  55                  60

Glu Asp His Glu Lys Val Val Glu Asn Ile Gln Met Trp Val Gln Asp
65                  70                  75                  80

Ser Pro Asn Lys Leu Tyr Phe Met Arg Arg Pro Asp Lys Tyr Ala Phe
                85                  90                  95

Ile Ser Arg Pro Glu Leu Tyr Leu Leu Thr Pro Lys Thr Ser Asp His
                100                 105                 110

Met Glu Ile Pro Ser Gly Asp Gln Trp Thr Ile Asp Val Lys Gln Lys
            115                 120                 125

Phe Val Ser Glu Tyr Phe His Arg Glu Pro Val Val Pro Pro Glu Met
130                 135                 140

Glu Gly Phe Leu Tyr Leu Lys Ser Asp Gly Arg Lys Ser Trp Lys Lys
145                 150                 155                 160

His Tyr Phe Val Leu Arg Pro Ser Gly Leu Tyr Tyr Ala Pro Lys Ser
                165                 170                 175

Lys Lys Pro Thr Thr Lys Asp Leu Thr Cys Leu Met Asn Leu His Ser
                180                 185                 190

Asn Gln Val Tyr Thr Gly Ile Gly Trp Glu Lys Lys Tyr Lys Ser Pro
                195                 200                 205

Thr Pro Trp Cys Ile Ser Ile Lys Leu Thr Ala Leu Gln Met Lys Arg
            210                 215                 220

Ser Gln Phe Ile Lys Tyr Ile Cys Ala Glu Asp Glu Met Thr Phe Lys
225                 230                 235                 240
```

-continued

```
Lys Trp Leu Val Ala Leu Arg Ile Ala Lys Asn Gly Ala Glu Leu Leu
                245                 250                 255

Glu Asn Tyr Glu Arg Ala Cys Gln Ile Arg Arg Glu Thr Leu Gly Pro
                260                 265                 270

Ala Ser Ser Met Ser Ala Ala Ser Ser Thr Ala Ile Ser Glu Val
                275                 280                 285

Pro His Ser Leu Ser His His Gln Arg Thr Pro Ser Val Ala Ser Ser
                290                 295                 300

Ile Gln Leu Ser Ser His Met Met Asn Asn Pro Thr His Pro Leu Ser
305                 310                 315                 320

Val Asn Val Arg Asn Gln Ser Pro Ala Ser Phe Ser Val Asn Ser Cys
                325                 330                 335

Gln Gln Ser His Pro Ser Arg Thr Ser Ala Lys Leu
                340                 345
```

(2) INFORMATION FOR SEQ ID NO:54:

(i) SEQUENCE CHARACTERISTICS:
       (A) LENGTH: 11 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:54:

```
Thr Gly Thr Ser Lys Ser Gln Glu Ala Ile Ile
1               5               10
```

(2) INFORMATION FOR SEQ ID NO:55:

(i) SEQUENCE CHARACTERISTICS:
       (A) LENGTH: 12 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:55:

```
Asn Thr Tyr Lys Arg Ile Lys Pro Thr Ser Cys Leu
1               5                   10
```

(2) INFORMATION FOR SEQ ID NO:56:

(i) SEQUENCE CHARACTERISTICS:
       (A) LENGTH: 15 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:56:

```
Gln Gln Pro Val Arg Glu Cys Arg Thr Pro Gly Arg Val Thr Leu
1               5                   10                  15
```

(2) INFORMATION FOR SEQ ID NO:57:

(i) SEQUENCE CHARACTERISTICS:
       (A) LENGTH: 67 amino acids
       (B) TYPE: amino acid
       (C) STRANDEDNESS:
       (D) TOPOLOGY: linear (ii) MOLECULE TYPE: peptide

```
           (xi) SEQUENCE DESCRIPTION: SEQ ID NO:57:

Pro Ser His Phe Gly Trp Asn Phe Arg Gly Trp Glu Gly Ala Leu Asp
1               5                   10                  15

Leu Lys Met Pro Lys Leu Thr Tyr Lys Leu Arg Arg Val Phe Ile Thr
            20              25              30

Asn Phe His Cys Cys Ser Ser Phe Pro Ser Phe Val Phe Phe Phe His
            35              40              45

Pro Phe Phe Ser Ser Val His Gln Cys Met Thr Phe Lys Ala Thr Tyr
    50              55              60

Ser Pro Ser
65

(2) INFORMATION FOR SEQ ID NO:58:

(i) SEQUENCE CHARACTERISTICS:
         (A) LENGTH: 11 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:58:

Lys Pro Asn Ser Ser Asp Pro Gly Ile Leu
1               5                   10
```

What is claimed is:

1. An isolated polypeptide comprising the amino acid sequence of SEQ ID NO:18.

2. An isolated nucleic acid molecule comprising a nucleotide sequence encoding the amino acid sequence of SEQ ID 18.

3. The nucleic acid molecule of claim 2, wherein the nucleic acid comprises the nucleotide sequence of SEQ ID NO:17.

4. A vector comprising the nucleic acid molecule of claim 2.

5. An expression vector comprising the nucleic acid molecule of claim 2 in operative association with a nucleotide regulatory sequence that controls expression of the nucleic acid in a host cell.

6. A host cell engineered to contain the nucleic acid of claim 2.

7. The host cell of claim 6 wherein the host cell is prokaryotic.

8. The host cell of claim 6 wherein the host cell is eukaryotic.

9. A host cell engineered to express the nucleic acid of claim 2.

10. The host cell of claim 9 wherein the host cell is prokaryotic.

11. The host cell of claim 9 wherein the host cell is eukaryotic.

12. An antibody specific for the polypeptide of claim 1.

13. The antibody of claim 12 is a monoclonal antibody.

14. A method of producing a GRB-10 polypeptide, comprising incubating the cell of claim 9 under conditions whereby the nucleic acid molecule is expressed and the cell produces GRB-10 polypeptide, and the GRB-10 polypeptide is produced.

* * * * *